United States Patent
Lee et al.

(10) Patent No.: US 8,895,558 B2
(45) Date of Patent: Nov. 25, 2014

(54) ARYLPIPERAZINE-CONTAINING PYRROLE 3-CARBOXAMIDE DERIVATIVES FOR TREATING DEPRESSIVE DISORDERS

(75) Inventors: Jinhwa Lee, Yongin-si (KR); Suk Youn Kang, Yongin-si (KR); Eun-Jung Park, Yongin-si (KR); Kwang-Seop Song, Yongin-si (KR); Min Ju Kim, Yongin-si (KR); Hee Jeong Seo, Yongin-si (KR); Suk Ho Lee, Yongin-si (KR); Jeongmin Kim, Yongin-si (KR); Ae Nim Pae, Seoul (KR); Woo-Kyu Park, Daejeon (KR)

(73) Assignee: Green Cross Corporation, Gyeonggi-do (KR)

( * ) Notice: Subject to any disclaimer, the term of this patent is extended or adjusted under 35 U.S.C. 154(b) by 330 days.

(21) Appl. No.: 13/121,551

(22) PCT Filed: Sep. 23, 2009

(86) PCT No.: PCT/KR2009/005415
§ 371 (c)(1),
(2), (4) Date: Mar. 29, 2011

(87) PCT Pub. No.: WO2010/038948
PCT Pub. Date: Apr. 8, 2010

(65) Prior Publication Data
US 2011/0178091 A1    Jul. 21, 2011

Related U.S. Application Data

(60) Provisional application No. 61/102,192, filed on Oct. 2, 2008.

(51) Int. Cl.
| | | |
|---|---|---|
| C07D 207/34 | (2006.01) | |
| C07D 401/12 | (2006.01) | |
| C07D 401/04 | (2006.01) | |
| C07D 405/04 | (2006.01) | |
| C07D 417/12 | (2006.01) | |
| A61K 31/496 | (2006.01) | |
| A61K 31/498 | (2006.01) | |
| C07D 405/12 | (2006.01) | |
| C07D 207/50 | (2006.01) | |
| C07D 207/36 | (2006.01) | |
| C07D 401/14 | (2006.01) | |

(52) U.S. Cl.
CPC ............ *C07D 207/34* (2013.01); *C07D 417/12* (2013.01); *C07D 401/12* (2013.01); *C07D 405/12* (2013.01); *C07D 207/50* (2013.01); *C07D 207/36* (2013.01); *C07D 401/04* (2013.01); *C07D 401/14* (2013.01)
USPC ................. 514/249; 514/253.06; 514/253.09; 514/254.04; 514/254.01; 544/353; 544/363; 544/364; 544/368; 544/372

(58) Field of Classification Search
None
See application file for complete search history.

(56) References Cited

U.S. PATENT DOCUMENTS 3,705,899 A     12/1972  Regnier et al.
7,491,821 B2 *  2/2009   Brotherton-Pleiss et al.  544/295

FOREIGN PATENT DOCUMENTS

| JP | 61-100566 A | 5/1986 |
|---|---|---|
| KR | 10-2008-0027943 A | 3/2008 |
| WO | 03/028728 * | 4/2003 |
| WO | 2007/020194 * | 2/2007 |

OTHER PUBLICATIONS

CA Registry No. 902873-31-8, entered into the Registry File on Aug. 21, 2006, supplied by Aurora Fine Chemicals.*
CA Registry No. 1115953-04-2, entered into the Registry File on Mar. 5, 2009, supplied by Aurora Fine Chemicals.*
Pinna et al. Farmaco 54(8), p. 542-550 (1999).*
CA Registry No. 1100290-70-7, entered into the Registry File on Feb. 3, 2009, supplied by UkrOrgSynthesis.*
CA Registry No. 1100125-76-5, entered into the Registry File on Feb. 3, 2009, supplied by UkrOrgSynthesis.*
Kang et al. Bioorganic & Medicinal Chemistry Letters, vol. 20, pp. 1705-1711 (2010).*

* cited by examiner

*Primary Examiner* — Emily Bernhardt
(74) *Attorney, Agent, or Firm* — Sughrue Mion, PLLC

(57) ABSTRACT

The present invention relates to novel arylpiperazine-containing pyrrole 3-carboxamide derivatives of formula (I) or a pharmaceutically acceptable salt thereof which is useful for preventing or treating depressive disorders. The present invention also provides a method for preparing the arylpiperazine-containing pyrrole 3-carboxamide derivatives or the pharmaceutically acceptable salt thereof, a pharmaceutical composition containing same, and a method for preventing or treating depressive disorders.

3 Claims, No Drawings

ARYLPIPERAZINE-CONTAINING PYRROLE 3-CARBOXAMIDE DERIVATIVES FOR TREATING DEPRESSIVE DISORDERS

FIELD OF THE INVENTION

The present invention relates to a novel arylpiperazine-containing pyrrole 3-carboxamide derivatives for treating depressive disorders.

BACKGROUND OF THE INVENTION

Depressive disorders involve all major bodily functions, mood, and thoughts, affecting the ways in which an individual eats and sleeps, feel about themselves, and think. Without treatment, depression symptoms can last for weeks, months or years. Depression is the leading cause of disability in the United States. An increasing number of treatment options have become more available over the past two decades for individuals with major depression disorder. The clinical description of depression is complex, covering a broad range of symptoms that lack a unifying biological hypothesis. Depression has both genetic and environmental components, with linkage studies suggesting it is a polygenic disorder. Modern treatment for depression, which focuses exclusively on agents that modulate monoamine neurotransmission, began with a monoamine oxidase inhibitor (MAOI). MAOIs increase serotonin and norepinephrine concentrations in the brain by inhibiting the MAO enzyme. They are highly effective in treating depression but are used only scarcely owing to potentially dangerous drug interaction effects.

A second breakthrough in depression treatment came from chlorpromazine derivatives. Imipramine, one such derivative, was exceptionally effective in patients who had severe depression. Imipramine is a tricyclic antidepressant (TCA) that acts by inhibiting cellular reuptake mechanisms for norepinephrine and serotonin to increase activity within these G protein-coupled receptor (GPCR) families. Imipramine retains activity at GPCRs, but this activity contributes to unattractive side effects. Subsequently, structural analogs of diphenhydramine were discovered as novel antidepressants. The phenoxyphenylpropylamine was used to identify fluoxetine, the first selective serotonine reuptake inhibitor (SSRI). The remarkable success of fluoxetine as an antidepressant extended to the identification of other SSRIs including paroxetine, citalopram, fluvoxamine, and sertraline. SSRIs became a family of antidepressants considered to be the current standard of drug treatment. It is thought that one cause of depression is an inadequate amount of serotonin. SSRIs are said to work by preventing the reuptake of serotonin by the presynaptic neuron, thus maintaining higher levels of 5-HT in the synapse. These antidepressants typically have fewer adverse events and side effects than the tricyclics or the MAOIs, although such effects as drowsiness, dry mouth, nervousness, anxiety, insomnia, decreased appetite, and decreased ability to function sexually may occur.

Although there are a number of treatments currently available, there are still clear opportunities for improvement of existing therapies. Much research has been focused to address unmet medical needs of currently available drug therapies: slow onset of action, inability to achieve full remission, difficulty of targeting significant populations of nonresponding patients, and minimalization of residual side effects including sexual dysfunction. Recent developments include serotonin+norepinephrine reuptake inhibitors (SNRIs), and norepinephrine+dopamine reuptake inhibitors (NDRIs), implying multiple neurotransmitter pathways in the spectrum of disorders that incorporate major depression [Pacher, P. et al., Curr. Med. Chem. 2004, 11, 925-943]. It is the hope that drugs acting by newer mechanisms will meet some, if not all, of these unmet needs.

Along the line, SARI (serotonin antagonist/reuptake inhibitor) drugs that block both the serotonin 5-HT$_2$ receptors and the serotonin transporters have been developed. Typical examples are Bristol-Myers Squibb's nefazodone [DeBattista, C. et al., Biol. Psychiatry, 1998, 44, 341], Yamanouchi's YM-992 [Hatanaka, K. et al., Neuropharmacology, 1997, 35(11), 1621], and Lilly's LY367265 [Pullar, I. A. et al., Eur. J. Pharmacol. 2000, 407(1-2), 39]. These compounds demonstrated improved results in the treatment of central nervous system disorders, compared with either the serotonin 5-HT$_2$ receptors or the selective serotonin reuptake inhibitors only, in clinical effects, side effects, reduction in drug action time, etc. [Avila, A. et al., J. Clin. Psychopharmacol., 2003, 23(5), 509]. Nefazodone is most closely related to trazodone in terms of chemical structure [Temple, D. L, Jr. et al., U.S. Pat. No. 4,338,317]. Unlike most SSRIs, nefazodone has no negative effects on libido or sexual functioning. Nefazodone's claimed advantages over other antidepressants include reduced possibility of disturbed sleep or sexual dysfunction, and ability to treat some patients who did not respond to other antidepressant drugs [Greene, D. S. et al., Clin. Pharmacokinet., 1997, 33(4), 260]. However, nefazodone is a potent inhibitor of the CYP3A4 isoenzyme both in vitro and in vivo [Kent, J. M. Lancet, 2000, 355, 911-918]. In the end, its sale was discontinued in 2003 in some countries, due to the small possibility of hepatic injury, which could lead to the need for a liver transplant, or even death. At 2004, Bristol-Myers Squibb withdrew nefazodone in the United States.

In this regard, there is an urgent need on the discovery of new drugs that act as a mode of nefazodone, but have better developability characteristics. This new class of antidepressants would significantly broaden the physicians' and patients' choice.

SUMMARY OF THE INVENTION

It is a primary object of the present invention to provide a novel arylpiperazine-containing pyrrole 3-carboxamide compound of formula (I) or a pharmaceutically acceptable salt thereof, which is useful for preventing or treating depressive disorders.

It is other object of the present invention to provide a method for preparing the inventive compound.

It is another object of the present invention to provide a pharmaceutical composition for preventing or treating depressive disorders, comprising the inventive compound as an active ingredient.

It is a further object of the present invention to provide a method for preventing or treating depressive disorders in a mammal, which comprises administering the inventive compound.

In accordance with one aspect of the present invention, there is provided a compound of formula (I) or a pharmaceutically acceptable salt thereof:

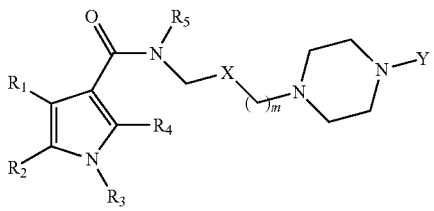

(I)

wherein:

$R_1$ represents hydrogen, hydroxy, $C_{1-3}$ alkyl, or $C_{1-3}$ alkoxy;

$R_2$ represents hydrogen, halogen, carbocycle, substituted carbocycle, aryl, substituted aryl, heteroaryl, substituted heteroaryl, heterocycle, substituted heterocycle, $C_{1-8}$ alkyl, substituted $C_{1-8}$ alkyl, hydroxy, acyloxy, $C_{1-6}$ alkoxy, substituted $C_{1-6}$ alkoxy, $C_{3-5}$ alkenyloxy, substituted $C_{3-5}$ alkenyloxy, $C_{3-5}$ alkynyloxy, substituted $C_{3-5}$ alkynyloxy, aryloxy, substituted aryloxy, heteroaryloxy, substituted heteroaryloxy, $C_{2-6}$ alkenyl, $C_{2-6}$ alkynyl, —$(CH_2)_n$—$C_{3-6}$ carbocycle, substituted $C_{2-6}$ alkenyl, $C_{2-6}$ alkynyl or —$(CH_2)_n$—$C_{3-6}$ carbocycle having one or two alkoxy or halogen groups, or —$(CH_2)_n$—R', R' being phenyl, furanyl, benzofuranyl, thienyl, benzothienyl, pyridinyl, pyridiminyl, pyrazinyl, pyridizinyl, tetrahydrofuranyl, tetrahydropyranyl, dioxanyl, 1,4-benzodioxanyl or benzo[1,3]dioxolyl, each being optionally substituted with one or more halogen, $C_{1-3}$ alkyl, or $C_{1-3}$ alkoxy groups, each optionally having one to three fluorine substituents, and n being 1 or 2;

$R_3$ represents hydrogen, $C_{1-5}$ alkyl, substituted $C_{1-5}$ alkyl, $C_{3-7}$ cycloalkyl, substituted $C_{3-7}$ cycloalkyl, aryl, substituted aryl, heteroaryl, substituted heteroaryl, heterocycloalkyl, or substituted heterocycloalkyl;

$R_4$ represents hydrogen, halogen, $C_{1-4}$ alkyl, or substituted $C_{1-4}$ alkyl;

$R_5$ represents hydrogen, or $C_{1-3}$ alkyl;

X is —$CH_2$—, —CH(OH)—, —CHF—, —$CF_2$— or —$CH(CH_2)F$—;

Y is

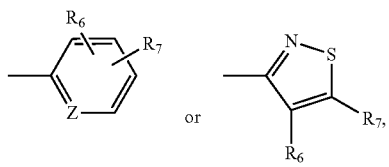

Z being N or CH, and $R_6$ and $R_7$ being each independently hydrogen, halogen, $C_{1-3}$ alkyl, $C_{1-3}$ alkoxy, cyano, monofluoromethyl, difluoromethyl, or trifluoromethyl, or $R_6$ and $R_7$, together with the aryl ring to which they are bonded, form a 5- to 7-membered saturated or unsaturated heterocyclic ring or aryl ring which is optionally substituted by one or more $C_{1-3}$ alkyl, $C_{1-3}$ alkoxy, halogen, trifluoromethyl or cyano groups; and m is 0 to 3.

In accordance with other aspect of the present invention, there is provided a method for preparing the compound of formula (I) or the pharmaceutically acceptable salt thereof, which comprises conducting an amide coupling reaction of pyrrole 3-carboxylic acid with arylpiperazinyl alkyl amine or its salt thereof.

In accordance with another aspect of the present invention, there is provided a pharmaceutical composition for preventing or treating depressive disorders, which comprises the compound of formula (I) or the pharmaceutically acceptable salt thereof as an active ingredient, and a pharmaceutically acceptable carrier.

In accordance with further aspect of the present invention, there is provided a method for preventing or treating depressive disorders in a mammal, which comprises administering the compound of formula (I) or the pharmaceutically acceptable salt thereof to the mammal.

DETAILED DESCRIPTION OF THE INVENTION

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five-to seven-membered rings may contain a double bond in the ring structure. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional subsituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein, the term "alkenyloxy" referes to —$OR_b$, where $R_b$ is alkenyl as defined above.

As used herein, the term "alkynyloxy" referes to —$OR_c$, where $R_c$ is alkynyl as defined above.

As used herein, the term "aralkoxy" refers to the group —$OR_aR_d$, wherein $R_a$ is alkyl and $R_d$ is aryl as defined above.

As used herein, the term "aryloxy" refers to the group —$OR_d$, wherein $R_d$ is aryl as defined above.

As used herein, the term "heteroaryloxy" refers to —$OR_e$, where $R_e$ is heteroaryl as defined above.

As used herein, the term "mercapto" refers to the group —SH.

As used herein, the term "sulfanyl" refers to the group —$SR_f$, wherein $R_f$ is substituted alkyl, substituted carbocycle, aryl, heteroaryl or heterocyclic, as defined above.

As used herein, the term "sulfinyl" refers to the group —S—(O)$R_f$, wherein $R_f$ is substituted alkyl, substituted carbocycle, aryl, heteroaryl or heterocyclic, as defined above.

As used herein, the term "sulfonyl" refers to the group —$S(O)_2R_f$, wherein $R_f$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted with substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted with substituted alkyl, substituted carbocycle, aryl, heteroaryl or heterocyclic, as defined above.

As used herein, the term "sulfonylamino" refers to the group —$NHS(O)_2R_f$ wherein $R_f$ is substituted alkyl, substituted carbocycle, aryl, heteroaryl or heterocyclic, as defined above.

As used herein, the term "carboxyamide" refers to the group —$NHC(O)R_f$ wherein $R_f$ is substituted alkyl, substituted carbocycle, aryl, heteroaryl or heterocyclic, as defined above.

As used herein, the term "carboxy" refers to the group —C(O)OH. The carboxy group is optionally substituted with substituted alkyl, substituted carbocycle, aryl, heteroaryl or heterocyclic, as defined above.

As used herein, the term "aminocarbonyl" refers to the group —$C(O)NH_2$. The aminocarbonyl group is optionally substituted with substituted alkyl, substituted carbocycle, aryl, heteroaryl or heterocyclic, as defined above.

As used herein, the term "ureido" refers to the group —NHC(O)NHR$_f$ wherein R$_f$ is hydrogen, alkyl, carbocycle or aryl as defined above.

As used herein, the term "guanidino" refers to the group —NHC(=NH)NH$_2$.

As used herein, the term "acyl" refers to the group —C(O)R$_f$, wherein R$_f$ is alkyl, carbocycle, or heterocyclic as defined above.

As used herein, the term "aroyl" refers to the group —C(O)R$_d$, wherein R$_d$ is aryl as defined above.

As used herein, the term "heteroaroyl" refers to the group —C(O)R$_e$, wherein R$_e$ is heteroaryl as defined above.

As used herein, the term "acyloxy" refers to the group —OC(O)R$_f$, wherein R$_f$ is alkyl, carbocycle, or heterocyclic as defined above.

As used herein, the term "aroyloxy" refers to the group —OC(O)R$_d$, wherein R$_d$ is aryl as defined herein.

As used herein, the term "heteroaroyloxy" refers to the group —OC(O)R$_e$, wherein R$_e$ is heteroaryl as defined herein.

As used herein, the term "pharmaceutically acceptable salt(s)", refers to those salts of compounds of the invention that are safe and effective for topical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

Preferred compounds useful in the present invention are selected from the group consisting of:

N-(3-(4-(3-chlorophenyl)piperazin-1-yl)propyl)-1,2-dimethyl-5-phenyl-1H-pyrrole-3-carboxamide;

N-(3-(4-(3-chlorophenyl)piperazin-1-yl)propyl)-1,2-dimethyl-5-phenyl-1H-pyrrole-3-carboxamide hydrochloride;

N-(3-(4-(2,3-dimethylphenyl)piperazin-1-yl)propyl)-1,2-dimethyl-5-phenyl-1H-pyrrole-3-carboxamide;

N-(3-(4-(3-chlorophenyl)piperazin-1-yl)propyl)-1-ethyl-2-methyl-5-phenyl-1H-pyrrole-3-carboxamide;

N-(3-(4-(2,3-dimethylphenyl)piperazin-1-yl)propyl)-1-ethyl-2-methyl-5-phenyl-1H-pyrrole-3-carboxamide;

N-(3-(4-(3-chlorophenyl)piperazin-1-yl)propyl)-2-methyl-5-phenyl-1-propyl-1H-pyrrole-3-carboxamide;

N-(3-(4-(2,3-dimethylphenyl)piperazin-1-yl)propyl)-2-methyl-5-phenyl-1-propyl-1H-pyrrole-3-carboxamide;

N-(3-(4-(3-chlorophenyl)piperazin-1-yl)propyl)-2-methyl-5-phenyl-1-(piperidin-1-yl)-1H-pyrrole-3-carboxamide;

N-(3-(4-(2,3-dimethylphenyl)piperazin-1-yl)propyl)-2-methyl-5-phenyl-1-(piperidin-1-yl)-1H-pyrrole-3-carboxamide;

N-(3-(4-(2,3-dichlorophenyl)piperazin-1-yl)propyl)-1,2-dimethyl-5-phenyl-1H-pyrrole-3-carboxamide;

N-(3-(4-(2,3-dichlorophenyl)piperazin-1-yl)propyl)-1-ethyl-2-methyl-5-phenyl-1H-pyrrole-3-carboxamide;

N-(3-(4-(2,3-dichlorophenyl)piperazin-1-yl)propyl)-2-methyl-5-phenyl-1-propyl-1H-pyrrole-3-carboxamide;

N-(3-(4-(2,3-dichlorophenyl)piperazin-1-yl)propyl)-2-methyl-5-phenyl-1-(piperidin-1-yl)-1H-pyrrole-3-carboxamide;

N-(3-(4-(3-chlorophenyl)piperazin-1-yl)propyl)-1-(4-fluorophenyl)-2-methyl-5-phenyl-1H-pyrrole-3-carboxamide;

N-(3-(4-(2,3-dimethylphenyl)piperazin-1-yl)propyl)-1-(4-fluorophenyl)-2-methyl-5-phenyl-1H-pyrrole-3-carboxamide;

N-(3-(4-(2,3-dichlorophenyl)piperazin-1-yl)propyl)-1-(4-fluorophenyl)-2-methyl-5-phenyl-1H-pyrrole-3-carboxamide;

1-Benzyl-N-(3-(4-(3-chlorophenyl)piperazin-1-yl)propyl)-2-methyl-5-phenyl-1H-pyrrole-3-carboxamide;

1-Benzyl-N-(3-(4-(2,3-dimethylphenyl)piperazin-1-yl)propyl)-2-methyl-5-phenyl-1H-pyrrole-3-carboxamide;

1-Benzyl-N-(3-(4-(2,3-dichlorophenyl)piperazin-1-yl)propyl)-2-methyl-5-phenyl-1H-pyrrole-3-carboxamide;

N-(3-(4-(3-chlorophenyl)piperazin-1-yl)propyl)-1-(cyclohexylmethyl)-2-methyl-5-phenyl-1H-pyrrole-3-carboxamide;

1-(Cyclohexylmethyl)-N-(3-(4-(2,3-dimethylphenyl)piperazin-1-yl)propyl)-2-methyl-5-phenyl-1H-pyrrole-3-carboxamide;

1-(Cyclohexylmethyl)-N-(3-(4-(2,3-dichlorophenyl)piperazin-1-yl)propyl)-2-methyl-5-phenyl-1H-pyrrole-3-carboxamide;

N-(3-(4-(3-chlorophenyl)piperazin-1-yl)propyl)-2-methyl-5-phenyl-1H-pyrrole-3-carboxamide;

N-(3-(4-(2,3-dimethylphenyl)piperazin-1-yl)propyl)-2-methyl-5-phenyl-1H-pyrrole-3-carboxamide;

N-(3-(4-(2,3-dichlorophenyl)piperazin-1-yl)propyl)-2-methyl-5-phenyl-1H-pyrrole-3-carboxamide;

N-(3-(4-(3-chlorophenyl)piperazin-1-yl)propyl)-1-isobutyl-2-methyl-5-phenyl-1H-pyrrole-3-carboxamide;

N-(3-(4-(2,3-dimethylphenyl)piperazin-1-yl)propyl)-1-isobutyl-2-methyl-5-phenyl-1H-pyrrole-3-carboxamide;

N-(3-(4-(2,3-dichlorophenyl)piperazin-1-yl)propyl)-1-isobutyl-2-methyl-5-phenyl-1H-pyrrole-3-carboxamide;

N-(3-(4-(2,3-dimethylphenyl)piperazin-1-yl)propyl)-1-ethyl-2-methyl-5-phenyl-1H-pyrrole-3-carboxamide hydrochloride;

N-(3-(4-(2,3-dimethylphenyl)piperazin-1-yl)propyl)-1-ethyl-2-methyl-5-phenyl-1H-pyrrole-3-carboxamide hydrochloride;

N-(3-(4-(2,3-dichlorophenyl)piperazin-1-yl)propyl)-N,2-dimethyl-5-phenyl-1-propyl-1H-pyrrole-3-carboxamide hydrochloride;

1-benzyl-N-(3-(4-(2,3-dimethylphenyl)piperazin-1-yl)propyl)-N,2-dimethyl-5-phenyl-1H-pyrrole-3-carboxamide hydrochloride;

N-(4-(4-(2,3-dimethylphenyl)piperazin-1-yl)butyl)-2-methyl-5-phenyl-1-propyl-1H-pyrrole-3-carboxamide hydrochloride;

N-(4-(4-(2,3-dichlorophenyl)piperazin-1-yl)butyl)-2-methyl-5-phenyl-1-propyl-1H-pyrrole-3-carboxamide hydrochloride;

N-(4-(4-(2,3-dimethylphenyl)piperazin-1-yl)butyl)-1,2-dimethyl-5-phenyl-1H-pyrrole-3-carboxamide hydrochloride;

N-(4-(4-(2,3-dichlorophenyl)piperazin-1-yl)butyl)-1,2-dimethyl-5-phenyl-1H-pyrrole-3-carboxamide hydrochloride;

N-(3-(4-(2,3-dichlorophenyl)piperazin-1-yl)propyl)-N,1,2-trimethyl-5-phenyl-1H-pyrrole-3-carboxamide hydrochloride;

N-(2-(4-(2,3-dichlorophenyl)piperazin-1-yl)ethyl)-2-methyl-5-phenyl-1H-pyrrole-3-carboxamide hydrochloride;

N-(2-(4-(2,3-dichlorophenyl)piperazin-1-yl)ethyl)-2-methyl-5-phenyl-1-propyl-1H-pyrrole-3-carboxamide hydrochloride;

N-(4-(4-(2,3-dimethylphenyl)piperazin-1-yl)butyl)-2-methyl-5-phenyl-1H-pyrrole-3-carboxamide hydrochloride;

N-(4-(4-(2,3-dichlorophenyl)piperazin-1-yl)butyl)-2-methyl-5-phenyl-1H-pyrrole-3-carboxamide hydrochloride;

N-(4-(4-(2,3-dimethylphenyl)piperazin-1-yl)butyl)-1-ethyl-2-methyl-5-phenyl-1H-pyrrole-3-carboxamide hydrochloride;

N-(4-(4-(2,3-dichlorophenyl)piperazin-1-yl)butyl)-1-ethyl-2-methyl-5-phenyl-1H-pyrrole-3-carboxamide hydrochloride;

5-(4-chlorophenyl)-N-(3-(4-(2,3-dimethylphenyl)piperazin-1-yl)propyl)-2-methyl-1H-pyrrole-3-carboxamide hydrochloride;

5-(4-chlorophenyl)-N-(3-(4-(2,3-dichlorophenyl)piperazin-1-yl)propyl)-2-methyl-1H-pyrrole-3-carboxamide hydrochloride;

5-(4-chlorophenyl)-N-(4-(4-(2,3-dimethylphenyl)piperazin-1-yl)butyl)-2-methyl-1H-pyrrole-3-carboxamide hydrochloride;

5-(4-chlorophenyl)-N-(4-(4-(2,3-dichlorophenyl)piperazin-1-yl)butyl)-2-methyl-1H-pyrrole-3-carboxamide hydrochloride;

N-(2-(4-(2,3-dichlorophenyl)piperazin-1-yl)ethyl)-2-methyl-5-phenyl-1H-pyrrole-3-carboxamide hydrochloride;

N-(2-(4-(2,3-dichlorophenyl)piperazin-1-yl)ethyl)-1-ethyl-2-methyl-5-phenyl-1H-pyrrole-3-carboxamide hydrochloride;

N-(2-(4-(2,3-dichlorophenyl)piperazin-1-yl)ethyl)-5-(4-methoxyphenyl)-2-methyl-1H-pyrrole-3-carboxamide hydrochloride;

N-(2-(4-(2,3-dichlorophenyl)piperazin-1-yl)ethyl)-5-(4-methoxyphenyl)-1,2-dimethyl-1H-pyrrole-3-carboxamide hydrochloride;

N-(2-(4-(2,3-dichlorophenyl)piperazin-1-yl)ethyl)-1-ethyl-5-(4-methoxyphenyl)-2-methyl-1H-pyrrole-3-carboxamide hydrochloride;

N-(2-(4-(2,3-dichlorophenyl)piperazin-1-yl)ethyl)-5-(4-methoxyphenyl)-2-methyl-1-propyl-1H-pyrrole-3-carboxamide hydrochloride;

N-(3-(4-(2,3-dichlorophenyl)piperazin-1-yl)propyl)-5-(4-methoxyphenyl)-2-methyl-1H-pyrrole-3-carboxamide hydrochloride;

N-(3-(4-(2,3-dichlorophenyl)piperazin-1-yl)propyl)-5-(4-methoxyphenyl)-1,2-dimethyl-1H-pyrrole-3-carboxamide hydrochloride;

N-(3-(4-(2,3-dichlorophenyl)piperazin-1-yl)propyl)-1-ethyl-5-(4-methoxyphenyl)-2-methyl-1H-pyrrole-3-carboxamide hydrochloride;

N-(3-(4-(2,3-dichlorophenyl)piperazin-1-yl)propyl)-5-(4-methoxyphenyl)-2-methyl-1-propyl-1H-pyrrole-3-carboxamide hydrochloride;

N-(4-(4-(2,3-dichlorophenyl)piperazin-1-yl)butyl)-5-(4-methoxyphenyl)-2-methyl-1H-pyrrole-3-carboxamide hydrochloride;

N-(4-(4-(2,3-dichlorophenyl)piperazin-1-yl)butyl)-5-(4-methoxyphenyl)-1,2-dimethyl-1H-pyrrole-3-carboxamide hydrochloride;

N-(4-(4-(2,3-dichlorophenyl)piperazin-1-yl)butyl)-1-ethyl-5-(4-methoxyphenyl)-2-methyl-1H-pyrrole-3-carboxamide hydrochloride;

N-(4-(4-(2,3-dichlorophenyl)piperazin-1-yl)butyl)-5-(4-methoxyphenyl)-2-methyl-1-propyl-1H-pyrrole-3-carboxamide hydrochloride;

N-(4-(4-(2,3-dichlorophenyl)piperazin-1-yl)butyl)-1-ethyl-5-(4-methoxyphenyl)-2-methyl-1H-pyrrole-3-carboxamide hydrochloride;

5-(4-chlorophenyl)-N-(3-(4-(2,3-dimethylphenyl)piperazin-1-yl)propyl)-1,2-dimethyl-1H-pyrrole-3-carboxamide hydrochloride;

5-(4-chlorophenyl)-N-(3-(4-(2,3-dichlorophenyl)piperazin-1-yl)propyl)-1,2-dimethyl-1H-pyrrole-3-carboxamide hydrochloride;

5-(4-chlorophenyl)-N-(3-(4-(2,3-dimethylphenyl)piperazin-1-yl)propyl)-1-ethyl-2-methyl-1H-pyrrole-3-carboxamide hydrochloride;

5-(4-chlorophenyl)-N-(3-(4-(2,3-dichlorophenyl)piperazin-1-yl)propyl)-1-ethyl-2-methyl-1H-pyrrole-3-carboxamide hydrochloride;

5-(4-chlorophenyl)-N-(3-(4-(2,3-dimethylphenyl)piperazin-1-yl)propyl)-2-methyl-1-propyl-1H-pyrrole-3-carboxamide hydrochloride;

5-(4-chlorophenyl)-N-(3-(4-(2,3-dichlorophenyl)piperazin-1-yl)propyl)-2-methyl-1-propyl-1H-pyrrole-3-carboxamide hydrochloride;

5-(4-chlorophenyl)-N-(2-(4-(2,3-dichlorophenyl)piperazin-1-yl)ethyl)-2-methyl-1H-pyrrole-3-carboxamide hydrochloride;

5-(4-chlorophenyl)-N-(2-(4-(2,3-dichlorophenyl)piperazin-1-yl)ethyl)-1,2-dimethyl-1H-pyrrole-3-carboxamide hydrochloride;

5-(4-chlorophenyl)-N-(2-(4-(2,3-dichlorophenyl)piperazin-1-yl)ethyl)-1-ethyl-2-methyl-1H-pyrrole-3-carboxamide hydrochloride;

5-(4-chlorophenyl)-N-(2-(4-(2,3-dichlorophenyl)piperazin-1-yl)ethyl)-2-methyl-1-propyl-1H-pyrrole-3-carboxamide hydrochloride;

1-butyl-N-(3-(4-(2,3-dichlorophenyl)piperazin-1-yl)propyl)-2-methyl-5-phenyl-1H-pyrrole-3-carboxamide hydrochloride;

N-(3-(4-(2,3-dichlorophenyl)piperazin-1-yl)propyl)-1-hexyl-2-methyl-5-phenyl-1H-pyrrole-3-carboxamide hydrochloride;

N-(3-(4-(2,3-dichlorophenyl)piperazin-1-yl)propyl)-5-(4-methoxyphenyl)-2-methyl-1H-pyrrole-3-carboxamide hydrochloride;

N-(3-(4-(2,3-dichlorophenyl)piperazin-1-yl)propyl)-5-(4-methoxyphenyl)-1,2-dimethyl-1H-pyrrole-3-carboxamide hydrochloride;

N-(3-(4-(2,3-dichlorophenyl)piperazin-1-yl)propyl)-1-ethyl-5-(4-methoxyphenyl)-2-methyl-1H-pyrrole-3-carboxamide hydrochloride;

N-(2-(4-(2,3-dichlorophenyl)piperazin-1-yl)ethyl)-2,4-dimethyl-5-phenyl-1H-pyrrole-3-carboxamide hydrochloride;

N-(3-(4-(2,3-dichlorophenyl)piperazin-1-yl)propyl)-2,4-dimethyl-5-phenyl-1H-pyrrole-3-carboxamide hydrochloride;

N-(4-(4-(2,3-dichlorophenyl)piperazin-1-yl)butyl)-2,4-dimethyl-5-phenyl-1H-pyrrole-3-carboxamide hydrochloride;

N-(3-(4-(2,3-dichlorophenyl)piperazin-1-yl)propyl)-1,2,4-trimethyl-5-phenyl-1H-pyrrole-3-carboxamide hydrochloride;

N-(3-(4-(2,3-dichlorophenyl)piperazin-1-yl)propyl)-1-ethyl-2,4-dimethyl-5-phenyl-1H-pyrrole-3-carboxamide hydrochloride;

N-(3-(4-(2,3-dichlorophenyl)piperazin-1-yl)propyl)-2,4-dimethyl-5-phenyl-1-propyl-1H-pyrrole-3-carboxamide hydrochloride;

N-(3-(4-(2,3-dichlorophenyl)piperazin-1-yl)propyl)-5-(3-methoxyphenyl)-2-methyl-1-propyl-1H-pyrrole-3-carboxamide hydrochloride;

N-(3-(4-(2,3-dichlorophenyl)piperazin-1-yl)propyl)-5-(3-methoxyphenyl)-2-methyl-1H-pyrrole-3-carboxamide hydrochloride;

N-(3-(4-(2,3-dichlorophenyl)piperazin-1-yl)propyl)-2-methyl-5-(pyridin-2-yl)-1H-pyrrole-3-carboxamide dihydrochloride;

N-(3-(4-(2,3-dichlorophenyl)piperazin-1-yl)propyl)-1,2-dimethyl-5-(pyridin-2-yl)-1H-pyrrole-3-carboxamide dihydrochloride;

N-(3-(4-(2,3-dichlorophenyl)piperazin-1-yl)propyl)-2-methyl-1-propyl-5-(pyridin-2-yl)-1H-pyrrole-3-carboxamide dihydrochloride;

N-(2-(4-(2,3-dichlorophenyl)piperazin-1-yl)ethyl)-2-methyl-5-(pyridin-2-yl)-1H-pyrrole-3-carboxamide dihydrochloride;

N-(2-(4-(2,3-dichlorophenyl)piperazin-1-yl)ethyl)-1,2-dimethyl-5-(pyridin-2-yl)-1H-pyrrole-3-carboxamide dihydrochloride;

N-(2-(4-(2,3-dichlorophenyl)piperazin-1-yl)ethyl)-2-methyl-1-propyl-5-(pyridin-2-yl)-1H-pyrrole-3-carboxamide dihydrochloride;

N-(3-(4-(2,3-dichlorophenyl)piperazin-1-yl)propyl)-2-methyl-5-(pyridin-3-yl)-1H-pyrrole-3-carboxamide;

N-(3-(4-(2,3-dichlorophenyl)piperazin-1-yl)propyl)-1,2-dimethyl-5-(pyridin-3-yl)-1H-pyrrole-3-carboxamide;

N-(3-(4-(2,3-dichlorophenyl)piperazin-1-yl)propyl)-2-methyl-1-propyl-5-(pyridin-3-yl)-1H-pyrrole-3-carboxamide;

N-(2-(4-(2,3-dichlorophenyl)piperazin-1-yl)ethyl)-2-methyl-5-(pyridin-3-yl)-1H-pyrrole-3-carboxamide;

N-(2-(4-(2,3-dichlorophenyl)piperazin-1-yl)ethyl)-1,2-dimethyl-5-(pyridin-3-yl)-1H-pyrrole-3-carboxamide;

N-(2-(4-(2,3-dichlorophenyl)piperazin-1-yl)ethyl)-2-methyl-1-propyl-5-(pyridin-3-yl)-1H-pyrrole-3-carboxamide;

N-(3-(4-(2,3-dichlorophenyl)piperazin-1-yl)propyl)-2-methyl-5-(pyridin-4-yl)-1H-pyrrole-3-carboxamide;

N-(3-(4-(2,3-dichlorophenyl)piperazin-1-yl)propyl)-1,2-dimethyl-5-(pyridin-4-yl)-1H-pyrrole-3-carboxamide;

N-(3-(4-(2,3-dichlorophenyl)piperazin-1-yl)propyl)-2-methyl-1-propyl-5-(pyridin-4-yl)-1H-pyrrole-3-carboxamide;

N-(2-(4-(2,3-dichlorophenyl)piperazin-1-yl)ethyl)-2-methyl-5-(pyridin-4-yl)-1H-pyrrole-3-carboxamide;

N-(2-(4-(2,3-dichlorophenyl)piperazin-1-yl)ethyl)-1,2-dimethyl-5-(pyridin-4-yl)-1H-pyrrole-3-carboxamide;

N-(2-(4-(2,3-dichlorophenyl)piperazin-1-yl)ethyl)-2-methyl-1-propyl-5-(pyridin-4-yl)-1H-pyrrole-3-carboxamide;

2-chloro-N-(3-(4-(2,3-dichlorophenyl)piperazin-1-yl)propyl)-5-phenyl-1H-pyrrole-3-carboxamide;

2-chloro-N-(3-(4-(2,3-dichlorophenyl)piperazin-1-yl)propyl)-1-methyl-5-phenyl-1H-pyrrole-3-carboxamide;

2-chloro-N-(3-(4-(2,3-dichlorophenyl)piperazin-1-yl)propyl)-1-propyl-5-(pyridin-4-yl)-1H-pyrrole-3-carboxamide;

N-(3-(4-(2,3-dichlorophenyl)piperazin-1-yl)propyl)-5-phenyl-1H-pyrrole-3-carboxamide;

N-(3-(4-(2,3-dichlorophenyl)piperazin-1-yl)propyl)-1-methyl-5-phenyl-1H-pyrrole-3-carboxamide;

N-(3-(4-(2,3-dichlorophenyl)piperazin-1-yl)propyl)-5-phenyl-1-propyl-1H-pyrrole-3-carboxamide;

5-tert-Butyl-N-(3-(4-(2,3-dichlorophenyl)piperazin-1-yl)propyl)-2-methyl-1H-pyrrole-3-carboxamide hydrochloride;

5-tert-Butyl-N-(3-(4-(2,3-dichlorophenyl)piperazin-1-yl)propyl)-1,2-dimethyl-1H-pyrrole-3-carboxamide;

N-(3-(4-(2-carbamoylbenzofuran-5-yl)piperazin-1-yl)propyl)-1,2-dimethyl-5-phenyl-1H-pyrrole-3-carboxamide;

N-(3-(4-(2-carbamoylbenzofuran-5-yl)piperazin-1-yl)propyl)-2-methyl-5-phenyl-1-propyl-1H-pyrrole-3-carboxamide;

1,2-dimethyl-5-phenyl-N-(3-(4-(quinolin-8-yl)piperazin-1-yl)propyl)-1H-pyrrole-3-carboxamide;

2-methyl-5-phenyl-1-propyl-N-(3-(4-(quinolin-8-yl)piperazin-1-yl)propyl)-1H-pyrrole-3-carboxamide;

N-(3-(4-(benzo[d]isothiazol-3-yl)piperazin-1-yl)propyl)-1,2-dimethyl-5-phenyl-1H-pyrrole-3-carboxamide;

N-(3-(4-(benzo[d]isothiazol-3-yl)piperazin-1-yl)propyl)-2-methyl-5-phenyl-1-propyl-1H-pyrrole-3-carboxamide;

5-(But-3-enyl)-N-(3-(4-(2,3-dichlorophenyl)piperazin-1-yl)propyl)-2-methyl-1H-pyrrole-3-carboxamide;

5-(But-3-enyl)-N-(3-(4-(2,3-dichlorophenyl)piperazin-1-yl)propyl)-1,2-dimethyl-1H-pyrrole-3-carboxamide;

5-Butyl-N-(3-(4-(2,3-dichlorophenyl)piperazin-1-yl)propyl)-2-methyl-1H-pyrrole-3-carboxamide;

5-Butyl-N-(3-(4-(2,3-dichlorophenyl)piperazin-1-yl)propyl)-1,2-dimethyl-1H-pyrrole-3-carboxamide;

N-(3-(4-(2,3-dichlorophenyl)piperazin-1-yl)propyl)-2,5-dimethyl-1H-pyrrole-3-carboxamide;

N-(3-(4-(2,3-dichlorophenyl)piperazin-1-yl)propyl)-1,2,5-trimethyl-1H-pyrrole-3-carboxamide;

N-(3-(4-(2,3-dichlorophenyl)piperazin-1-yl)propyl)-5-(4-hydroxybutyl)-2-methyl-1H-pyrrole-3-carboxamide;

N-(3-(4-(2,3-dichlorophenyl)piperazin-1-yl)propyl)-5-(4-hydroxybutyl)-1,2-dimethyl-1H-pyrrole-3-carboxamide;

N-(3-(4-(2,3-dihydrobenzo[b][1,4]dioxin-5-yl)piperazin-1-yl)propyl)-1,2-dimethyl-5-phenyl-1H-pyrrole-3-carboxamide;

N-(3-(4-(2,3-dihydrobenzo[b][1,4]dioxin-5-yl)piperazin-1-yl)propyl)-2-methyl-5-phenyl-1-propyl-1H-pyrrole-3-carboxamide;

1,2-dimethyl-5-(pyridin-2-yl)-N-(3-(4-(quinoxalin-5-yl)piperazin-1-yl)propyl)-1H-pyrrole-3-carboxamide;

2-methyl-1-propyl-5-(pyridin-2-yl)-N-(3-(4-(quinoxalin-5-yl)piperazin-1-yl)propyl)-1H-pyrrole-3-carboxamide;

1,2-dimethyl-5-(pyridin-2-yl)-N-(3-(4-(quinolin-8-yl)piperazin-1-yl)propyl)-1H-pyrrole-3-carboxamide dihydrochloride;

2-methyl-1-propyl-5-(pyridin-2-yl)-N-(3-(4-(quinolin-8-yl)piperazin-1-yl)propyl)-1H-pyrrole-3-carboxamide dihydrochloride;

2-methyl-5-(pyridin-2-yl)-N-(3-(4-(quinolin-8-yl)piperazin-1-yl)propyl)-1H-pyrrole-3-carboxamide;

N-(3-(4-(benzo[d][1,3]dioxol-4-yl)piperazin-1-yl)propyl)-1,2-dimethyl-5-phenyl-1H-pyrrole-3-carboxamide;

N-(3-(4-(benzo[d][1,3]dioxol-4-yl)piperazin-1-yl)propyl)-2-methyl-5-phenyl-1-propyl-1H-pyrrole-3-carboxamide;

N-(3-(4-(2,3-dichlorophenyl)piperazin-1-yl)-2-hydroxypropyl)-1,2-dimethyl-5-phenyl-1H-pyrrole-3-carboxamide hydrochloride;

N-(3-(4-(2,3-dichlorophenyl)piperazin-1-yl)-2-hydroxypropyl)-2-methyl-5-phenyl-1-propyl-1H-pyrrole-3-carboxamide hydrochloride;

N-(3-(4-(2,3-dichlorophenyl)piperazin-1-yl)propyl)-5-(4-methoxybutyl)-1,2-dimethyl-1H-pyrrole-3-carboxamide hydrochloride;

2-methyl-5-phenyl-N-(3-(4-(quinolin-6-yl)piperazin-1-yl)propyl)-1H-pyrrole-3-carboxamide;

1,2-dimethyl-5-phenyl-N-(3-(4-(quinolin-6-yl)piperazin-1-yl)propyl)-1H-pyrrole-3-carboxamide;

2-methyl-5-(pyridin-2-yl)-N-(3-(4-(quinolin-6-yl)piperazin-1-yl)propyl)-1H-pyrrole-3-carboxamide;

1,2-dimethyl-5-(pyridin-2-yl)-N-(3-(4-(quinolin-6-yl)piperazin-1-yl)propyl)-1H-pyrrole-3-carboxamide;

1,2-dimethyl-N-(3-(4-(2-methylquinolin-8-yl)piperazin-1-yl)propyl)-5-phenyl-1H-pyrrole-3-carboxamide;

2-methyl-N-(3-(4-(2-methylquinolin-8-yl)piperazin-1-yl)propyl)-5-phenyl-1-propyl-1H-pyrrole-3-carboxamide;

N-(3-(4-(3-chloro-2-methylphenyl)piperazin-1-yl)propyl)-1,2-dimethyl-5-phenyl-1H-pyrrole-3-carboxamide;

N-(3-(4-(3-chloro-2-methylphenyl)piperazin-1-yl)propyl)-2-methyl-5-phenyl-1-propyl-1H-pyrrole-3-carboxamide;

5-tert-Butyl-N-(2-(4-(2,3-dichlorophenyl)piperazin-1-yl)ethyl)-1,2-dimethyl-1H-pyrrole-3-carboxamide;

N-(3-(4-(2,3-dichlorophenyl)piperazin-1-yl)propyl)-2,5-dimethyl-1-phenyl-1H-pyrrole-3-carboxamide;

N-(3-(4-(2,3-dimethylphenyl)piperazin-1-yl)propyl)-2,5-dimethyl-1-phenyl-1H-pyrrole-3-carboxamide;

N-(3-(4-(3-chloro-2-fluorophenyl)piperazin-1-yl)propyl)-1,2-dimethyl-5-phenyl-1H-pyrrole-3-carboxamide;

N-(3-(4-(3-chloro-2-fluorophenyl)piperazin-1-yl)propyl)-2-methyl-5-phenyl-1-propyl-1H-pyrrole-3-carboxamide;

5-tert-Butyl-N-(3-(4-(3-chloro-2-fluorophenyl)piperazin-1-yl)propyl)-1,2-dimethyl-1H-pyrrole-3-carboxamide;

N-(3-(4-(3-chloro-2-fluorophenyl)piperazin-1-yl)propyl)-2,5-dimethyl-1-phenyl-1H-pyrrole-3-carboxamide;

N-(3-(4-(3-chloro-2-methylphenyl)piperazin-1-yl)propyl)-2,5-dimethyl-1-phenyl-1H-pyrrole-3-carboxamide;

5-tert-Butyl-N-(3-(4-(3-chloro-2-methylphenyl)piperazin-1-yl)propyl)-1,2-dimethyl-1H-pyrrole-3-carboxamide;

5-tert-Butyl-N-(3-(4-(2,3-dimethylphenyl)piperazin-1-yl)propyl)-1,2-dimethyl-1H-pyrrole-3-carboxamide;

N-(2-(4-(2,3-dichlorophenyl)piperazin-1-yl)ethyl)-2,5-dimethyl-1-phenyl-1H-pyrrole-3-carboxamide;

5-tert-Butyl-N-(3-(4-(2,3-dimethylphenyl)piperazin-1-yl)propyl)-2-methyl-1-propyl-1H-pyrrole-3-carboxamide;

5-tert-Butyl-N-(3-(4-(2,3-dichlorophenyl)piperazin-1-yl)propyl)-2-methyl-1-propyl-1H-pyrrole-3-carboxamide;

5-tert-Butyl-N-(3-(4-(2,3-dichlorophenyl)piperazin-1-yl)propyl)-1-ethyl-2-methyl-1H-pyrrole-3-carboxamide;

N-(2-(4-(3-chloro-2-fluorophenyl)piperazin-1-yl)ethyl)-1,2-dimethyl-5-phenyl-1H-pyrrole-3-carboxamide;

N-(2-(4-(3-chloro-2-methylphenyl)piperazin-1-yl)ethyl)-1,2-dimethyl-5-phenyl-1H-pyrrole-3-carboxamide;

1,2-dimethyl-N-(2-(4-(2-methylquinolin-8-yl)piperazin-1-yl)ethyl)-5-phenyl-1H-pyrrole-3-carboxamide;

5-tert-Butyl-N-(2-(4-(3-chloro-2-fluorophenyl)piperazin-1-yl)ethyl)-1,2-dimethyl-1H-pyrrole-3-carboxamide;

5-tert-Butyl-N-(2-(4-(3-chloro-2-methylphenyl)piperazin-1-yl)ethyl)-1,2-dimethyl-1H-pyrrole-3-carboxamide;

5-tert-Butyl-1,2-dimethyl-N-(2-(4-(2-methylquinolin-8-yl)piperazin-1-yl)ethyl)-1H-pyrrole-3-carboxamide;

5-tert-Butyl-N-(2-(4-(2,3-dimethylphenyl)piperazin-1-yl)ethyl)-1,2-dimethyl-1H-pyrrole-3-carboxamide;

5-tert-Butyl-N-(3-(4-(2,3-dimethylphenyl)piperazin-1-yl)propyl)-1-ethyl-2-methyl-1H-pyrrole-3-carboxamide;

5-tert-Butyl-N-(3-(4-(2,3-dichlorophenyl)piperazin-1-yl)-2-hydroxypropyl)-1,2-dimethyl-1H-pyrrole-3-carboxamide;

N-(3-(4-(2,3-dichlorophenyl)piperazin-1-yl)propyl)-4-methoxy-1,2-dimethyl-5-phenyl-1H-pyrrole-3-carboxamide;

N-(2-(4-(2,3-Dichlorophenyl)piperazin-1-yl)ethyl)-4-methoxy-1,2-dimethyl-5-phenyl-1H-pyrrole-3-carboxamide;

1,2-dimethyl-5-phenyl-N-(2-(4-(quinolin-8-yl)piperazin-1-yl)ethyl)-1H-pyrrole-3-carboxamide;

N-(3-(4-(3-chloro-2-methylphenyl)piperazin-1-yl)-2-hydroxypropyl)-1,2-dimethyl-5-phenyl-1H-pyrrole-3-carboxamide;

N-(2-(4-(2,3-dichlorophenyl)piperazin-1-yl)-3-fluoropropyl)-1,2-dimethyl-5-phenyl-1H-pyrrole-3-carboxamide hydrochloride;

N-(2-(4-(2,3-dichlorophenyl)piperazin-1-yl)-3-fluoropropyl)-2-methyl-5-phenyl-1-propyl-1H-pyrrole-3-carboxamide hydrochloride;

N-(3-(4-(2,3-dichlorophenyl)piperazin-1-yl)-2,2-difluoropropyl)-1,2-dimethyl-5-phenyl-1H-pyrrole-3-carboxamide;

5-tert-Butyl-N-(3-(4-(2,3-dimethylphenyl)piperazin-1-yl)-2-hydroxypropyl)-1,2-dimethyl-1H-pyrrole-3-carboxamide;

5-tert-Butyl-N-(4-(4-(2,3-dimethylphenyl)piperazin-1-yl)butyl)-1,2-dimethyl-1H-pyrrole-3-carboxamide;

N-(2-(4-(2,3-dimethylphenyl)piperazin-1-yl)ethyl)-4-methoxy-1,2-dimethyl-5-phenyl-1H-pyrrole-3-carboxamide;

N-(3-(4-(2,3-dimethylphenyl)piperazin-1-yl)propyl)-4-methoxy-1,2-dimethyl-5-phenyl-1H-pyrrole-3-carboxamide; and N-(3-(4-(2,3-dichlorophenyl)piperazin-1-yl)propyl)-4-hydroxy-1,2-dimethyl-5-phenyl-1H-pyrrole-3-carboxamide.

General Synthetic Sequence

The following synthetic schemes are merely illustrative of the methods by which the compounds of the invention may be prepared and are not intended to limit the scope of the invention as defined in the appended claims.

The inventive target compounds were prepared by amide coupling with acid and amine at the final stage (Reaction Scheme 1). Pyrrole 3-carboxylic acid and arylpiperazinyl alkyl amine were used as acid and amine functionality, respectively.

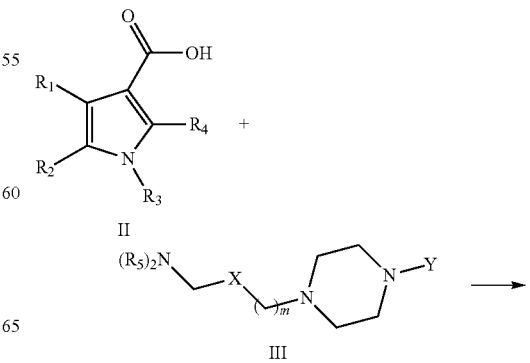

Reaction Scheme 1

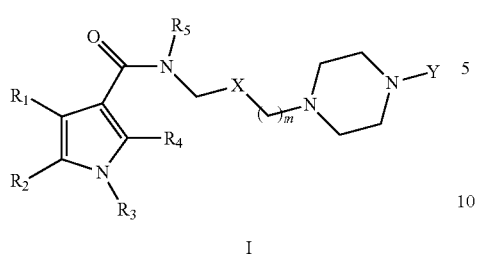

I

In Reaction Scheme 1, $R_1$ to $R_5$, X, Y, and m have the same meaning as defined above.

Preparation of pyrrole derivatives, especially comprising 5-phenyl and 3-carboxylic acid, started from alkylation of phenylacetophenone group to ethyl acetoacetate (1) (Vanotti, E. et al., PCT Patent No. WO2005/013986, 2005), as shown in Reaction Scheme 2. Under the conditions of NaH in THF, 2-bromoacetophenone (2) was reacted on 2-position of ethyl acetoacetate (1) to produce alkylated acetoacetate (3). Cyclization of ethyl phenylacetonylacetoacetate (3) to ethyl 2-methyl-5-phenyl-1H-pyrrole-3-carboxylate (4) was accomplished with ammonium acetate in acetic acid at 80° C. Various alkyl groups were installed at nitrogen of pyrrole under the conditions of sodium hydride and alkyl iodide in DMF. Treatment of pyrrole ester (5) with sodium hydroxide in refluxed ethanol proceeded to afford pyrrole 3-carboxylic acid (6).

Reaction Scheme 2

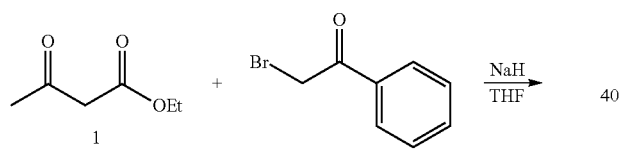

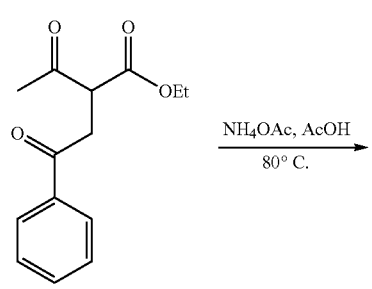

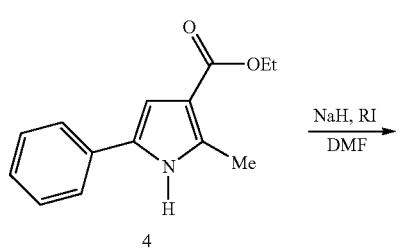

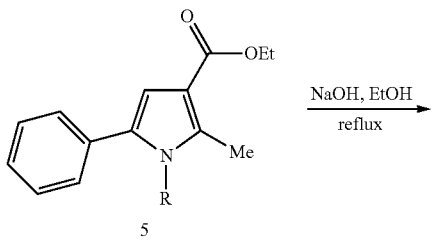

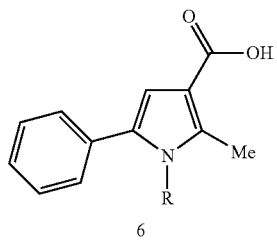

(R = H, Me, Et, nPr, etc)

Direct cyclization from acetoacetate (3) to N-substituted pyrrole compounds could be accomplished with use of neutral amine instead of ammonium acetate to produce the corresponding pyrrole compounds as shown in Reaction Scheme 3. Treatment of ester (3) with neutral amine or aniline derivatives in the presence of p-toluenesulfonic acid as a catalyst in ethanol at 80° C. afforded N-substituted pyrrole 3-carboxylic acid ethyl ester (5). For instance, when a benzylamine was used as amine, N-benzylated pyrrole compound was produced. Similarly, 4-fluorophenyl substituted pyrrole derivatives could be prepared when 4-fluoroaniline was selected. Hydrolysis of ester to carboxylic acid was accomplished as described before.

Reaction Scheme 3

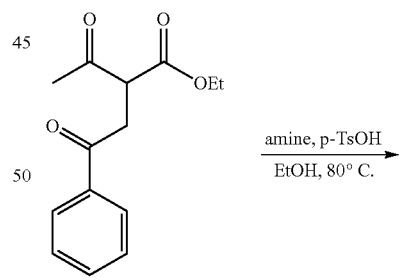

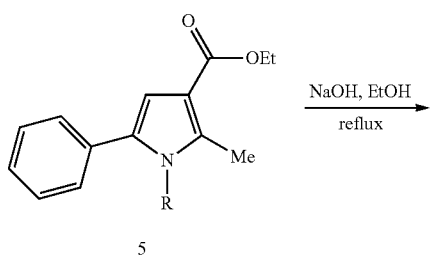

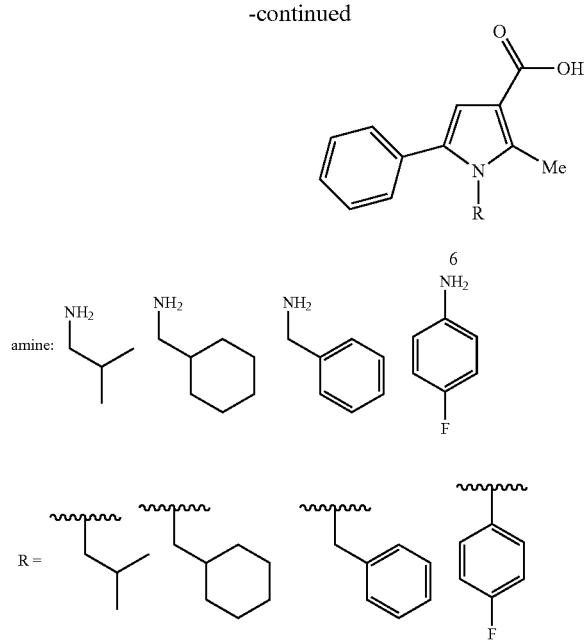
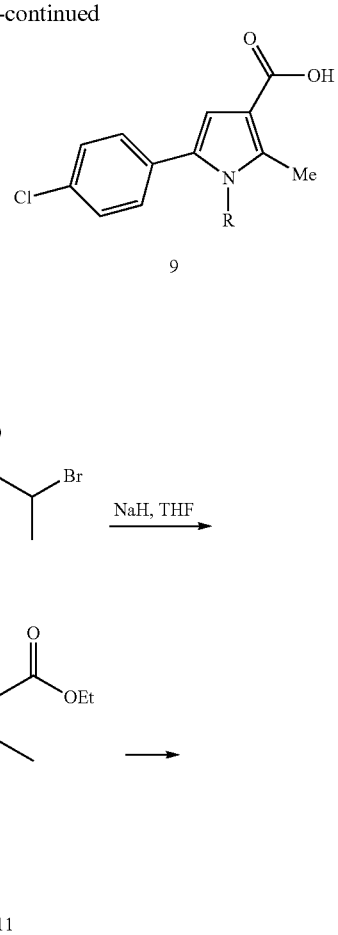

Alternative derivatization of pyrrole moiety started from alkylation to ethyl acetoacetate (1). Installation of chlorine to para-position of phenyl was accomplished by using of 2-bromo-4'-chloroacetophenone (7) instead of 2-bromoacetophone (2) as shown in Reaction Scheme 4. Alkylation on nitrogen position and hydrolysis produced carboxylic acids of structure (9). In an analogous method described previously, various substituted pyrrole derivatives could be prepared with a particular bromoketone. The C4-methylated pyrroles were prepared when 2-bromopropiophenone (10) was used. Carboxylic acid (12) was prepared in an analogous way as described above.

Reaction Scheme 4

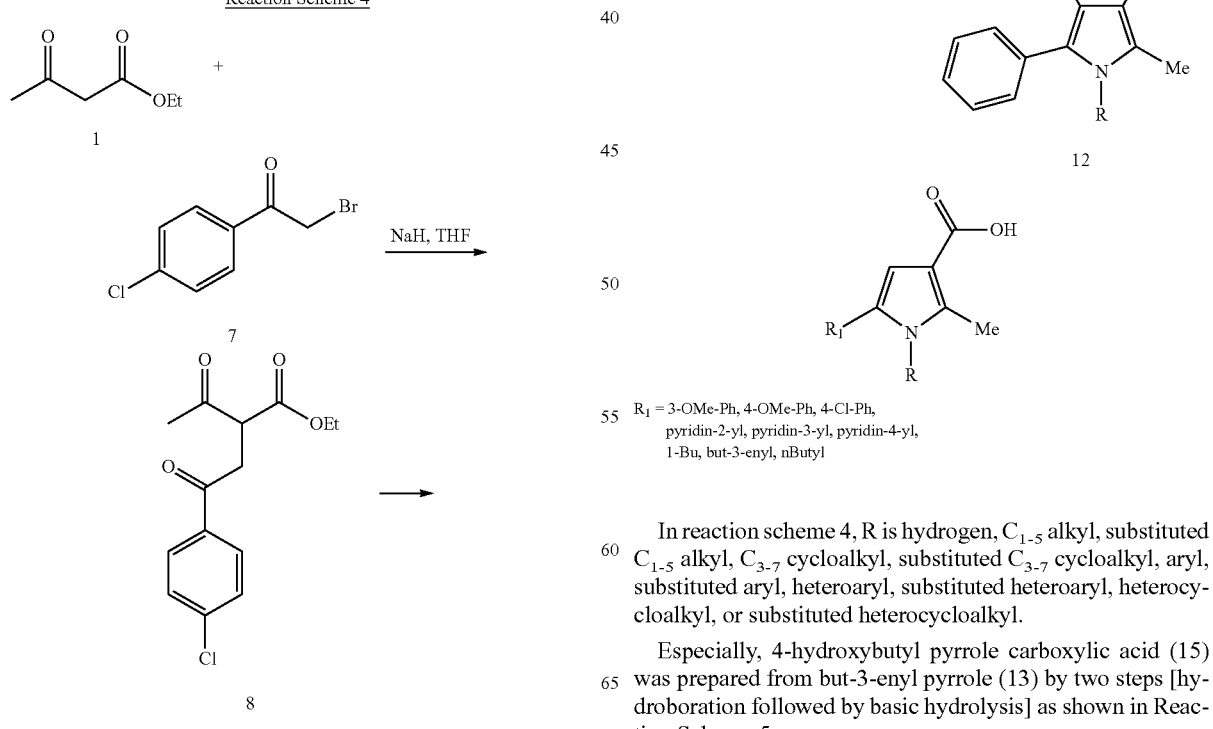

$R_1$ = 3-OMe-Ph, 4-OMe-Ph, 4-Cl-Ph, pyridin-2-yl, pyridin-3-yl, pyridin-4-yl, 1-Bu, but-3-enyl, nButyl In reaction scheme 4, R is hydrogen, $C_{1-5}$ alkyl, substituted $C_{1-5}$ alkyl, $C_{3-7}$ cycloalkyl, substituted $C_{3-7}$ cycloalkyl, aryl, substituted aryl, heteroaryl, substituted heteroaryl, heterocycloalkyl, or substituted heterocycloalkyl.

Especially, 4-hydroxybutyl pyrrole carboxylic acid (15) was prepared from but-3-enyl pyrrole (13) by two steps [hydroboration followed by basic hydrolysis] as shown in Reaction Scheme 5.

Reaction Scheme 5

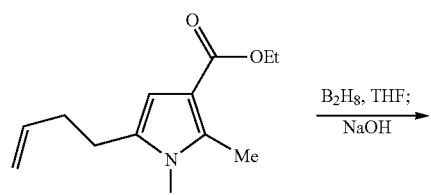

13

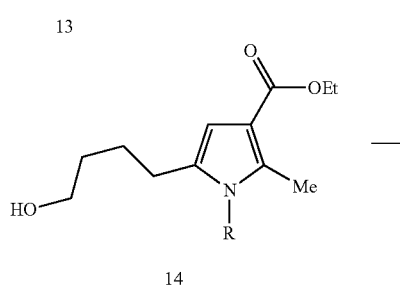

14

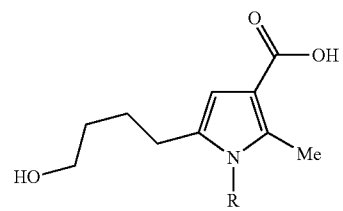

15

In reaction scheme 5, R is hydrogen, $C_{1-5}$ alkyl, substituted $C_{1-5}$ alkyl, $C_{3-7}$ cycloalkyl, substituted $C_{3-7}$ cycloalkyl, aryl, substituted aryl, heteroaryl, substituted heteroaryl, heterocycloalkyl, or substituted heterocycloalkyl.

Bromination of the ester (16) with copper(II) bromide was performed to produced the 4-bromopyrrole (17) at low temperature (such as 0° C.) in good yields as shown in Reaction Scheme 6. N-Methylation of (17) using MeI in the presence of NaH as a base converted the pyrrole (17) to the corresponding N-methylpyrrole intermediate (18). The acid intermediate (19) was obtained by hydrolysis of (18) with alcoholic NaOH at heating conditions. Treatment of this bromide (19) with NaOMe in the presence of CuI gave the target methoxy compound (20) in quantitative yield.

Reaction Scheme 6

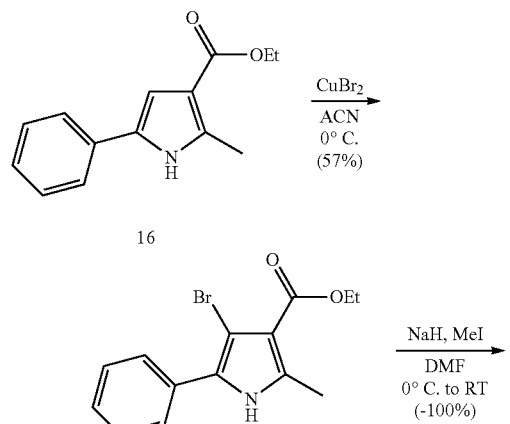

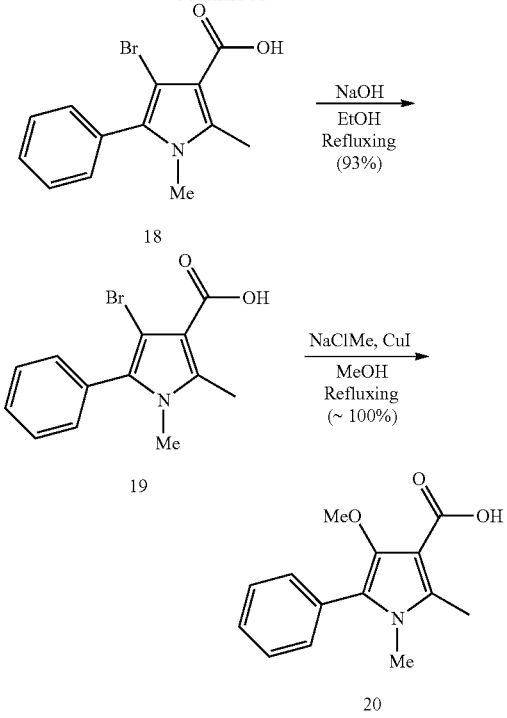

For the synthesis of 2-chloro derivatives, 2-bromoacetophenone (2) was reacted with ethyl cyanoacetate (21) with the similar method described in scheme 1, as shown in Reaction Scheme 7. With HCl gas, nitrile group was converted to the corresponding chloroimidate and subsequent cyclization occurred in situ to produce 2-chlropyrrole compound (23) in 85% yield. N-alkylation of pyrrole and subsequent hydrolysis of ethyl ester were accomplished in an analogous method demonstrated in Reaction Scheme 2. Hydrogenation of 2-chloro-5-phenylpyrrole compounds (24) transformed 24 to the corresponding 5-phenylpyrroles (26) smoothly.

Reaction Scheme 7

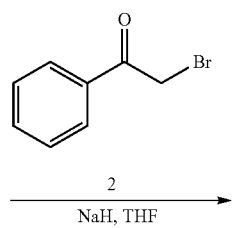

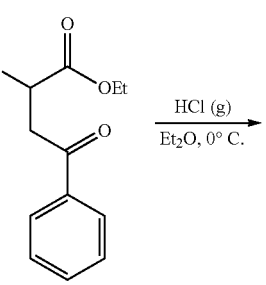

22

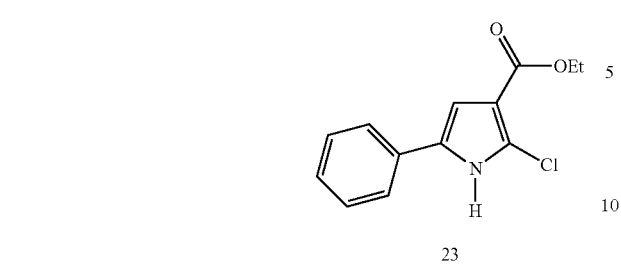
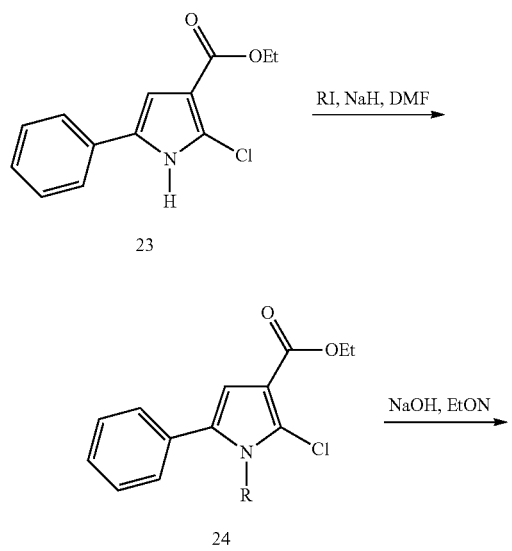
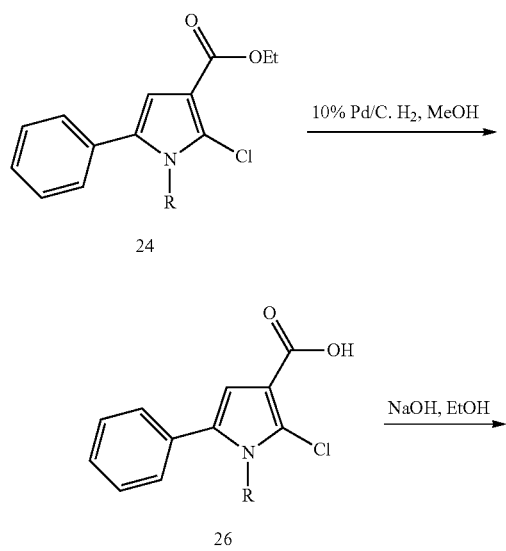
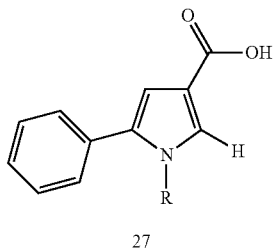

In reaction scheme 7, R is hydrogen, $C_{1-5}$ alkyl, substituted $C_{1-5}$ alkyl, $C_{3-7}$ cycloalkyl, substituted $C_{3-7}$ cycloalkyl, aryl, substituted aryl, heteroaryl, substituted heteroaryl, heterocycloalkyl, or substituted heterocycloalkyl.

Preparation of arylpiperazine moiety containing $C_2$ linker started from 2-bromophthalimide (28) and 2,3-dichlorophenylpiperazine (29) (Robarge, M. J. et al., *J. Med. Chem.* 2001, 44, 3175-3186). Treatment of 2-bromophthalimide (28) with 2,3-dichlorophenylpiperazine hydrochloride (29) in the presence of potassium carbonate in DMF at room temperature afforded N-protected amine (30) as shown in Reaction Scheme 8. Compound (30) was treated with hydrazine in ethanol at 80° C. to give amine (31). Liquid amine (31) was transformed to hydrochloride salt form with 4N HCl in dioxane efficiently. Similarly, 3-chlorophenylpiperazine and 2,3-dimethylphenylpiperazine were utilized for preparation of the corresponding amine building blocks (32) and (33), respectively.

Reaction Scheme 8

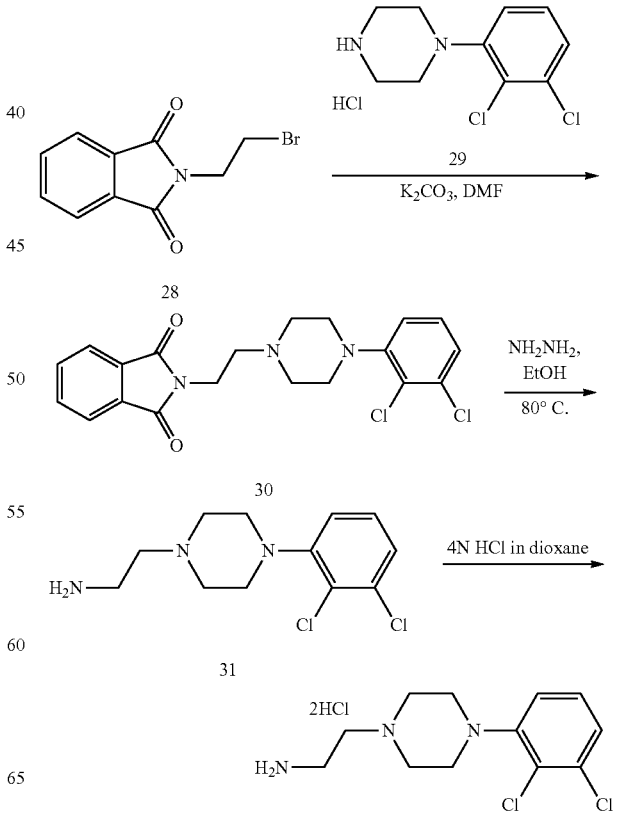

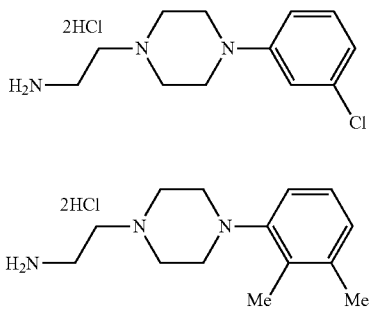

For the preparation of C₃ linker arylpiperazine parts, 3-bromopropylamine was selected as starting material. Protection on primary amine was performed with 3-bromopropylamine hydrobromide (34) and CbzCl under di-phase methylene chloride and 3N NaOH aqueous solution to give N-Cbz bromopropylamine (35) as shown in Reaction Scheme 9. Installation of bromopropylamine to arylpiperazine proceeded with potassium carbonate described before to afford protected alkylated arylpiperazine (36). The Cbz group of structure (36) was deprotected with iodotrimethylsilane in acetonitrile to synthesize amine (37) as oil. Transformation of neutral amine to the corresponding hydrochloride form was accomplished with 4N HCl in dioxane. Similarly, 3-chlorophenylarylpiperazine and 2,3-dimethylphenylpiperazine were used for preparation of amine building blocks (38) and (39), respectively.

Reaction Scheme 9

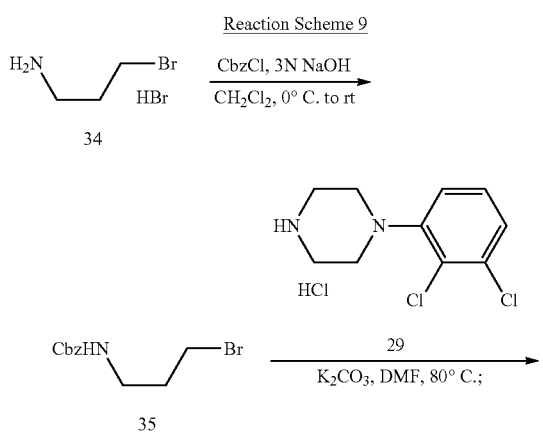

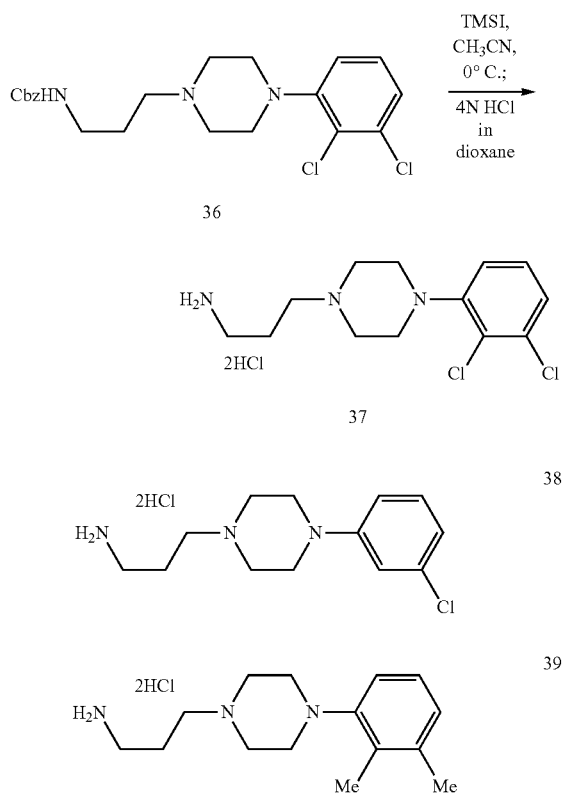

As shown in Scheme 10, the synthesis of 3-(4-(2-methoxyphenyl)piperazin-1-yl)propan-1-amine (43), and the like, wherein the alkyl chain between the piperazine and the terminal amine corresponds to two carbons through four carbons, commenced with N-(2-bromoethyl)phthalimide, N-(3-bromopropyl)phthalimide (40), and N-(4-bromobutyl) phthalimide by adopting a reported procedure [Robarge, M. J. et al., *J. Med. Chem.* 2001, 44, 3175-3186]. For example, N-(3-bromopropyl)phthalimide (40) was reacted with 1-(2-methoxyphenyl)piperazine (41) in the presence of potassium carbonate in a suitable solvent such as DMF at rt afforded the corresponding alkylated product (42) as shown in Reaction Scheme 10. Hydrazinolysis of the alkylated product (42), followed by treatment of HCl solution generated 3-(4-(2,3-dichlorophenyl)piperazin-1-yl)propan-1-amine as a HCl salt form (43). Commercially available arylpiperazine derivatives were used for the corresponding arylpiperazinyl-propylamine.

Reaction Scheme 10

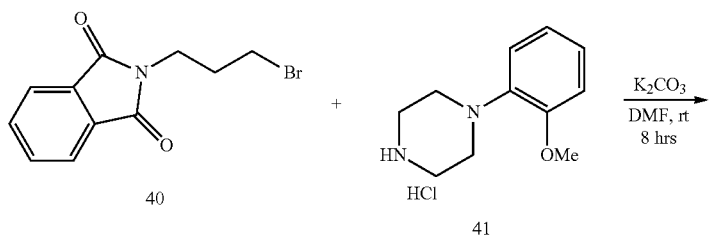

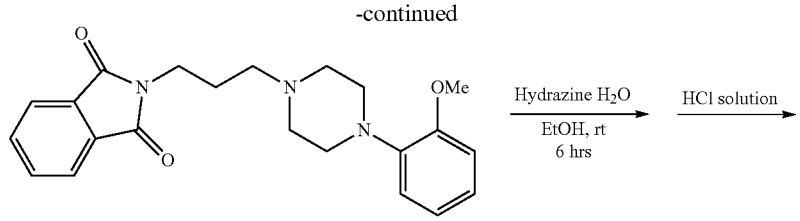

42

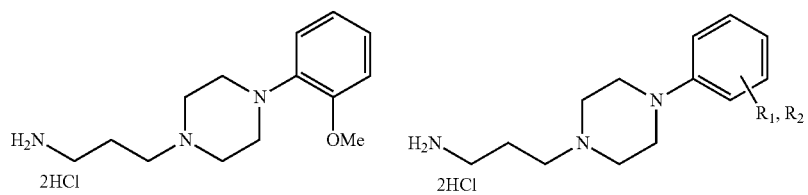

43

$R_1, R_2$ = 2-CF$_3$, 3-OMe, 2-Br, 4-Br, 2-CN,
2,4-diF, 3,4-diCl, 2-OEt, 2-F, 3/4-tiF.

Preparation of arylpiperazine containing N-methylated alkyl substituent started with 3-aminopropan-1-ol (44) as shown in Reaction Scheme 11. Protection of amine (44) with CbzCl under the condition of triethylamine in methylene chloride afforded alcohol (45). Alcohol (45) was protected with TBS group with TBSCl (tert-butylchlorodimethylsilane) and imidazole in DMF to afford TBS ether (46). Treatment of TBS ether (46) with sodium hydride and iodomethane in DMF proceeded to N-methylated product (47). Deprotection of TBS group to afford alcohol (48) proceeded with tetrabutylammonium fluoride in THF and subsequent transformation alcohol (48) to bromide (49) was accomplished with carbon tetrabromide and triphenylphosphine in acetonitrile. Having N-protected bromide (49), arylpiperazine was installed to produce aminoalkylated arylpiperazine (51) with similar methods described before. Both 3-chlorophenyl (52) and 2,3-dimethyl derivatives (53) were produced in an analogous way, respectively.

Reaction Scheme 11

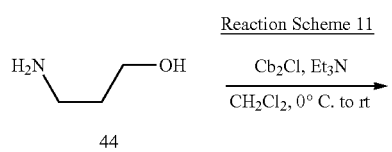

44

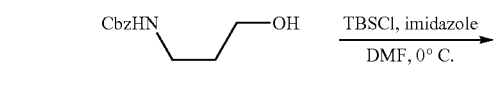

45

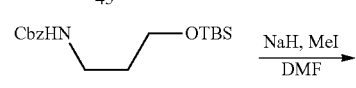

46

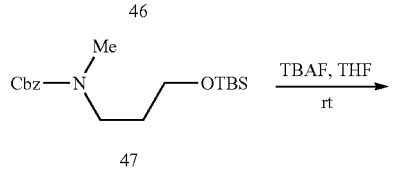

47

-continued

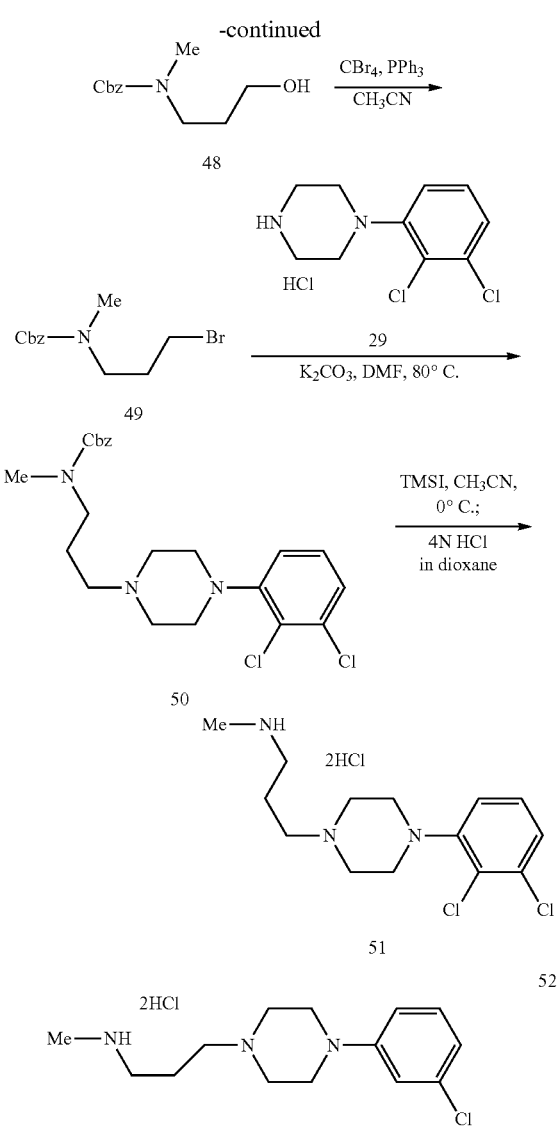

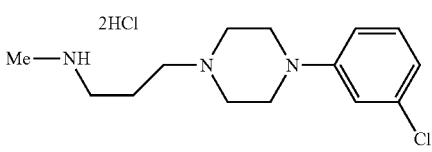

52

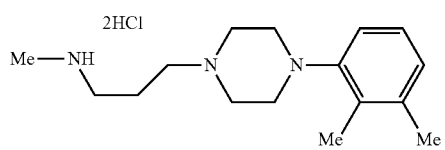
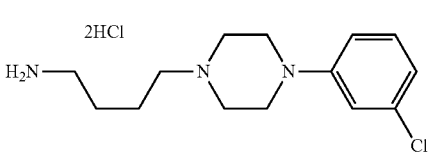
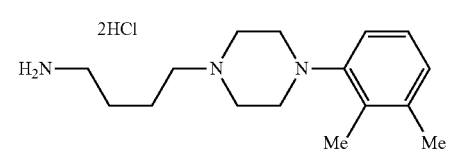

Arylpiperazine connecting primary amine via a $C_4$ linker was synthesized with similar method as described in scheme 11. Instead of 3-aminopropan-1-ol (44), 4-aminobutan-1-ol (54) was used as shown in Reaction Scheme 12. Protection amino alcohol (54) with CbzCl proceeded to afford alcohol (55). Treatment of alcohol (55) with carbon tetrabromide and triphenylphosphine in acetonitrile transformed alcohol (55) to bromide (56). Coupling of bromide (56) and 2,3-dichlorophenylpiperazine dihydrochloride (29) proceeded smoothly with potassium bicarbonate to produce alkylated arylpiperazine (57). The Cbz group deprotection of alkylated arylpiperazine (57) followed by HCl salt formation was accomplished with treatment of iodotrimethylsilane and subsequent use of 4N HCl in dioxane. With similar methods, 3-chlorophenyl and 2,3-dimehtyl versions (59) and (60) were also produced, respectively.

For the derivatization of arylpiperazine alkylamine, various arylpiperazines were synthesized and a particular alkylamine moiety was connected as described in Reaction Scheme 13. At first, N-Arylpiperazines were prepared via condensation of the requisite anilines such as 3-chloro-2-methylaniline (61) with bis(2-chloroethyl)amine (62), following a reported procedure [Martin, G. E. et al., *J. Med. Chem.* 1989, 32, 1052-1056] as shown in Reaction Scheme 13. Using the method, other arylpiperazine derivatives could be prepared with various anilines.

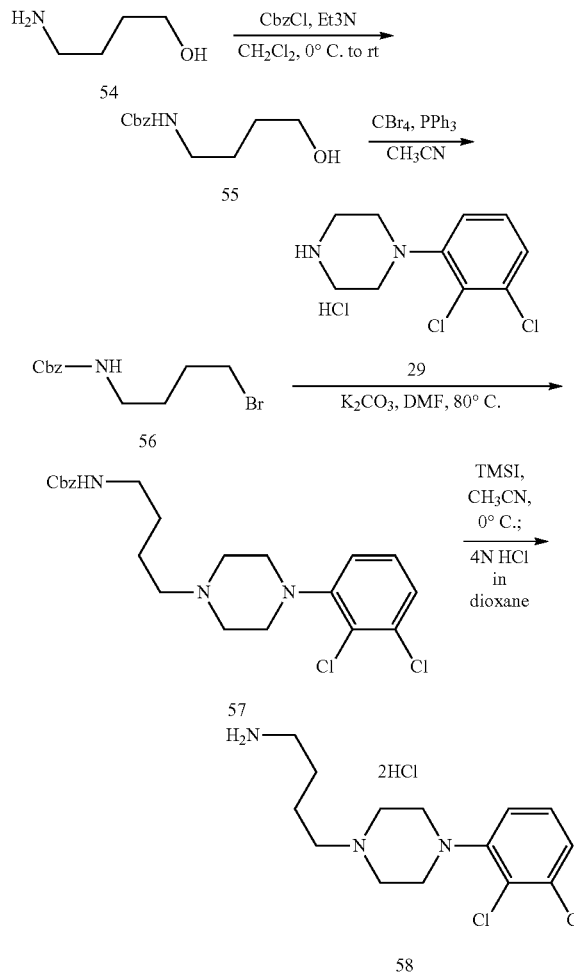

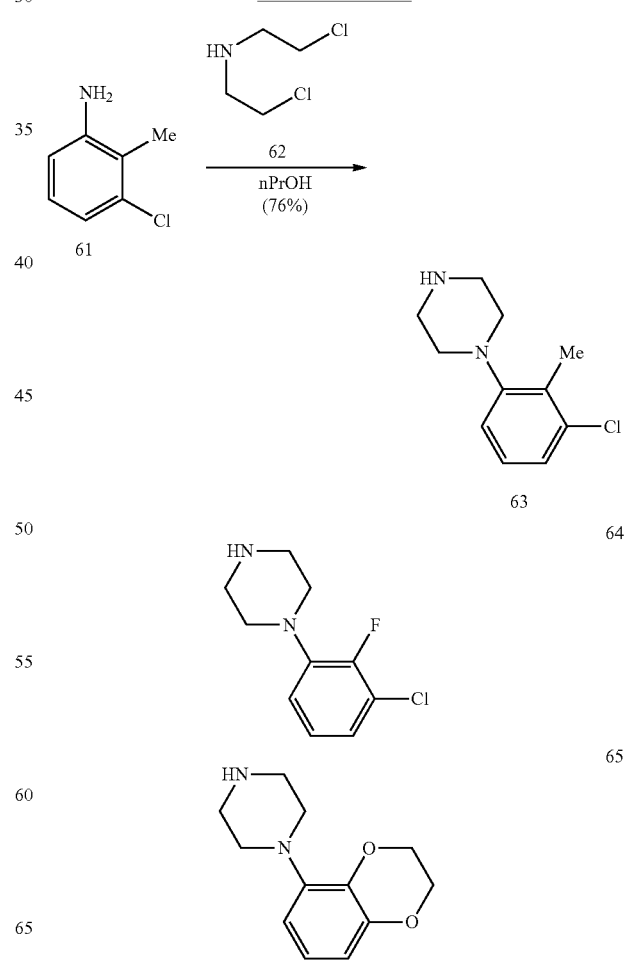

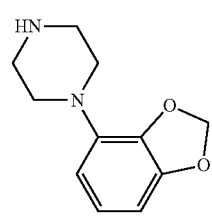

66

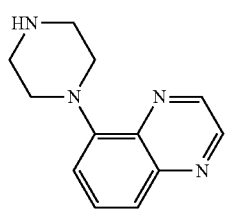

67

Next, 8-(piperazin-1-yl)quinoline (72) was prepared as depicted in Reaction Scheme 14 [Zhou, D. et al,. *Bioorg. Med. Chem.* 2008, 16, 6707-6723]. Reaction of commercially available 8-hydroxyquinoline (68) with trifluoromethanesulfonic anhydride (triflic anhydride) in the presence of base produced the corresponding triflate (69). Buchwald coupling [Buchwald, S. L. et al., *J. Am. Chem. Soc.* 1998, 120, 4960] between quinolin-8-yl trifluoromethanesulfonate (69) and 1-tent-butyl-4-piperazine carboxylate (70) afforded compound 71 in 72% yield for the two steps. Deprotection of Boc group of compound 71 using HCl in refluxed methanol produced quinolinyl piperazine (72). Using the method, various arylpiperazines showed in Reaction Scheme 14 were prepared.

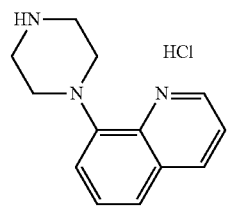

72

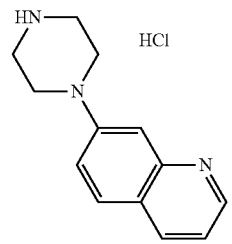

73

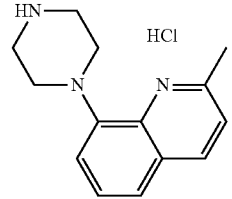

74

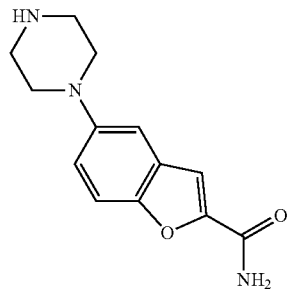

75

Coupling reaction of commercially available 3-chloro-1,2-benzisothiazole (76) with excess piperazine affords a heteroarylpiperazine compound (77) at refluxing conditions in moderate yield as shown in Reaction Scheme 15. A phthalimide intermediate (78) is prepared by alkylation of the heteroarylpiperazine (77) with the appropriate N-bromoalkylphthalimide (40) in the presence of K$_2$CO$_3$ as a base. The phthalimide (78) can be converted to a primary amine compound (79), and then subsequently acidified with 4M HCl in dioxane to provide the target intermediate as HCl salt form.

Reaction Scheme 14

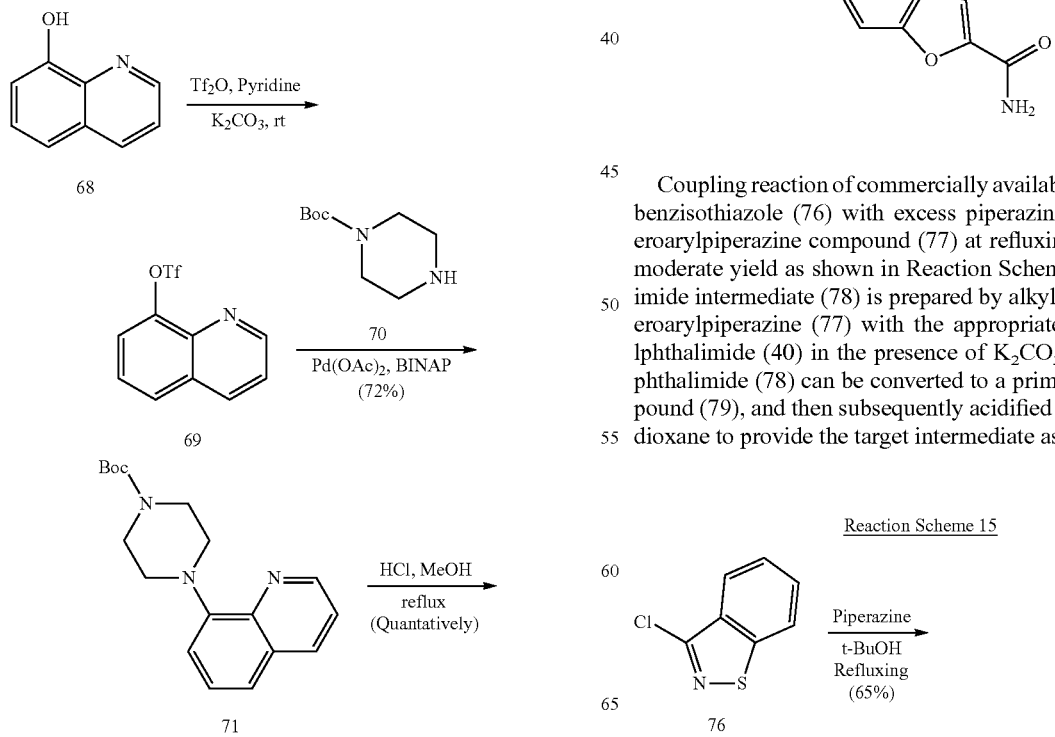

Reaction Scheme 15

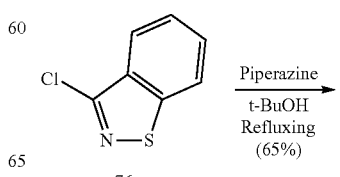

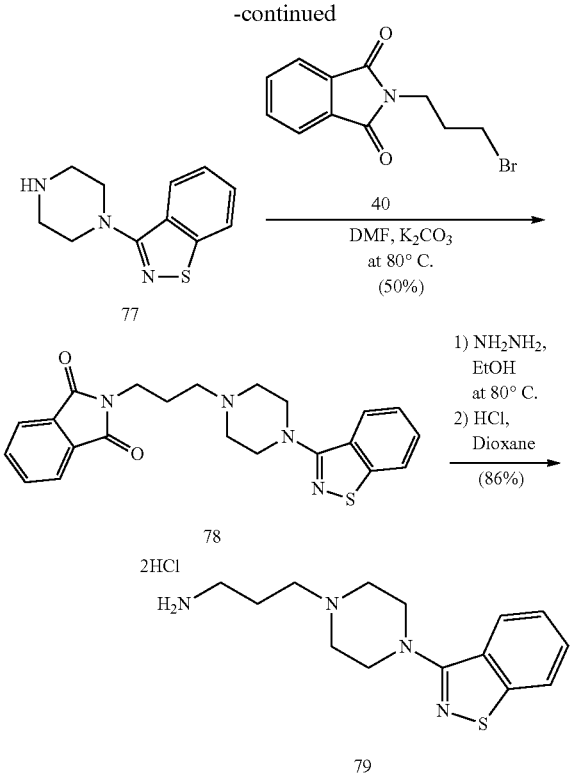

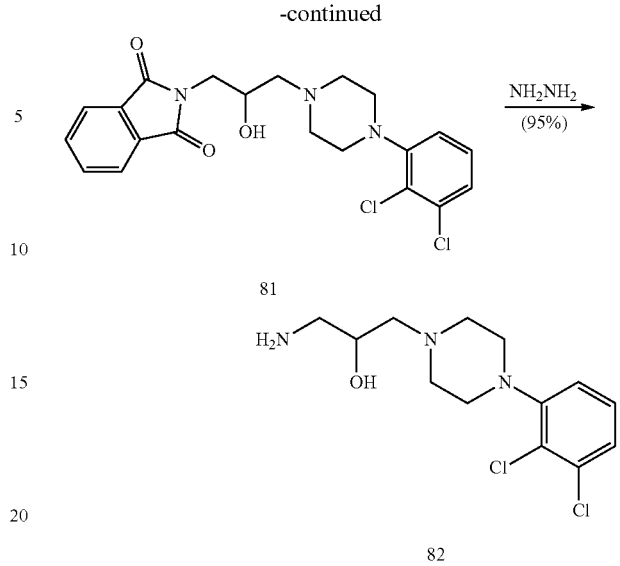

In order to increase hydrophilicity for compounds such as 3-(4-(2,3-dichlorophenyl)piperazin-1-yl)propan-1-amine (37), a compound such as 1-amino-3-(4-(2,3-dichlorophenyl) piperazin-1-yl)propan-2-ol (82) was prepared as shown in Reaction Scheme 16. Thus, commercially available N-(2,3-epoxypropyl)phthalimide (80) was treated with 1-(2,3-dichlorophenyl)piperazine (29) in the presence of base such as triethylamine in a suitable solvent such as THF at 80° C. produced the alcohol (81) in about 91% yield. Subsequently, hydrazinolysis of compound 81 generated 1-amino-3-(4-(2, 3-dichlorophenyl)piperazin-1-yl)propan-2-ol (82) as a white solid in 95% yield.

Another variation involves difluorination for compounds such as 3-(4-(2,3-dichlorophenyl)piperazin-1-yl)propan-1-amine (37) as demonstrated in Reaction Scheme 17. Thus, the alcohol (81) generated in Scheme 16 was oxidized using Swern oxidation conditions to provide the corresponding ketone (83) in 89% yield. Treatment of ketone (83) with DAST (diethylaminosulfur trifluoride) gave the corresponding difluoride (84) in 21% yield. Treatment of difluoride (84) with hydrazine produced 3-(4-(2,3-dichlorophenyl)piperazin-1-yl)-2,2-difluoropropan-1-amine (85) in quantitative yield.

Reaction Scheme 16

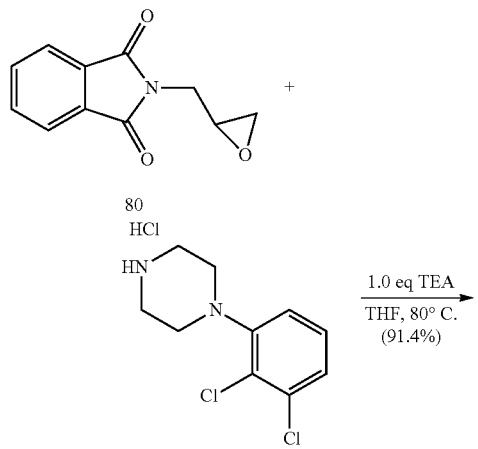

Reaction Scheme 17

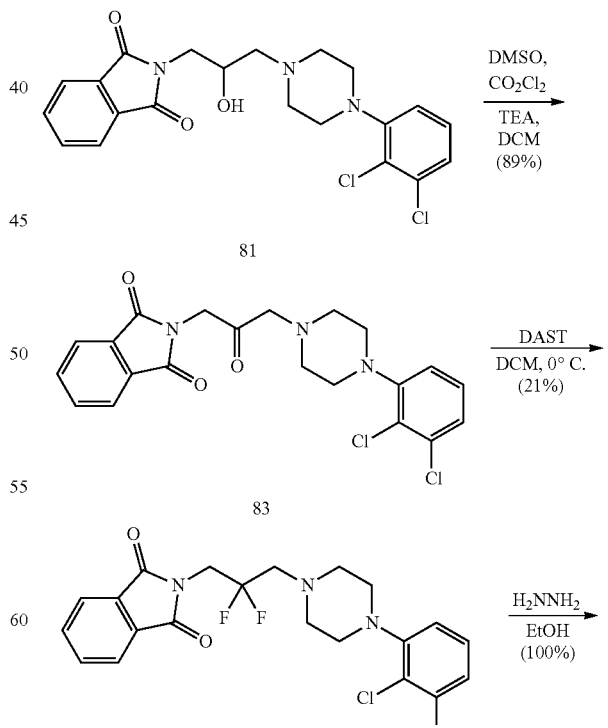

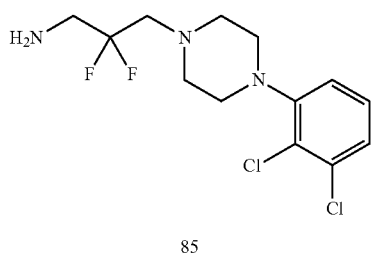

85

Coupling reaction of acid part and amino alkyl arylpiperazine part was conducted as follows. With prepared 2-methyl-5-phenyl-1H-pyrrole-3-carboxylic acid (6a) and 3-(4-(2,3-dichlorophenyl)piperazin-1-yl)propan-1-amine (37), amide coupling underwent under conditions such as EDCI, HOBT and NMM in methylene chloride or DMF produce amide (86a) as shown in Reaction Scheme 18. After reaction completes, purification was performed using preparative reverse phase column with acetonitrile and water, and then 0.2% TFA acetonitrile and water solution if it was necessary. The neutral product (86a) was converted to HCl salt form (86b) by treatment of (86a) with HCl solution in methanol.

Reaction Scheme 18

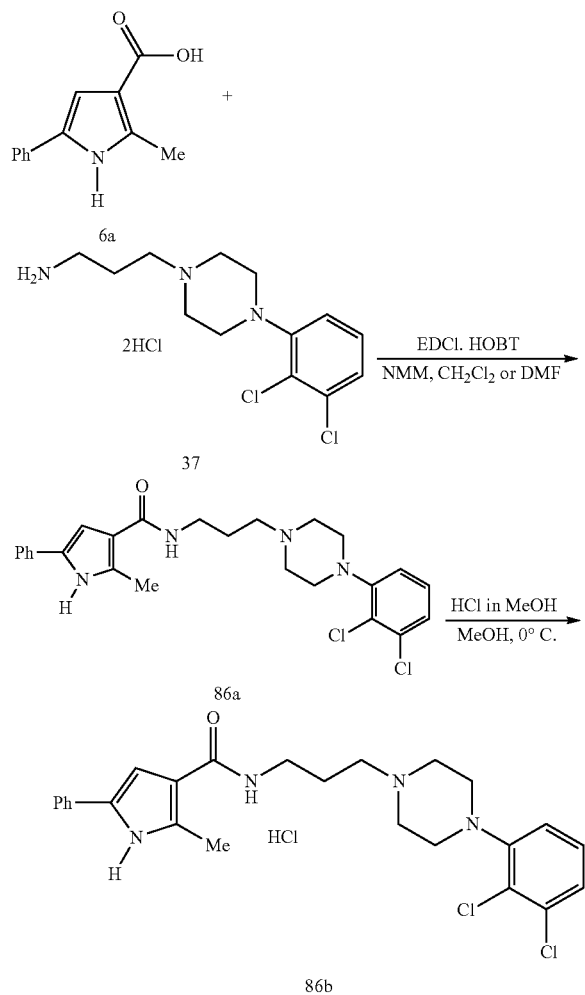

Treatment of methoxypyrrole derivative (87) with BBr₃ at cold temperature produces a corresponding hydroxypyrrole derivative (88) as shown in Reaction Scheme 19.

Reaction Scheme 19

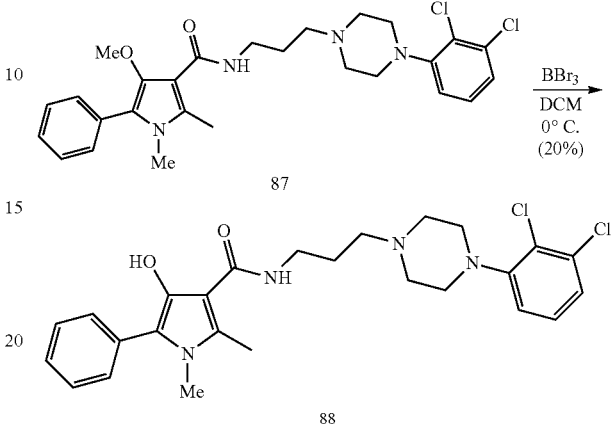

The inventive arylpiperazine-containing pyrrole 3-carboxamide compound of formula (I) is effective for preventing or treating depressive disorders.

Accordingly, the present invention provides a pharmaceutical composition for preventing or treating depressive disorders, which comprises the compound of formula (I) or the pharmaceutically acceptable salt thereof as an active ingredient and a pharmaceutically acceptable carrier.

Further, the present invention provides a method for preventing or treating depressive disorders in a mammal, which comprises administering the compound of formula (I) or the pharmaceutically acceptable salt thereof to the mammal.

As used herein, the term "depressive disorders" refers to mental illnesses characterized by a profound and persistent feeling of sadness or despair and/or a loss of interest in things that once were pleasurable. Disturbance in sleep, appetite, and mental processes are a common accompaniment.

The pharmaceutical composition may be administered orally, intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerin or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg/Kg, and preferably from 1 mg to 100 mg/Kg of the compound of Formula (I) or its pharmaceutically acceptable salt.

The suitable daily dosage for oral administration is about 0.01 mg/Kg to 40 mg/Kg of the compound of Formula (I) or its pharmaceutically acceptable salt, may be administered 1 to 6 times a day, depending on the patient's condition.

EXAMPLES

As used herein the symbols and conventions used describing the processes, schemes and examples of the present invention are consistent with those used in the contemporary scientific literature, for example, the *Journal of the American Chemical Society or the Journal of Biological Chemistry*. Unless otherwise noted, all starting materials were obtained from commercial suppliers and used without further purification.

Hz (Hertz)
$T_r$ (retention time)
MeOH (methanol)
TFA (trifluoroacetic acid)
EtOH (ethanol)
DMSO (dimethylsulfoxide)
DCM (dichloromethane)
DMF (N,N-dimethylformamide)
CDI (1,1-carbonyldiimidazole)
HOSu (N-hydroxysuccinimide)
HOBT (1-hydroxybenzotriazole)
Boc (tert-butyloxycarbonyl)
mCPBA (meta-chloroperbenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)phosphinic chloride);
EDCI (1-ethyl-3-[3-dimethylaminopropyl]carbodiimide hydrochloride)
MeI (iodomethane)
LDA (lithium diisopropylamide)
DIPEA (diisopropylethylamine)
NaSMe (sodium thiomethoxide)

TLC (thin layer chromatography)
RP (reverse phase)
i-PrOH (isopropanol)
TEA (triethylamine)
THF (tetrahydrofuran)
EtOAc (ethyl acetate)
HOAc (acetic acid)
Ac (acetyl)
Bn (benzyl)

While the invention has been described with respect to the specific embodiments, it should be recognized that various modifications and changes may be made by those skilled in the art to the invention which also falls within the scope of the invention as defined as the appended claims.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are of the highest available purity unless otherwise indicated. Microwave reaction was conducted with a Biotage microwave reactor. $^1$H NMR spectra were recorded on either a Jeol ECX-400 spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad). Mass spectra were obtained with Micromass, Quattro LC Triple Quadruple Tandem Mass Spectometer, ESI or Agilent, 1100LC/MSD, ESI. For preparative HPLC, ca 100 mg of a product was injected in 1 ml of DMSO onto a SunFire™ Prep C18 OBD 5 um 19×100 mm Column with a 10 min gradient from 10% $CH_3CN$ to 90% $CH_3CN$ in $H_2O$. For normal phase preparative column chromatography Biotage SP1 system and Isolera system were used with tBuOMe or Ethyl acetate and hexane as solvent. Flash chromatography was carried using Merck silica gel 60 (230-400 mesh). Most of the reactions were monitored by thin-layer chromatography on 0.25 mm E. Merck silica gel plates (60E-254), visualized with UV light using a 5% ethanolic phosphomolybdic acid or p-anisaldehyde solution.

The following synthetic schemes are merely illustrative of the methods by which the compounds of the invention may be prepared and are not intended to limit the scope of the invention as defined in the appended claims.

Preparation Example 1

Ethyl 2-methyl-5-phenyl-1H-pyrrole-3-carboxylate

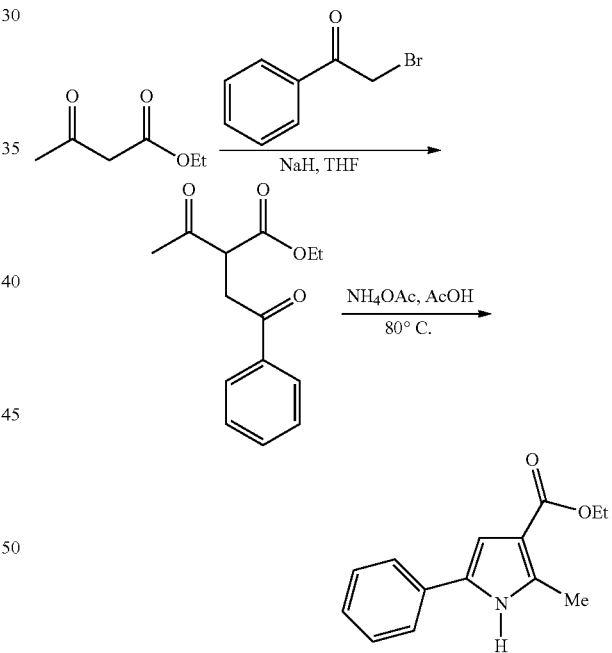

Step 1: Ethyl 2-acetyl-4-oxo-4-phenylbutanoate

To a solution of ethyl acetoacetate (10 g, 76.8 mmol) in tetrahydrofuran (50 ml) at 0° C. was added sodium hydride (4 g, 60% in mineral oil, 100 mmol) portionly. The reaction mixture was stirred for minutes, and 2-bromoacetophenone (16.8 g, 84.5 mmol) in tetrahydrofuran (20 ml) was added dropwisely. After warming the mixture to room temperature, it was stirred for 4 hours. The resulting solution was quenched with water and normal work-up accomplished with diethyl ether. The organic layer was dried with $MgSO_4$, and purified by silica gel column chromatography (EtOAc:Hx=1:5) to produce desired compound (19 g, 98%) as light yellow color oil.
MH+249

Step 2: Ethyl 2-methyl-5-phenyl-1H-pyrrole-3-carboxylate

Ethyl 2-acetyl-4-oxo-4-phenylbutanoate (19 g, 76.8 mmol) was treated with NH₄OAc (29.4 g, 384 mmol) in acetic acid (100 ml) at room temperature. After stirring 10 minutes, the reaction mixture was heated to 80° C. for overnight. After cooling to room temperature, acetic acid was evaporated under reduced pressure and water (50 ml) was added. With diethyl ether, organic layer was extracted. Purification by normal phase preparative LC provided desired compound (13.3 g, 76%) as yellow solid.
¹H NMR (400 MHz, CDCl₃) δ 8.45 (brs, 1H), 7.45 (dd, J=8.4, 1.6 Hz, 2H), 7.36 (t, J=7.6 Hz, 2H), 7.20 (dd, J=7.2, 1.1Hz, 1H), 6.84 (d, J=2.8 Hz, 1H), 4.29 (q, J=7.2 Hz, 2H), 2.59 (s, 3H), 1.36 (t, J=6.8 Hz, 3H).
MH+230

Preparation Example 2

1,2-Dimethyl-5-phenyl-1H-pyrrole-3-carboxylic acid

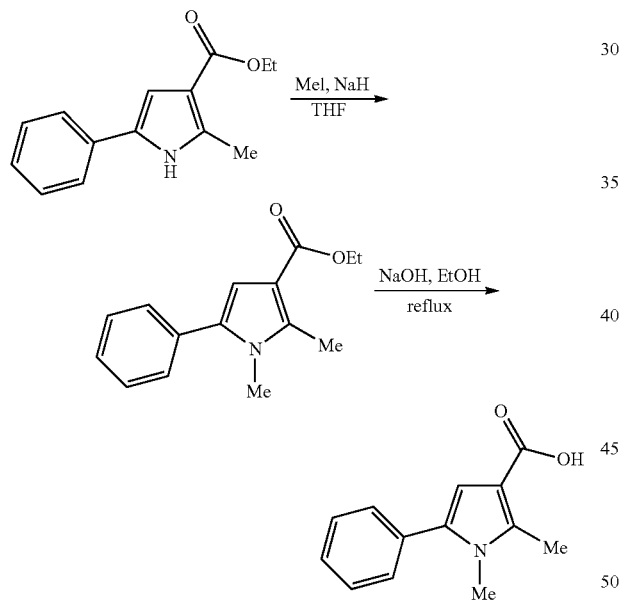

Step 1: Ethyl 1,2-dimethyl-5-phenyl-1H-pyrrole-3-carboxylate

To ethyl 2-methyl-5-phenyl-1H-pyrrole-3-carboxylate (3 g, 13 mmol) in THF (50 ml) was added iodomethane (4 ml, 65 mmol) and sodium hydride (630 mg, 60% in mineral oil, 15.6 mmol) at 0° C. After warming the reaction mixture to room temperature, it was stirred for 1 day. Water (20 ml) was added and extracted organic layer with diethyl ether. With normal-phase preparative LC, purification preceded to gave title compound (3 g, 94%) as yellow solid.
¹H NMR (400 MHz, CDCl₃) δ 7.42-7.31 (m, 5H), 6.58 (s, 1H), 4.28 (q, J=7.2 Hz, 2H), 3.50 (s, 3H), 2.60 (s, 3H), 1.34 (t, J=7.2 Hz, 3H).
MH+244

Step 2: 1,2-Dimethyl-5-phenyl-1H-pyrrole-3-carboxylic acid

To the solution of Ethyl 1,2-dimethyl-5-phenyl-1H-pyrrole-3-carboxylic acid (3 g, 13 mmol) in EtOH (50 ml) was added NaOH (1.6 g, 39 mmol) at room temperature. The reaction mixture was refluxed for 1 day with LC-MS monitoring. After reaction complete, EtOH was evaporated under reduced pressure. Water (50 ml) was added and washed aqueous layer with diethyl ether twice. 1N HCl solution was added to aqueous layer until pH<3. And extraction was accomplished with EtOAc. Organic layer was dried with MgSO₄ and evaporated in vacuo to provide title compound (2.6 g, 95%) as yellow soild. Without further purification, acid was used for the reaction of amide coupling.

Preparation Example 3

1-Ethyl-2-methyl-5-phenyl-1H-pyrrole-3-carboxylic acid

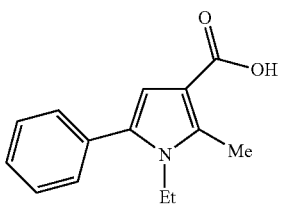 [SMILES: CCn1c(-c2ccccc2)cc(C(=O)O)c1C]

¹H NMR (400 MHz, CDCl₃) δ 7.42-7.34 (m, 5H), 6.55 (s, 1H), 4.29 (q, J=6.8 Hz, 2H), 2.62 (s, 3H), 1.19 (t, J=6.8 Hz, 3H).
MH+230

Preparation Example 4

1-Ethyl-2-methyl-5-phenyl-1H-pyrrole-3-carboxylic acid

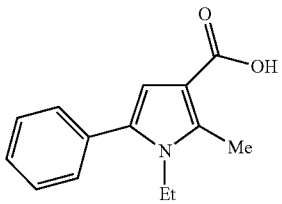 [SMILES: CCn1c(-c2ccccc2)cc(C(=O)O)c1C]

¹H NMR (400 MHz, CDCl₃) δ 7.43-7.30 (m, 5H), 6.60 (s, 1H), 3.94 (q, J=7.6 Hz, 2H), 2.64 (s, 3H), 1.21 (t, J=7.6 Hz, 3H).
MH+230

Preparation Example 5

2-Methyl-5-phenyl-1-propyl-1H-pyrrole-3-carboxylic acid

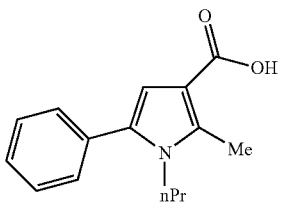

$^1$H NMR (400 MHz, CDCl$_3$) δ 7.42-7.34 (m, 5H), 6.55 (s, 1H), 3.84 (dd, J=9.2, 8.0 Hz, 2H), 2.62 (s, 3H), 1.59-1.53 (m, 2H), 0.76 (t, J=7.6 Hz, 3H).
MH+244

Preparation Example 6

1-(4-Fluorophenyl)-2-methyl-5-phenyl-1H-pyrrole-3-carboxylic acid

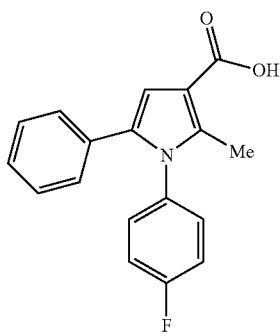 [SMILES: Cc1c(C(=O)O)cc(-c2ccccc2)n1-c1ccc(F)cc1]

$^1$H NMR (400 MHz, CDCl$_3$) δ 7.26-7.00 (m, 9H), 6.85 (s, 1H), 2.42 (s, 3H).
MH+296

Preparation Example 7

1-Benzyl-2-methyl-5-phenyl-1H-pyrrole-3-carboxylic acid

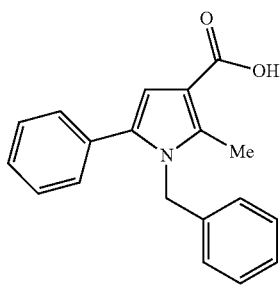 [SMILES: Cc1c(C(=O)O)cc(-c2ccccc2)n1Cc1ccccc1]

$^1$H NMR (400 MHz, CDCl$_3$) δ 7.33-7.24 (m, 8H), 6.92 (d, J=7.6 Hz, 2H), 6.74 (s, 1H), 5.14 (s, 2H), 2.48 (s, 3H).
MH+292

Preparation Example 8

5-(4-chlorophenyl)-2-methyl-1H-pyrrole-3-carboxylic acid

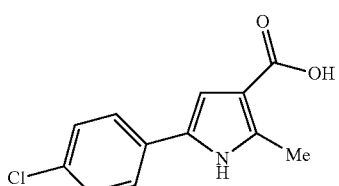

MH+236

Preparation Example 9

5-(4-chlorophenyl)-1,2-dimethyl-1H-pyrrole-3-carboxylic acid

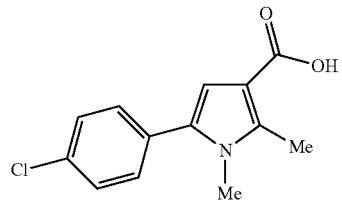 [SMILES: Cc1c(C(=O)O)cc(-c2ccc(Cl)cc2)n1C]

MH+250

Preparation Example 10

5-(4-chlorophenyl)-1-ethyl-2-methyl-1H-pyrrole-3-carboxylic acid

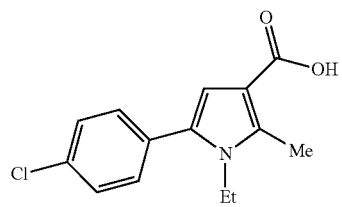 [SMILES: CCn1c(-c2ccc(Cl)cc2)cc(C(=O)O)c1C]

MH+264

Preparation Example 11

Ethyl 5-(4-hydroxybutyl)-2-methyl-1H-pyrrole-3-carboxylate

A solution of olefin (1.00 g, 4.8 mmol) in dry THF (16 mL) was treated under N$_2$ with BH$_3$-THF (14.5 mL of a 1.0 M THF solution, 14.5 mmol). The reaction mixture was stirred for 18 h at room temperature and then quenched by addition of MeOH (10 mL), 6 M aqueous NaOH (3.5 mL), and 30% H$_2$O$_2$ (5.5 mL). The resulting mixture was then stirred at 50° C. for 1 h and worked up (extraction with EtOAc). The organic layer was dried with MgSO4, and purified by silica gel column chromatography (EtOAc:Hx=1:4) to produce desired compound (0.8 g, 70%) as light yellow color oil.
MH+225

Preparation Example 12

4-Methoxy-1,2-dimethyl-5-phenyl-1H-pyrrole-3-carboxylic acid

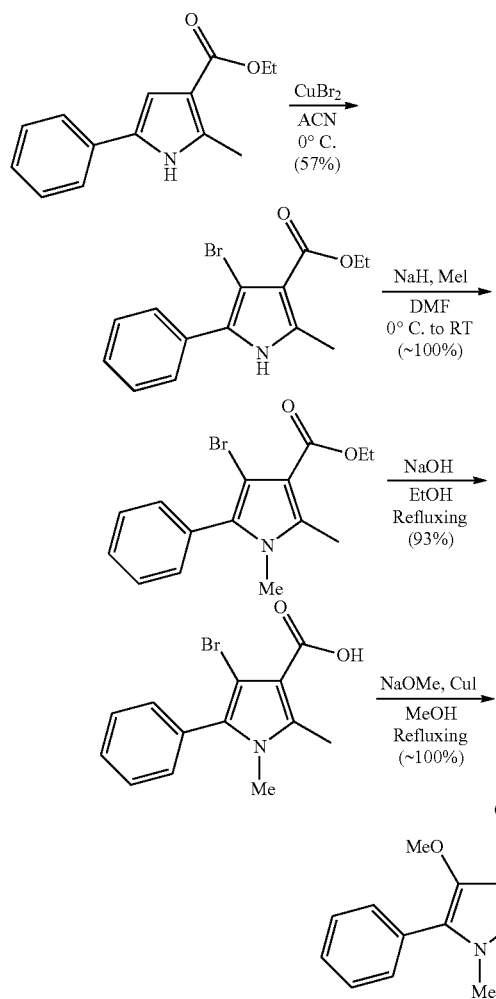

To a solution of ethyl 2-methyl-5-phenyl-1H-pyrrole-3-carboxylate (4.59 g, 20 mmol) in acetonitrile (200 mL) was added CuBr$_2$ (15.4 g, 69 mmol) at 0° C. The reaction mixture was held at 0° C. under magnetic stirring. After 4~5 hours, the mixture was poured into water (250 mL) and extracted with ethyl acetate (300~400 mL). The organic phase was dried over MgSO$_4$ and evaporated under vacuum. The residue was further purified by flash column chromatography to provide the intermediate ethyl 4-bromo-2-methyl-5-phenyl-1H-pyrrole-3-carboxylate (3.31 g, 11.4 mmol, 57%).

$^1$H NMR (400 MHz, CDCl$_3$) δ 7.59 (d, J=8.0 Hz, 2H), 7.41 (t, J=8.0 Hz, 2H), 7.31 (t, J=7.2 Hz, 1H), 4.32 (q, J=7.2 Hz, 2H), 2.55 (s, 1H), 1.37 (t, J=8.8 Hz, 3H).

MH+279

Ethyl 4-bromo-2-methyl-5-phenyl-1H-pyrrole-3-carboxylate (3.31 g, 11.4 mmol) was dissolved into anhydrous DMF (50 mL). After stirring at 0° C. for 15 min, to this solution was added NaH (60%, 0.55 g, 13.7 mmol). The mixture was held at 0° C. for 10 min and then MeI (2.13 mL, 34.2 mmol) was added to the mixture. The reaction mixture was gradually warmed to RT and stirred overnight. The mixture was poured into brine (100 mL) and extracted with ethyl acetate (200 mL). The organic phase was dried over MgSO$_4$ and evaporated under vacuum. The residue was further purified by flash column chromatography to provide the crude intermediate ethyl 4-bromo-1,2-dimethyl-5-phenyl-1H-pyrrole-3-carboxylate (4.23 g, 13.1 mmol, 115%).

A mixture of the ethyl 4-bromo-1,2-dimethyl-5-phenyl-1H-pyrrole-3-carboxylate (3.43 g, 10.7 mmol) and NaOH (1.28 g, 31.9 mmol) in EtOH (15 mL) was refluxed overnight and then cooled to room temperature. The reaction mixture was poured into 1M HCl solution (100 mL) and extracted with ethyl acetate (200 mL). The organic phase was dried over MgSO$_4$ and evaporated under vacuum. The residue 4-bromo-1,2-dimethyl-5-phenyl-1H-pyrrole-3-carboxylic acid was used without further purification for the next step (2.91 g, 9.91 mmol, 93%).

The mixture of the 4-bromo-1,2-dimethyl-5-phenyl-1H-pyrrole-3-carboxylic acid (2.91 g, 9.91 mmol), NaOMe (11.3 mL, 25% wt in MeOH) and CuI (566 mg, 2.97 mmol) in MeOH (35 mL) was refluxed overnight. The reaction mixture was poured into 1M HCl solution (100 mL) and extracted with ethyl acetate (200 mL). The organic phase was dried over MgSO$_4$ and evaporated under vacuum to provide the title compound (2.56 g, 10.4 mmol, 105%).

$^1$H NMR (400 MHz, CDCl$_3$) δ 7.48-7.44 (m, 2H), 7.42-7.36 (m, 3H), 3.55 (s, 1H), 3.36 (s, 1H), 2.59 (s, 1H).

MH+246.

Preparation Example 13

Ethyl 2-chloro-5-phenyl-1H-pyrrole-3-carboxylate

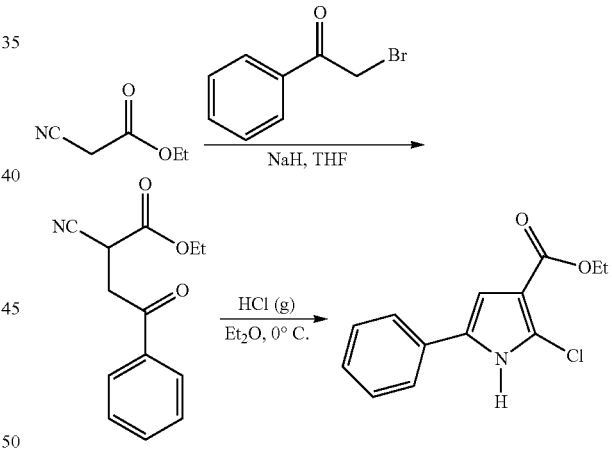

Step 1: Ethyl 2-cyano-4-oxo-4-phenylbutanoate

To a solution of ethyl 2-cyanoacetate (10 g, 88.4 mmol) in tetrahydrofuran (50 ml) at 0° C. was added sodium hydride (4.2 g, 60% in mineral oil, 105 mmol) portionly. The reaction mixture was stirred for 30 minutes, and 2-bromoacetophenone (20 g, 100 mmol) in tetrahydrofuran (20 ml) was added dropwisely. After warming the mixture to room temperature, it was stirred for 4 hours. The resulting solution was quenched with water and normal work-up accomplished with diethyl ether. The organic layer was dried with MgSO$_4$, and purified by silica gel column chromatography (EtOAc:Hx=1:3) to produce desired compound (19 g, 98%) as light yellow color oil.

MH+232

Step 2: Ethyl 2-chloro-5-phenyl-1H-pyrrole-3-carboxylate

To a solution of ethyl 2-cyano-4-oxo-4-phenylbutanoate (8 g, 34.6 mmol) in Et$_2$O (100 ml) was bubbled HCl gas at 0° C. for 30 min. After reaction mixture was stirred for 1 day at 0° C., the resulting solution was evaporated under reduced pressure. The residue was purified with silica gel column (EtOAc:Hx=1:3) to produce title compound (7.3 g, 84.5%) as light yellow solid.

MH+250

Preparation Example 14

Ethyl 5-phenyl-1H-pyrrole-3-carboxylate

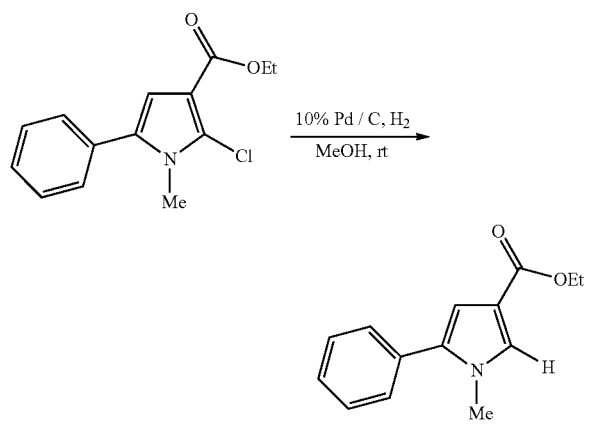

Ethyl 2-chloro-1-methyl-5-phenyl-1H-pyrrole-3-carboxylate (2.4 g, 9.1 mmol) and 10% Pd/C (100 mg) was dissolved in methanol (50 ml) at room temperature. The reaction mixture was hydrogenated for 6 hrs at room temperature and the resulting solution was filtered. After evaporated under reduced pressure, the residue was purified with normal phase preparative column chromatography to produce title compound (1.9g, 91%) as white solid.

MH+230

Preparation Example 15

3-(4-(3-chlorophenyl)piperazin-1-yl)propan-1-amine dihydrochloride

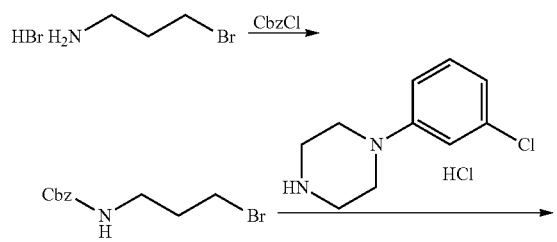

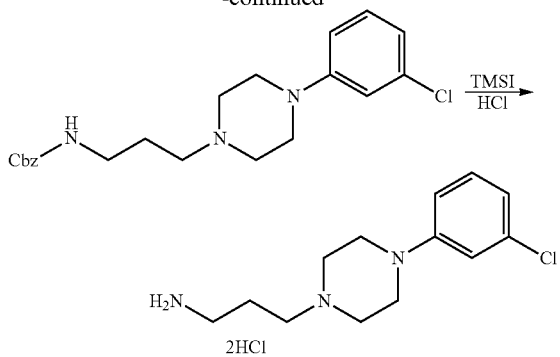

Step 1: Benzyl 3-bromopropylcarbamate

Benzylchloroformate (8.6 ml, 60 mmol) was added to a stirred mixture of 3-bromopropylamine hydrobromide (6.6 g, 30 mmol) in methylene chloride (100 ml) and 3N sodium hydroxide solution (100 ml) at 0° C. After stirring two phase reaction mixture at room temperature for overnight, organic layer was separated and washed with water twice (30 ml×2). After drying with MgSO$_4$, the volatile solvent was evaporated under reduced pressure. The residue was purified with silica gel column chromatography (EtOAc:Hx=1:4) to obtain desire compound (8.6 g, 98%) as colorless oil.

$^1$H NMR (400 MHz, CDCl$_3$) δ 7.40-7.30 (m, 5H), 5.10 (s, 2H), 3.72 (brs, 2H), 2.25-2.18 (m, 2H), 1.98 (br, 2H), 1.81-1.78 (m, 3H).

MH+272

Step 2: Benzyl 3-(4-(3-chlorophenyl)piperazin-1-yl)propylcarbamate 1-(3-Chlorophenyl)piperazine hydrochloride (5 g, 25.4 mmol), benzyl 3-bromopropylcarbamate (8.3 g, 30.5 mmol) and potassium carbonate (10.5 g, 75.9 mmol) were heated to 80° C. in dimethylformamide (100 ml) for overnight under nitrogen condition. After the reaction complete, the reaction mixture was cooled to room temperature and water was added. The organic layer was extracted with ethyl acetate, and washed with water and brine. After drying with MgSO$_4$, the organic layer was filtered and evaporated under reduced pressure to give the title compound (7.2 g, 73%) as light yellow oil, which was used in the deprotection reaction without further purification.

Step 3: 3-(4-(3-chlorophenyl)piperazin-1-yl)propan-1-amine dihydrochloride

Iodotrimethylsilane (9.2 ml, 55.6 mmol) was added to a solution of Benzyl 3-(4-(3-chlorophenyl)piperazin-1-yl)propylcarbamate (7.2 g, 18.6 mmol) in acetonitrile (100 ml) at 0° C. After the reaction mixture was warmed to room temperature, it was stirred for 30 minutes. And then it was quenched with MeOH (10 ml), and stirred for an additional 10 minutes. After volatiles were evaporated under reduced pressure, the residue was dissolved in 3N HCl (30 ml) and washed with ether twice (50 ml×2). The aqueous solution was neutralized to pH>9 with aqueous NH$_4$OH. Extraction with methylene chloride and drying with MgSO4 followed by evaporation yielded the neutral desire product as clear viscous oil. 4N HCl in dioxane (8 ml, 32 mmol) was added and stirred 30 minutes.

And then evaporation in vacuo gave the desired HCl salt compound (4.19 g, 89%) as light yellow solid.
MH+254

Preparation Example 16

2-(4-(2,3-dichlorophenyl)piperazin-1-yl)ethanamine dihydrochloride

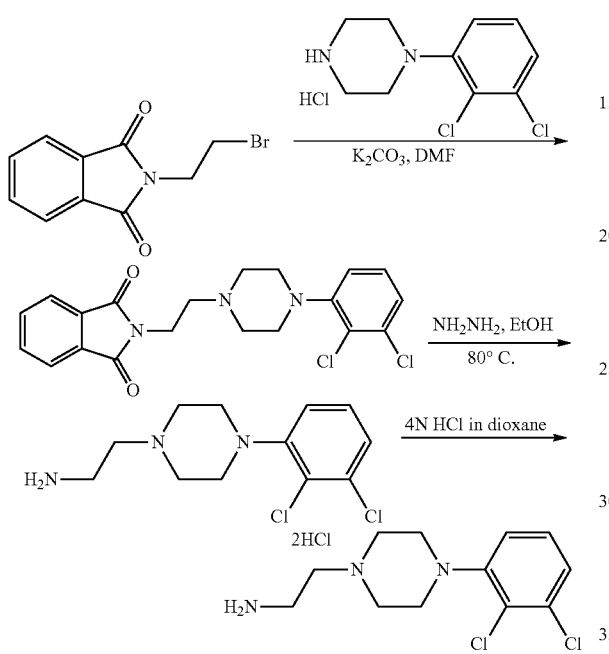

Step 1: 2-(2-(4-(2,3-dichlorophenyl)piperazin-1-yl)ethyl)isoindoline-1,3-dione 1-(2,3-Dichlorophenyl)piperazine hydrochloride (3.16 g, 11.8 mmol) and potassium carbonate (4.08 g, 29.5 mmol) were added to the solution of 2-(2-bromoethyl)isoindoline-1,3-dione (3 g, 11.8 mmol) in DMF (20 ml). The reaction mixture was stirred for overnight at room temperature. After reaction complete, water (40 ml) was added and then normal work-up was taken. The residue was purified with normal phase preparative column to afford title compound (3.87 g, 81% yield) as white solid.
MH+404

Step 2: 2-(4-(2,3-dichlorophenyl)piperazin-1-yl)ethanamine dihydrochloride

To a stirred solution of 2-(2-(4-(2,3-dichlorophenyl)piperazin-1-yl)ethyl)isoindoline-1,3-dione (3.87 g, 9.57 mmol) in ethanol (50 ml) was added hydrazine (3 ml) at room temperature. The reaction mixture was warmed to 80° C. and stirred for 1 day at that temperature. The resulting solution was cooled down to room temperature, and the volatiles were evaporated under reduced pressure. The residue was work-up with EtOAC and saturated sodium bicarbonate solution. After evaporation of organic layer under reduced pressure, it was poured into 1N HCl solution. The aqueous solution was washed with ethyl ether, and then basified with aqueous ammonia. Methylene chloride was used for work-up organic layer, dried with magnesium sulfate. After solvent was removed under reduced pressure, 4N HCl in dioxane (5 ml) was added at 0° C. and stirred 10 min to produce HCl salt form. Light yellow solid title compound (3.1 g, 89%) was obtained by evaporation and drying in vacuo volatile compounds.
MH+274(−2HCl)

Preparation Example 17

3-(4-(2,3-dichlorophenyl)piperazin-1-yl)-N-methyl-propan-1-amine dihydrochloride

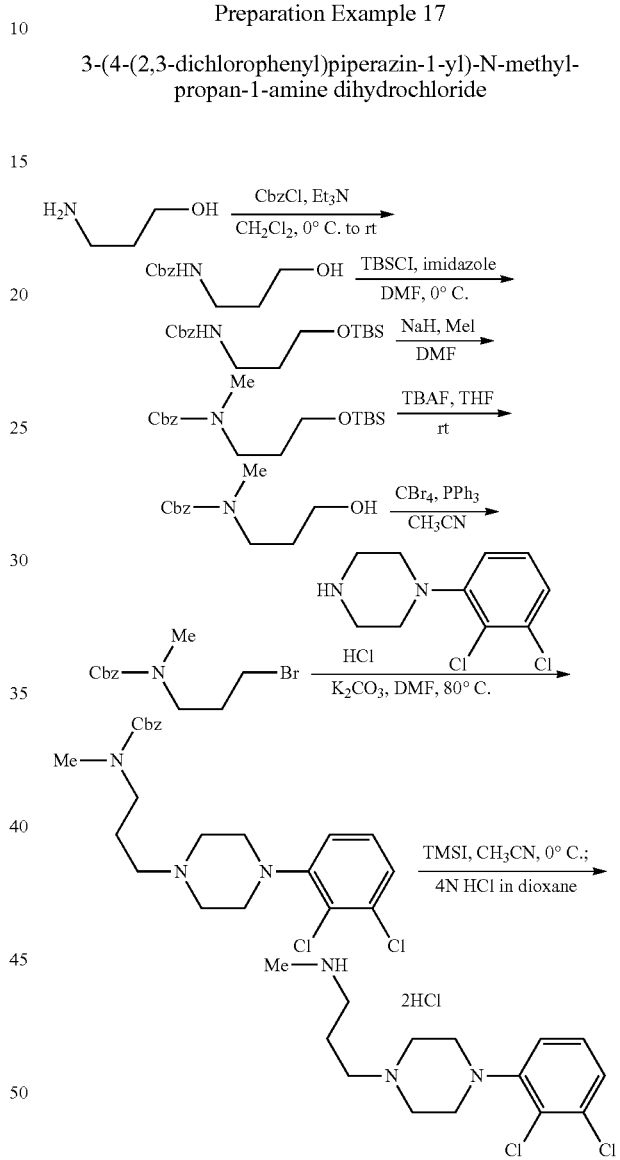

Step 1: Benzyl 3-hydroxypropylcarbamate

3-Aminopropan-1-ol (10 g, 133 mmol) was dissolved in methylene chloride (100 ml) at 0° C. Triethylamine (9 ml, 65 mmol) and CbzCl (10 ml, 66.8 mmol) were added slowly to the solution at 0° C. and warmed to room temperature. The reaction mixture was stirred for 1 hour at room temperature, and then diethyl ether (100 ml) and water (50 ml) were poured into the resulting solution. With diethyl ether normal work-up was taken, dried with magnesium sulfate. After evaporation the volatile material, the residue was purified with normal phase preparative column to produce title compound (15 g, 95%) as colorless oil.

$^1$H NMR (400 MHz, CDCl$_3$) δ 7.35-7.27 (m, 5H), 5.27 (brs, 1H), 5.09 (s, 2H), 3.71 (t, J=5.6 Hz, 2H), 3.32 (q, J=6 Hz, 2H), 1.74-1.69 (m, 2H).

MH+210

Step 2: Benzyl 3-(tert-butyldimethylsilyloxy)propylcarbamate

Benzyl 3-hydroxypropylcarbamate (15 g, 72 mmol) was treated with imidazole (10 g, 146.9 mmol) and TBSCl (12 g, 79.6 mmol) in DMF (10 ml) at 0° C. After warming up the reaction mixture to room temperature, it was stirred for 30 minutes. The resulting solution was quenched with water (50 ml), and then extracted with diethyl ether (50 ml×2) twice. After evaporation of volatile material under reduced pressure, the residue was purified with silica gel column chromatography (EtOAc:Hx=1:10) to afford title compound (23 g, 98%) as colorless oil.

MH+324

Step 3: benzyl 3-(tert-butyldimethylsilyloxy)propyl(methyl)carbamate

To the solution of benzyl 3-(tert-butyldimethylsilyloxy) propylcarbamate (5 g, 15.5 mmol) in tetrahydrofuran (20 ml), sodium hydride (1.24 g, 31 mmol, 60% in mineral oil) and iodomethane (3.86 ml, 62 mmol) were added slowly. The reaction temperature was warmed up to room temperature, and stirred for overnight. The reaction was completed quenched by water and organic material was extracted with ether. After evaporation of volatile material under reduced pressure, the residue was purified with silica gel column chromatography (EtOAC:Hx=1:10) to give title compound (4.9 g, 94%) as light yellow oil.

MH+338

Step 4: Benzyl 3-bromopropyl(methyl)carbamate

TBAF (12.8 ml, 1.0M solution in THF, 12.8 mmol) was added to the solution of benzyl 3-(tert-butyldimethylsilyloxy) propyl(methyl)carbamate (3.6 g, 10.7 mmol) in THF (30 ml). After reaction complete, water and EtOAC work-up and then drying were followed to give benzyl 3-hydroxypropyl (methyl)carbamate. After further purification, alcohol was treated with triphenylphosphine (3.35 g, 12.8 mmol) and carbon tetrabromide (12.8 mmol) in acetonitrile (20 ml). The reaction progress was monitored by TLC or LS/MS. After reaction complete, the organic layer was extracted and evaporated. The residue was purified with silica gel column chromatography (EtOAC:Hx=1:5) to give title compound (2.5 g, 82%, 2 steps) as light yellow oil.

Step 5: 3-(4-(2,3-dichlorophenyl)piperazin-1-yl)-N-methylpropan-1-amine dihydrochloride Benzyl 3-bromopropyl(methyl)carbamate was converted to title compound with method described at the preparation of 2-(4-(2,3-dichlorophenyl)piperazin-1-yl)ethanamine dihydrochloride.

Preparation Example 19

1-(3-chloro-2-methylphenyl)piperazine

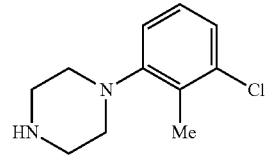 [SMILES: Cc1c(Cl)cccc1N1CCNCC1]

To a stirred solution of 3-chloro-2-methylaniline (21.6 g, 0.15 mol) in n-butanol (200 ml) was added bis(2-chloroethyl)amine hydrochloride (30 g, 0.17 mol) at room temperature and allowed to refluxed temperature for 2 days. After cooled to room temperature Na$_2$CO$_3$ (9 g, 0.08 mol) was added and then reaction mixture was refluxed 30 min. The resulting mixture was filtered with n-butanol (100 ml) and collected solid was dried under reduced pressure to be obtained title compound (24.8 g, 81%) as white solid.

MH+211

Preparation Example 20

8-(piperazin-1-yl)quinoline hydrochloride

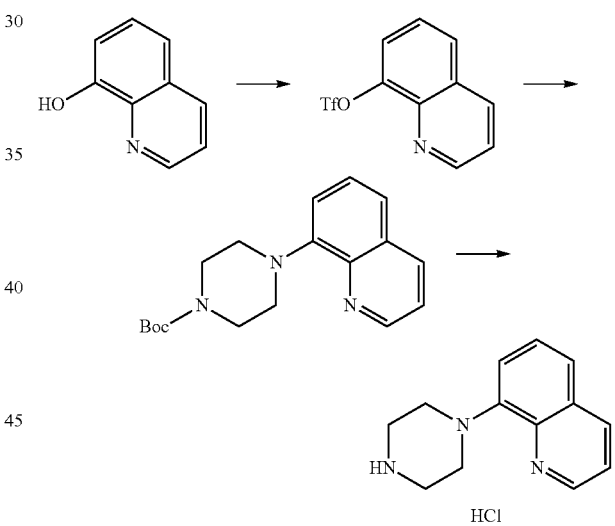

Step 1: quinolin-8-yl trifluoromethanesulfonate

To a solution of quinolin-8-ol (8 g, 0.055 mol) and K$_2$CO$_3$ (15.2 g, 0.110 mol) in pyridine (60 ml) at −20° C. were added with trifluoromethanesulfonic anhydride (14 ml, 0.083 mol) dropwise. After stirring for 1 hour at −20° C., the reaction mixture was stirred at room temperature for 2 days. The resulting solution was quenched with water, and normal work-up was preceded. The residue was purified with normal preparative column to provide title compound (13 g, 85%) as white solid.

Step 2: tert-butyl 4-(quinolin-8-yl)piperazine-1-carboxylate t-Butyl piperazine-1-carboxylate (8.6 g, 46 mmol) and quinolin-8-yl trifluoromethanesulfonate (11 g, 39.6 mmol)

were added to a solution of $Cs_2CO_3$ (18 g, 55 mmol), BINAP (1.07 g) and $Pd(OAc)_2$ (367 mg) in THF (100 ml). The reaction mixture was refluxed for 1 day and then cooled down to room temperature. The resulting solution was diluted with $Et_2O$ (100 ml) and then filtered with Celite. The organic solution was evaporated under reduced pressure, and the residue was purified with normal preparative column to give rise to desired compound (9.3 g, 74% yield) as light yellow solid.
MH+314

Step 3: 8-(piperazin-1-yl)quinoline hydrochloride tert-Butyl 4-(quinolin-8-yl)piperazine-1-carboxylate (2.4 g, 7.66 mmol) was dissolved in methanol (50 ml) and $SOCl_2$ was added to the solution dropwise at 0° C. The resulting solution was refluxed for 1 day and evaporated under reduced pressure. EtOAc (50 ml) was added to the residue and stirred for 2 hours to produce light yellow solid. The title compound was collected by filtration (1.7 g, 89%) as light yellow solid.
MH+214

Preparation Example 21

3-(4-(Benzo[d]isothiazol-3-yl)piperazin-1-yl)propan-1-amine dihydrochloride

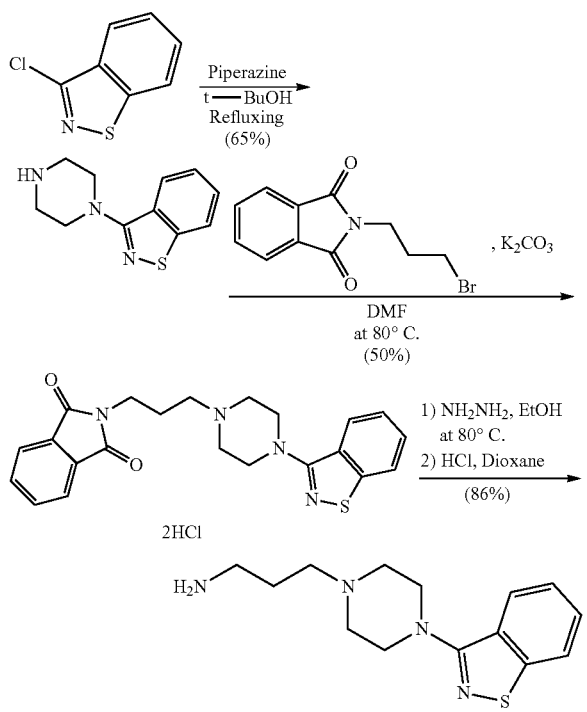

A mixture of piperazine (10.2 g, 0.118 mmol) and 3-chloro-1,2-benzisothiazole (4.0 g, 0.024 mmol) in t-BuOH (4 mL) was refluxed overnight. The reaction mixture was poured into water (100 mL) and extracted with toluene (200 mL). The organic phase was dried over $MgSO_4$ and evaporated until about 20 mL remained, under vacuum. The resulting suspension was cooled at 0-5° C. overnight. The precipitate was filtered and dried under vacuum to provide 3-(piperazin-1-yl)benzo[d]isothiazole as an intermediate (3.36 g, 15.4 mmol, 65%).
MH+220

A mixture of 3-(piperazin-1-yl)benzo[d]isothiazole (1.75 g, 8.0 mmol), N-(3-bromopropyl)-phthalimide (1.96 mmol, 7.3 mmol) and $K_2CO_3$ (2.21 g, 16.0 mol) in DMF (10 mL) was stirred at 80° C. for 3 hours. The reaction mixture was poured into water (100 mL) and extracted with ethyl acetate (150 mL). The organic phase was dried over $MgSO_4$ and evaporated under vacuum. The residue was further purified by flash column chromatography to provide 2-(3-(4-(benzo[d]isothiazol-3-yl)piperazin-1-yl)propyl)isoindoline-1,3-dione as an intermediate (1.49 g, 3.67 mmol, 50%).

To a solution of 2-(3-(4-(benzo[d]isothiazol-3-yl)piperazin-1-yl) propyl)isoindoline-1,3-dione (1.49 g, 3.67 mmol) in EtOH (25 mL) was added Hydrazine monohydrate (2.5 mL). The mixture was stirred at 80° C. for 1-2 hours and cooled to room temperature. The reaction mixture was poured into water (100 mL) and extracted with DCM (150 mL). The organic phase was dried over $MgSO_4$ and evaporated under vacuum. The residue was redissolved in ether (20~30 mL) and HCl solution (3 mL, 2M in ether) was added to the solution. The resulting precipitate was collected on a filter funnel and dried under vacuum to provide the title compound as HCl salt form (1.1 g, 3.15 mmol, 86%).

$^1$H NMR (400 MHz, $CD_3OD_3$) δ 8.04 (d, J=8.4 Hz, 1H), 7.94 (d, J=8.0 Hz, 1H), 7.55 (t, J=7.2 Hz, 1H), 7.45 (t, J=7.6 Hz, 1H), 4.24-4.14 (br, 2H), 3.85 (t, J=7.2 Hz, 1H), 3.76-3.66 (br, 2H), 3.59-3.32 (m, 9H), 3.08 (t, J=7.6 Hz, 1H), 2.34-2.30 (m, 1H), 2.25-2.17 (m, 2H).

MH+277

Preparation Example 22

1-Amino-3-(4-(2,3-dichlorophenyl)piperazin-1-yl)propan-2-ol

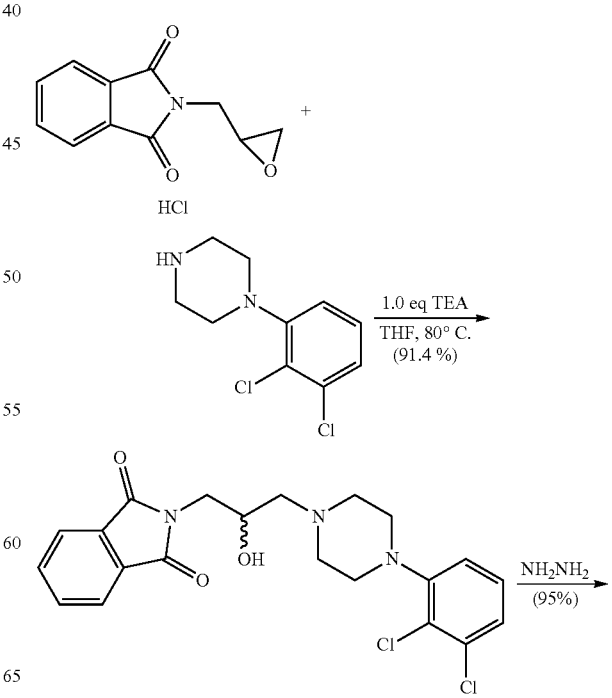

-continued

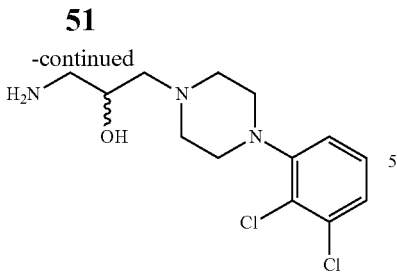

To a stirred solution of N-(2,3-epoxypropyl)phthalimide (10 g, 0.049 mol) in THF (100 mL) was added 1-(2,3-dichlorophenyl) piperazine HCl (8.7 g, 0.033 mol) and triethylamine (4.6 mL, 0.033 mol) at R.T., and then the resultant solution was heated at 80° C. overnight. The reaction was quenched with H₂O and extracted with DCM. The organic layer was washed with brine, dried over MgSO₄, filtered, and evaporated. The solid residue was solidified with DCM (20 mL)/diethyl ether (200 mL), filtered and dried in vacuo, which was used for the following synthesis without further purification. To the prepared white solid piperazine (13 g, 0.030 mol) in EtOH was added hydrazine monohydrate (20 mL) and the reaction solution was refluxed at 80° C. for 2 h. The reaction solution was cooled to R.T. and evaporated. The oily crude compound was extracted with EtOAc/H₂O and organic layer was combined and evaporated. The pale yellow solid was tritylated with ether to afford pure targeted amine (8.7 g, 95%) as white solid.

MH+304

Preparation Example 23

3-(4-(2,3-Dichlorophenyl)piperazin-1-yl)-2,2-difluoropropan-1-amine

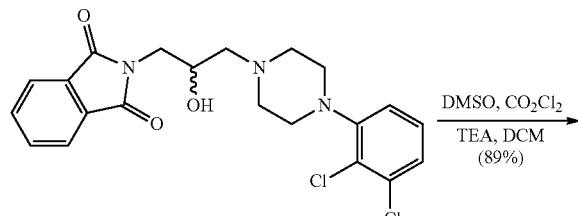

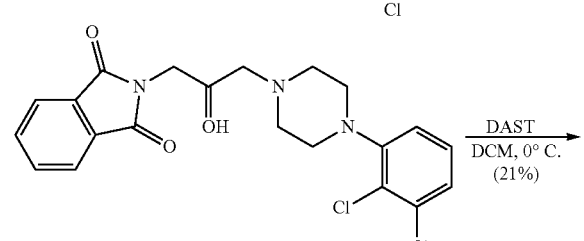

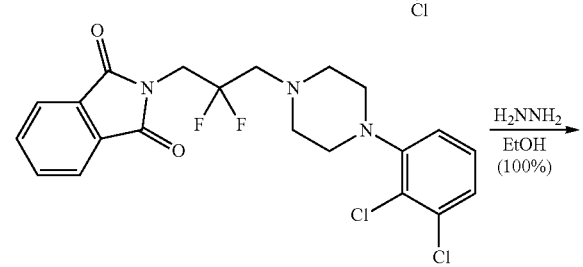

-continued

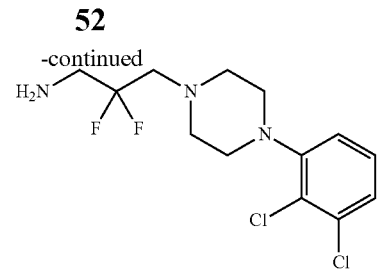

Step 1: 2-(3-(4-(2,3-Dichlorophenyl)piperazin-1-yl)-2-oxopropyl)isoindoline-1,3-dione To a stirred solution of oxalyl chloride (2.2 mL, 0.025 mol) in DCM (20 mL) was added dropwise a solution of DMSO (4 mL) in DCM (15 mL) at −60° C. The reaction mixture was warmed to −20° C. before a solution of (+/−)-hydroxy piperazine (5 g, 0.012 mol) in DCM (15 mL) was added. After the reaction mixture was stirred and allowed to warm to −10° C., triethylamine (8 mL, 0.058 mol) was added. The resultant mixture was warmed to R.T. and stirred for an additional 2 h, and then water was added. The aqueous layer was extracted with DCM, and the organic layers were combined, washed with brine, dried over MgSO₄, filtered, and evaporated. The oily residue was purified by flash column chromatography (Biotage SP1™) to obtain 4.4 g (0.010 mol; 89%).

MH+432

Step 2: 2-(3-(4-(2,3-Dichlorophenyl)piperazin-1-yl)-2,2-difluoropropyl)isoindoline-1,3-dione To a stirred solution of ketone (4.4 g, 0.010 mol) in DCM (90 mL) was added dropwise (diethylamino)sulfur trifluoride (DAST, 3.8 mL, 0.029 mol) at −78° C. The reaction mixture was stirred at R.T. for 3 h. The reaction was quenched with aqueous NaHCO₃ and extracted with DCM/H₂O, and then the organic layers were combined, washed with brine, dried over MgSO₄, filtered, and evaporated. The oily residue was purified by flash column chromatography (Biotage SP1™) to obtain 990 mg (2.2 mmol; 21%).

MH+454

Step 3: 3-(4-(2,3-Dichlorophenyl)piperazin-1-yl)-2,2-difluoropropan-1-amine

To the difluoro-piperazine (42, 1.2 g, 2.53 mmol) in EtOH (15 mL) was added hydrazine monohydrate (1.8 mL) and the reaction solution was refluxed at 80° C. for 1 h. The reaction solution was cooled to R.T. and evaporated. The oily crude compound was extracted with EtOAc/H₂O and the organic layer was combined and evaporated. The crude compound was diluted with MeOH (5 mL) and added 2N HCl in ether solution to afford targeted amine HCl salts (1.0 g, 100%) as white solid.

MH+360

Example 1

N-(3-(4-(3-chlorophenyl)piperazin-1-yl)propyl)-1,2-dimethyl-5-phenyl-1H-pyrrole-3-carboxamide

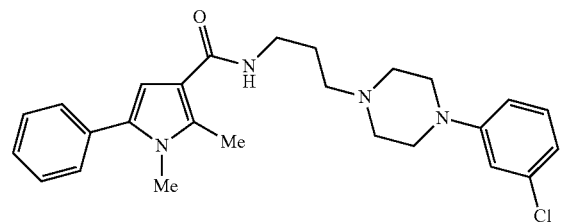

To the mixture of 1,2-Dimethyl-5-phenyl-1H-pyrrole-3-carboxylic acid (100 mg, 0.46 mmol) and 3-(4-(3-chlorophenyl) piperazin-1-yl)propan-1-amine dihydrochloride (152 mg, 0.46 mmol) in methylene chloride (5 ml) was added EDCI (178 mg, 0.92 mmol), HOBT (130 mg, 0.9 mmol) and NMM (0.3 ml, 1.8 mmol) continuously. After stirring for 1 day at room temperature, MeOH was added to the resulting solution, and filter off. After evaporation under reduced pressure, the residue was purified by reverse phase preparative HPLC to provided title compound (149 mg, 71%) as white solid.

$^1$H NMR (400 MHz, CDCl$_3$) δ 7.46 (brs, 1H), 7.24-7.13 (m, 6H), 6.87-6.73 (m, 4H), 6.27 (s, 1H), 3.54 (dd, J=11.2, 5.2 Hz, 2H), 3.48 (s, 3H), 3.25-3.19 (m, 5H), 2.64 (s, 3H), 2.60-2.44 (m, 6H), 1.80 (m, 2H).

MH+451

Example 2

N-(3-(4-(3-chlorophenyl)piperazin-1-yl)propyl)-1,2-dimethyl-5-phenyl-1H-pyrrole-3-carboxamide hydrochloride

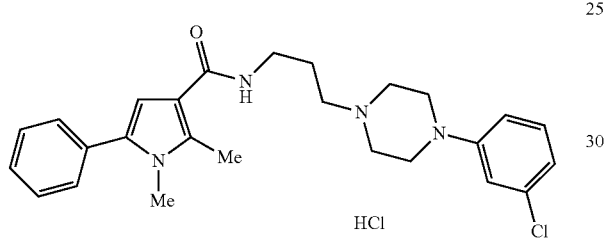

HCl solution (4N in dioxane, 0.5 ml) was added to the solution of N-(3-(4-(3-chlorophenyl)piperazin-1-yl)propyl)-1,2-dimethyl-5-phenyl-1H-pyrrole-3-carboxamide (100 mg) in methanol (5 ml). After stirring 10 minutes, the volatiles were evaporated under reduced pressure and dried in vacuo to produce HCl salt form as light yellow solid.

The following compounds of Example 3 to 202 were obtained by repeating the procedure of Example 1 and 2.

Example 3

N-(3-(4-(2,3-dimethylphenyl)piperazin-1-yl)propyl)-1,2-dimethyl-5-phenyl-1H-pyrrole-3-carboxamide

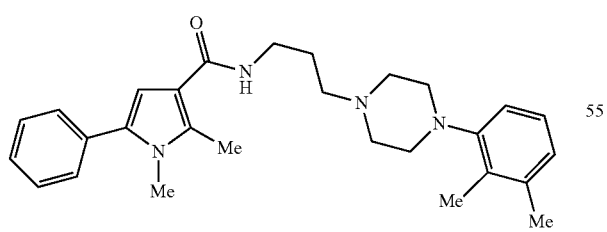

$^1$H NMR (400 MHz, CDCl$_3$) δ 7.43 (brs, 1H), 7.39-7.31 (m, 5H), 6.94 (t, J=7.6 Hz, 1H), 6.88 (d, J=7.2 Hz, 1H), 6.40 (s, 1H), 3.54 (dd, J=11.2, 5.6 Hz, 2H), 3.49 (s, 3H), 2.92 (t, J=4.0 Hz, 4H), 2.65 (s, 3H), 2.60 (t, J=5.2 Hz, 2H), 2.26 (s, 3H), 2.19 (s, 3H), 1.83-1.79 (m, 2H).

MH+445

Example 4

N-(3-(4-(3-chlorophenyl)piperazin-1-yl)propyl)-1-ethyl-2-methyl-5-phenyl-1H-pyrrole-3-carboxamide

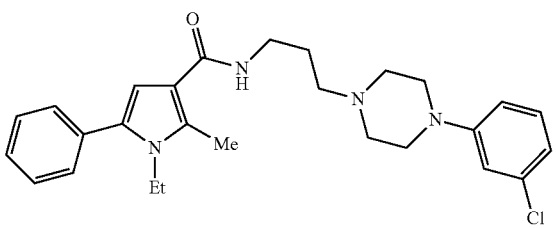 [SMILES: CCn1c(-c2ccccc2)cc(C(=O)NCCCN2CCN(c3cccc(Cl)c3)CC2)c1C]

$^1$H NMR (400 MHz, CDCl$_3$) δ 7.26-7.13 (m, 6H), 6.88-6.72 (m, 5H), 6.24 (s, 1H), 3.88 (q, J=7.2 Hz, 2H), 3.52 (dd, J=11.2, 5.2 Hz, 2H), 3.23-3.19 (m, 4), 2.65 (s, 3H), 2.65-2.56 (m, 6H), 1.81-1.78 (m, 2H), 1.18 (t, J=6.8 Hz, 3H).

MH+465

Example 5

N-(3-(4-(2,3-dimethylphenyl)piperazin-1-yl)propyl)-1-ethyl-2-methyl-5-phenyl-1H-pyrrole-3-carboxamide

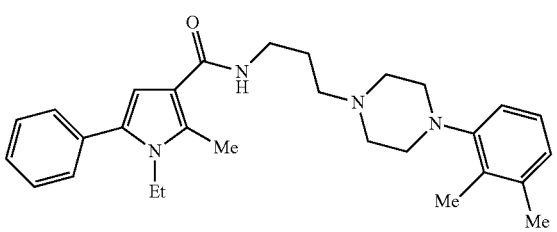 [SMILES: CCn1c(-c2ccccc2)cc(C(=O)NCCCN2CCN(c3cccc(C)c3C)CC2)c1C]

$^1$H NMR (400 MHz, CDCl$_3$) δ 7.03-7.35 (m, 7H), 6.96-6.87 (m, 2H), 6.64 (d, J=7.6 Hz, 1H), 6.37 (s, 1H), 3.91 (q, J=7.2 Hz, 2H), 3.54 (dd, J=11.6, 5.6 Hz, 2H), 2.92-2.89 (m, 3H), 2.67 (s, 3H), 2.60 (t, J=6.0 Hz, 3H), 2.56 (s, 3H), 2.19 (s, 3H), 1.81-1.77 (m, 2H), 1.19 (t, J=7.2 Hz, 3H).

MH+459

Example 6

N-(3-(4-(3-chlorophenyl)piperazin-1-yl)propyl)-2-methyl-5-phenyl-1-propyl-1H-pyrrole-3-carboxamide

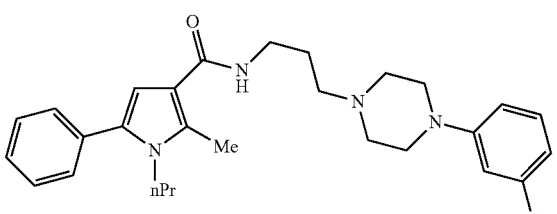

$^1$H NMR (400 MHz, CDCl$_3$) δ 7.40-7.28 (m, 2H), 7.24-7.20 (m, 1H), 7.18-7.13 (m, 5H), 6.87-6.71 (m, 4H), 6.23 (s,

1H), 3.80(t, J=7.6 Hz, 2H), 3.53 (dd, J=11.6, 5.6 Hz, 2H), 3.22-3.18 (m, 4H), 2.64 (s, 3H), 2.64-2.56 (m, 5H), 1.80 (t, J=4.0 Hz, 2H), 1.61-1.51 (m, 2H), 0.73 (t, J=7.2 Hz, 3H).
MH+479

Example 7

N-(3-(4-(2,3-dimethylphenyl)piperazin-1-yl)propyl)-2-methyl-5-phenyl-1-propyl-1H-pyrrole-3-carboxamide

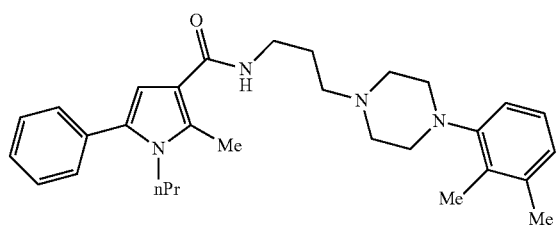

¹H NMR (400 MHz, CDCl₃) δ 7.38-7.26 (m, 6H), 6.96-6.87 (m, 3H), 6.63 (d, J=7.6 Hz, 1H), 6.36 (s, 1H), 3.84-3.80 (m, 3H), 3.53 (t, J=6.0 Hz, 2H), 2.91-2.88 (m, 6H), 2.65 (s, 3H), 2.61-2.57 (m, 5H), 2.25 (s, 3H), 2.19 (s, 3H), 1.79-1.77 (m, 2H), 1.55-1.54 (m, 2H), 0.74 (t, J=7.6 Hz, 3H).
MH+473

Example 8

N-(3-(4-(3-chlorophenyl)piperazin-1-yl)propyl)-2-methyl-5-phenyl-1-(piperidin-1-yl)-1H-pyrrole-3-carboxamide

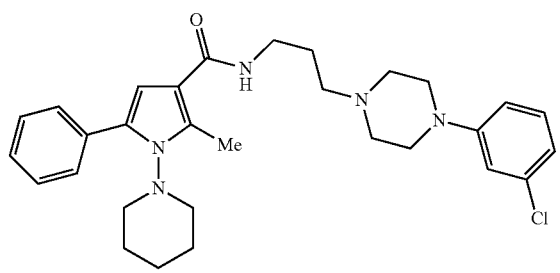 [SMILES: Cc1c(C(=O)NCCCN2CCN(c3cccc(Cl)c3)CC2)cc(-c2ccccc2)n1N1CCCCC1]

¹H NMR (400 MHz, CDCl₃) δ 7.31 (d, J=7.2 Hz, 2H), 7.19-7.17 (m, 1H), 7.12 (dd, J=15.2, 8.0 Hz, 2H), 6.84-6.82 (m, 2H), 6.73 (d, J=8.8 Hz, 1H), 6.18 (s, 1H), 3.51 (dd, J=11.6, 5.6 Hz, 2H), 3.33-3.28 (m, 2H), 3.22 (t, J=3.2 Hz, 4H), 3.05-3.02 (m, 2H), 2.72 (s, 3H), 2.63 (t, J=4.8 Hz, 3H), 2.57 (t, J=6.0 Hz, 2H), 1.93-1.90 (m, 2H), 1.82-1.74 (m, 3H), 1.62-1.48 (m, 5H), 1.37-1.18 (m, 5H).
MH+520

Example 9

N-(3-(4-(2,3-dimethylphenyl)piperazin-1-yl)propyl)-2-methyl-5-phenyl-1-(piperidin-1-yl)-1H-pyrrole-3-carboxamide

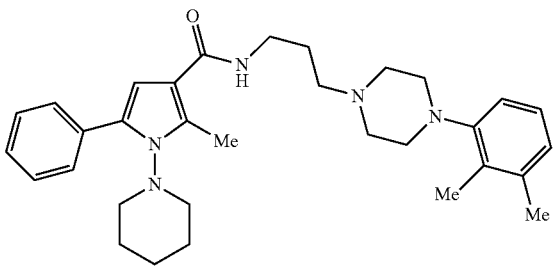 [SMILES: Cc1cccc(N2CCN(CCCNC(=O)c3cc(-c4ccccc4)n(N4CCCCC4)c3C)CC2)c1C]

¹H NMR (400 MHz, CDCl₃) δ 7.47-7.45 (m, 2H), 7.36-7.29 (m, 3H), 6.95 (t J=8.0 Hz, 1H), 6.88 (d, J=7.2 Hz, 1H), 6.67 (d, J=8.0 Hz, 1H), 6.30 (s, 1H), 3.53 (dd, J=11.2, 5.6 Hz, 2H), 3.33 (td, J=10.8, 3.2 Hz, 2H), 3.09-3.04 (m, 2H), 2.92-2.90 (m, 4H), 2.74 (s, 3H), 2.60 (t, J=6.0 Hz, 4H), 2.26 (s, 3H), 2.20 (s, 3H), 1.83-1.76 (m, 2H), 1.65-1.50 (m, 6H), 1.34-1.26 (m, 1H).
MH+514

Example 10

N-(3-(4-(2,3-dichlorophenyl)piperazin-1-yl)propyl)-1,2-dimethyl-5-phenyl-1H-pyrrole-3-carboxamide

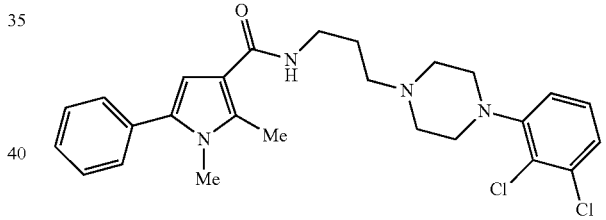

¹H NMR (400 MHz, CDCl₃) δ 7.39 (brs, 1H), 7.34-7.30 (m, 4H), 7.13 (dd, J=8.0, 1.6 Hz, 1H), 7.00 (t, J=8.4 Hz, 1H), 6.66 (dd, J=8.0, 1.2 Hz, 1H), 6.36 (s, 1H), 3.53 (dd, J=11.6, 5.6 Hz, 2H), 3.49 (s, 3H), 3.06 (brs, 4H), 2.68 (m, 5H), 2.65 (s, 3H), 2.61 (t, J=5.6 Hz, 2H), 1.83-1.77 (m, 2H).
MH+485

Example 11

N-(3-(4-(2,3-dichlorophenyl)piperazin-1-yl)propyl)-1-ethyl-2-methyl-5-phenyl-1H-pyrrole-3-carboxamide

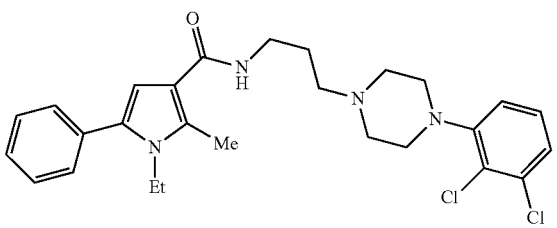 [SMILES: CCn1c(-c2ccccc2)cc(C(=O)NCCCN2CCN(c3cccc(Cl)c3Cl)CC2)c1C]

¹H NMR (400 MHz, CDCl₃) δ 7.38-7.32 (m, 5H), 7.14 (dd, J=8.4, 1.6 Hz, 1H), 7.01 (t, J=7.6 Hz, 1H), 6.66 (dd, J=8.0, 1.6 Hz, 1H), 6.34 (s, 1H), 3.91 (q, J=7.2 Hz, 2H), 3.53 (dd, J=11.2, 5.6 Hz, 2H), 3.06 (m, 4H), 2.67 (s, 3H), 2.61 (t, J=6.0 Hz, 2H), 1.83-1.73 (m, 3H), 1.37-1.25 (m, 2H), 1.19 (t, J=7.6 Hz, 3H).

MH+499

Example 12

N-(3-(4-(2,3-dichlorophenyl)piperazin-1-yl)propyl)-2-methyl-5-phenyl-1-propyl-1H-pyrrole-3-carboxamide

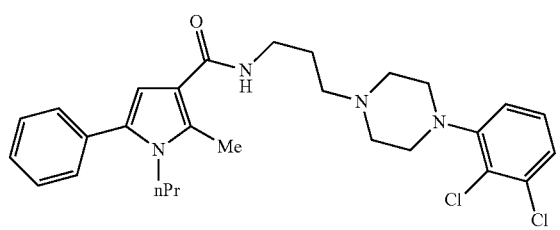

¹H NMR (400 MHz, CDCl₃) δ 7.41-7.27 (m, 6H), 7.14 (dd, J=8.4, 1.6 Hz, 1H), 7.00 (t, J=8.0 Hz, 1H), 6.65 (dd, J=8.4, 1.6 Hz, 1H), 6.34 (s, 1H), 3.82 (t, J=8.0 Hz, 2H), 3.56-4.51 (m, 2H), 3.20 (m, 4H), 2.66 (s, 3H), 2.59 (t, J=6.4 Hz, 3H), 1.83-1.74 (m, 3H), 1.60-1.51 (m, 5H), 0.81-0.73 (m, 4H).

MH+513

Example 13

N-(3-(4-(2,3-dichlorophenyl)piperazin-1-yl)propyl)-2-methyl-5-phenyl-1-(piperidin-1-yl)-1H-pyrrole-3-carboxamide

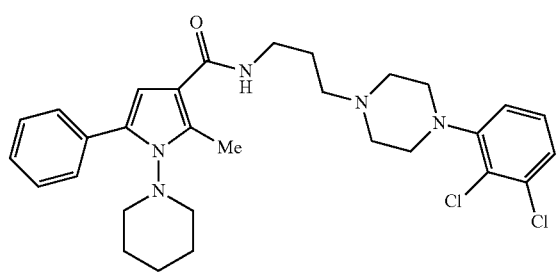 [SMILES: Cc1c(C(=O)NCCCN2CCN(c3cccc(Cl)c3Cl)CC2)cc(-c2ccccc2)n1N1CCCCC1]

¹H NMR (400 MHz, CDCl₃) δ 7.44-7.34 (m, 3H), 7.27-7.26 (m, 2H), 7.12 (dd, J=8.0, 1.2 Hz, 1H), 6.99 (t, J=8.4 Hz, 1H), 6.66 (d, J=8.0 Hz, 1H), 6.27 (s, 1H), 3.52 (dd, J=11.6, 6.0 Hz, 2H), 3.34-3.30 (m, 2H), 3.06-3.03 (m, 5H), 2.73 (s, 2H), 2.67-2.59 (m, 5H), 1.82-1.77 (m, 2H), 1.62-1.49 (m, 6H), 1.33-1.26 (m, 1H).

MH+554

Example 14

N-(3-(4-(3-chlorophenyl)piperazin-1-yl)propyl)-1-(4-fluorophenyl)-2-methyl-5-phenyl-1H-pyrrole-3-carboxamide

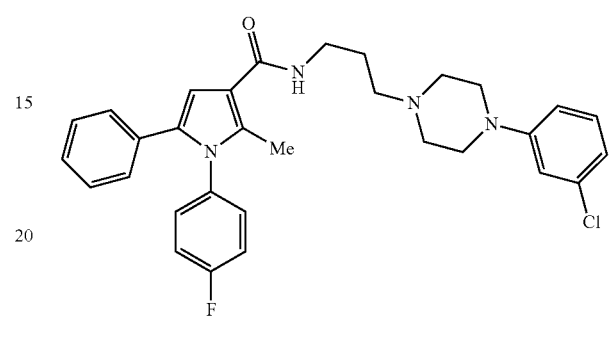

¹H NMR (400 MHz, CDCl₃) δ 7.47 (brs, 1H), 7.16 (t, J=8.0 Hz, 1H), 7.08-7.02 (m, 5H), 6.92 (t, J=8.0 Hz, 2H), 6.88-6.83 (m, 4H), 6.76 (dd, J=8.4, 1.6 Hz, 1H), 6.49 (s, 1H), 3.57 (dd, J=11.6, 5.6 Hz, 2H), 3.28 (t, J=5.2 Hz, 4H), 2.69-2.62 (m, 6H), 2.42 (s, 3H), 1.86-1.83 (m, 2H).

MH+531

Example 15

N-(3-(4-(2,3-dimethylphenyl)piperazin-1-yl)propyl)-1-(4-fluorophenyl)-2-methyl-5-phenyl-1H-pyrrole-3-carboxamide

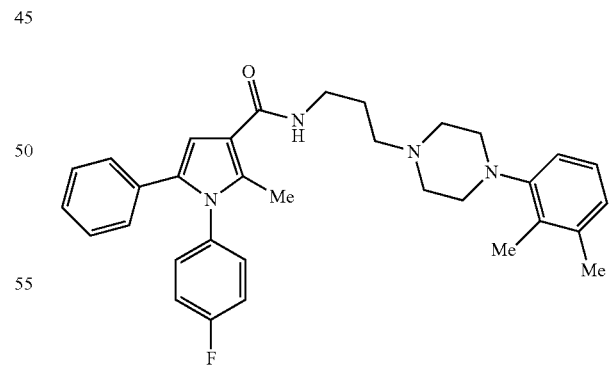

¹H NMR (400 MHz, CDCl₃) δ 7.56 (m, 1H), 7.15-7.01 (m, 9H), 7.01-6.87 (m, 2H), 6.71 (d, J=7.6 Hz, 1H), 6.60 (s, 1H), 3.57 (dd, J=11.2, 5.6 Hz, 2H), 2.95 (t, J=4.4 Hz, 4H), 2.68 (brs, 4H), 2.63 (t, J=5.6 Hz, 2H), 2.43 (s, 3H), 2.26 (s, 3H), 2.21 (s, 3H), 1.86-1.80 (m, 2H).

MH+525

Example 16

N-(3-(4-(2,3-dichlorophenyl)piperazin-1-yl)propyl)-1-(4-fluorophenyl)-2-methyl-5-phenyl-1H-pyrrole-3-carboxamide

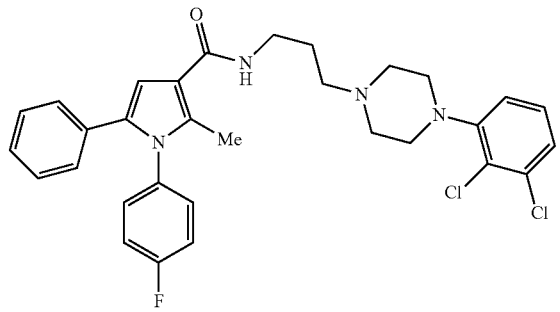 [SMILES: Cc1c(C(=O)NCCCN2CCN(c3cccc(Cl)c3Cl)CC2)cc(-c2ccccc2)n1-c1ccc(F)cc1]

$^1$H NMR (400 MHz, CDCl$_3$) δ 7.51 (brs, 1H), 7.26-7.4 (m, 7H), 6.99 (d, J=8.0 Hz, 3H), 6.70 (dd, J=8.0, 1.2 Hz, 1H), 6.57 (s, 1H), 3.57 (dd, J=11.6, 6.0 Hz, 2H), 3.10 (brs, 4H), 2.71 (brs, 4H), 2.64 (t, J=6.0 Hz, 2H), 2.43 (s, 3H), 1.84-1.81 (m, 2H).

MH+565

Example 17

1-Benzyl-N-(3-(4-(3-chlorophenyl)piperazin-1-yl)propyl)-2-methyl-5-phenyl-1H-pyrrole-3-carboxamide

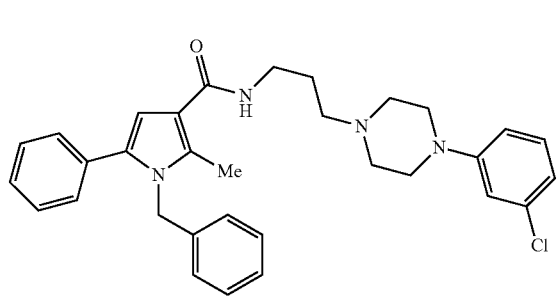 [SMILES: Cc1c(C(=O)NCCCN2CCN(c3cccc(Cl)c3)CC2)cc(-c2ccccc2)n1Cc1ccccc1]

$^1$H NMR (400 MHz, CDCl$_3$) δ 7.36-7.26 (m, 2H), 7.25-7.05 (m, 6H), 6.90 (d, J=7.2 Hz, 2H), 6.83-6.81 (m, 2H), 6.73 (dd, J=7.6, 1.6 Hz, 1H), 6.38 (s, 1H), 5.10 (s, 2H), 3.57-3.52 (m, 2H), 3.25-3.18 (m, 4H), 2.65 (t, J=5.2 Hz, 4H), 2.60 (t, J=6.0 Hz, 2H), 2.49 (s, 3H), 1.85-1.78 (m, 2H).

MH+527

Example 18

1-Benzyl-N-(3-(4-(2,3-dimethylphenyl)piperazin-1-yl)propyl)-2-methyl-5-phenyl-1H-pyrrole-3-carboxamide

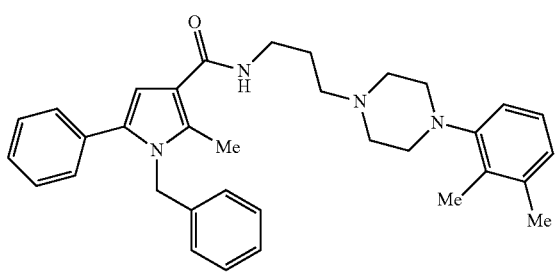 [SMILES: Cc1cccc(N2CCN(CCCNC(=O)c3cc(-c4ccccc4)n(Cc4ccccc4)c3C)CC2)c1C]

$^1$H NMR (400 MHz, CDCl$_3$) δ 7.47 (m, 1H), 7.29-7.20 (m, 8H), 6.94-6.86 (m, 4H), 6.66 (d, J=7.6 Hz, 1H), 6.50 (s, 1H), 5.12 (s, 2H), 3.55 (dd, J=10.8, 4.8 Hz, 2H), 2.92 (t, J=4.8 Hz, 4H), 2.67 (brs, 3H), 2.61 (t, J=5.6 Hz, 2H), 2.50 (s, 3H), 2.25 (s, 3H), 2.20 (s, 3H), 1.84-1.78 (m, 2H).

MH+521

Example 19

1-Benzyl-N-(3-(4-(2,3-dichlorophenyl)piperazin-1-yl)propyl)-2-methyl-5-phenyl-1H-pyrrole-3-carboxamide

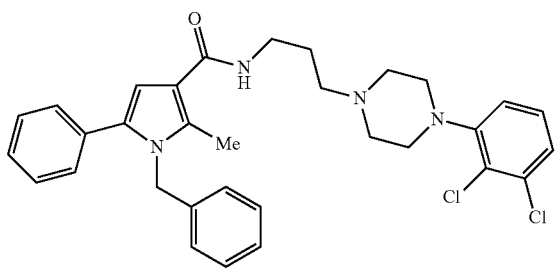 [SMILES: Cc1c(C(=O)NCCCN2CCN(c3cccc(Cl)c3Cl)CC2)cc(-c2ccccc2)n1Cc1ccccc1]

$^1$H NMR (400 MHz, CDCl$_3$) δ 7.45 (m, 1H), 7.30-7.21 (m, 6H), 7.12 (dd, J=8.0, 0.8 Hz, 1H), 6.97 (t, J=8.0 Hz, 1H), 6.90 (d, J=7.6 Hz, 2H), 6.65 (d, J=8.0 Hz, 1H), 6.47 (s, 1H), 5.11 (s, 2H), 3.55 (dd, J=11.6, 5.6 Hz, 2H), 3.07 (brs, 4H), 2.70 (brs, 4H), 2.62 (t, J=6.0 Hz, 2H), 2.50 (s, 3H), 1.83-1.79 (m, 2H).

MH+561

Example 20

N-(3-(4-(3-chlorophenyl)piperazin-1-yl)propyl)-1-(cyclohexylmethyl)-2-methyl-5-phenyl-1H-pyrrole-3-carboxamide

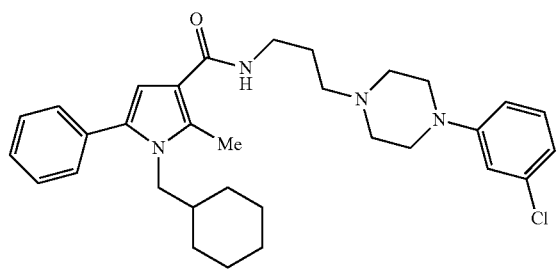 [SMILES: Cc1c(C(=O)NCCCN2CCN(c3cccc(Cl)c3)CC2)cc(-c2ccccc2)n1CC1CCCCC1]

$^1$H NMR (400 MHz, CDCl$_3$) δ 7.26-7.12 (m, 6H), 6.83-6.79 (m, 2H), 6.71 (dd, J=8.4, 2.4 Hz, 1H), 6.21 (s, 1H), 3.75 (d, J=4.8 Hz, 2H), 3.51 (dd, J=11.6, 5.6 Hz, 2H), 3.20 (t, J=5.2 Hz, 4H), 2.64-2.61 (m, 4H), 2.61 (s, 3H), 2.57 (t, J=6.0 Hz, 2H), 1.81-1.77 (m, 2H), 1.58-1.52 (m, 2H), 1.33-1.29 (m, 3H), 0.99-0.07 (m, 3H), 0.61-0.57 (m, 2H).

MH+533

Example 21

1-(Cyclohexylmethyl)-N-(3-(4-(2,3-dimethylphenyl)piperazin-1-yl)propyl)-2-methyl-5-phenyl-1H-pyrrole-3-carboxamide

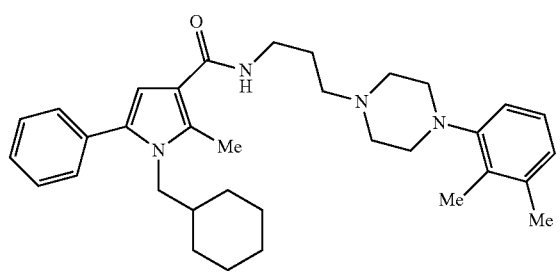 [SMILES: Cc1cccc(N2CCN(CCCNC(=O)c3cc(-c4ccccc4)n(CC4CCCCC4)c3C)CC2)c1C]

$^1$H NMR (400 MHz, CDCl$_3$) δ 7.37-7.31 (m, 5H), 6.95-6.87 (m, 2H), 6.61 (d, J=8.4 Hz, 1H), 6.36 (s, 1H), 3.77 (d, J=4.8 Hz, 2H), 3.51 (t, J=8.6 Hz, 2H), 2.89 (t, J=5.2 Hz, 4H), 2.65 (s, 3H), 2.57 (t, J=6.0 Hz, 2H), 2.25 (s, 3H), 2.19 (s, 3H), 1.81-1.77 (m, 2H), 1.58-1.52 (m, 2H), 1.33-1.29 (m, 3H), 0.99-0.07 (m, 3H), 0.61-0.57 (m, 2H).

MH+527

Example 22

1-(cyclohexylmethyl)-N-(3-(4-(2,3-dichlorophenyl)piperazin-1-yl)propyl)-2-methyl-5-phenyl-1H-pyrrole-3-carboxamide

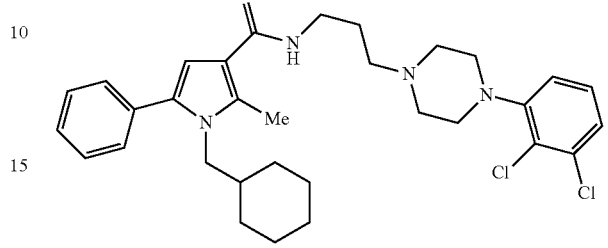

$^1$H NMR (400 MHz, CDCl$_3$) δ 7.39 (m, 1H), 7.33-7.26 (m, 4H), 7.13 (d, J=8.4 Hz, 1H), 6.99 (t, J=8.4 Hz, 1H), 6.61 (d, J=8.0 Hz, 1H), 6.32 (s, 1H), 3.77 (d, J=7.2 Hz, 2H), 3.55-3.49 (m, 2H), 3.04 (brs, 4H), 2.67 (brs, 4H), 2.64 (s, 3H), 2.60 (t, J=6.0 Hz, 3H), 1.82-1.76 (m, 2H), 1.53-1.52 (m, 2H), 1.41-1.25 (m, 4H), 0.98-0.96 (m, 3H), 0.61-0.58 (m, 2H).

MH+567

Example 23

N-(3-(4-(3-chlorophenyl)piperazin-1-yl)propyl)-2-methyl-5-phenyl-1H-pyrrole-3-carboxamide

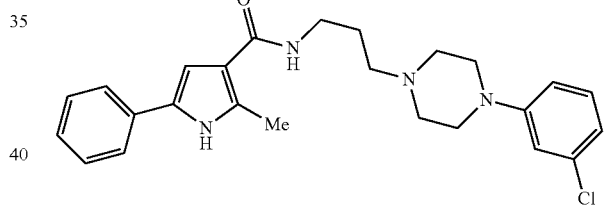

$^1$H NMR (400 MHz, CDCl$_3$) δ 8.28 (brs, 1H), 7.52-5.48 (m, 1H), 7.18-7.09 (m, 4H), 6.88-6.78 (m, 3H), 6.56 (s, 1H), 3.57-3.49 (m, 2H), 3.32-3.30 (m, 3H), 2.69-2.63 (m, 3H), 2.63 (s, 3H), 1.84-1.81 (m, 1H), 1.58 (brs, 5H), 1.31-1.26 (m, 2H), 0.88-0.84 (m, 2H).

MH+437

Example 24

N-(3-(4-(2,3-dimethylphenyl)piperazin-1-yl)propyl)-2-methyl-5-phenyl-1H-pyrrole-3-carboxamide

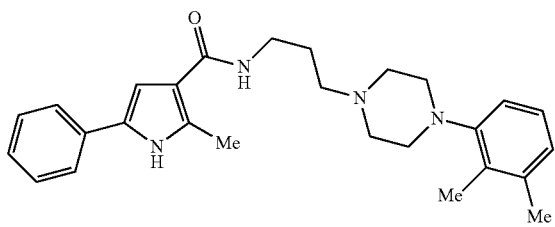 [SMILES: Cc1cccc(N2CCN(CCCNC(=O)c3cc(-c4ccccc4)[nH]c3C)CC2)c1C]

¹H NMR (400 MHz, CDCl₃) δ 8.41 (brs, 1H), 7.58 (m, 1H), 7.44-7.42 (m, 2H), 7.32-7.26 (m, 2H), 7.23-7.19 (m, 1H), 6.96-6.81 (m, 3H), 6.67 (d, J=2.4 Hz, 1H), 3.55 (dd, J=11.6, 5.6 Hz, 2H), 2.98 (t, J=4.8 Hz, 4H), 2.64 (s, 3H), 2.62-2.57 (m, 2H), 2.26 (s, 3H), 2.21 (S, 3H), 1.84-1.78 (m, 2H), 1.63-1.60 (m, 2H).

MH+431

Example 25

N-(3-(4-(2,3-dichlorophenyl)piperazin-1-yl)propyl)-2-methyl-5-phenyl-1H-pyrrole-3-carboxamide

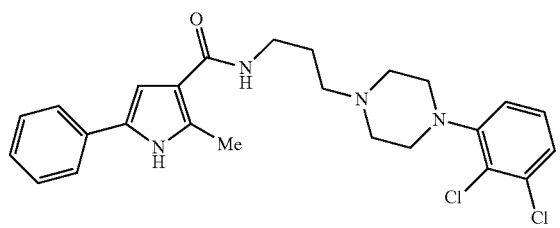 [SMILES: Cc1[nH]c(-c2ccccc2)cc1C(=O)NCCCN1CCN(c2cccc(Cl)c2Cl)CC1]

¹H NMR (400 MHz, CDCl₃) δ 8.46 (brs, 1H), 7.53 (m, 1H), 7.39 (d, J=7.6 Hz, 2H), 7.21-7.13 (m, 2H), 6.98 (t, J=8.0 Hz, 1H), 6.81 (d, J=8.0 Hz, 1H), 6.62 (d, J=2.4 Hz, 1H), 3.57-3.53 (m, 2H), 3.13 (brs, 4H), 2.71 (brs, 5H), 2.63 (s, 3H), 1.84-1.79 (m, 2H).

MH+471

Example 26

N-(3-(4-(3-chlorophenyl)piperazin-1-yl)propyl)-1-isobutyl-2-methyl-5-phenyl-1H-pyrrole-3-carboxamide

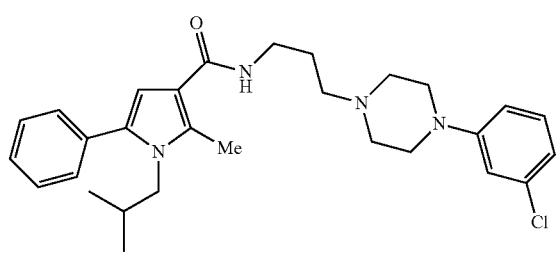 [SMILES: Cc1c(C(=O)NCCCN2CCN(c3cccc(Cl)c3)CC2)cc(-c2ccccc2)n1CC(C)C]

¹H NMR (400 MHz, CDCl₃) δ 7.45-7.26 (m, 2H), 7.23-7.12 (m, 5H), 6.84-6.79 (m, 2H), 6.71 (dd, J=8.4, 1.6 Hz, 1H), 6.23 (s, 1H), 3.73 (d, J=7.6 Hz, 2H), 3.52 (dd, J=12.0, 6.0 Hz, 2H), 3.20 (t, J=4.8 Hz, 4H), 2.65-2.57 (m, 6H), 2.63 (s, 3H), 1.82-1.76 (m, 2H), 1.72-1.65 (m, 2H), 0.60 (dd, J=6.4 Hz, 6H).

MH+493

Example 27

N-(3-(4-(2,3-dimethylphenyl)piperazin-1-yl)propyl)-1-isobutyl-2-methyl-5-phenyl-1H-pyrrole-3-carboxamide

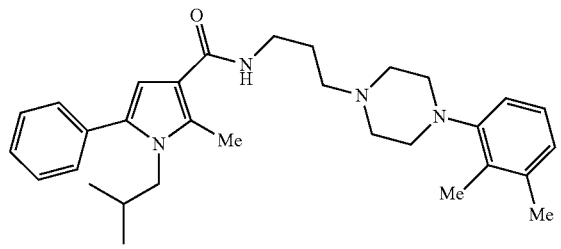 [SMILES: Cc1cccc(N2CCN(CCCNC(=O)c3cc(-c4ccccc4)n(CC(C)C)c3C)CC2)c1C]

¹H NMR (400 MHz, CDCl₃) δ 7.37-7.33 (m, 5H), 6.95-6.87 (m, 2H), 6.61 (d, J=8.0 Hz, 1H), 6.36 (s, 1H), 3.75 (d, J=8.0 Hz, 2H), 3.53 (t, J=5.6 Hz, 2H), 2.89 (t, J=4.0 Hz, 4H), 2.65 (s, 3H), 2.65-2.57 (br, 3H), 2.59 (t, J=5.6 Hz, 2H), 2.25 (s, 3H), 2.19 (s, 3H), 1.82-1.67 (m, 3H), 0.63 (d, J=6.8 Hz, 6H).

MH+487

Example 28

N-(3-(4-(2,3-dichlorophenyl)piperazin-1-yl)propyl)-1-isobutyl-2-methyl-5-phenyl-1H-pyrrole-3-carboxamide

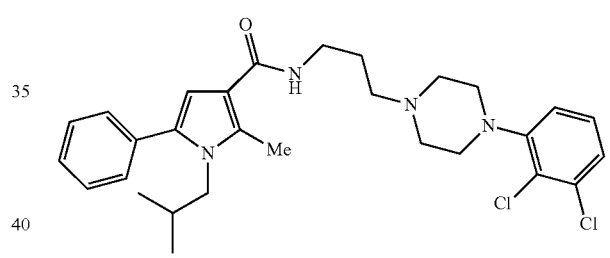

¹H NMR (400 MHz, CDCl₃) δ 7.41 (brs, 1H), 7.34-7.28 (m, 5H), 7.13 (d, J=8.0 Hz, 1H), 6.99 (t, J=8.0 Hz, 1H), 6.61 (d, J=8.0 Hz, 1H), 6.34 (s, 1H), 3.75 (d, J=7.6 Hz, 2H), 3.55-3.49 (m, 2H), 3.04 (brs, 4H), 2.67 (brs, 3H), 2.64 (s, 3H), 2.60 (t, J=5.6 Hz, 2H), 1.81-1.67 (m, 3H), 1.62 (brs, 1H), 0.62 (d, J=6.4 Hz, 6H).

MH+527

Example 29

N-(3-(4-(2,3-dimethylphenyl)piperazin-1-yl)propyl)-1-ethyl-N,2-dimethyl-5-phenyl-1H-pyrrole-3-carboxamide hydrochloride

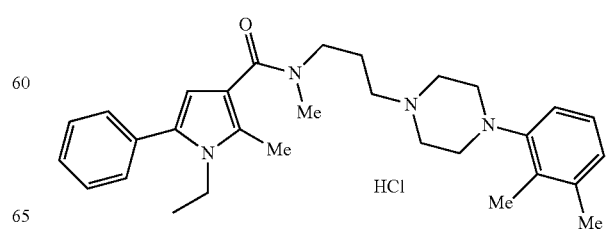

¹H NMR (400 MHz, MeOH-d₄) δ 7.43-7.34 (m, 5H), 7.07 (t, J=7.6 Hz, 1H), 6.96 (t, J=8.4 Hz, 2H), 3.97 (q, J=6.8 Hz, 2H), 3.63 (d, J=11.6 Hz, 2H), 3.52 (s, 3H), 3.47 (t, J=5.6 Hz, 2H), 3.32-3.10 (m, 5H), 2.25 (s, 3H), 2.24 (s, 3H), 2.09-2.06 (m, 2H), 1.12 (t, J=6.8 Hz, 3H).

MH+473 (—HCl)

Example 30

N-(3-(4-(2,3-dimethylphenyl)piperazin-1-yl)propyl)-1-ethyl-2-methyl-5-phenyl-1H-pyrrole-3-carboxamide hydrochloride

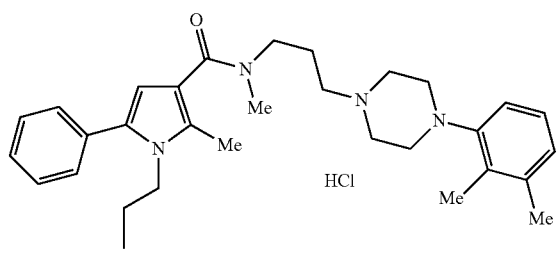 [SMILES: CCCn1c(-c2ccccc2)cc(C(=O)N(C)CCCN2CCN(c3cccc(C)c3C)CC2)c1C ; Cl]

¹H NMR (400 MHz, MeOH-d₄) δ 7.44-7.35 (m, 5H), 7.04 (t, J=7.5 Hz, 1H), 6.99 (t, J=8.1 Hz, 2H), 4.13 (t, J=6.9 Hz, 2H), 4.07 (s, 3H), 3.63-3.60 (m, 2H), 3.52 (s, 3H), 3.46-3.14 (m, 8H), 2.28 (s, 3H), 2.24 (s, 3H), 2.09-2.06 (m, 4H), 1.12 (t, J=6.8 Hz, 3H).

MH+487 (—HCl)

Example 31

N-(3-(4-(2,3-dichlorophenyl)piperazin-1-yl)propyl)-N,2-dimethyl-5-phenyl-1-propyl-1H-pyrrole-3-carboxamide hydrochloride

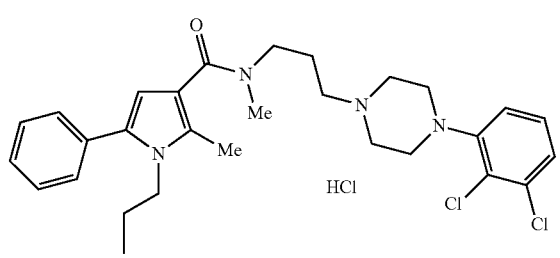 [SMILES: CCCn1c(-c2ccccc2)cc(C(=O)N(C)CCCN2CCN(c3cccc(Cl)c3Cl)CC2)c1C ; Cl]

¹H NMR (400 MHz, MeOH-d₄) δ 7.46-7.37 (m, 5H), 7.06 (t, J=7.5 Hz, 1H), 7.01 (m, 2H), 4.26 (t, J=6.9 Hz, 2H), 4.13 (s, 3H), 3.70-3.64 (m, 2H), 3.58 (s, 3H), 3.48-3.23 (m, 8H), 2.09-2.06 (m, 4H), 1.10 (t, J=6.8 Hz, 3H).

MH+527 (—HCl)

Example 32

1-benzyl-N-(3-(4-(2,3-dimethylphenyl)piperazin-1-yl)propyl)-N, 2-dimethyl-5-phenyl-1H-pyrrole-3-carboxamide hydrochloride

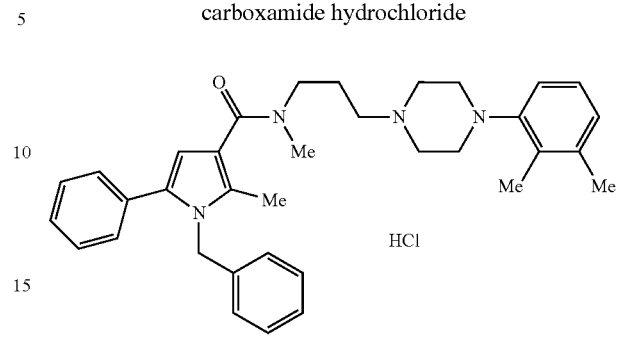

¹H NMR (400 MHz, MeOH-d₄) δ 7.48-7.45 (m, 3H), 7.29-7.20 (m, 6H), 6.94-6.86 (m, 4H), 5.12 (s, 2H), 3.56 (dd, J=10.8, 4.8 Hz, 2H), 3.57 (s, 3H), 2.68-2.30 (m, 8H), 2.26 (s, 3H), 2.22 (s, 3H), 1.84-1.78 (m, 2H).

MH+535 (—HCl)

Example 33

N-(4-(4-(2,3-dimethylphenyl)piperazin-1-yl)butyl)-2-methyl-5-phenyl-1-propyl-1H-pyrrole-3-carboxamide hydrochloride

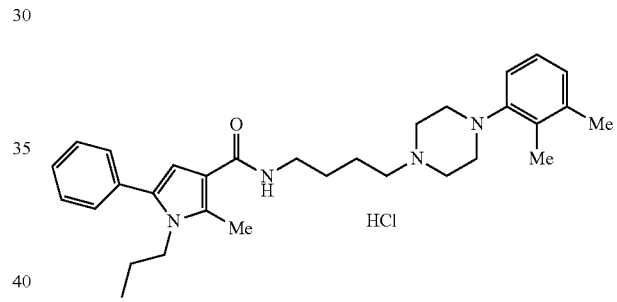

¹H NMR (400 MHz, MeOH-d₄) δ 7.42-7.31 (m, 5H), 7.07-7.03 (m, 1H), 6.93 (d, J=7.6 Hz, 2H), 3.89 (t, J=7.6 Hz, 2H), 3.63-3.59 (m, 2H), 3.38-3.32 (m, 2H), 3.22-3.06 (m, 7H), 2.57 (s, 3H), 2.25 (s, 3H), 2.23 (s, 3H), 1.86-1.83 (m, 2H), 1.69-1.67 (m, 2H), 1.50-1.47 (m, 2H), 0.70 (t, J=7.2 Hz, 3H).

MH+487 (—HCl)

Example 34

N-(4-(4-(2,3-dichlorophenyl)piperazin-1-yl)butyl)-2-methyl-5-phenyl-1-propyl-1H-pyrrole-3-carboxamide hydrochloride

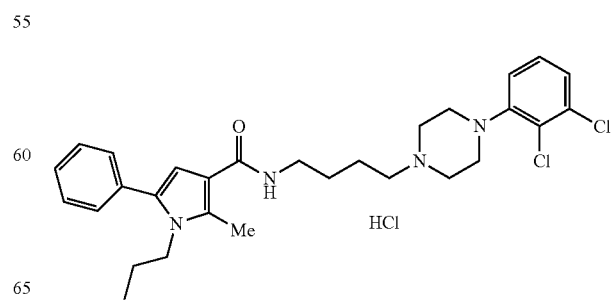

¹H NMR (400 MHz, MeOH-d₄) δ 7.42-7.38 (m, 2H), 7.35-7.30 (m, 3H), 7.29-7.25 (m, 2H), 7.16-7.14 (m, 1H), 3.89 (t, J=7.2 Hz, 2H), 3.66 (d, J=12.0 Hz, 2H), 3.51 (d, J=12.8 Hz, 2H), 3.40 (t, J=12.8 Hz, 2H), 3.19-3.15 (m, 4H), 2.57 (s, 3H), 1.93-1.84 (m, 2H), 1.70-1.69 (m, 2H), 1.50-1.48 (m, 2H), 0.69 (t, J=7.6 Hz, 3H).

MH+527 (—HCl)

Example 35

N-(4-(4-(2,3-dimethylphenyl)piperazin-1-yl)butyl)-1,2-dimethyl-5-phenyl-1H-pyrrole-3-carboxamide hydrochloride

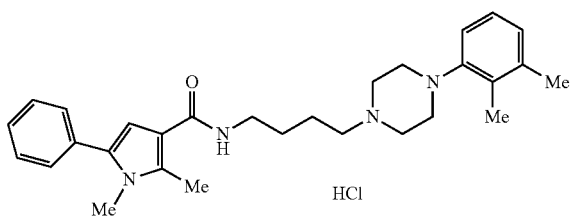 [SMILES: Cc1cccc(N2CCN(CCCCNC(=O)c3cc(-c4ccccc4)n(C)c3C)CC2)c1C ; Cl]

¹H NMR (400 MHz, MeOH-d₄) δ 7.43-7.31 (m, 3H), 7.08-6.94 (m, 3H), 3.65-3.61 (m, 2H), 3.50 (s, 3H), 3.43-3.30 (m, 4H), 3.28-3.11 (m, 7H), 2.56 (s, 3H), 2.25 (s, 3H), 2.24 (s, 3H), 1.93-1.85 (m, 2H), 1.79-1.71 (m, 2H).

MH+459 (—HCl)

Example 36

N-(4-(4-(2,3-dichlorophenyl)piperazin-1-yl)butyl)-1,2-dimethyl-5-phenyl-1H-pyrrole-3-carboxamide hydrochloride

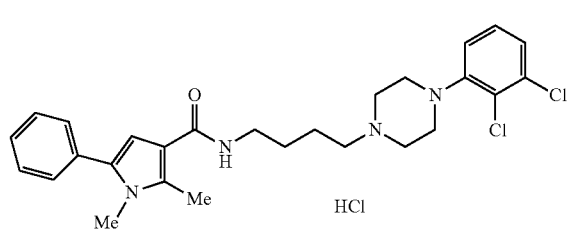 [SMILES: Cc1c(C(=O)NCCCCN2CCN(c3cccc(Cl)c3Cl)CC2)cc(-c2ccccc2)n1C ; Cl]

¹H NMR (400 MHz, MeOH-d₄) δ 7.42-7.26 (m, 6H), 7.16-7.13 (m, 2H), 3.66 (d, J=12.0 Hz, 2H), 3.54-3.49 (m, 2H), 3.50 (s, 3H), 3.41-3.29 (m, 4H), 3.28-3.11 (m, 2H), 2.56 (s, 3H), 1.89-1.82 (m, 2H), 1.72-1.69 (m, 2H).

MH+499 (—HCl)

Example 37

N-(3-(4-(2,3-dichlorophenyl)piperazin-1-yl)propyl)-N,1,2-trimethyl-5-phenyl-1H-pyrrole-3-carboxamide hydrochloride

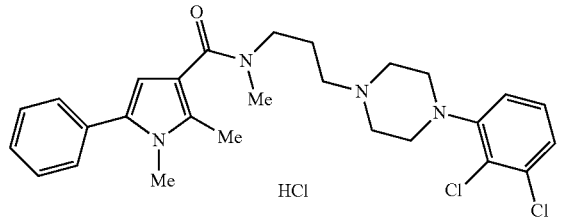 [SMILES: Cc1c(C(=O)N(C)CCCN2CCN(c3cccc(Cl)c3Cl)CC2)cc(-c2ccccc2)n1C ; Cl]

¹H NMR (400 MHz, CDCl₃) δ 7.43-7.26 (m, 6H), 7.19-7.04 (m, 2H), 3.68-3.64 (m, 2H), 3.52 (s, 3H), 3.33 (s, 3H), 3.30-3.22 (m, 8H), 2.38 (s, 3H).

MH+499 (—HCl).

Example 38

N-(2-(4-(2,3-dichlorophenyl)piperazin-1-yl)ethyl)-2-methyl-5-phenyl-1H-pyrrole-3-carboxamide hydrochloride

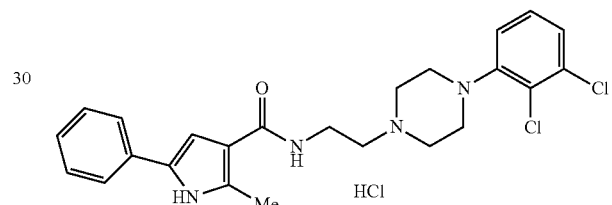

¹H NMR (400 MHz, CDCl₃) δ 7.57-7.55 (m, 2H), 7.35-7.27 (m, 4H), 7.20-7.16 (m, 2H), 3.83 (d, J=12.0 Hz, 2H), 3.76 (t, J=5.2 Hz, 2H), 3.56 (t, J=13.6 Hz, 2H), 3.45 (t, J=5.6 Hz, 2H), 3.36 (t, J=9.6 Hz, 2H), 3.20 (t, J=9.6 Hz, 2H), 2.56 (s, 3H).

MH+457 (—HCl)

Example 39

N-(2-(4-(2,3-dichlorophenyl)piperazin-1-yl)ethyl)-2-methyl-5-phenyl-1-propyl-1H-pyrrole-3-carboxamide hydrochloride

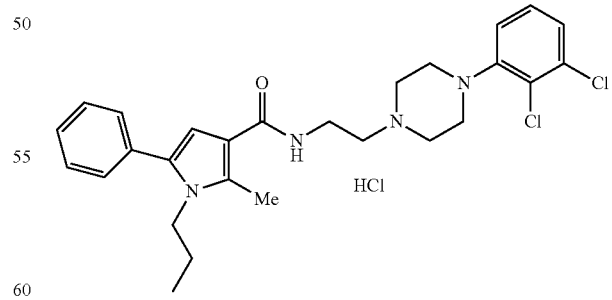

¹H NMR (400 MHz, CDCl₃) δ 7.43-7.40 (m, 2H), 7.35-7.31 (m, 3H), 7.28-7.26 (m, 2H), 7.19-7.16 (m, 1H), 6.45 (brs, 1H), 3.90 (t, J=7.2 Hz, 2H), 3.82 (d, J=11.6 Hz, 2H), 3.72 (t, J=5.6 Hz, 2H), 3.55 (d, J=13.2 Hz, 2H), 3.50-3.11 (m, 8H), 1.53-1.44 (m, 2H), 0.70 (t, J=7.6 Hz, 3H).

MH+499 (—HCl)

Example 40

N-(4-(4-(2,3-dimethylphenyl)piperazin-1-yl)butyl)-2-methyl-5-phenyl-1H-pyrrole-3-carboxamide hydrochloride

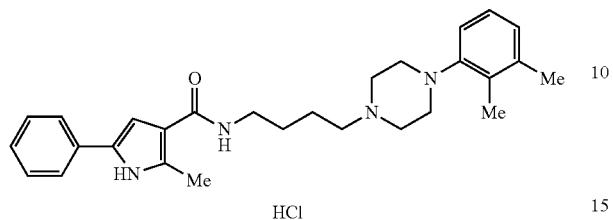

$^1$H NMR (400 MHz, MeOH-d$_4$) δ 7.54 (d, J=7.2 Hz, 2H), 7.32 (t, J=7.6 Hz, 2H), 7.16 (t, J=7.2 Hz, 1H), 7.05 (t, J=7.6 Hz, 1H), 6.96-6.93 (m, 2H), 3.63 (d, J=11.6 Hz, 2H), 3.43 (t, J=6.8 Hz, 2H), 3.33-3.06 (m, 8H), 2.53 (s, 3H), 2.25 (s, 3H), 2.23 (s, 3H), 1.91-1.84 (m, 2H), 1.76-1.69 (m, 2H). MH+445 (—HCl).

Example 41

N-(4-(4-(2,3-dichlorophenyl)piperazin-1-yl)butyl)-2-methyl-5-phenyl-1H-pyrrole-3-carboxamide hydrochloride

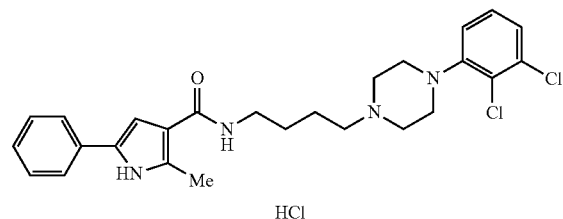 [SMILES: Cc1[nH]c(-c2ccccc2)cc1C(=O)NCCCCN1CCN(c2cccc(Cl)c2Cl)CC1 ; Cl]

$^1$H NMR (400 MHz, MeOH-d$_4$) δ 7.57 (d, J=7.6 Hz, 2H), 7.33 (t, J=7.6 Hz, 2H), 7.27-7.14 (m, 4H), 3.67 (d, J=8.8 Hz, 2H), 3.51-3.48 (m, 4H), 3.32-3.21 (m, 4H), 2.54 (s, 3H), 1.91 (brs, 2H), 1.76 (brs, 2H).
MH+485 (—HCl)

Example 42

N-(4-(4-(2,3-dimethylphenyl)piperazin-1-yl)butyl)-1-ethyl-2-methyl-5-phenyl-1H-pyrrole-3-carboxamide hydrochloride

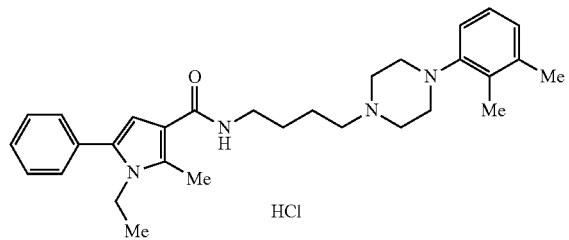 [SMILES: CCn1c(-c2ccccc2)cc(C(=O)NCCCCN2CCN(c3cccc(C)c3C)CC2)c1C ; Cl]

$^1$H NMR (400 MHz, MeOH-d$_4$) δ 7.42-7.32 (m, 5H), 7.05 (t, J=8.0 Hz, 1H), 6.94 (d, J=7.6 Hz, 2H), 3.95 (q, J=7.2 Hz, 2H), 3.64 (d, J=11.6 Hz, 2H), 3.40 (t, J=6.4 Hz, 2H), 3.33- 3.08 (m, 5H), 2.58 (s, 3H), 2.25 (s, 3H), 2.23 (s, 3H), 1.86-1.83 (m, 2H), 1.72-1.68 (m, 2H), 1.12 (t, J=6.8 Hz, 3H). MH+473 (—HCl)

Example 43

N-(4-(4-(2,3-dichlorophenyl)piperazin-1-yl)butyl)-1-ethyl-2-methyl-5-phenyl-1H-pyrrole-3-carboxamide hydrochloride

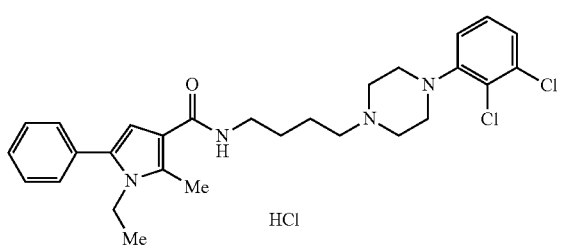 [SMILES: CCn1c(-c2ccccc2)cc(C(=O)NCCCCN2CCN(c3cccc(Cl)c3Cl)CC2)c1C ; Cl]

$^1$H NMR (400 MHz, MeOH-d$_4$) δ 7.42-7.26 (m, 7H), 7.13 (dd, J=6.8, 2.8 Hz, 1H),3.95 (q, J=6.8 Hz, 2H), 3.67 (d, J=12.0 Hz, 2H), 3.52 (d, J=12.8 Hz, 2H), 3.39 (t, J=6.8 Hz, 2H), 3.33-3.11 (m, 5H), 2.58 (s, 1H), 1.87-1.84 (m, 2H), 1.71-1.67 (m, 2H), 1.12 (t, J=6.8 Hz, 3H).
MH+513(—HCl)

Example 44

5-(4-chlorophenyl)-N-(3-(4-(2,3-dimethylphenyl)piperazin-1-yl)propyl)-2-methyl-1H-pyrrole-3-carboxamide hydrochloride

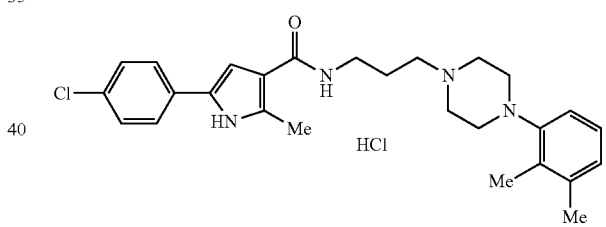

$^1$H NMR (400 MHz, MeOH-d$_4$) δ 7.52 (d, J=8.8 Hz, 2H), 7.32 (d, J=8.4 Hz, 2H), 7.06 (t, J=8.0 Hz, 1H), 6.96 (t, J=8.4 Hz, 2H), 3.63 (d, J=11.2 Hz, 2H), 3.49 (t, J=6.4 Hz, 2H), 3.30-3.11 (m, 8H), 2.54 (s, 3H), 2.25 (s, 3H), 2.24 (s, 3H), 2.12-2.06 (m, 2H). MH+465(—HCl)

Example 45

5-(4-chlorophenyl)-N-(3-(4-(2,3-dichlorophenyl)piperazin-1-yl)propyl)-2-methyl-1H-pyrrole-3-carboxamide hydrochloride

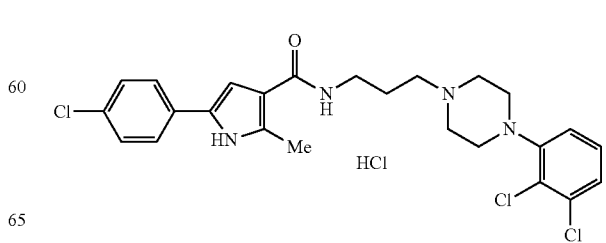

¹H NMR (400 MHz, MeOH-d₄) δ 7.53 (d, J=8.4 Hz, 2H), 7.35-7.28 (m, 3H), 7.18 (dd, J=6.4, 3.2 Hz, 2H), 3.68 (d, J=12.0 Hz, 2H), 3.37 (d, J=13.2 Hz, 2H), 3.50 (t, J=6.0 Hz, 2H), 3.36-3.18 (m, 5H), 2.26 (s, 3H), 2.13-2.07 (m, 2H). MH+505(—HCl)

Example 46

5-(4-chlorophenyl)-N-(4-(4-(2,3-dimethylphenyl)piperazin-1-yl)butyl)-2-methyl-1H-pyrrole-3-carboxamide hydrochloride

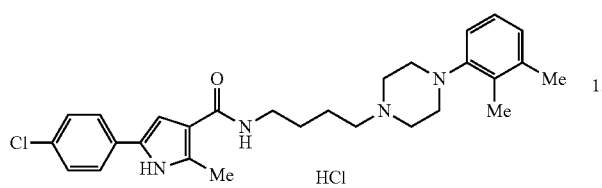

¹H NMR (400 MHz, MeOH-d₄) δ 7.51 (d, J=8.8 Hz, 2H), 7.31 (d, J=8.8 Hz, 2H), 7.05 (t, J=8.0 Hz, 1H), 6.94 (d, J=7.6 Hz, 2H), 3.63 (d, J=11.6Hz, 2H), 3.41 (t, J=6.8 Hz, 2H), 3.33-2.99 (m, 8H), 2.53 (s, 3H), 2.25 (s, 3H), 2.23 (s, 3H), 1.90-1.83 (m, 2H), 1.75-1.67 (m, 2H).
MH+479 (—HCl)

Example 47

5-(4-chlorophenyl)-N-(4-(4-(2,3-dichlorophenyl)piperazin-1-yl)butyl)-2-methyl-1H-pyrrole-3-carboxamide hydrochloride

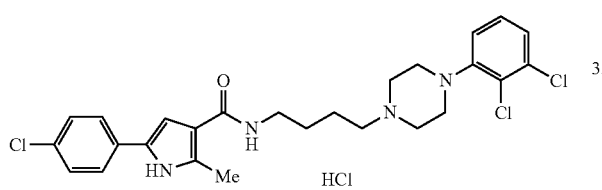

¹H NMR (400 MHz, MeOH-d₄) δ 7.51 (d, J=8.8 Hz, 2H), 7.33-7.25 (m, 4H), 7.13 (dd, J=7.2, 2.4 Hz, 1H), 3.67 (d, J=12.0 Hz, 2H), 3.52 (d, J=12.8 Hz, 2H), 3.40 (t, J=6.8 Hz, 2H), 3.33-3.28 (m, 4H), 3.14 (t, J=12.4 Hz, 2H), 2.52 (s, 3H), 1.90-1.83 (m, 2H), 1.74-1.67 (m, 2H). MH+521 (—HCl)

Example 48

N-(2-(4-(2,3-dichlorophenyl)piperazin-1-yl)ethyl)-2-methyl-5-phenyl-1H-pyrrole-3-carboxamide hydrochloride

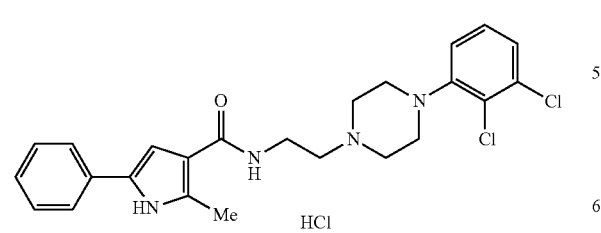

¹H NMR (400 MHz, MeOH-d₄) δ 7.43-7.26 (m, 6H), 7.17 (dd, J=6.8, 2.8 Hz, 2H), 3.82 (d, J=12.4 Hz, 2H), 3.72 (t, J=5.2 Hz, 2H), 3.56 (d, J=12.4 Hz, 2H), 3.44-3.14 (m, 4H), 2.59 (s, 3H).
MH+471 (—HCl)

Example 49

N-(2-(4-(2,3-dichlorophenyl)piperazin-1-yl)ethyl)-1-ethyl-2-methyl-5-phenyl-1H-pyrrole-3-carboxamide hydrochloride

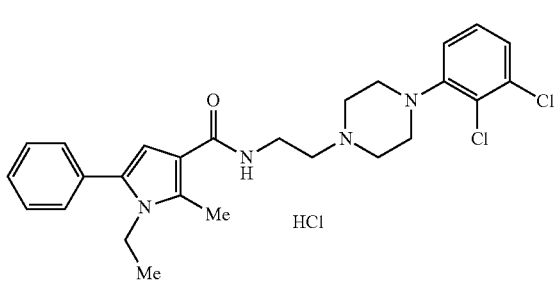 [SMILES: CCn1c(-c2ccccc2)cc(C(=O)NCCN2CCN(c3cccc(Cl)c3Cl)CC2)c1C ; Cl]

¹H NMR (400 MHz, MeOH-d₄) δ 7.43-7.26 (m, 7H), 7.17 (dd, J=6.4, 2.8 Hz, 1H), 3.96 (q, J=6.8 Hz, 2H), 3.82 (d, J=12.4 Hz, 2H), 3.73 (t, J=5.2 Hz, 2H), 3.55 (d, J=13.2 Hz, 2H), 3.43 (t, J=5.6 Hz, 3.38-3.15 (m, 4H), 2.61 (s, 3H), 1.12 (t, J=7.2 Hz, 3H).

MH+485 (—HCl)

Example 50

N-(2-(4-(2,3-dichlorophenyl)piperazin-1-yl)ethyl)-5-(4-methoxyphenyl)-2-methyl-1H-pyrrole-3-carboxamide hydrochloride

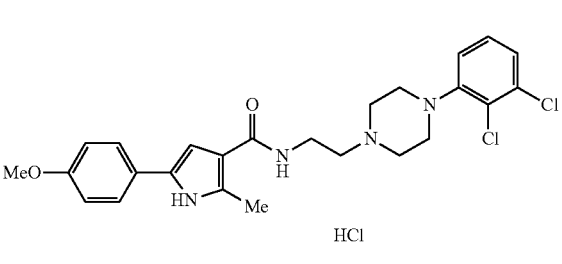 [SMILES: COc1ccc(-c2cc(C(=O)NCCN3CCN(c4cccc(Cl)c4Cl)CC3)c(C)[nH]2)cc1 ; Cl]

MH+487 (—HCl)

Example 51

N-(2-(4-(2,3-dichlorophenyl)piperazin-1-yl)ethyl)-5-(4-methoxyphenyl)-1,2-dimethyl-1H-pyrrole-3-carboxamide hydrochloride

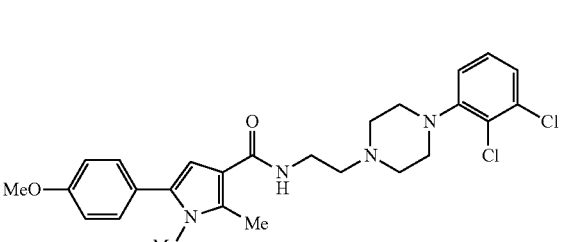

MH+501 (—HCl)

Example 52

N-(2-(4-(2,3-dichlorophenyl)piperazin-1-yl)ethyl)-1-ethyl-5-(4-methoxyphenyl)-2-methyl-1H-pyrrole-3-carboxamide hydrochloride

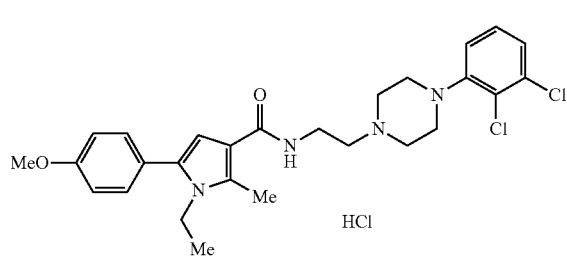 [SMILES: CCn1c(-c2ccc(OC)cc2)cc(C(=O)NCCN2CCN(c3cccc(Cl)c3Cl)CC2)c1C ; Cl]

MH+515 (—HCl)

Example 53

N-(2-(4-(2,3-dichlorophenyl)piperazin-1-yl)ethyl)-5-(4-methoxyphenyl)-2-methyl-1-propyl-1H-pyrrole-3-carboxamide hydrochloride

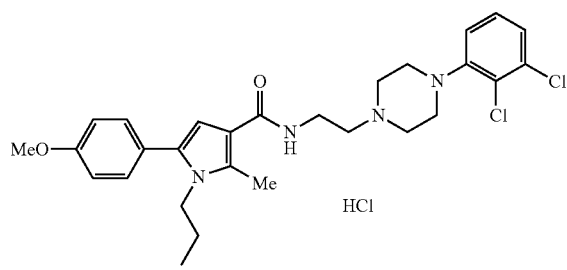 [SMILES: CCCn1c(-c2ccc(OC)cc2)cc(C(=O)NCCN2CCN(c3cccc(Cl)c3Cl)CC2)c1C ; Cl]

MH+529 (—HCl)

Example 54

N-(3-(4-(2,3-dichlorophenyl)piperazin-1-yl)propyl)-5-(4-methoxyphenyl)-2-methyl-1H-pyrrole-3-carboxamide hydrochloride

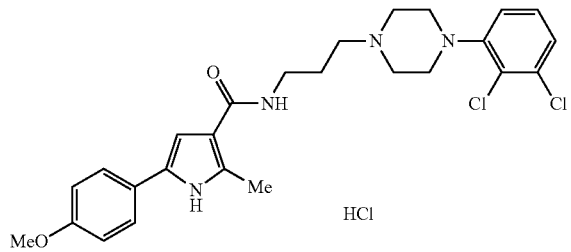 [SMILES: COc1ccc(-c2cc(C(=O)NCCCN3CCN(c4cccc(Cl)c4Cl)CC3)c(C)[nH]2)cc1 ; Cl]

MH+501 (—HCl)

Example 55

N-(3-(4-(2,3-dichlorophenyl)piperazin-1-yl)propyl)-5-(4-methoxyphenyl)-1,2-dimethyl-1H-pyrrole-3-carboxamide hydrochloride

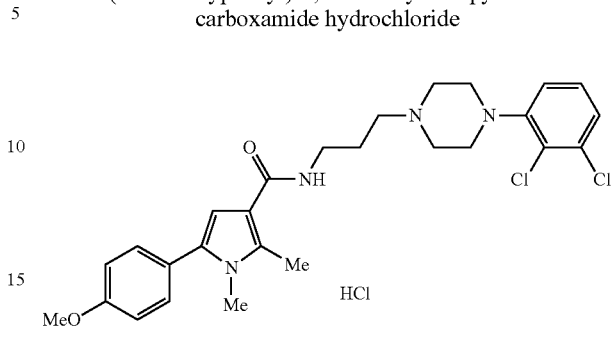

MH+515 (—HCl)

Example 56

N-(3-(4-(2,3-dichlorophenyl)piperazin-1-yl)propyl)-1-ethyl-5-(4-methoxyphenyl)-2-methyl-1H-pyrrole-3-carboxamide hydrochloride

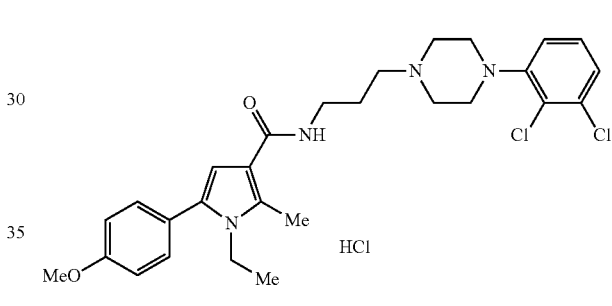

MH+529 (—HCl)

Example 57

N-(3-(4-(2,3-dichlorophenyl)piperazin-1-yl)propyl)-5-(4-methoxyphenyl)-2-methyl-1-propyl-1H-pyrrole-3-carboxamide hydrochloride

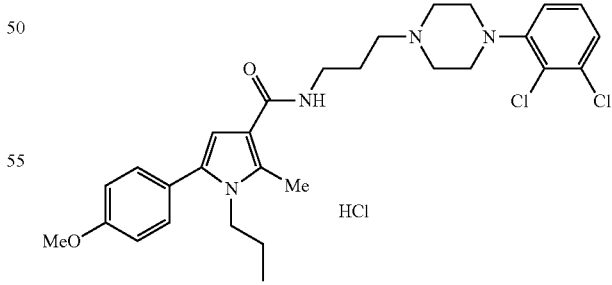

$^1$H NMR (400 MHz, CD$_3$OD) δ 7.31-7.28 (m, 2H), 7.26-7.23 (m, 2H), 7.19-7.16 (m, 1H), 6.95 (d, J=8.0 Hz, 2H), 3.84 (t, J=7.6 Hz, 2H), 3.81 (s, 3H), 3.68-3.65 (m, 2H), 3.56-3.53 (m, 2H), 3.49-3.45 (m, 2H), 3.34-3.17 (m, 6H), 2.58 (s, 3H), 2.11-2.04 (m, 2H), 1.53-1.44 (m, 2H), 0.70 (t, J=7.6 Hz, 3H).
MH+543

Example 58
N-(4-(4-(2,3-dichlorophenyl)piperazin-1-yl)butyl)-5-(4-methoxyphenyl0-2-methyl-1H-pyrrole-3-carboxamide hydrochloride
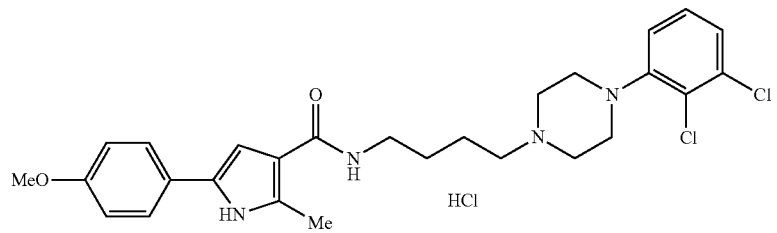 [SMILES: COc1ccc(-c2cc(C(=O)NCCCCN3CCN(c4cccc(Cl)c4Cl)CC3)c(C)[nH]2)cc1 ; Cl]
MH+515 (—HCl)
Example 59
N-(4-(4-(2,3-dichlorophenyl)piperazin-1-yl)butyl)-5-(4-methoxyphenyl)-1,2-dimethyl-1H-pyrrole-3-carboxamide hydrochloride
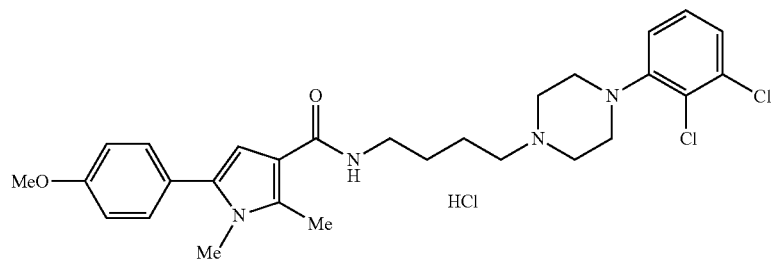 [SMILES: COc1ccc(-c2cc(C(=O)NCCCCN3CCN(c4cccc(Cl)c4Cl)CC3)c(C)n2C)cc1 ; Cl]
MH+529 (—HCl)
Example 60
N-(4-(4-(2,3-dichlorophenyl)piperazin-1-yl)butyl)-1-ethyl-5-(4-methoxyphenyl)-2-methyl-1H-pyrrole-3-carboxamide hydrochloride
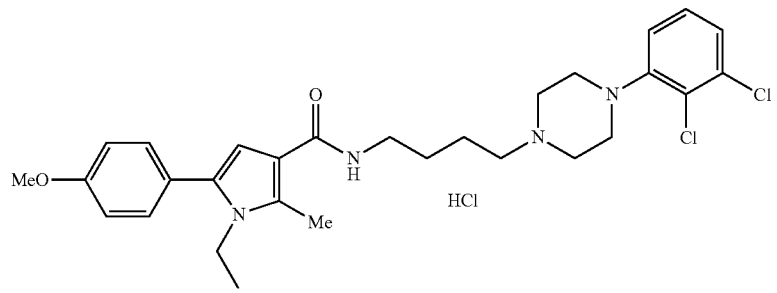 [SMILES: CCn1c(-c2ccc(OC)cc2)cc(C(=O)NCCCCN2CCN(c3cccc(Cl)c3Cl)CC2)c1C ; Cl]
MH+543 (—HCl)

Example 61

5-(4-chlorophenyl)-N-(3-(4-(2,3-dimethylphenyl)piperazin-1-yl)propyl)-1,2-dimethyl-1H-pyrrole-3-carboxamide hydrochloride

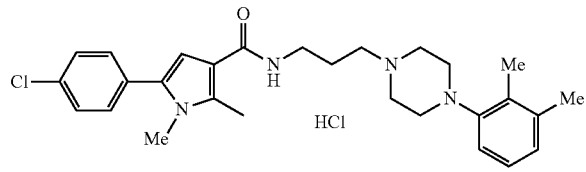 [SMILES: Cc1cccc(N2CCN(CCCNC(=O)c3cc(-c4ccc(Cl)cc4)n(C)c3C)CC2)c1C ; Cl]

$^1$H NMR (400 MHz, MeOH-d$_4$) δ 7.38 (dd, J=8.0, 20.8 Hz, 4H), 7.07 (d, J=7.6 Hz, 1H), 7.03-6.97 (m, 2H), 3.66 (brs, 1H), 3.51-3.48 (m, 5H), 3.38-3.37 (brs, 1H), 3.33-3.32 (m, 1H), 2.26 (d, J=1.6 Hz, 3H), 2.26 (d, 2.4 Hz, 6H), 2.13-2.10 (m, 2H).
MH+479 (—HCl)

Example 62

5-(4-chlorophenyl)-N-(3-(4-(2,3-dichlorophenyl)piperazin-1-yl)propyl)-1,2-dimethyl-1H-pyrrole-3-carboxamide hydrochloride

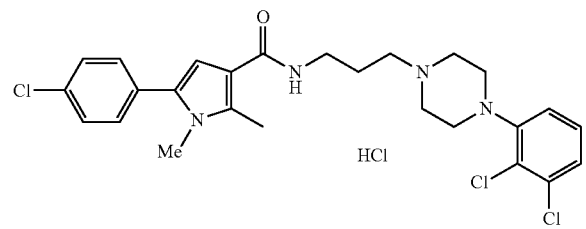 [SMILES: Cc1c(C(=O)NCCCN2CCN(c3cccc(Cl)c3Cl)CC2)cc(-c2ccc(Cl)cc2)n1C ; Cl]

$^1$H NMR (400 MHz, MeOH-d$_4$) 7.38 (dd, J=8.4, 2.4 Hz, 4H), 7.30-7.27 (m, 2H), 7.18-7.16 (m, 1H), 3.66 (d, J=11.2 Hz, 2H), 3.54 (d, J=12.8 Hz, 2H), 3.50 (s, 3H), 3.47 (t, J=6.4 Hz, 2H), 3.33 (s, 3H), 3.26-3.19 (m, 2H), 2.58 (s, 3H), 2.10-2.06 (m, 2H).
MH+519 (—HCl)

Example 63

5-(4-chlorophenyl)-N-(3-(4-(2,3-dimethylphenyl)piperazin-1-yl)propyl)-1-ethyl-2-methyl-1H-pyrrole-3-carboxamide hydrochloride

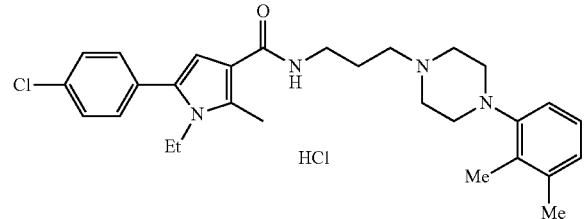 [SMILES: CCn1c(-c2ccc(Cl)cc2)cc(C(=O)NCCCN2CCN(c3cccc(C)c3C)CC2)c1C ; Cl]

$^1$H NMR (400 MHz, MeOH-d$_4$) δ 7.43-7.41 (m, 2H), 7.36-7.34 (m, 2H), 7.07 (t, J=7.6 Hz, 1H), 6.99-6.95 (m, 2H), 3.95 (q, J=6.8 Hz, 2H), 3.64 (d, J=10.0 Hz, 2H), 3.48 (t, J=6.0 Hz, 2H), 3.33-3.28 (m, 2H), 3.26-3.16 (m, 6H), 2.59 (d, J=2.0 Hz, 3H), 2.25 (s, 6H), 2.10-2.07 (m, 2H), 1.13 (t, J=7.2 Hz, 3H).
MH+493 (—HCl)

Example 64

5-(4-chlorophenyl)-N-(3-(4-(2,3-dichlorophenyl)piperazin-1-yl)propyl)-1-ethyl-2-methyl-1H-pyrrole-3-carboxamide hydrochloride

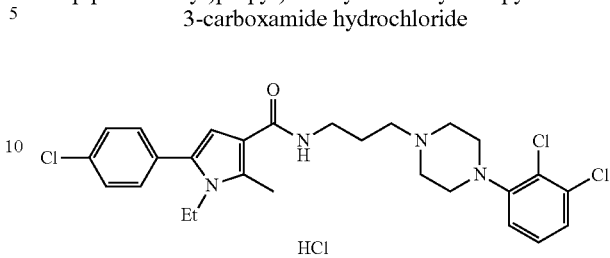

$^1$H NMR (400 MHz, MeOH-d$_4$) δ 7.43-7.41 (m, 2H), 7.36-7.34 (m, 2H), 7.30-7.29 (m, 2H), 7.18-7.16 (m, 2H), 3.95 (q, J=6.8 Hz, 2H), 3.67 (d, J=12.0 Hz, 2H), 3.54 (d, J=12.4 Hz, 2H), 3.47 (t, J=6.4 Hz, 2H), 3.34-3.17 (m, 6H), 2.60 (s, 3H), 2.10-2.06 (m, 2H), 1.13 (t, J=7.2 Hz, 3H).
MH+534 (—HCl)

Example 65

5-(4-chlorophenyl)-N-(3-(4-(2,3-dimethylphenyl)piperazin-1-yl)propyl)-2-methyl-1-propyl-1H-pyrrole-3-carboxamide hydrochloride

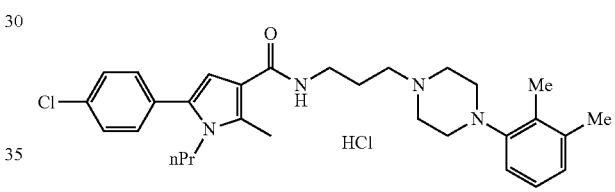

$^1$H NMR (400 MHz, MeOH-d$_4$) δ 7.43-7.41 (m, 2H), 7.35-7.32 (m, 2H), 7.10-7.05 (m, 1H), 6.99-6.95 (m, 2H), 3.89 (t, J=7.6 Hz, 2H), 3.64 (d, J=10.8 Hz, 2H), 3.48 (t, J=6.4 Hz, 2H), 3.36-3.17 (m, 6H), 2.59 (s, 3H), 2.25 (s, 6H), 2.12-2.05 (m, 2H), 1.52-1.46 (m, 2H), 0.71 (t, J=7.2 Hz, 3H).
MH+507 (—HCl)

Example 66

5-(4-chlorophenyl)-N-(3-(4-(2,3-dichlorophenyl)piperazin-1-yl)propyl)-2-methyl-1-propyl-1H-pyrrole-3-carboxamide hydrochloride

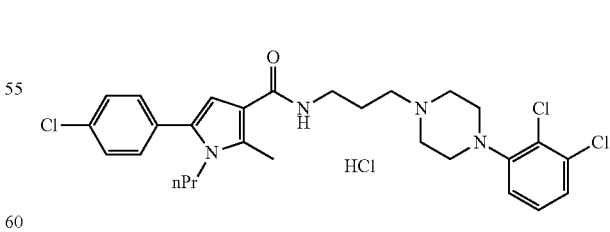

$^1$H NMR (400 MHz, MeOH-d$_4$) δ 7.43-7.41 (m, 2H), 7.34-7.32 (m, 2H), 7.30-7.26 (m, 2H), 7.20-7.16 (m, 1H), 3.89 (t, J=7.6 Hz, 2H), 3.67 (d, J=11.6 Hz, 2H), 3.54 (d, J=12.4 Hz, 2H), 3.47 (t. J=6.0 Hz, 2H), 3.34-3.17 (m, 4H), 2.59 (s, 3H), 2.11-2.07 (m, 2H), 1.54-1.44 (m, 2H), 0.71 (t, J=7.2 Hz, 3H).
MH+547 (—HCl)

Example 67

5-(4-chlorophenyl)-N-(2-(4-(2,3-dichlorophenyl)piperazin-1-ypethyl)-2-methyl-1H-pyrrole-3-carboxamide hydrochloride

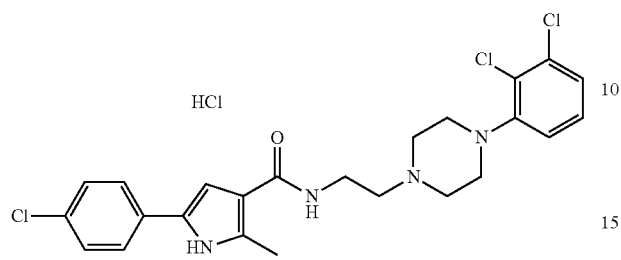

$^1$H NMR (400 MHz, MeOH-d$_4$) δ 7.43-7.40 (m, 2H), 7.38-7.34 (m, 2H), 7.30-7.26 (m, 2H), 7.17-7.14 (m, 1H), 3.80 (d, J=10.2 Hz, 2H), 3.75 (t, J=9.4 Hz, 2H), 3.56 (d, J=10.1 Hz, 2H), 3.42 (t, J=4 Hz, 2H), 3.34 (d, J=8.8 Hz, 2H), 3.24 (t, J=10.4 Hz, 2H), 2.54 (s, 3H).
MH+491 (—HCl)

Example 68

5-(4-chlorophenyl)-N-(2-(4-(2,3-dichlorophenyl)piperazin-1-yl)ethyl)-1,2-dimethyl-1H-pyrrole-3-carboxamide hydrochloride

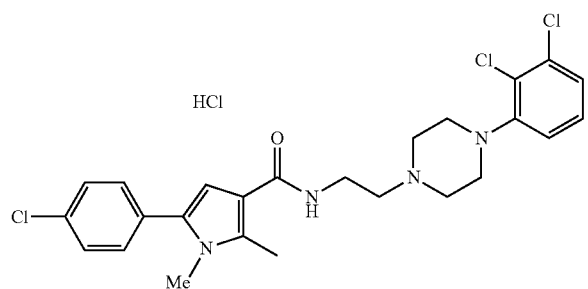 [SMILES: Cc1c(C(=O)NCCN2CCN(c3cccc(Cl)c3Cl)CC2)cc(-c2ccc(Cl)cc2)n1C ; Cl]

$^1$H NMR (400 MHz, MeOH-d$_4$) δ 7.43-7.40 (m, 2H), 7.38-7.34 (m, 2H), 7.30-7.26 (m, 2H), 7.18-7.15 (m, 1H), 3.82 (d, J=10.2 Hz, 2H), 3.72 (t, J=10.3 Hz, 2H), 3.56 (d, J=10.1 Hz, 2H), 3.50 (s, 3H), 3.42 (t, J=4 Hz, 2H), 3.36 (dd, J=2.0, 8.5 Hz, 2H), 3.24 (t, J=10.4 Hz, 2H), 2.59 (s, 3H).
MH+505 (—HCl)

Example 69

5-(4-chlorophenyl)-N-(2-(4-(2,3-dichlorophenyl)piperazin-1-ypethyl)-1-ethyl-2-methyl-1H-pyrrole-3-carboxamide hydrochloride

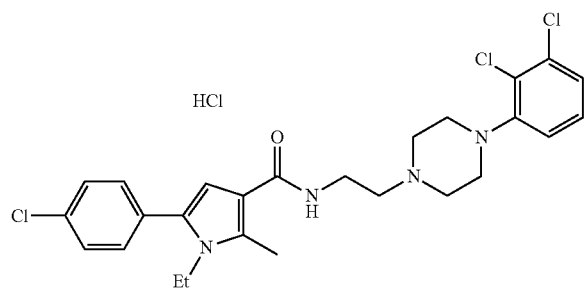 [SMILES: CCn1c(-c2ccc(Cl)cc2)cc(C(=O)NCCN2CCN(c3cccc(Cl)c3Cl)CC2)c1C ; Cl]

$^1$H NMR (400 MHz, MeOH-d$_4$) δ 7.42 (d, J=8.4 Hz, 2H), 7.36-7.31 (m, 2H), 7.30-7.26 (m, 2H), 7.18-7.14 (m, 1H), 3.96 (q, J=7.6 Hz, 2H), 3.82 (d, J=12.4 Hz, 2H), 3.73 (t, J=5.2 Hz, 2H), 3.54 (d, J=13.2 Hz, 2H), 3.43 (t, J=8.4 Hz, 2H), 3.36 (dd, J=2.4, 12.0 Hz, 2H), 3.18 (t, J=11.6 Hz, 2H), 2.60 (s, 3H), 1.12 (t, J=7.2 Hz, 3H).
MH+519 (—HCl)

Example 70

5-(4-chlorophenyl)-N-(2-(4-(2,3-dichlorophenyl)piperazin-1-ypethyl)-2-methyl-1-propyl-1H-pyrrole-3-carboxamide hydrochloride

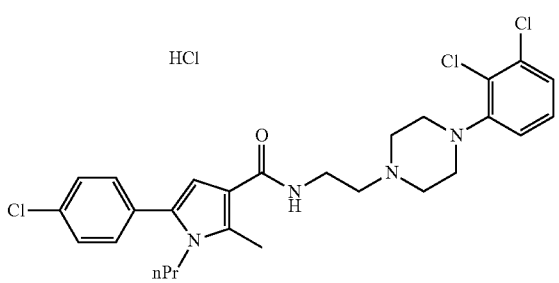

$^1$H NMR (400 MHz, MeOH-d$_4$) δ 7.43-7.40 (m, 2H), 7.35-7.33 (m, 2H), 7.30-7.28 (m, 2H), 7.18-7.15 (m, 1H), 3.90 (t, J=7.6 Hz, 2H), 3.82 (d, J=12.4 Hz, 2H), 3.72 (t, J=5.2 Hz, 2H), 3.52 (d, J=13.2 Hz, 2H), 3.43 (t, J=8.4 Hz, 2H), 3.36 (dd, J=2.4, 12.0 Hz, 2H), 3.18 (t, J=11.6 Hz, 2H), 2.60 (s, 3H), 1.52-1.46 (m, 2H), 0.71 (t, J=7.2 Hz, 3H).
MH+533 (—HCl)

Example 71

1-butyl-N-(3-(4-(2,3-dichlorophenyl)piperazin-1-yl)propyl)-2-methyl-5-phenyl-1H-pyrrole-3-carboxamide hydrochloride

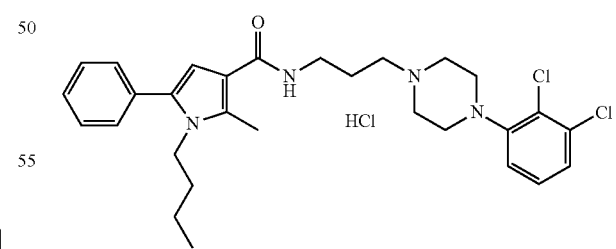

$^1$H NMR (400 MHz, MeOH-d$_4$) δ 7.43-7.42 (m, 3H), 7.41-7.39 (m, 2H), 7.36-7.26 (m, 2H), 7.18-7.16 (m, 1H), 3.93 (t, J=7.6 Hz, 2H), 3.67 (d, J=12.0 Hz, 2H), 3.54 (d, J=13.2 Hz, 2H), 3.48 (t, J=6.4 Hz, 2H), 3.34-3.18 (m, 4H), 2.59 (s, 3H), 2.12-2.05 (m, 2H), 1.48-1.40 (m, 2H), 1.14-1.08 (m, 2H), 0.73 (t, J=7.6 Hz, 3H).
MH+527 (—HCl)

Example 72

N-(3-(4-(2,3-dichlorophenyl)piperazin-1-yl)propyl)-1-hexyl-2-methyl-5-phenyl-1H-pyrrole-3-carboxamide hydrochloride

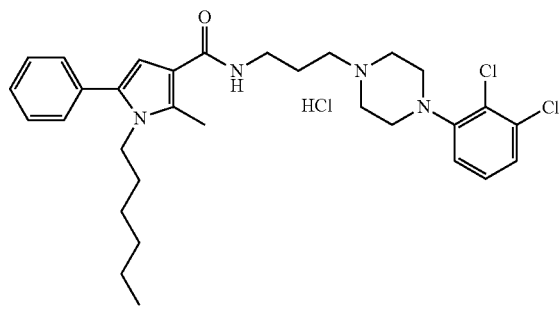 [SMILES: CCCCCCn1c(-c2ccccc2)cc(C(=O)NCCCN2CCN(c3cccc(Cl)c3Cl)CC2)c1C ; Cl]

$^1$H NMR (400 MHz, MeOH-d$_4$) δ 7.43-7.42 (m, 3H), 7.41-7.39 (m, 2H), 7.36-7.27 (m, 2H), 7.20-7.16 (m, 1H), 3.93 (t, J=7.6 Hz, 2H), 3.67 (d, J=11.6 Hz, 2H), 3.55 (d, J=12.8 Hz, 2H), 3.47 (t, J=6.4 Hz, 2H), 3.34-3.17 (m, 4H), 2.59 (s, 3H), 2.11-2.04 (m, 2H), 1.44-1.42 (m, 2H), 1.17-1.11 (m, 2H), 1.10-1.07 (m, 4H), 0.78 (t, J=6.8 Hz, 3H).
MH+555 (—HCl)

Example 73

N-(3-(4-(2,3-dichlorophenyl)piperazin-1-yl)propyl)-5-(4-methoxyphenyl)-2-methyl-1H-pyrrole-3-carboxamide hydrochloride

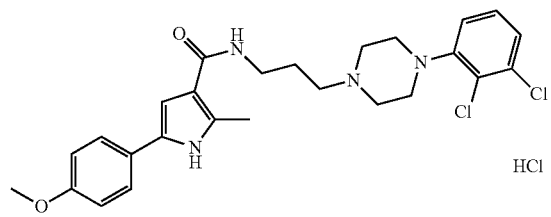 [SMILES: COc1ccc(-c2cc(C(=O)NCCCN3CCN(c4cccc(Cl)c4Cl)CC3)c(C)[nH]2)cc1 ; Cl]

$^1$H NMR (400 MHz, CD$_3$OD) δ 7.46 (d, J=8.4Hz, 2H), 7.31-7.23 (m, 2H), 7.16 (dd, J=6.4, 2.8Hz, 1H), 7.29-7.24 (d, J=8.8 Hz, 2H), 3.78 (s, 3H), 3.68-3.65 (m, 2H), 3.57-3.53 (m, 2H), 3.50-3.47 (m, 2H), 3.28-3.17 (m, 6H), 2.53 (s, 3H), 2.12-2.07 (m, 2H).
MH+501

Example 74

N-(3-(4-(2,3-dichlorophenyl)piperazin-1-yl)propyl)-5-(4-methoxyphenyl)-1,2-dimethyl-1H-pyrrole-3-carboxamide hydrochloride

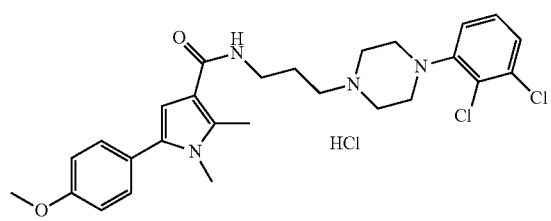 [SMILES: COc1ccc(-c2cc(C(=O)NCCCN3CCN(c4cccc(Cl)c4Cl)CC3)c(C)n2C)cc1 ; Cl]

$^1$H NMR (400 MHz, CD$_3$OD) δ 7.31-7.24 (m, 4H), 7.18-7.16 (m, 1H), 6.97-6.94 (m, 2H), 3.81 (s, 3H), 3.68-3.65 (m, 2H), 3.57-3.53 (m, 2H), 3.49-3.46 (m, 5H), 3.34-3.17 (m, 6H), 2.57 (s, 3H), 2.11-2.04 (m, 2H).
MH+515

Example 75

N-(3-(4-(2,3-dichlorophenyl)piperazin-1-yl)propyl)-1-ethyl-5-(4-methoxyphenyl)-2-methyl-1H-pyrrole-3-carboxamide hydrochloride

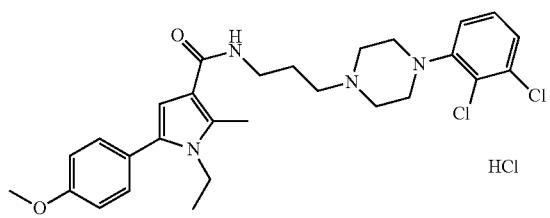 [SMILES: CCn1c(-c2ccc(OC)cc2)cc(C(=O)NCCCN2CCN(c3cccc(Cl)c3Cl)CC2)c1C ; Cl]

$^1$H NMR (400 MHz, CD$_3$OD) δ 7.32-7.25 (m, 4H), 7.18-7.16 (m, 1H), 6.96 (d, J=8.8 Hz, 2H), 3.91 (q, J=7.2 Hz, 2H), 3.81 (s, 3H), 3.68-3.65 (m, 2H), 3.57-3.54 (m, 2H), 3.48-3.45 (m, 2H), 3.34-3.17 (m, 6H), 2.59 (s, 3H), 2.10-2.05 (m, 2H), 1.11 (t, J=6.8 Hz, 3H).
MH+529

Example 76

N-(2-(4-(2,3-dichlorophenyl)piperazin-1-yl)ethyl)-2,4-dimethyl-5-phenyl-1H-pyrrole-3-carboxamide hydrochloride

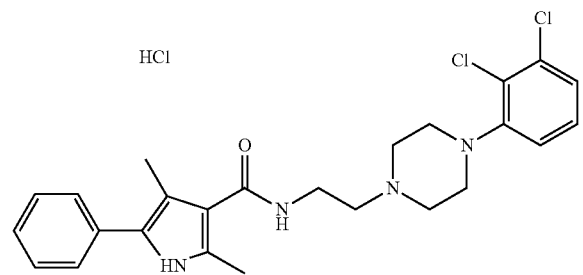 [SMILES: Cc1[nH]c(-c2ccccc2)c(C)c1C(=O)NCCN1CCN(c2cccc(Cl)c2Cl)CC1 ; Cl]

$^1$H NMR (400 MHz, MeOH-d$_4$) δ 7.40-7.31 (m, 4H), 7.30-7.28 (m, 2H), 7.26-7.18 (m, 1H), 7.16-7.15 (m, 1H), 3.84-3.80 (m, 4H), 3.56 (d, J=12.8 Hz, 2H), 3.49-3.43 (m, 2H), 3.38 (d, J=11.2 Hz, 2H), 3.21 (t, J=11.2 Hz, 2H), 2.45 (s, 3H), 2.30 (s, 3H).
MH+471 (—HCl)

Example 77

N-(3-(4-(2,3-dichlorophenyl)piperazin-1-yl)propyl)-2,4-dimethyl-5-phenyl-1H-pyrrole-3-carboxamide hydrochloride

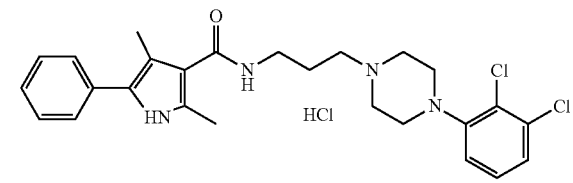 [SMILES: Cc1[nH]c(-c2ccccc2)c(C)c1C(=O)NCCCN1CCN(c2cccc(Cl)c2Cl)CC1 ; Cl]

¹H NMR (400 MHz, MeOH-d₄) δ 7.41-7.35 (m, 4H), 7.31-7.28 (m, 2H), 7.26-7.20 (m, 1H), 7.18-7.16 (m, 1H), 3.70 (d, J=11.6 Hz, 2H), 3.58-3.53 (m, 4H), 3.36-3.19 (m, 6H), 2.43 (s, 3H), 2.28 (s, 3H), 2.20-2.12 (m, 2H).
MH+485 (—HCl)

Example 78

N-(4-(4-(2,3-dichlorophenyl)piperazin-1-yl)butyl)-2,4-dimethyl-5-phenyl-1H-pyrrole-3-carboxamide hydrochloride

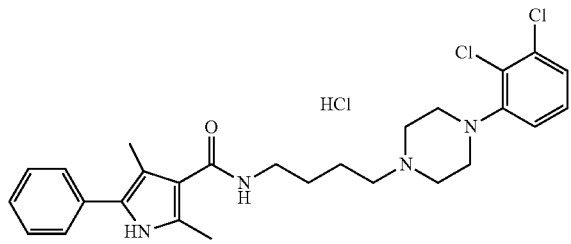 [SMILES: Cc1[nH]c(-c2ccccc2)c(C)c1C(=O)NCCCCN1CCN(c2cccc(Cl)c2Cl)CC1 ; Cl]

¹H NMR (400 MHz, MeOH-d₄) δ 7.42-7.36 (m, 4H), 7.30-7.28 (m, 2H), 7.25-7.21 (m, 1H), 7.17-7.14 (m, 1H), 3.68 (d, J=11.6 Hz, 2H), 3.56-3.550 (m, 4H), 3.35-3.17 (m, 6H), 2.42 (s, 3H), 2.26 (s, 3H), 1.97-1.89 (m, 2H), 1.82-1.75 (m, 2H).
MH+499 (—HCl)

Example 79

N-(3-(4-(2,3-dichlorophenyl)piperazin-1-yl)propyl)-1,2,4-trimethyl-5-phenyl-1H-pyrrole-3-carboxamide hydrochloride

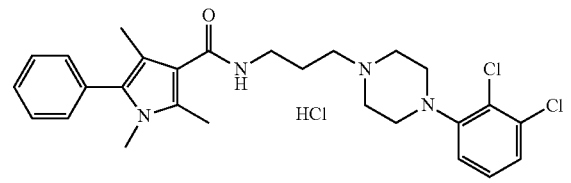 [SMILES: Cc1c(C(=O)NCCCN2CCN(c3cccc(Cl)c3Cl)CC2)c(C)n(C)c1-c1ccccc1 ; Cl]

¹H NMR (400 MHz, MeOH-d₄) δ 7.46-7.42 (m, 2H), 7.38-7.31 (m, 1H), 7.30-7.23 (m, 4H), 7.20-7.15 (m, 1H), 3.70 (d, J=11.6 Hz, 2H), 3.58-3.53 (m, 4H), 3.37-3.10 (m, 6H), 3.35 (s, 3H), 2.42 (s, 3H), 2.19-2.12 (m, 2H), 2.06 (s, 3H).
MH+499 (—HCl)

Example 80

N-(3-(4-(2,3-dichlorophenyl)piperazin-1-yl)propyl)-1-ethyl-2,4-dimethyl-5-phenyl-1H-pyrrole-3-carboxamide hydrochloride

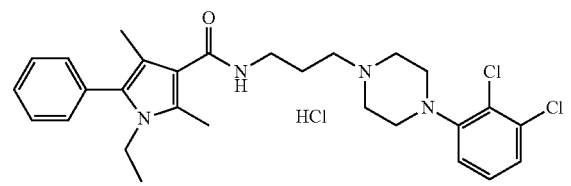 [SMILES: CCn1c(C)c(C(=O)NCCCN2CCN(c3cccc(Cl)c3Cl)CC2)c(C)c1-c1ccccc1 ; Cl]

¹H NMR (400 MHz, MeOH-d₄) δ 7.46-7.39 (m, 2H), 7.38-7.36 (m, 1H), 7.30-7.24 (m, 4H), 7.18-7.14 (m, 1H), 3.80 (q, J=7.2 Hz, 2H), 3.70 (d, J=12.0 Hz, 2H), 3.63-3.42 (m, 4H), 3.46-3.14 (m, 6H), 2.44 (s, 3H), 2.19-207 (m, 2H), 2.01 (s, 3H), 1.03 (t, J=6.8 Hz, 3H).
MH+513 (—HCl)

Example 81

N-(3-(4-(2,3-dichlorophenyl)piperazin-1-yl)propyl)-2,4-dimethyl-5-phenyl-1-propyl-1H-pyrrole-3-carboxamide hydrochloride

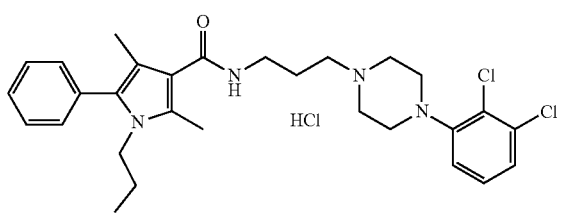 [SMILES: CCCn1c(C)c(C(=O)NCCCN2CCN(c3cccc(Cl)c3Cl)CC2)c(C)c1-c1ccccc1 ; Cl]

¹H NMR (400 MHz, MeOH-d₄) δ 7.45-7.42 (m, 2H), 7.39-7.37 (m, 1H), 7.35-7.18 (m, 4H), 7.17-7.18 (m, 1H), 3.76-3.68 (m, 4H), 3.57-3.53 (m, 4H), 3.36-3.18 (m, 4H), 2.44 (s, 3H), 2.18-2.11 (m, 2H), 2.02 (s, 3H), 1.47-1.40 (m, 2H), 0.66 (t, J=7.2 Hz, 3H).
MH+527 (—HCl)

Example 82

N-(3-(4-(2,3-dichlorophenyl)piperazin-1-yl)propyl)-5-(3-methoxyphenyl)-2-methyl-1-propyl-1H-pyrrole-3-carboxamide hydrochloride

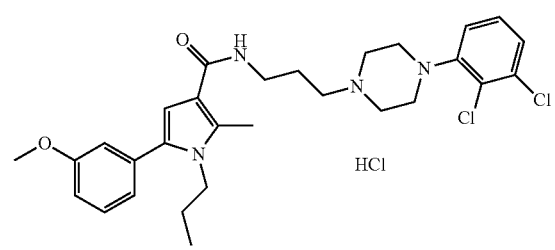 [SMILES: CCCn1c(-c2cccc(OC)c2)cc(C(=O)NCCCN2CCN(c3cccc(Cl)c3Cl)CC2)c1C ; Cl]

MH+543

Example 83

N-(3-(4-(2,3-dichlorophenyl)piperazin-1-yl)propyl)-5-(3-methoxyphenyl)-2-methyl-1H-pyrrole-3-carboxamide hydrochloride

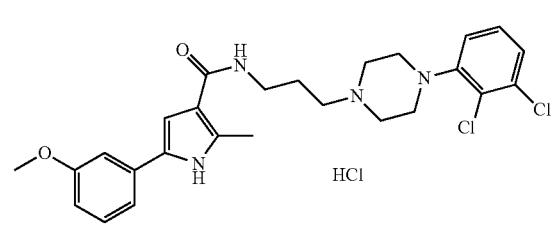 [SMILES: COc1cccc(-c2cc(C(=O)NCCCN3CCN(c4cccc(Cl)c4Cl)CC3)c(C)[nH]2)c1 ; Cl]

¹H NMR (400 MHz, CD₃OD) δ 7.31-7.21 (m, 3H), 7.18-7.11 (m, 3H), 6.74 (dd, J=8.4, 2.4Hz, 1H), 3.81 (s, 3H), 3.68-3.62 (m, 4H), 3.57-3.54 (m, 2H), 3.50-3.47 (m, 2H), 3.34-3.16 (m, 4H), 2.54 (s, 3H), 2.09-2.06 (m, 2H).
MH+501

Example 84

N-(3-(4-(2-Methoxyphenyl)piperazin-1-yl)propyl)-2-methyl-5-phenyl-1-propyl-1H-pyrrole-3-carboxamide

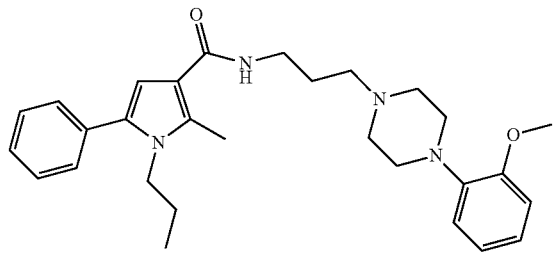 [SMILES: CCCn1c(-c2ccccc2)cc(C(=O)NCCCN2CCN(c3ccccc3OC)CC2)c1C]

¹H NMR (400 MHz, DMSO-d₆) δ 7.72 (brs, 1H), 7.39-7.28 (m, 5H), 6.92-6.86 (m, 2H), 6.83-6.78 (m, 2H), 6.46 (s, 1H), 3.80 (d, J=8.0 Hz, 2H), 3.72 (s, 3H), 3.18 (q, J=6.8 Hz, 2H), 2.95-2.87 (m, 4H), 2.50 (s, 3H), 2.52-2.42 (m, 4H), 2.36-2.32 (m, 2H), 1.64-1.60 (m, 2H), 1.43-1.37 (m, 2H), 0.62 (t, J=7.2 Hz, 3H).
MH+475.

Example 85

1,2-dimethyl-5-phenyl-N-(3-(4-(3-(trifluoromethyl)phenyl)piperazin-1-yl)propyl)-1H-pyrrole-3-carboxamide hydrochloride

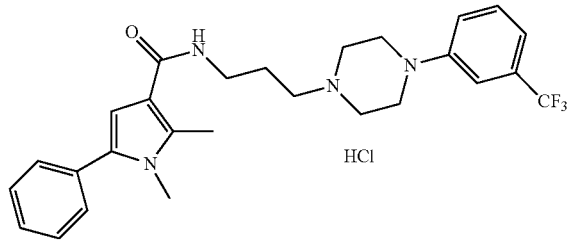 [SMILES: Cc1c(C(=O)NCCCN2CCN(c3cccc(C(F)(F)F)c3)CC2)cc(-c2ccccc2)n1C ; Cl]

¹H NMR (400 MHz, CD₃OD) δ 7.48-7.43 (m, 1H), 7.41-7.31 (m, 5H), 7.27 (m, 2H), 7.19-7.18 (m, 1H), 3.96-3.93 (m, 2H), 3.70-3.63 (m, 2H), 3.47 (s, 4H), 3.28-3.20 (m, 4H), 2.57 (s, 3H), 2.11-2.08 (m, 2H).
MH+485

Example 86

2-methyl-5-phenyl-1-propyl-N-(3-(4-(3-(trifluoromethyl)phenyl)piperazin-1-yl)propyl)-1H-pyrrole-3-carboxamide hydrochloride

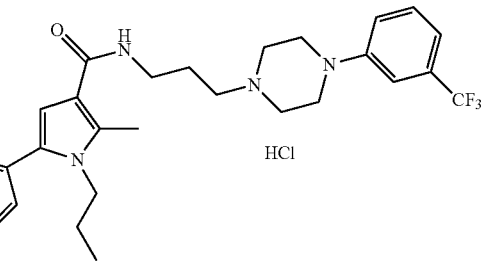

¹H NMR (400 MHz, CD₃OD) δ 7.48-7.39 (m, 3H), 7.35-7.33 (m, 3H), 7.28-7.27 (m, 2H), 7.19-7.18 (m, 1H), 3.96-3.88 (m, 4H), 3.73-3.64 (m, 3H), 3.50-3.47 (m, 2H), 3.26-3.17 (m, 4H), 2.57 (s, 3H), 2.11-2.08 (m, 2H), 1.53-1.44 (m, 2H), 0.69 (t, J=7.6Hz, 3H).
MH+513

Example 87

N-(3-(4-(4-methoxyphenyl)piperazin-1-yl)propyl)-2-methyl-5-phenyl-1-propyl-1H-pyrrole-3-carboxamide dihydrochloride

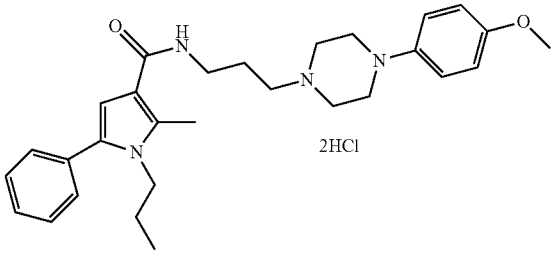 [SMILES: CCCn1c(-c2ccccc2)cc(C(=O)NCCCN2CCN(c3ccc(OC)cc3)CC2)c1C ; "2HCl"]

¹H NMR (400 MHz, CD₃OD) δ 7.43-7.32 (m, 7H), 7.03-6.99 (m, 2H), 3.92-3.88 (m, 2H), 3.83 (s, 3H), 3.84-3.62 (m, 8H), 3.62 (s, 3H), 3.51-3.48 (m, 2H), 3.33-3.32 (m, 2H), 2.59 (s, 3H), 2.10 (m, 2H), 1.50-1.48 (m, 2H), 0.70 (t, J=7.2Hz, 3H).
MH+475

Example 88

N-(3-(4-(2-bromophenyl)piperazin-1-yl)propyl)-2-methyl-5-phenyl-1-propyl-1H-pyrrole-3-carboxamide

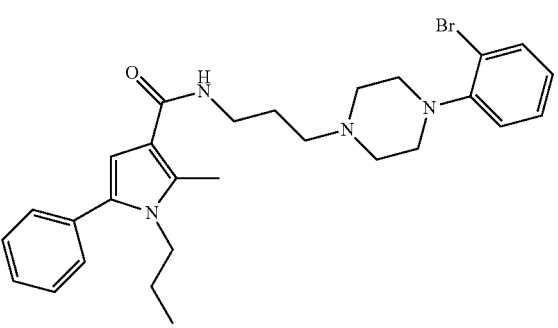 [SMILES: CCCn1c(-c2ccccc2)cc(C(=O)NCCCN2CCN(c3ccccc3Br)CC2)c1C]

¹H NMR (400 MHz, CDCl₃) δ 7.53 (dd, J=8.0, 1.2Hz, 1H), 7.34 (m, 5H), 7.12 (td, J=8.0, 1.2Hz, 1H), 6.89 (td, J=7.6, 1.2Hz, 1H), 6.74 (dd, J=8.0, 1.6Hz, 1H), 3.82 (t, J=7.6Hz, 2H), 3.55-3.51 (m, 2H), 3.05 (m, 4H), 2.65 (s, 3H), 2.60 (t, J=6.0Hz, 3H), 1.82-1.76 (m, 2H), 1.63-1.50(m, 5H), 0.74 (t, J=7.6Hz, 3H).
MH+523

Example 89

N-(3-(4-(2-bromophenyl)piperazin-1-yl)propyl)-1,2-dimethyl-5-phenyl-1H-pyrrole-3-carboxamide

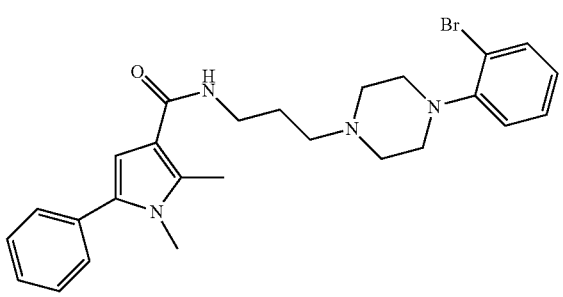 [SMILES: Cc1c(C(=O)NCCCN2CCN(c3ccccc3Br)CC2)cc(-c2ccccc2)n1C]

¹H NMR (400 MHz, CD₃OD) δ 7.61-7.59 (m, 1H), 7.43-7.32 (m, 6H), 7.23-7.21 (m, 1H), 7.05-7.02 (m, 1H), 3.63 (s, 3H), 3.54-3.45 (m, 4H), 3.33-3.15 (m, 8H), 2.59 (s, 3H), 2.07 (m, 2H).
MH+495

Example 90

N-(3-(4-(2-cyanophenyl)piperazin-1-yl)propyl)-2-methyl-5-phenyl-1-propyl-1H-pyrrole-3-carboxamide hydrochloride

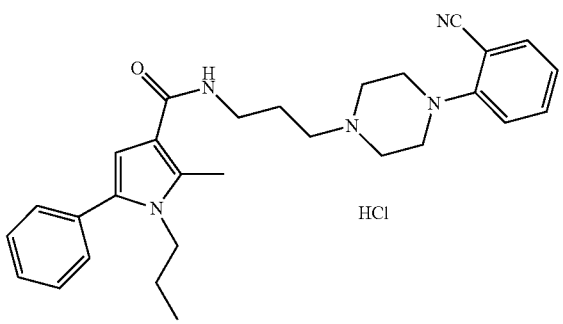 [SMILES: CCCn1c(-c2ccccc2)cc(C(=O)NCCCN2CCN(c3ccccc3C#N)CC2)c1C ; Cl]

¹H NMR (400 MHz, CD₃OD) δ 7.61-7.59 (m, 1H), 7.43-7.32 (m, 6H), 7.23-7.21 (m, 1H), 7.05-7.02 (m, 1H), 3.91-3.88 (m, 2H), 3.72-3.67 (m, 4H), 3.48-3.45 (m, 2H), 3.30-3.25 (m, 6H), 2.59 (s, 3H), 2.09-2.06 (m, 2H), 1.52-1.46 (m, 2H), 0.70 (t, J=7.6Hz, 3H).
MH+470.

Example 91

N-(3-(4-(2,3-dichlorophenyl)piperazin-1-yl)propyl)-2-methyl-5-(pyridin-2-yl)-1H-pyrrole-3-carboxamide dihydrochloride

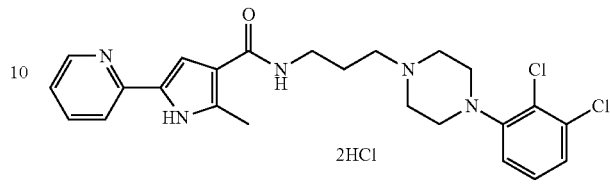

¹H NMR (400 MHz, MeOH-d₄) δ 8.55 (dd, J=8.0, 6.0 Hz, 1H), 8.45 (dt, J=1.6, 8.8 Hz, 1H), 8.13 (d, J=8.4 Hz, 1H), 7.68 (dt, J=1.2, 7.2 Hz, 1H), 7.59-7.56 (m, 1H), 7.31-7.28 (m, 2H), 7.15-7.10 (m, 1H), 3.70 (d, J=12.0 Hz, 2H), 3.54 (d, J=13.6 Hz, 2H), 3.50 (t, J=6.8 Hz, 2H), 3.37-3.31 (m, 4H), 3.21 (d, J=12.4 Hz, 2H), 2.46 (s, 3H), 2.14-2.11 (m, 2H).
MH+472 (−2HCl)

Example 92

N-(3-(4-(2,3-dichlorophenyl)piperazin-1-yl)propyl)-1,2-dimethyl-5-(pyridin-2-yl)-1H-pyrrole-3-carboxamide dihydrochloride

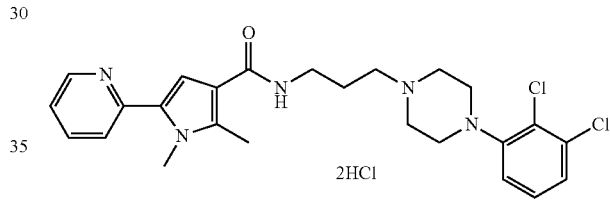

¹H NMR (400 MHz, MeOH-d₄) δ 8.74 (d, J=6.0 Hz, 1H), 8.58 (dt, J=1.6, 8.0 Hz, 1H), 8.13 (d, J=8.4 Hz, 1H), 7.90 (t, J=6.4 Hz, 1H), 7.31-7.28 (m, 2H), 7.26-7.25 (m, 1H), 7.18-7.15 (m, 1H), 3.73 (s, 3H), 3.68 (d, J=12.0 Hz, 2H), 3.53 (d, J=12.4 Hz, 2H), 3.48 (t, J=6.4 Hz, 2H), 3.33-3.28 (m, 2H), 3.23-3.19 (m, 2H), 2.65 (s, 3H), 2.13-2.09 (m, 2H).
MH+486 (−2HCl).

Example 93

N-(3-(4-(2,3-dichlorophenyl)piperazin-1-yl)propyl)-2-methyl-1-propyl-5-(pyridin-2-yl)-1H-pyrrole-3-carboxamide dihydrochloride

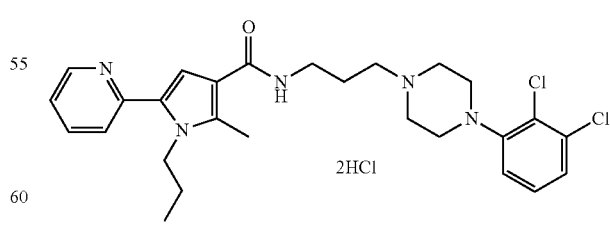

¹H NMR (400 MHz, MeOH-d₄) δ 8.77 (dd, J=1.2, 6.0 Hz, 1H), 8.61 (dt, J=1.6, 8.4 Hz, 1H), 8.12 (d, J=8.0 Hz, 1H), 7.94 (dt, J=1.2, 7.2 Hz, 1H), 7.31-7.28 (m, 2H), 7.26-7.25 (m, 1H), 7.18-7.15 (m, 1H), 4.14 (t, J=7.2 Hz, 2H), 3.79 (d, J=12.4 Hz, 2H), 3.54 (d, J=13.6 Hz, 2H), 3.48 (t, J=6.4 Hz, 2H), 3.33-

3.28 (m, 2H), 3.21 (d, J=12.0 Hz, 2H), 2.45 (s, 3H), 2.12-2.10 (m, 2H), 1.59-1.56 (m, 2H), 0.76 (t, J=7.2 Hz, 3H).

MH+514 (−2HCl)

Example 94

N-(2-(4-(2,3-dichlorophenyl)piperazin-1-yl)ethyl)-2-methyl-5-(pyridin-2-yl)-1H-pyrrole-3-carboxamide dihydrochloride

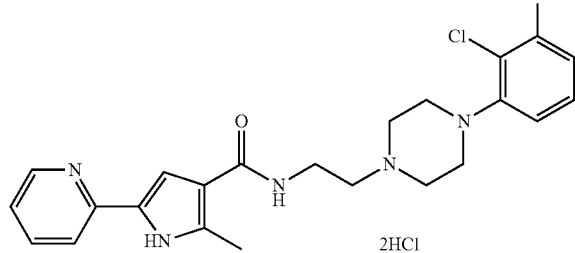

¹H NMR (400 MHz, MeOH-d₄) δ 8.56 (d, J=6.0 Hz, 1H), 8.46 (dt, J=1.6, 8.8 Hz, 1H), 8.14 (d, J=8.4 Hz, 1H), 7.69 (t, J=6.4 Hz, 1H), 7.63 (s, 1H), 7.31-7.22 (m, 2H), 7.18-7.14 (m, 1H), 3.86 (d, J=12.4 Hz, 2H), 3.80 (t, J=5.6 Hz, 2H), 3.54 (d, J=13.6 Hz, 2H), 3.49 (t, J=5.6 Hz, 2H), 3.33-3.28 (m, 2H), 2.63 (s, 3H).

MH+458 (−2HCl)

Example 95

N-(2-(4-(2,3-dichlorophenyl)piperazin-1-yl)ethyl)-1,2-dimethyl-5-(pyridin-2-yl)-1H-pyrrole-3-carboxamide dihydrochloride

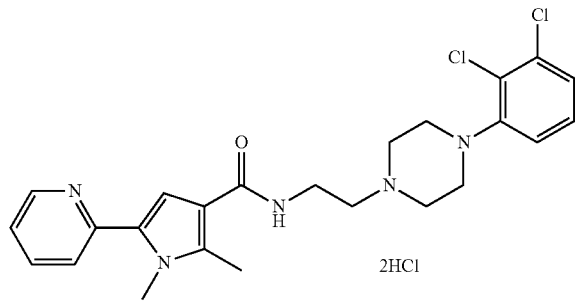 [SMILES: Cc1c(C(=O)NCCN2CCN(c3cccc(Cl)c3Cl)CC2)cc(-c2ccccn2)n1C]

¹H NMR (400 MHz, MeOH-d₄) δ 8.75 (d, J=5.2 Hz, 1H), 8.58 (t, J=7.6 Hz, 1H), 8.14 (d, J=8.4 Hz, 1H), 7.90 (t, J=6.4 Hz, 1H), 7.29-7.25 (m, 3H), 7.19-7.15 (m, 1H), 3.84 (d, J=12.0 Hz, 2H), 3.79 (t, J=5.6 Hz, 2H), 3.74 (s, 3H), 3.53 (d, J=13.2 Hz, 2H), 3.47 (t, J=5.6 Hz, 2H), 3.42-3.21 (m, 2H), 2.66 (s, 3H).

MH+472 (−2HCl)

Example 96

N-(2-(4-(2,3-dichlorophenyl)piperazin-1-yl)ethyl)-2-methyl-1-propyl-5-(pyridin-2-yl)-1H-pyrrole-3-carboxamide dihydrochloride

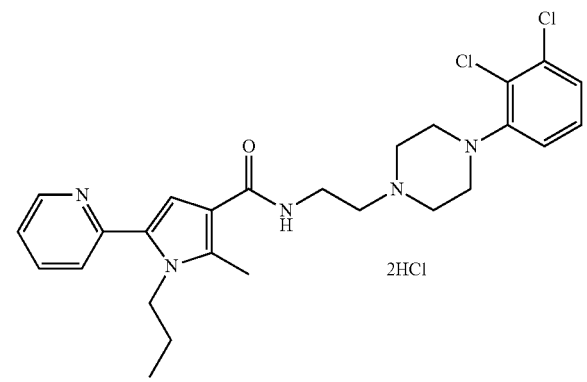 [SMILES: CCCn1c(-c2ccccn2)cc(C(=O)NCCN2CCN(c3cccc(Cl)c3Cl)CC2)c1C]

¹H NMR (400 MHz, MeOH-d₄) δ 8.78 (d, J=6.0 Hz, 1H), 8.61 (t, J=8.4 Hz, 1H), 8.13 (d, J=8.4 Hz, 1H), 7.94 (t, J=6.8 Hz, 1H), 7.29-7.19 (m, 3H), 7.18-7.15 (m, 1H), 4.15 (t, J=7.2 Hz, 2H), 3.84 (d, J=12.0 Hz, 2H), 3.78 (t, J=5.2 Hz, 2H), 3.54 (d, J=12.8 Hz, 2H), 3.47 (t, J=5.6 Hz, 2H), 3.39-3.30 (m, 2H), 2.68 (s, 3H), 1.59-1.56 (m, 2H), 0.75 (t, J=7.2 Hz, 3H).

MH+500 (−2HCl)

Example 97

N-(3-(4-(2,4-difluorophenyl)piperazin-1-yl)propyl)-1,2-dimethyl-5-phenyl-1H-pyrrole-3-carboxamide hydrochloride

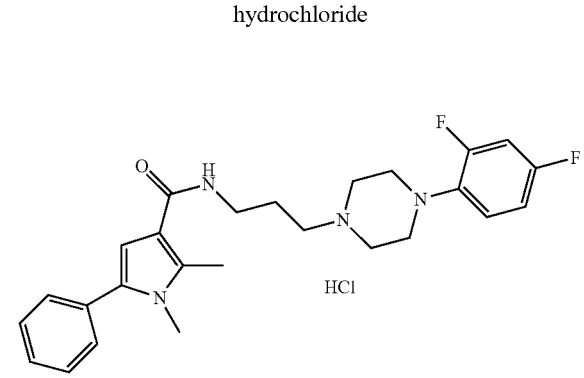

¹H NMR (400 MHz, DMSO-d₆) δ 11.08 (bs, 1H), 7.92 (br 1H), 7.43-7.29 (m, 5H), 7.25-7.19 (m, 1H), 7.14-7.08 (m, 1H), 7.02-6.97 (m, 1H), 6.58 (s, 1H), 3.53-3.46 (m, 2H), 3.44 (s, 3H), 3.37-3.34 (m, 2H), 3.24-3.09 (m, 8H), 2.51 (s, 3H), 1.94-1.91 (m, 2H).

MH+453

Example 98

N-(3-(4-(2,4-difluorophenyl)piperazin-1-yl)propyl)-2-methyl-5-phenyl-1-propyl-1H-pyrrole-3-carboxamide hydrochloride

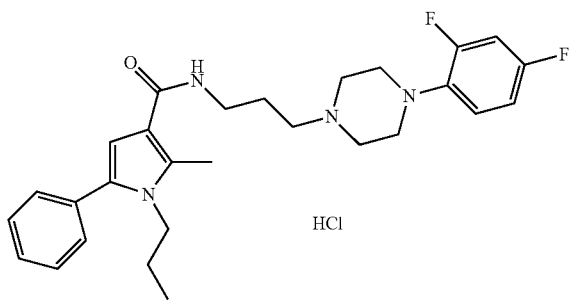 [SMILES: CCCn1c(-c2ccccc2)cc(C(=O)NCCCN2CCN(c3ccc(F)cc3F)CC2)c1C ; Cl]

$^1$H NMR (400 MHz, DMSO-d$_6$) δ 11.02 (bs, 1H), 7.91 (br 1H), 7.43-7.40 (m, 2H), 7.34-7.30 (m, 3H), 7.25-7.19 (m, 1H), 7.14-7.09 (m, 1H), 6.53 (s, 1H), 3.81 (t, J=7.6Hz, 2H), 3.53-3.46 (m, 2H), 3.37-3.32 (m, 2H), 3.23-3.10 (m, 8H), 2.52 (s, 3H), 1.96-1.90 (m, 2H), 1.46-1.37 (m, 2H), 0.63 (t, J=7.6Hz, 3H).
MH+481

Example 99

N-(3-(4-(2,3-dichlorophenyl)piperazin-1-yl)propyl)-2-methyl-5-(pyridin-3-yl)-1H-pyrrole-3-carboxamide

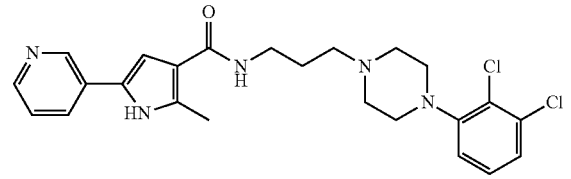 [SMILES: Cc1[nH]c(-c2cccnc2)cc1C(=O)NCCCN1CCN(c2cccc(Cl)c2Cl)CC1]

$^1$H NMR (400 MHz, CDCl$_3$) δ 8.80 (d, J=2.0 Hz, 1H), 8.41 (dd, J=1.2, 4.8 Hz, 1H), 7.72 (td, J=2.0, 8.0 Hz, 1H), 7.24-7.13 (m, 2H), 7.00 (t, J=8.0 Hz, 1H), 6.79 (dd, J=1.2, 8.0 Hz, 1H), 6.69 (s, 1H), 3.55 (t, J=6.0 Hz, 2H), 3.10 (brs, 4H), 2.71 (brs, 4H), 2.65-2.62 (m, 2H), 2.61 (s, 3H), 1.85-1.79 (m, 2H).
MH+472.

Example 100

N-(3-(4-(2,3-dichlorophenyl)piperazin-1-yl)propyl)-1,2-dimethyl-5-(pyridin-3-yl)-1H-pyrrole-3-carboxamide

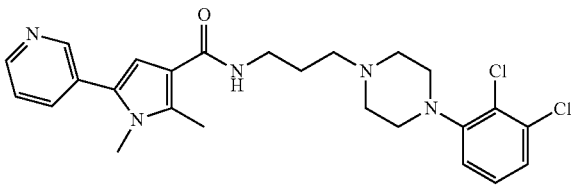 [SMILES: Cc1c(C(=O)NCCCN2CCN(c3cccc(Cl)c3Cl)CC2)cc(-c2cccnc2)n1C]

$^1$H NMR (400 MHz, CDCl$_3$) δ 8.64 (d, J=1.6 Hz, 1H), 8.55 (dd, J=1.2, 4.8 Hz, 1H), 7.62 (td, J=2.0, 8.0 Hz, 1H), 7.26-7.24 (m, 1H), 7.16-7.13 (m, 1H), 7.02 (t, J=8.0 Hz, 1H), 6.65 (dd, J=1.2, 8.0 Hz, 1H), 6.44 (s, 1H), 3.55-3.52 (m, 3H), 3.51 (s, 3H), 3.04 (brs, 4H), 2.67 (brs, 2H), 2.65 (s, 3H), 2.61 (t, J=5.6 HZ, 2H), 1.83-1.77 (m, 2H).
MH+486

Example 101

N-(3-(4-(2,3-dichlorophenyl)piperazin-1-yl)propyl)-2-methyl-1-propyl-5-(pyridin-3-yl)-1H-pyrrole-3-carboxamide

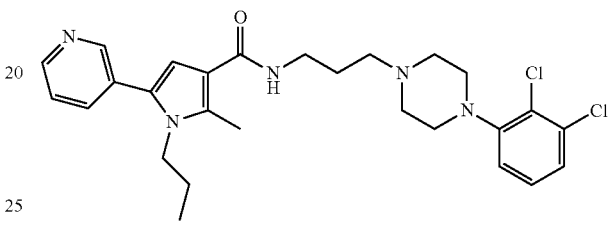

$^1$H NMR (400 MHz, CDCl$_3$) δ 8.63 (d, J=2.0 Hz, 1H), 8.57 (dd, J=1.6, 4.8 Hz, 1H), 7.60 (td, J=2.0, 8.0 Hz, 1H), 7.26-7.22 (m, 1H), 7.14 (dd, J=1.2, 8.0 Hz, 1H), 7.03 (t, J=8.0 Hz, 1H), 6.64 (dd, J=1.2, 8.0 Hz, 1H), 6.40 (s, 1H), 3.81 (t, J=8.0 Hz, 2H), 3.53 (t, J=6.0 Hz, 2H), 3.03 (brs, 4H), 2.67 (brs, 3H), 2.66 (s, 3H), 2.60 (t, J=6.0 Hz, 2H), 1.83-1.77 (m, 2H), 1.60-1.50 (m, 2H), 0.76 (t, J=7.2 Hz, 3H).
MH+514

Example 102

N-(2-(4-(2,3-dichlorophenyl)piperazin-1-yl)ethyl)-2-methyl-5-(pyridin-3-yl)-1H-pyrrole-3-carboxamide

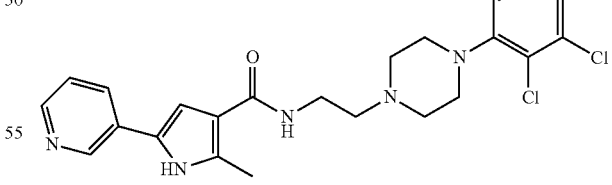

$^1$H NMR (400 MHz, CDCl$_3$) δ 8.99 (brs, 1H), 8.78 (d, J=2.0 Hz, 1H), 8.45 (dd, J=1.2, 4.8 Hz, 1H), 7.75 (td, J=1.6, 8.0 Hz, 1H), 7.31-7.28 (m, 1H), 7.18-7.13 (m, 2H), 6.98 (dd, J=2.8, 6.8 Hz, 1H), 6.63 (d, J=2.8 Hz, 1H), 6.43 (t, J=4.4 Hz, 1H), 3.58-3.53 (m, 2H), 3.09 (brs, 4H), 2.71-2.66 (m, 5H), 2.63 (s, 3H), 1.72 (brs, 2H).
MH+458

Example 103

N-(2-(4-(2,3-dichlorophenyl)piperazin-1-yl)ethyl)-1,2-dimethyl-5-(pyridin-3-yl)-1H-pyrrole-3-carboxamide

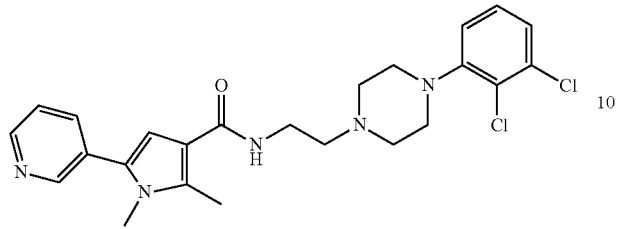

¹H NMR (400 MHz, CDCl₃) δ 8.65 (d, J=2.0 Hz, 1H), 8.58 (dd, J=1.6, 4.8 Hz, 1H), 7.67 (td, J=2.0, 8.0 Hz, 1H), 7.35 (dd, J=5.2, 8.0 Hz, 1H), 7.19-7.12 (m, 2H), 6.96 (dd, J=2.4, 7.2 Hz, 1H), 6.58 (brs, 1H), 6.37 (s, 1H), 3.61-3.58 (m, 2H), 3.51 (s, 3H), 3.12 (brs, 4H), 2.81 (brs, 6H), 2.65 (s, 3H).
MH+472

Example 104

N-(2-(4-(2,3-dichlorophenyl)piperazin-1-yl)ethyl)-2-methyl-1-propyl-5-(pyridin-3-yl)-1H-pyrrole-3-carboxamide

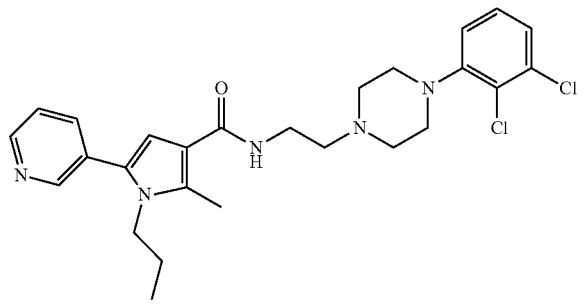 [SMILES: CCCn1c(-c2cccnc2)cc(C(=O)NCCN2CCN(c3cccc(Cl)c3Cl)CC2)c1C]

¹H NMR (400 MHz, CDCl₃) δ 8.63 (d, J=1.6 Hz, 1H), 8.58 (dd, J=1.2, 4.8 Hz, 1H), 7.67 (td, J=2.0, 8.0 Hz, 1H), 7.35 (dd, J=4.8, 8.0 Hz, 1H), 7.20-7.13 (m, 2H), 6.96 (dd, J=1.6, 7.6 Hz, 1H), 6.35 (s, 1H), 3.82 (d, J=8.0 Hz, 2H), 3.65 (brs, 2H), 3.17 (brs, 4H), 2.91 (brs, 5H), 2.65 (s, 3H), 1.61-1.54 (m, 2H), 0.77 (t, J=7.6 Hz, 3H).
MH+500

Example 105

N-(3-(4-(2,3-dichlorophenyl)piperazin-1-yl)propyl)-2-methyl-5-(pyridin-4-yl)-1H-pyrrole-3-carboxamide

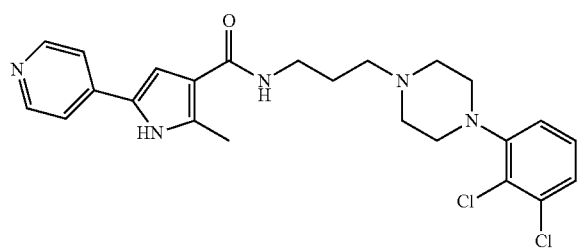 [SMILES: Cc1[nH]c(-c2ccncc2)cc1C(=O)NCCCN1CCN(c2cccc(Cl)c2Cl)CC1]

¹H NMR (400 MHz, CDCl₃) δ 8.77 (d, J=2.4 Hz, 1H), 8.40 (dd, J=1.6, 4.8 Hz, 1H), 7.70 (td, J=2.4, 8.4 Hz, 1H), 7.17-7.12 (m, 2H), 6.98 (t, J=8.0 Hz, 1H), 6.78 (dd, J=1.2, 8.0, 1H), 6.67 (s, 1H), 3.54 (t, J=6.0 Hz, 2H), 3.08 (brs, 4H), 2.69 (brs, 3H), 2.65-2.61 (m, 2H), 2.60 (s, 3H), 1.83-1.77 (m, 2H).
MH+472

Example 106

N-(3-(4-(2,3-dichlorophenyl)piperazin-1-yl)propyl)-1,2-dimethyl-5-(pyridin-4-yl)-1H-pyrrole-3-carboxamide

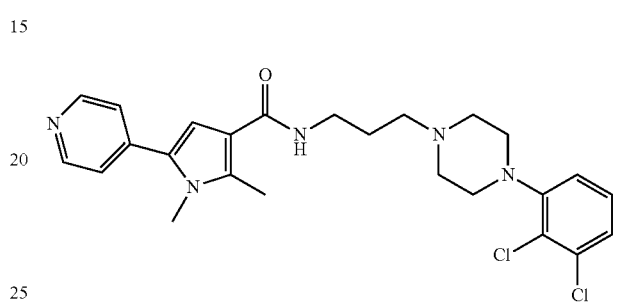

¹H NMR (400 MHz, CDCl₃) δ 8.64 (d, J=1.2 Hz, 1H), 8.55 (dd, J=1.6, 4.8 Hz, 1H), 7.61 (td, J=2.0, 8.0 Hz, 1H), 7.26-7.24 (m, 1H), 7.14 (dd, J=2.8, 6.8 Hz, 1H), 7.02 (t, J=8.4 Hz, 1H), 6.65 (dd, J=1.2, 8.0 Hz, 1H), 6.43 (s, 1H), 3.55-3.51 (m, 2H), 3.51 (s, 3H), 3.04 (brs, 4H), 2.67 (brs, 2H), 2.65 (s, 3H), 2.61 (t, J=6.4 Hz, 2H), 1.83-1.77 (m, 2H).
MH+486

Example 107

N-(3-(4-(2,3-dichlorophenyl)piperazin-1-yl)propyl)-2-methyl-1-propyl-5-(pyridin-4-yl)-1H-pyrrole-3-carboxamide

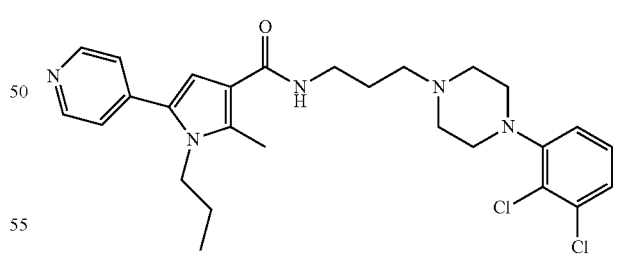

¹H NMR (400 MHz, CDCl₃) δ 8.62 (d, J=1.2 Hz, 1H), 8.56 (dd, J=1.6, 4.8 Hz, 1H), 7.60 (td, J=2.0, 7.6 Hz, 1H), 7.26-7.24 (m, 1H), 7.14 (dd, J=1.2, 8.0 Hz, 1H), 7.03 (t, J=8.0 Hz, 1H), 6.64 (dd, J=1.2, 8.0 Hz, 1H), 6.40 (s, 1H), 3.81 (t, J=8.0 Hz, 2H), 3.53 (t, J=6.0 Hz, 2H), 3.03 (brs, 4H), 2.67 (brs, 4H), 2.66 (s, 3H), 2.60 (t, J=6.0 Hz, 2H), 1.81-1.78 (m, 2H), 1.58-1.52 (m, 2H), 0.76 (t, J=7.2 Hz, 3H).
MH+514

Example 108

N-(2-(4-(2,3-dichlorophenyl)piperazin-1-yl)ethyl)-2-methyl-5-(pyridin-4-yl)-1H-pyrrole-3-carboxamide

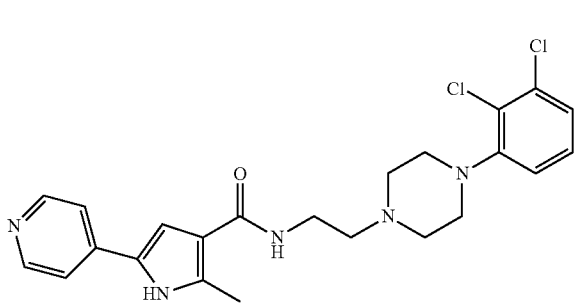 [SMILES: Cc1[nH]c(-c2ccncc2)cc1C(=O)NCCN1CCN(c2cccc(Cl)c2Cl)CC1]

$^1$H NMR (400 MHz, CDCl$_3$) δ 9.31 (brs, 1H), 8.80 (d, J=2.0 Hz, 1H), 8.45 (dd, J=1.2, 4.8 Hz, 1H), 7.60 (td, J=2.0, 8.0 Hz, 1H), 7.31-7.29 (m, 1H), 7.19-7.14 (m, 2H), 6.98 (dd, J=2.8, 6.4 Hz, 1H), 6.65 (d, J=2.8 Hz, 1H), 6.46 (t, J=4.8 Hz, 1H), 3.56 (dd, J=6.0, 11.2 Hz, 2H), 3.10 (brs, 4H), 2.72 (brs, 4H), 2.70-2.67 (m, 2H), 2.63 (s, 3H).

MH+458

Example 109

N-(2-(4-(2,3-dichlorophenyl)piperazin-1-yl)ethyl)-1,2-dimethyl-5-(pyridin-4-yl)-1H-pyrrole-3-carboxamide

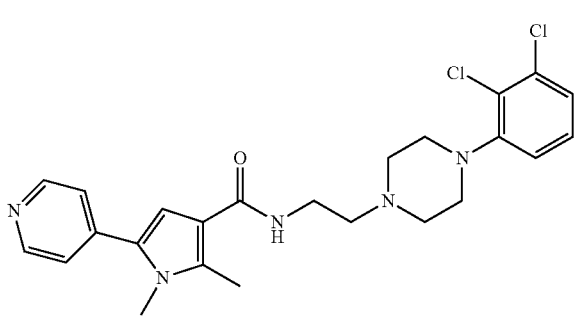 [SMILES: Cc1c(C(=O)NCCN2CCN(c3cccc(Cl)c3Cl)CC2)cc(-c2ccncc2)n1C]

$^1$H NMR (400 MHz, CDCl$_3$) δ 8.65 (d, J=2.0 Hz, 1H), 8.57 (dd, J=1.6, 4.8 Hz, 1H), 7.67 (td, J=2.0, 8.0 Hz, 1H), 7.37-7.34 (m, 1H), 7.22-7.13 (m, 2H), 6.95 (dd, J=2.0, 7.6 Hz, 1H), 6.66 (brs, 1H), 6.38 (s, 1H), 3.63-3.61 (m, 2H), 3.51 (s, 3H), 3.14 (brs, 4H), 2.84 (brs, 5H), 2.65 (s, 3H).

MH+472.

Example 110

N-(2-(4-(2,3-dichlorophenyl)piperazin-1-yl)ethyl)-2-methyl-1-propyl-5-(pyridin-4-yl)-1H-pyrrole-3-carboxamide

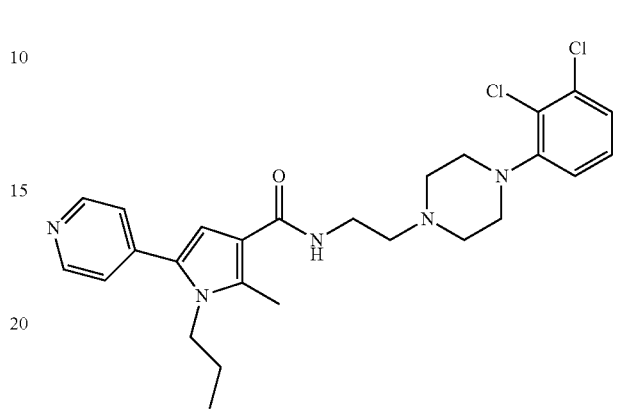

$^1$H NMR (400 MHz, CDCl$_3$) δ 8.64 (d, J=2.0 Hz, 1H), 8.58 (dd, J=1.6, 5.2 Hz, 1H), 7.66 (td, J=1.6, 7.6 Hz, 1H), 7.37-7.34 (m, 1H), 7.20-7.13 (m, 2H), 6.96 (dd, J=2.0, 7.6 Hz, 1H), 6.63 (brs, 1H), 6.34 (s, 1H), 3.84-3.80 (m, 2H), 3.62-3.61 (m, 2H), 3.14 (brs, 4H), 2.93 (brs, 5H), 2.65 (s, 3H), 1.59-1.54 (m, 2H), 0.77 (t, J=7.2 Hz, 3H).

MH+500

Example 111

N-(3-(4-(3,4-dichlorophenyl)piperazin-1-yl)propyl)-1,2-dimethyl-5-phenyl-1H-pyrrole-3-carboxamide hydrochloride

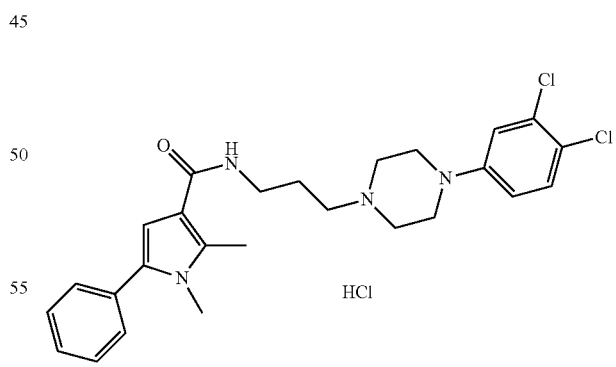

$^1$H NMR (400 MHz, DMSO-d$_6$) δ 11.09 (bs, 1H), 7.92 (br 1H), 7.43-7.28 (m, 6H), 7.21 (d, J=2.8Hz, 1H), 6.96 (dd, J=9.2, 3.2Hz, 1H), 6.58 (s, 1H), 3.87-3.84 (m, 2H), 3.51-3.47 (m, 2H), 3.44 (s, 3H), 3.23-3.13 (m, 4H), 3.09-3.02 (m, 4H), 2.50 (s, 3H), 1.94-1.90 (m, 2H).

MH+485

Example 112

N-(3-(4-(3,4-dichlorophenyl)piperazin-1-yl)propyl)-2-methyl-5-phenyl-1-propyl-1H-pyrrole-3-carboxamide hydrochloride

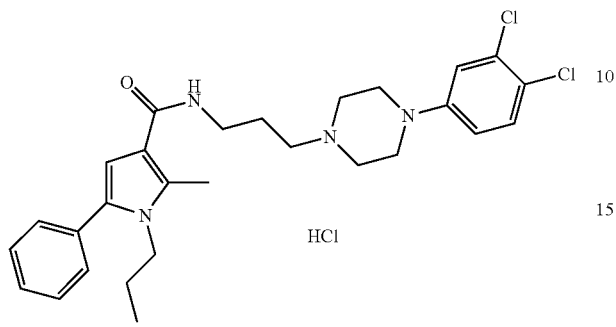

$^1$H NMR (400 MHz, DMSO-d$_6$) δ 10.98 (bs, 1H), 7.90 (br 1H), 7.43-7.30 (m, 6H), 7.21 (d, J=2.8Hz, 1H), 6.97 (dd, J=8.8, 2.8Hz, 1H), 6.53 (s, 1H), 3.87-3.79 (m, 4H), 3.53-3.47 (m, 2H), 3.22-3.13 (m, 4H), 3.10-3.02 (m, 4H), 2.52 (s, 3H), 1.93-1.90 (m, 2H), 1.46-1.37 (m, 2H), 0.63 (t, J=7.2Hz, 3H).
MH+513

Example 113

N-(3-(4-(3-Methoxyphenyl)piperazin-1-yl)propyl)-2-methyl-5-phenyl-1-propyl-1H-pyrrole-3-carboxamide

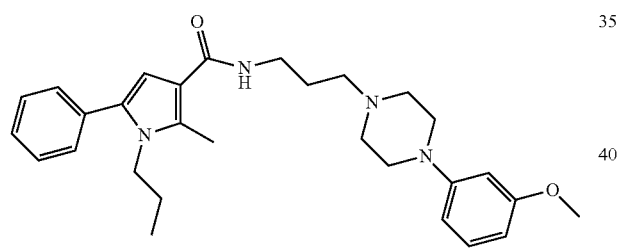

$^1$H NMR (400 MHz, DMSO-d$_6$) δ 7.73 (brs, 1H), 7.36-7.29 (m, 5H), 7.08 (t, J=8.0 Hz, 1H), 6.50 (d, J=7.6 Hz, 1H), 6.46 (s, 1H), 6.42 (s, 1H), 6.35 (d, J=6.0 Hz, 1H), 3.80 (d, J=7.6 Hz, 2H), 3.68 (s, 3H), 3.21-3.19 (m, 2H), 3.14-3.02 (m, 4H), 2.51 (s, 3H), 2.52-2.35 (m, 6H), 1.72-1.65 (m, 2H), 1.46-1.36 (m, 2H), 0.63 (t, J=7.2 Hz, 3H).
MH+475

Example 114

2-chloro-N-(3-(4-(2,3-dichlorophenyl)piperazin-1-yl)propyl)-5-phenyl-1H-pyrrole-3-carboxamide

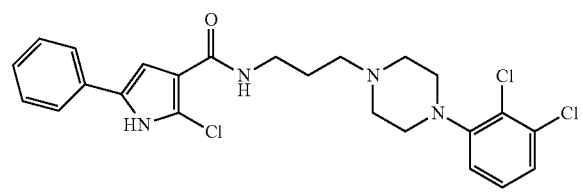 [SMILES: O=C(NCCCN1CCN(c2cccc(Cl)c2Cl)CC1)c1cc(-c2ccccc2)[nH]c1Cl]

$^1$H NMR (400 MHz, CDCl$_3$) δ 8.68 (brs, 1H), 7.42 (d, J=7.2 Hz, 2H), 7.34 (t, J=7.2 Hz, 2H), 7.28-7.13 (m, 3H), 7.04 (t, J=8.0 Hz, 1H), 6.94-6.84 (m, 2H), 3.56 (dd, J=6.0, 12.0 Hz, 2H), 3.08 (brs, 4H), 2.68 (brs, 4H), 2.60 (t, J=6.4 Hz, 2H), 1.86-1.80 (m, 2H).
MH+491

Example 115

2-chloro-N-(3-(4-(2,3-dichlorophenyl)piperazin-1-yl)propyl)-1-methyl-5-phenyl-1H-pyrrole-3-carboxamide

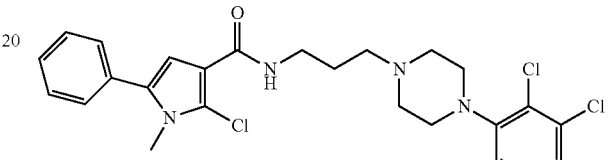

$^1$H NMR (400 MHz, CDCl$_3$) δ 7.41-7.32 (m, 4H), 7.17-7.14 (m, 2H), 7.07 (t, J=7.6 Hz, 1H), 6.80 (d, J=8.0 Hz, 1H), 6.60 (s, 1H), 3.57 (s, 3H), 3.56-3.54 (m, 2H), 3.07 (brs, 4H), 2.68 (brs, 4H), 2.61-2.58 (m, 2H), 1.83 (t, J=6.0 Hz, 2H), 1.60 (brs, 2H).
MH+505

Example 116

2-chloro-N-(3-(4-(2,3-dichlorophenyl)piperazin-1-yl)propyl)-1-propyl-5-(pyridin-4-yl)-1H-pyrrole-3-carboxamide

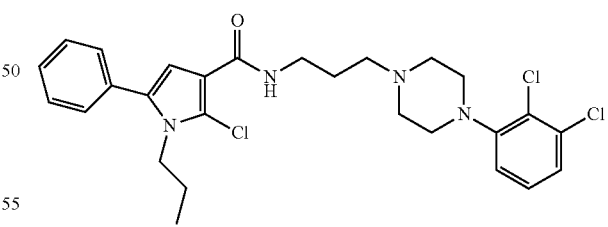

$^1$H NMR (400 MHz, CDCl$_3$) δ 7.42-7.38 (m, 3H), 7.37-30 (m, 2H), 7.18-7.14 (m, 2H), 7.07 (t, J=8.0 Hz, 1H), 6.80 (dd, J=1.2, 8.0 Hz, 1H), 6.56 (s, 1H), 3.91 (t, J=8.0 Hz, 2H), 3.55 (q, J=6.0 Hz, 2H), 3.06 (brs, 4H), 2.68 (brs, 3H), 2.59 (t, J=6.4 Hz, 2H), 1.86-1.80 (m, 2H), 1.65-1.56 (m, 2H), 0.75 (t, J=7.2 Hz, 3H).
MH+533

Example 117

N-(3-(4-(4-Bromophenyl)piperazin-1-yl)propyl)-1,2-dimethyl-5-phenyl-1H-pyrrole-3-carboxamide

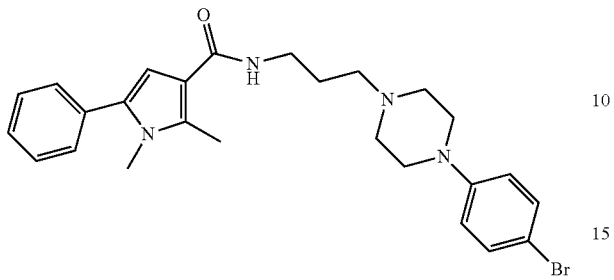

$^1$H NMR (400 MHz, DMSO-d$_6$) δ 7.71 (brs, 1H), 7.36-7.25 (m, 6H), 6.85 (d, J=9.2 Hz, 2H), 6.49 (s, 1H), 3.43 (s, 3H), 3.20 (q, J=6.4 Hz, 2H), 3.12-3.07 (m, 4H), 2.49 (s, 3H), 2.50-2.43 (m, 4H), 2.36-2.32 (m, 2H), 1.67-1.60 (m, 2H).
MH+495

Example 118

N-(3-(4-(2-Ethoxyphenyl)piperazin-1-yl)propyl)-1,2-dimethyl-5-phenyl-1H-pyrrole-3-carboxamide

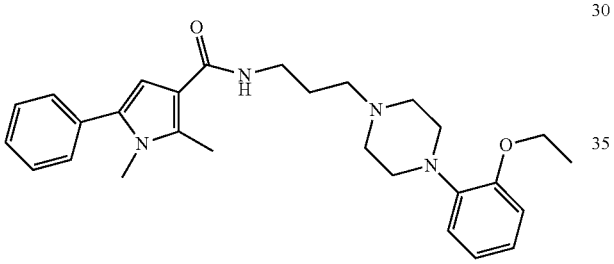

$^1$H NMR (400 MHz, DMSO-d$_6$) δ 7.76 (brs, 1H), 7.40-7.34 (m, 4H), 7.31-7.27 (m, 1H), 6.91-6.86 (m, 2H), 6.85-6.81 (m, 2H), 6.52 (s, 1H), 3.97 (q, J=6.8 Hz, 2H), 3.44 (s, 3H), 3.21-3.18 (m, 2H), 3.05-2.95 (m, 4H), 2.55 (s, 3H), 2.62-2.32 (m, 6H), 1.72-1.65 (m, 2H), 1.30 (t, J=6.8 Hz, 3H).
MH+461

Example 119

N-(3-(4-(2-Fluorophenyl)piperazin-1-yl)propyl)-1,2-dimethyl-5-phenyl-1H-pyrrole-3-carboxamide

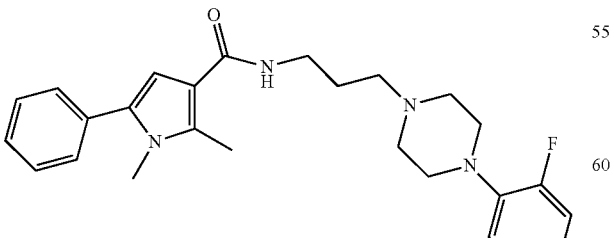

$^1$H NMR (400 MHz, DMSO-d$_6$) δ 7.72 (brs, 1H), 7.39-7.34 (m, 4H), 7.31-7.27 (m, 1H), 7.11-7.04 (m, 2H), 6.99-6.93 (m, 2H), 6.51 (s, 1H), 3.44 (s, 3H), 3.20 (q, J=6.4 Hz, 2H), 3.05-2.96 (m, 4H), 2.50 (s, 3H), 2.61-2.31 (m, 6H), 1.69-1.62 (m, 2H).
MH+435

Example 120

N-(3-(4-(3,4-Difluorophenyl)piperazin-1-yl)propyl)-1,2-dimethyl-5-phenyl-1H-pyrrole-3-carboxamide

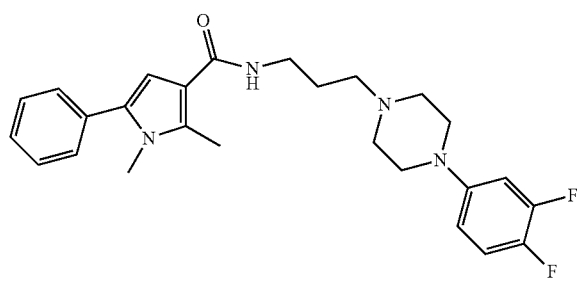 [SMILES: Cc1c(C(=O)NCCCN2CCN(c3ccc(F)c(F)c3)CC2)cc(-c2ccccc2)n1C]

$^1$H NMR (400 MHz, DMSO-d$_6$) δ 7.74 (brs, 1H), 7.37-7.31 (m, 4H), 7.29-7.25 (m, 1H), 7.21 (q, J=9.6 Hz, 1H), 6.96-6.93 (m, 1H), 6.70-6.67 (m, 1H), 6.49 (s, 1H), 3.43 (s, 3H), 3.22-3.17 (m, 2H), 3.12-3.05 (m, 4H), 2.49 (s, 3H), 2.51-2.42 (m, 6H), 1.69-1.62 (m, 2H).
MH+453

Example 121

1,2-Dimethyl-5-phenyl-N-(3-(4-(pyridin-2-yl)piperazin-1-yl)propyl)-1H-pyrrole-3-carboxamide

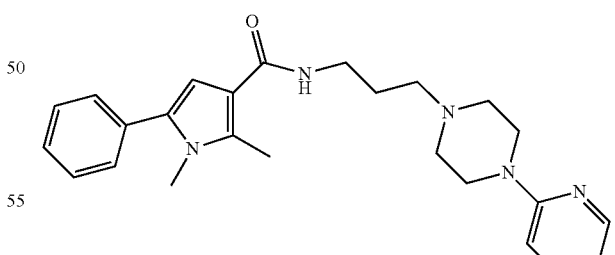

$^1$H NMR (400 MHz, DMSO-d$_6$) δ 8.09 (brs, 1H), 7.82-7.75 (m, 1H), 7.52-7.48 (m, 1H), 7.43-7.26 (m, 5H), 6.85-6.78 (m, 1H), 6.69-6.61 (m, 1H), 6.52 (s, 1H), 3.44 (s, 3H), 3.24-3.19 (m, 2H), 3.36-3.25 (m, 4H), 2.50 (s, 3H), 2.66-2.28 (m, 6H), 1.79-1.72 (m, 2H).
MH+418

Example 122

N-(3-(4-(2-Methoxyphenyl)piperazin-1-yl)propyl)-1,2-dimethyl-5-phenyl-1H-pyrrole-3-carboxamide

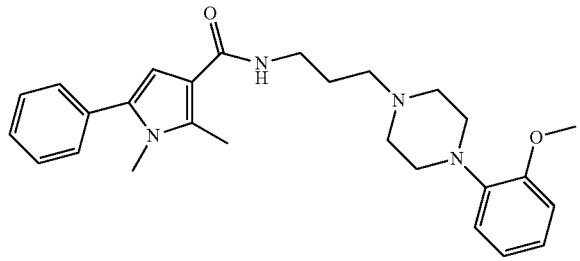 [SMILES: COc1ccccc1N1CCN(CCCNC(=O)c2cc(-c3ccccc3)n(C)c2C)CC1]

$^1$H NMR (400 MHz, DMSO-d$_6$) δ 7.75 (brs, 1H), 7.40-7.33 (m, 4H), 7.31-7.27 (m, 1H), 6.92-6.90 (m, 2H), 6.83-6.82 (m, 2H), 6.51 (s, 1H), 3.73 (s, 3H), 3.44 (s, 3H), 3.23-3.18 (m, 2H), 3.05-2.92 (m, 4H), 2.50 (s, 3H), 2.61-2.32 (m, 6H), 1.69-1.62 (m, 2H).
MH+447

Example 123

N-(3-(4-(3-Methoxyphenyl)piperazin-1-yl)propyl)-1,2-dimethyl-5-phenyl-1H-pyrrole-3-carboxamide

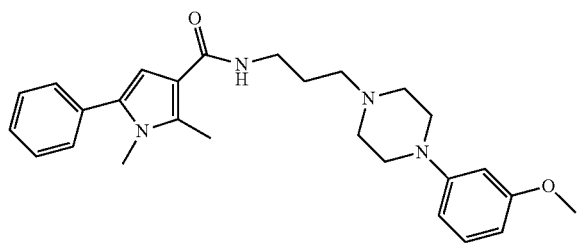 [SMILES: COc1cccc(N2CCN(CCCNC(=O)c3cc(-c4ccccc4)n(C)c3C)CC2)c1]

$^1$H NMR (400 MHz, DMSO-d$_6$) δ 7.74 (brs, 1H), 7.36-7.27 (m, 4H), 7.08 (t, J=8.4 Hz, 1H), 6.50 (s, 1H), 6.48 (s, 1H), 6.41 (s, 1H), 6.34 (d, J=7.2 Hz, 1H), 3.68 (s, 3H), 3.44 (s, 3H), 3.21 (q, J=6.4 Hz, 2H), 3.13-3.05 (m, 4H), 2.50 (s, 3H), 2.61-2.32 (m, 6H), 1.72-1.62 (m, 2H).
MH+447

Example 124

N-(3-(4-(2,3-dichlorophenyl)piperazin-1-yl)propyl)-5-phenyl-1H-pyrrole-3-carboxamide

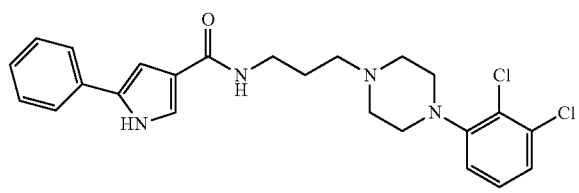 [SMILES: O=C(NCCCN1CCN(c2cccc(Cl)c2Cl)CC1)c1c[nH]c(-c2ccccc2)c1]

$^1$H NMR (400 MHz, CDCl$_3$) δ 9.99 (brs, 1H), 7.75 (t, J=4.4 Hz, 1H), 7.53-7.48 (m, 2H), 7.44-7.43 (m, 1H), 7.28-7.25 (m, 2H), 7.21-7.18 (m, 1H), 7.14 (dd, J=8.0, 1.6 Hz, 1H), 7.00 (t, J=8.0 Hz, 1H), 6.83 (dd, J=1.2, 8.0 Hz, 1H), 6.75 (t, J=2.0 Hz, 1H), 3.57 (dd, J=5.6, 11.2 Hz, 2H), 3.11 (brs, 4H), 2.69 (brs, 4H), 2.61 (t, J=6.0 Hz, 2H), 1.82-1.75 (m, 2H).MH+457

Example 125

N-(3-(4-(2,3-dichlorophenyl)piperazin-1-yl)propyl)-1-methyl-5-phenyl-1H-pyrrole-3-carboxamide

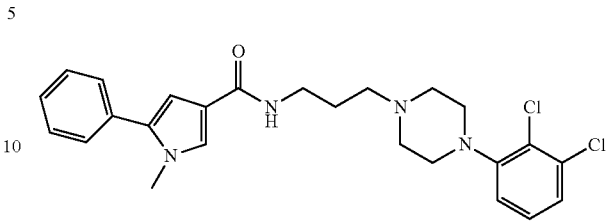

$^1$H NMR (400 MHz, CDCl$_3$) δ 7.45 (t, J=2.4 Hz, 1H), 7.36-7.32 (m, 4H), 7.30 (d, J=2.0 Hz, 1H), 7.14 (dd, J=1.2, 8.0 Hz, 1H), 7.00 (t, J=8.4 Hz, 1H), 6.74 (dd, J=1.2, 8.0 Hz, 1H), 6.46 (dd, J=1.6 Hz, 1H), 3.64 (s, 3H), 3.55 (q, J=5.6 Hz, 2H), 3.09 (brs, 4H), 2.69 (brs, 4H), 2.62 (t, J=6.0 Hz, 2H), 1.83-1.77 (m, 2H), 1.65 (brs, 1H).MH+471

Example 126

N-(3-(4-(2,3-dichlorophenyl)piperazin-1-yl)propyl)-5-phenyl-1-propyl-1H-pyrrole-3-carboxamide

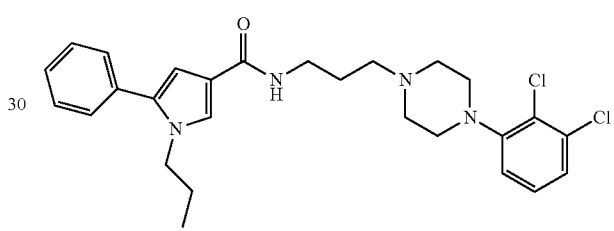

$^1$H NMR (400 MHz, CDCl$_3$) δ 7.52 (t, J=2.0 Hz, 1H), 7.36-7.30 (m, 6H), 7.14 (dd, J=1.2, 8.0 Hz, 1H), 7.01 (t, J=8.0 Hz, 1H), 6.72 (dd, J=1.2, 8.0 Hz, 1H), 6.42 (d, J=2.0 Hz, 1H), 3.86 (t, J=7.2 Hz, 2H), 3.55 (q, J=5.6 Hz, 2H), 3.08 (brs, 4H), 2.69 (brs, 4H), 2.61 (t, J=6.0 Hz, 2H), 1.83-1.77 (m, 2H), 1.71-1.61 (m, 3H), 0.79 (t, J=7.6 Hz, 3H).MH+499

Example 127

5-tert-butyl-N-(3-(4-(2,3-dichlorophenyl)piperazin-1-yl)propyl)-2-methyl-1H-pyrrole-3-carboxamide hydrochloride

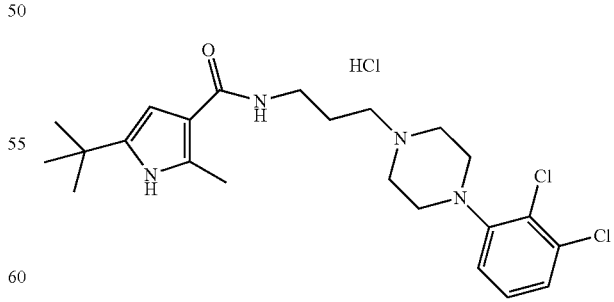

$^1$H NMR (400 MHz, CDCl$_3$) δ 7.78 (brs, 1H), 7.19-7.10 (m, 2H), 6.99 (brs, 1H), 6.93 (dd, J=7.2, 2.0 Hz, 1H), 5.98 (d, J=2.8 Hz, 1H), 3.50 (q, J=6.0 Hz, 2H), 3.13 (brs, 4H), 2.69 (brs, 4H), 2.59 (t, J=6.4 Hz, 2H), 2.54 (s, 3H), 1.82-1.76 (m, 2H), 1.23 (s, 9H).

Example 128

5-tert-butyl-N-(3-(4-(2,3-dichlorophenyl)piperazin-1-yl)propyl)-1,2-dimethyl-1H-pyrrole-3-carboxamide

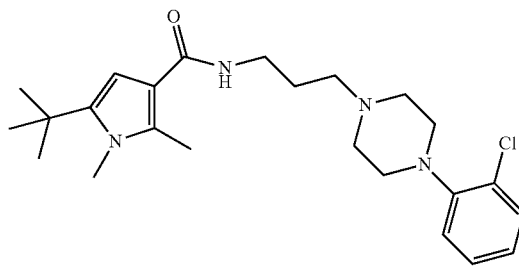

$^{1}$H NMR (400 MHz, CDCl$_3$) δ 7.17-7.10 (m, 2H), 6.92 (dd, J=2.0, 2.4 Hz, 1H), 6.87 (brs, 1H), 5.99 (s 1H), 3.58 (s, 3H), 3.49 (q, J=5.6 Hz, 2H), 3.11 (brs, 4H), 2.68 (brs, 4H), 2.58 (t, J=6.8 Hz, 2H), 2.55 (s, 3H), 1.80-1.77 (m, 2H), 1.33 (s, 9H).
MH+465

Example 129

N-(3-(4-(2-carbamoylbenzofuran-5-yl)piperazin-1-yl)propyl)-1,2-dimethyl-5-phenyl-1H-pyrrole-3-carboxamide

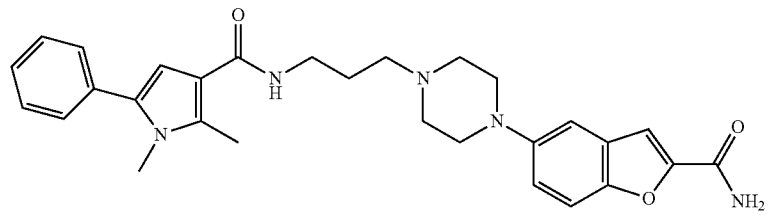 [SMILES: Cc1c(C(=O)NCCCN2CCN(c3ccc4oc(C(N)=O)cc4c3)CC2)cc(-c2ccccc2)n1C]

$^{1}$H NMR (400 MHz, CDCl$_3$) δ 7.36-7.30 (m, 6H), 7.16 (d, J=7.6 Hz, 1H), 7.01 (t, J=8.0 Hz, 1H), 6.72 (dd, J=2.0, 7.6 Hz, 1H), 6.44 (d, J=2.0 Hz, 1H), 3.55-3.51 (m, 2H), 3.51 (s, 3H), 3.06 (brs, 4H), 2.66 (brs, 2H), 2.64 (s, 3H), 2.61 (t, J=6.4 Hz, 2H), 1.83-1.77 (m, 2H).
MH+499

Example 130

N-(3-(4-(2-carbamoylbenzofuran-5-yl)piperazin-1-yl)propyl)-2-methyl-5-phenyl-1-propyl-1H-pyrrole-3-carboxamide

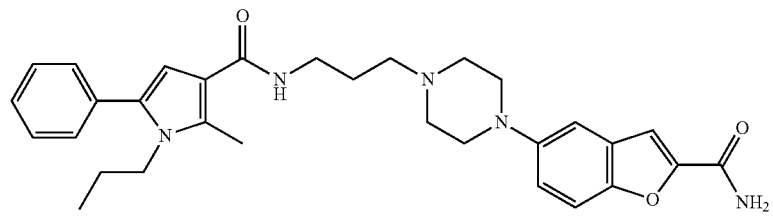 [SMILES: CCCn1c(-c2ccccc2)cc(C(=O)NCCCN2CCN(c3ccc4oc(C(N)=O)cc4c3)CC2)c1C]

$^{1}$H NMR (400 MHz, CDCl$_3$) δ 7.37-7.31 (m, 6H), 7.14 (d, J=7.6 Hz, 1H), 7.00 (t, J=8.0 Hz, 1H), 6.72 (dd, J=2.0, 7.6 Hz, 1H), 6.44 (d, J=2.0 Hz, 1H), 3.81 (t, J=8.0 Hz, 2H), 3.53 (t, J=6.0 Hz, 2H), 3.03 (brs, 4H), 2.67 (brs, 4H), 2.66 (s, 3H), 2.60 (t, J=6.0 Hz, 2H), 1.81-1.78 (m, 2H), 1.58-1.52 (m, 2H), 0.76 (t, J=7.2 Hz, 3H).
MH+527

Example 131

1,2-dimethyl-5-phenyl-N-(3-(4-(quinolin-8-yl)piperazin-1-yl)propyl)-1H-pyrrole-3-carboxamide

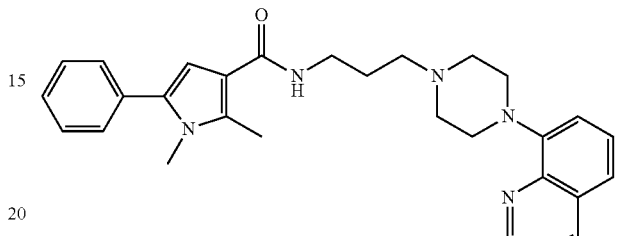

$^{1}$H NMR (400 MHz, CDCl$_3$) δ 8.88 (dd, J=1.6, 4.0 Hz, 1H), 8.10 (dd, J=1.6, 8.0 Hz, 1H), 7.45-7.31 (m, 8H), 7.13 (dd, J=3.6, 5.2 Hz, 1H), 6.46 (brs, 1H), 6.30 (s, 1H), 3.58 (q, J=6.0 Hz, 2H), 3.50 (s, 3H), 3.46 (brs, 3H), 2.87 (brs, 3H), 2.72 (t, J=6.0 Hz, 2H), 2.64 (s, 3H), 1.58-1.52 (m, 2H).
MH+467

Example 132

2-methyl-5-phenyl-1-propyl-N-(3-(4-(quinolin-8-yl)piperazin-1-yl)propyl)-1H-pyrrole-3-carboxamide

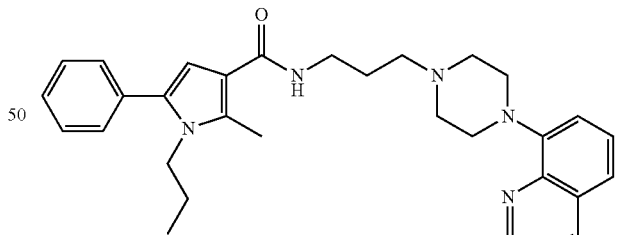

¹H NMR (400 MHz, CDCl₃) δ 8.90 (dd, J=1.6, 4.0 Hz, 1H), 8.12 (dd, J=1.6, 8.0 Hz, 1H), 7.46-7.30 (m, 8H), 7.14 (dd, J=4.0, 5.2 Hz, 1H), 6.50 (brs, 1H), 6.31 (s, 1H), 3.86 (t, J=7.2 Hz, 2H), 3.55 (q, J=5.6 Hz, 2H), 3.08 (brs, 4H), 2.69 (brs, 4H), 2.61 (t, J=6.0 Hz, 2H), 1.83-1.77 (m, 2H), 1.71-1.61 (m, 3H), 0.79 (t, J=7.6 Hz, 3H).
MH+467

Example 133

N-(3-(4-(benzo[d]isothiazol-3-yl)piperazin-1-yl)propyl)-1,2-dimethyl-5-phenyl-1H-pyrrole-3-carboxamide

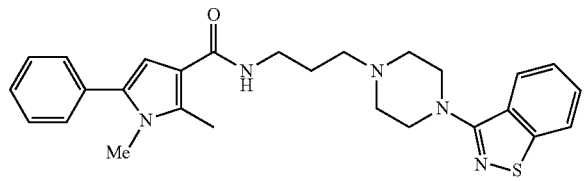 [SMILES: Cc1c(C(=O)NCCCN2CCN(c3nsc4ccccc34)CC2)cc(-c2ccccc2)n1C]

¹H NMR (400 MHz, CDCl₃) δ 7.89 (d, J=8.0 Hz, 1H), 7.83 (d, J=8.4 Hz, 1H), 7.47 (t, J=7.2 Hz, 1H), 7.35 (t, J=6.8 Hz, 1H), 7.31-7.24 (m, 5H), 7.16 (br, 1H), 6.31 (s, 1H), 3.61-3.59 (m, 4H), 3.54 (q, J=6.0 Hz, 2H), 3.48 (s, 3H), 2.74-2.72 (m, 4H), 2.64 (s, 3H), 2.62 (t, J=6.4 Hz, 2H), 1.85-1.79 (m, 2H).
MH+474

Example 134

N-(3-(4-(Benzo[d]isothiazol-3-yl)piperazin-1-yl)propyl)-2-methyl-5-phenyl-1-propyl-1H-pyrrole-3-carboxamide

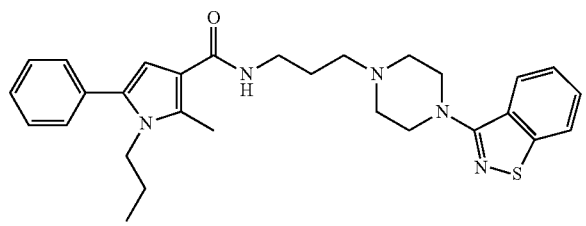 [SMILES: CCCn1c(-c2ccccc2)cc(C(=O)NCCCN2CCN(c3nsc4ccccc34)CC2)c1C]

¹H NMR (400 MHz, CDCl₃) δ 7.88 (d, J=8.0 Hz, 1H), 7.82 (d, J=8.0 Hz, 1H), 7.47 (t, J=7.2 Hz, 1H), 7.35 (t, J=7.2 Hz, 1H), 7.31-7.24 (m, 5H), 7.06 (br, 1H), 6.27 (s, 1H), 3.82-3.79 (m, 2H), 3.59-3.57 (m, 4H), 3.53 (q, J=6.0 Hz, 2H), 2.73-2.71 (m, 4H), 2.64 (s, 3H), 2.61 (t, J=6.4 Hz, 2H), 1.85-1.79 (m, 2H), 1.59-1.51 (m, 2H), 0.73 (t, J=7.6 Hz, 3H). MH+502

Example 135

5-(but-3-enyl)-N-(3-(4-(2,3-dichlorophenyl)piperazin-1-yl)propyl)-2-methyl-1H-pyrrole-3-carboxamide

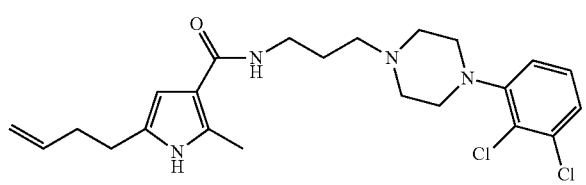 [SMILES: C=CCCc1cc(C(=O)NCCCN2CCN(c3cccc(Cl)c3Cl)CC2)c(C)[nH]1]

¹H NMR (400 MHz, CDCl₃) δ 7.77 (brs, 1H), 7.17-7.10 (m, 2H), 6.97 (brs, 1H), 6.93 (dd, J=2.0, 2.0 Hz, 1H), 6.01 (d, J=2.8 Hz, 1H), 5.87-5.78 (m, 1H), 5.06-5.00 (m, 2H), 3.49 (q, J=6.0 Hz, 2H), 3.10 (brs, 4H), 2.68 (brs, 4H), 262-2.57 (m, 4H), 2.54 (s, 3H), 2.33 (t, J=6.8 Hz, 2H), 1.80-1.77 (m, 2H).
MH+448

Example 136

5-(but-3-enyl)-N-(3-(4-(2,3-dichlorophenyl)piperazin-1-yl)propyl)-1,2-dimethyl-1H-pyrrole-3-carboxamide

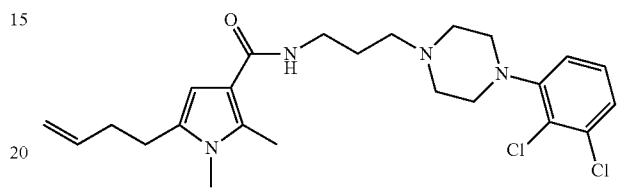

¹H NMR (400 MHz, CDCl₃) δ 7.17-7.10 (m, 2H), 6.93 (dd, J=2.0, 2.0 Hz, 1H), 6.01 (s 1H), 5.87-5.77 (m, 1H), 5.04-4.98 (m, 2H), 3.51-3.47 (m, 4H), 3.39 (s, 3H), 3.11 (brs, 4H), 2.68 (brs, 4H), 2.59-2.56 (m, 2H), 2.55 (s, 3H), 2.35-2.31 (m, 2H), 1.78 (t, J=6.0 Hz, 2H).
MH+462

Example 137

5-butyl-N-(3-(4-(2,3-dichlorophenyl)piperazin-1-yl)propyl)-2-methyl-1H-pyrrole-3-carboxamide

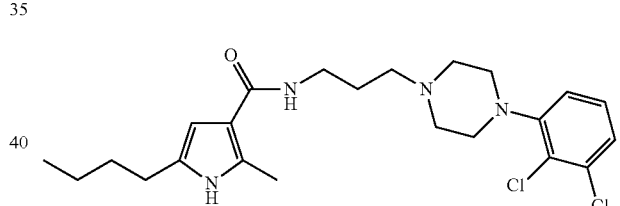

¹H NMR (400 MHz, CDCl₃) δ 7.73 (brs, 1H), 7.17-7.11 (m, 2H), 6.94 (dd, J=2.0, 2.4 Hz, 1H), 5.98 (d, J=2.8 Hz, 1H), 3.49 (q, J=5.6 Hz, 2H), 3.11 (brs, 4H), 2.68 (brs, 4H), 2.58 (t, J=6.0 Hz, 2H), 2.53 (s, 3H), 2.48 (t, J=7.6 Hz, 2H), 1.81-1.75 (m, 2H), 1.53-1.49 (m, 2H), 1.36-1.26 (m, 2H), 0.86 (t, J=7.6 Hz, H).
MH+450

Example 138

5-butyl-N-(3-(4-(2,3-dichlorophenyl)piperazin-1-yl)propyl)-1,2-dimethyl-1H-pyrrole-3-carboxamide

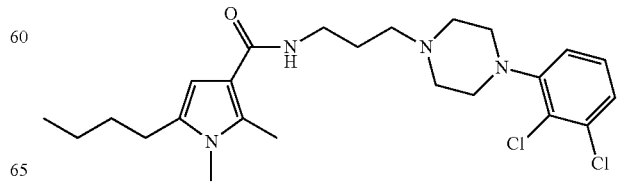

¹H NMR (400 MHz, CDCl₃) δ 7.17-7.11 (m, 2H), 6.93(dd, J=2.0, 2.0 Hz, 1H), 5.99 (s, 1H), 3.49 (q, J=5.6 Hz, 2H), 3.38 (s, 3H), 3.11 (brs, 4H), 2.68 (brs, 4H), 2.58 (t, J=6.4 Hz, 2H), 2.55 (s, 3H), 2.49 (dd, J=7.6, 8.0 Hz, 2H), 1.81-1.75 (m, 2H), Example 139

N-(3-(4-(2,3-dichlorophenyl)piperazin-1-yl)propyl)-2,5-dimethyl-1H-pyrrole-3-carboxamide

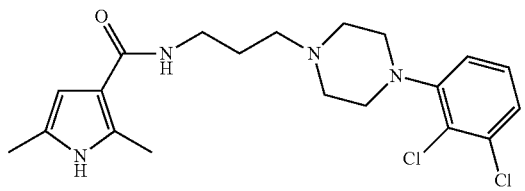 [SMILES: Cc1cc(C(=O)NCCCN2CCN(c3cccc(Cl)c3Cl)CC2)c(C)[nH]1]

MH+408

Example 140

N-(3-(4-(2,3-dichlorophenyl)piperazin-1-yl)propyl)-1,2,5-trimethyl-1H-pyrrole-3-carboxamide

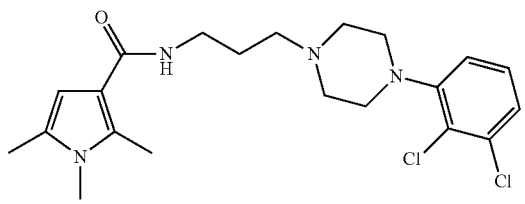 [SMILES: Cc1cc(C(=O)NCCCN2CCN(c3cccc(Cl)c3Cl)CC2)c(C)n1C]

¹H NMR (400 MHz, CDCl₃) δ 7.18-7.14 (m, 2H), 6.95 (dd, J=2.4, 2.4 Hz, 1H), 6.01 (s, 1H), 3.51-3.46 (m, 2H), 3.10 (brs, 4H), 2.68 (brs, 4H), 2.59-2.55 (m, 2H), 2.54 (s, 3H), 2.16 (s, 3H), 1.81-1.74 (m, 2H).
MH+422.

Example 141

N-(3-(4-(2,3-dichlorophenyl)piperazin-1-yl)propyl)-5-(4-hydroxybutyl)-2-methyl-1H-pyrrole-3-carboxamide

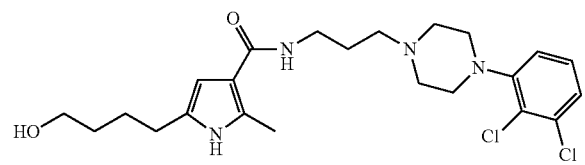 [SMILES: Cc1[nH]c(CCCCO)cc1C(=O)NCCCN1CCN(c2cccc(Cl)c2Cl)CC1]

¹H NMR (400 MHz, CDCl₃) δ 7.88 (brs, 1H), 7.19-7.13 (m, 2H), 6.94(dd, J=2.0, 2.8 Hz, 1H), 5.99 (d, J=2.8 Hz, 1H), 3.61 (t, J=6.0 Hz, 2H), 3.49 (q, J=6.0 Hz, 2H), 3.10 (brs, 4H), 2.68 (brs, 4H), 2.63-2.54 (m, 4H), 2.52 (s, 3H), 1.81-1.75 (m, 2H), 1.70-1.54 (m, 4H).
MH+466.

Example 142

N-(3-(4-(2,3-dichlorophenyl)piperazin-1-yl)propyl)-5-(4-hydroxybutyl)-1,2-dimethyl-1H-pyrrole-3-carboxamide

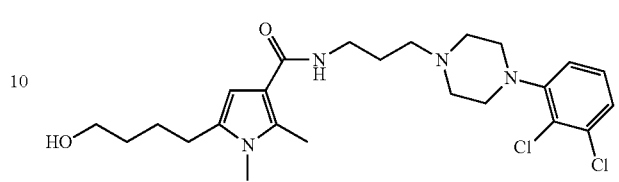

¹H NMR (400 MHz, CDCl₃) δ 7.16-7.14 (m, 2H), 6.94(dd, J=2.4, 2.4 Hz, 1H), 5.99(s, 1H), 3.58 (t, J=6.4 Hz, 3H), 3.48 (t, J=6.4 Hz, 2H), 3.40 (s, 3H), 3.10 (brs, 4H), 2.67 (brs, 4H), 2.59-2.50 (m, 4H), 2.53 (s, 3H), 1.81-1.75 (m, 2H), 1.70-1.53 (m, 4H).
MH+480

Example 143

N-(3-(4-(2,3-dihydrobenzo[b][1,4]dioxin-5-yl)piperazin-1-yl)propyl)-1,2-dimethyl-5-phenyl-1H-pyrrole-3-carboxamide

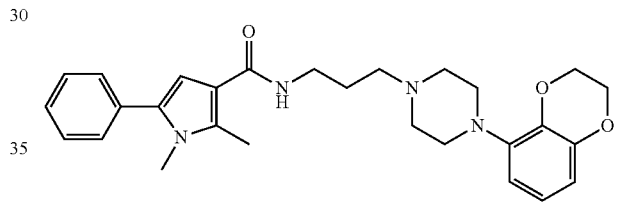

¹H NMR (400 MHz, CDCl₃) δ 7.42-7.27 (m, 6H), 6.70 (t, J=8.4 Hz, 1H), 6.59 (dd, J=1.6, 8.4 Hz, 1H), 6.37 (dd, J=1.6, 8.4 Hz, 1H), 6.35 (s, 1H), 4.34-4.28 (m, 2H), 4.27-4.22 (m, 2H), 3.53 (quartet, J=5.6 Hz, 2H), 3.49 (s, 3H), 3.11 (brs, 4H), 2.79-2.57 (m, 9H), 1.86-1.75 (m, 2H).
MH+475.

Example 144

N-(3-(4-(2,3-dihydrobenzo[b][1,4]dioxin-5-yl)piperazin-1-yl)propyl)-2-methyl-5-phenyl-1-propyl-1H-pyrrole-3-carboxamide

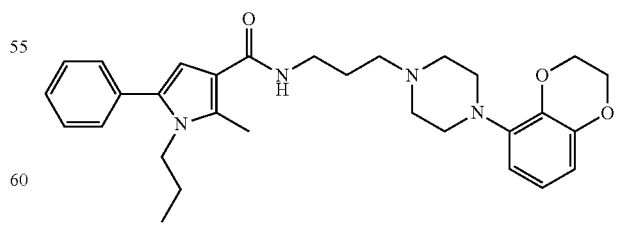

¹H NMR (400 MHz, CDCl₃) δ 7.38-7.27 (m, 5H), 6.69 (t, J=8.4 Hz, 1H), 6.58 (dd, J=8.4, 1.6 Hz, 1H), 6.34 (dd, J=8.4, 1.6 Hz, 1H), 6.30 (s, 1H), 4.35-4.29 (m, 2H), 4.26-4.21 (m, 2H), 3.85-3.78 (m, 2H), 3.52 (quartet, J=5.6 Hz, 2H), 3.08

(brs, 4H), 2.76-2.55 (m, 8H), 1.85-1.76 (m, 2H), 1.56 (quartet, J=7.6 Hz, 2H), 0.74 (t, J=7.2 Hz, 3H).
MH+503

Example 145

1,2-dimethyl-5-(pyridin-2-yl)-N-(3-(4-(quinoxalin-5-yl)piperazin-1-yl)propyl)-1H-pyrrole-3-carboxamide

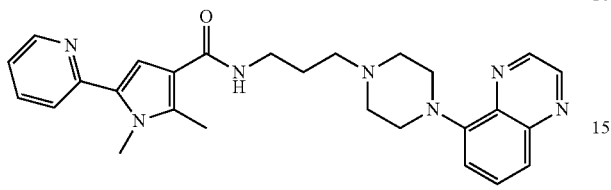

¹H NMR (400 MHz, CDCl₃) δ 8.57-8.55 (m, 1H), 8.32 (dd, J=3.2, 6.0 Hz, 2H), 7.50-7.46 (m, 1H), 7.41-7.39 (m, 2H), 7.13 (dd, J=1.6, 8.0 Hz, 1H), 7.10-7.06 (m, 1H), 6.98 (t, J=8.0 Hz, 1H), 6.70 (dd, J=1.6, 8.0 Hz, 1H), 6.67 (s, 1H), 3.84 (s, 3H), 3.54 (q, J=6.0 Hz, 2H), 3.08 (brs, 4H), 2.71 (brs, 3H), 2.64 (s, 3H), 2.61 (t, J=5.6 Hz, 4H), 1.82-1.77 (m, 2H).
MH+469 (—HCl)

Example 146

2-methyl-1-propyl-5-(pyridin-2-yl)-N-(3-(4-(quinoxalin-5-yl)piperazin-1-yl)propyl)-1H-pyrrole-3-carboxamide

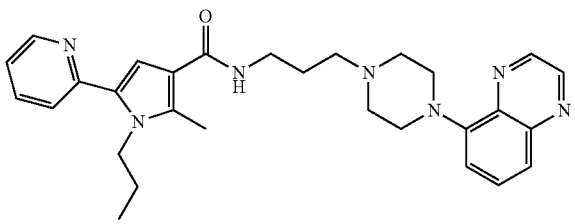 [SMILES: CCCn1c(-c2ccccn2)cc(C(=O)NCCCN2CCN(c3cccc4nccnc34)CC2)c1C]

¹H NMR (400 MHz, CDCl₃) δ 8.53 (d, J=4.8 Hz, 1H), 8.32 (dd, J=3.2, 6.0 Hz, 2H), 7.60-7.45 (m, 3H), 7.20-7.06 (m, 3H), 6.96-6.90 (m, 2H), 4.39 (t, J=7.6 Hz, 2H), 3.56 (q, J=5.6 Hz, 2H), 3.38 (brs, 5H), 3.03 (brs, 5H), 2.65 (s, 3H), 2.14 (brs, 2H), 1.67-1.58 (m, 2H), 0.81 (t, J=7.2 Hz, 3H).
MH+497 (—HCl)

Example 147

1,2-dimethyl-5-(pyridin-2-yl)-N-(3-(4-(quinolin-8-yl)piperazin-1-yl)propyl)-1H-pyrrole-3-carboxamide dihydrochloride

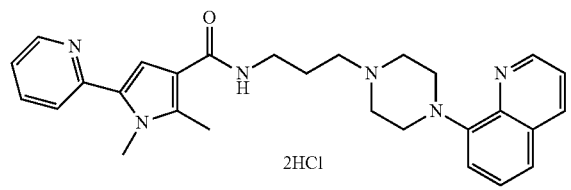 [SMILES: Cc1c(C(=O)NCCCN2CCN(c3cccc4cccnc34)CC2)cc(-c2ccccn2)n1C]

¹H NMR (400 MHz, MeOH-d₄) δ 8.88 (dd, J=1.6, 4.0 Hz, 1H), 8.52 (dd, J=4.0, 4.8 Hz, 1H), 8.11 (dd, J=1.6, 8.0 Hz, 1H), 7.67 (t, J=4.8 Hz, 1H), 7.43 (d, J=7.2 Hz, 1H), 7.39-7.25 (m, 5H), 7.04-7.00 (m, 1H), 6.96 (dd, J=8.0, 7.6 Hz, 1H), 6.71 (s, 1H), 3.59-3.55 (m, 2H), 3.50 (brs, 1H), 2.88 (brs, 4H), 2.69 (t, J=5.6 Hz, 2H), 2.65 (s, 3H), 1.87-1.81 (m, 2H).
MH+469 (–2HCl)

Example 148

2-methyl-1-propyl-5-(pyridin-2-yl)-N-(3-(4-(quinolin-8-yl)piperazin-1-yl)propyl)-1H-pyrrole-3-carboxamide dihydrochloride

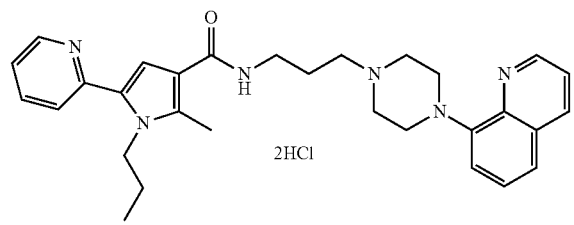 [SMILES: CCCn1c(-c2ccccn2)cc(C(=O)NCCCN2CCN(c3cccc4cccnc34)CC2)c1C]

¹H NMR (400 MHz, MeOH-d₄) δ 8.88 (dd, J=1.6, 4.0 Hz, 1H), 8.51-8.50 (m, 1H), 8.11 (dd, J=1.6, 8.4 Hz, 1H), 7.62 (t, J=2.4 Hz, 1H), 7.42 (dd, J=1.2, 8.4 Hz, 1H), 7.39-7.33 (m, 3H), 7.24 (dd, J=1.6, 8.0 Hz, 1H), 7.02-6.95 (m, 2H), 6.71 (s, 1H), 3.57 (q, J=5.6 Hz, 2H), 3.49 (brs, 4H), 2.88 (brs, 4H), 2.71-2.66 (m, 2H), 2.66 (s, 3H), 1.87-1.81 (m, 2H), 1.65-1.58 (m, 2H), 0.79 (t, J=7.2 Hz, 3H).
MH+497 (—HCl)

Example 149

2-methyl-5-(pyridin-2-yl)-N-(3-(4-(quinolin-8-yl)piperazin-1-yl)propyl)-1H-pyrrole-3-carboxamide

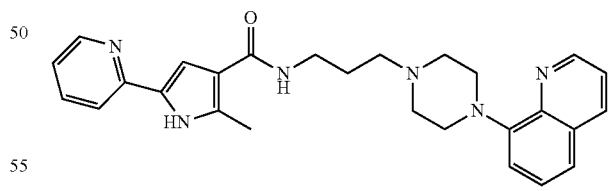

¹H NMR (400 MHz, MeOH-d₄) δ 8.86 (dd, J=1.6, 4.0 Hz, 1H), 8.51-8.50 (m, 1H), 8.11 (dd, J=1.6, 8.4 Hz, 1H), 7.62 (t, J=2.4 Hz, 1H), 7.42 (dd, J=1.2, 8.4 Hz, 1H), 7.39-7.33 (m, 3H), 7.24 (dd, J=1.6, 8.0 Hz, 1H), 7.02-6.95 (m, 2H), 6.71 (s, 1H), 3.49 (brs, 4H), 2.88 (brs, 4H), 2.71-2.66 (m, 2H), 2.66 (s, 3H), 1.65-1.58 (m, 2H).
MH+455 (—HCl)

Example 150

N-(3-(4-(benzo[d][1,3]dioxol-4-yl)piperazin-1-yl)propyl)-1,2-dimethyl-5-phenyl-1H-pyrrole-3-carboxamide

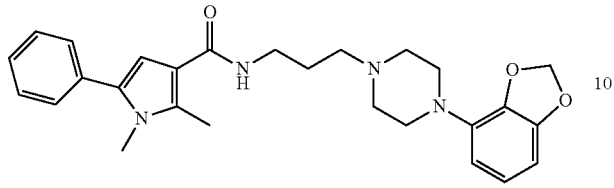

¹H NMR (400 MHz, CDCl₃) δ 7.42-7.35 (m, 1H), 7.29-7.17 (m, 5H), 6.47 (t, J=8.0 Hz, 1H), 6.59 (dd, J=8.0, 1.2 Hz, 1H), 6.34 (dd, J=8.0, 1.2 Hz, 1H), 6.32 (s, 1H), 5.92 (s, 2H), 3.53 (quartet, J=5.6 Hz, 2H), 3.49 (s, 3H), 3.24 (br t, J=4.4 Hz, 4H), 2.71-2.52 (m, 7H), 2.58 (t, J=6.0 Hz, 2H), 1.79 (quartet, J=6.0 Hz, 2H).
MH+461

Example 151

N-(3-(4-(benzo[d][1,3]dioxol-4-yl)piperazin-1-yl)propyl)-2-methyl-5-phenyl-1-propyl-1H-pyrrole-3-carboxamide

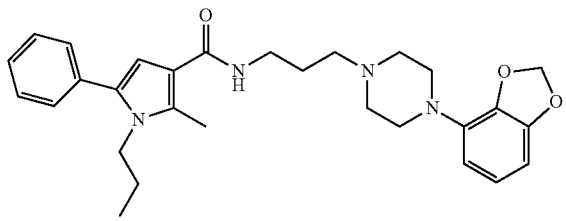 [SMILES: CCCn1c(-c2ccccc2)cc(C(=O)NCCCN2CCN(c3cccc4c3OCO4)CC2)c1C]

¹H NMR (400 MHz, CDCl₃) δ 7.32-7.19 (m, 6H), 6.73 (t, J=8.0 Hz, 1H), 6.53 (dd, J=8.0, 1.2 Hz, 1H), 6.32 (dd, J=8.0, 1.2 Hz, 1H), 6.28 (s, 1H), 5.92 (s, 2H), 3.81 (t, J=7.6 Hz, 2H), 3.52 (quartet, J=5.6 Hz, 2H), 3.21 (brs, 4H), 2.71-2.61 (m, 7H), 2.58 (t, J=6.0 Hz, 2H), 1.79 (quartet, J=6.0 Hz, 2H), 1.56 (sextet, J=7.2 Hz, 2H), 0.74 (t, J=7.2 Hz, 3H).
MH+489

Example 152

N-(3-(4-(2,3-dichlorophenyl)piperazin-1-yl)-2-hydroxypropyl)-1,2-dimethyl-5-phenyl-1H-pyrrole-3-carboxamide hydrochloride

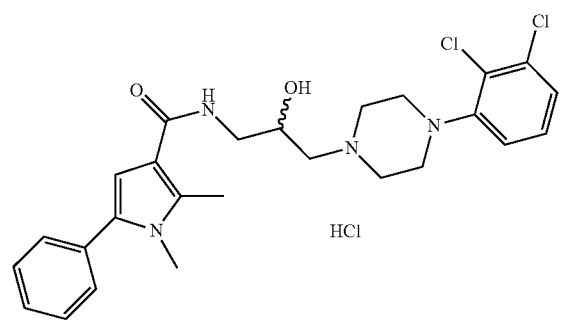 [SMILES: Cc1c(C(=O)NCC(O)CN2CCN(c3cccc(Cl)c3Cl)CC2)cc(-c2ccccc2)n1C ; Cl]

MH+501

Example 153

N-(3-(4-(2,3-dichlorophenyl)piperazin-1-yl)-2-hydroxypropyl)-2-methyl-5-phenyl-1-propyl-1H-pyrrole-3-carboxamide hydrochloride

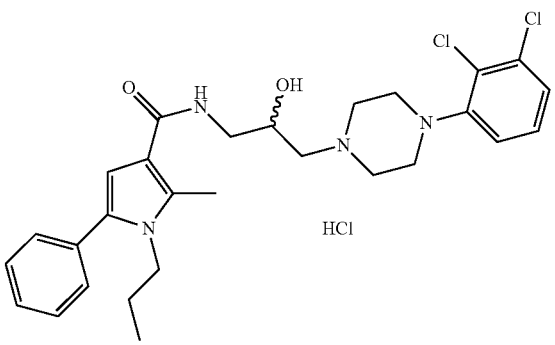 [SMILES: CCCn1c(-c2ccccc2)cc(C(=O)NCC(O)CN2CCN(c3cccc(Cl)c3Cl)CC2)c1C ; Cl]

MH+529

Example 154

N-(3-(4-(2,4-Dichlorophenyl)piperazin-1-yl)propyl)-1,2-dimethyl-5-phenyl-1H-pyrrole-3-carboxamide hydrochloride

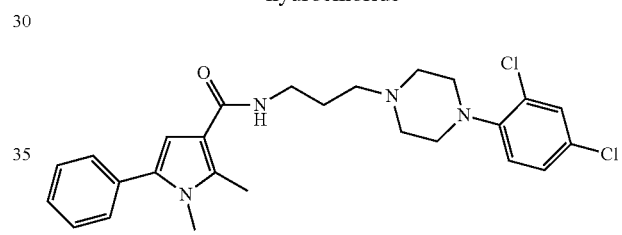

¹H NMR (400 MHz, DMSO-d₆) δ 10.95 (brs, 1H), 7.91 (brs, 1H), 7.57 (d, J=2.0 Hz, 1H), 7.43-7.28 (m, 6H), 7.19 (d, J=8.4 Hz, 1H), 6.58 (s, 1H), 4.38-4.28 (m, 4H), 3.54-3.52 (m, 2H), 3.44 (s, 3H), 3.38-3.35 (m, 2H), 3.25-3.13 (m, 4H), 2.51 (s, 3H), 1.94-1.91 (m, 2H).
MH+485

Example 155

N-(3-(4-(4-Fluorophenyl)piperazin-1-yl)propyl)-1,2-dimethyl-5-phenyl-1H-pyrrole-3-carboxamide

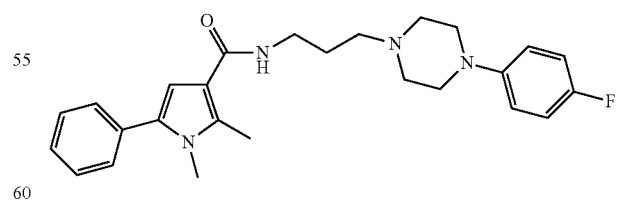

¹H NMR (400 MHz, DMSO-d₆) δ 7.70 (brs, 1H), 7.36-7.25 (m, 5H), 7.00 (t, J=8.8 Hz, 2H), 6.91-6.88 (m, 2H), 6.49 (s, 1H), 3.43 (s, 3H), 3.20 (q, J=6.0 Hz, 2H), 3.08-3.01 (m, 4H), 2.49 (s, 3H), 2.54-2.46 (m, 4H), 2.39-2.32 (m, 2H), 1.68-1.62 (m, 2H).
MH+435

Example 156

N-(3-(4-(2,5-Ddichlorophenyl)piperazin-1-yl)propyl)-1,2-dimethyl-5-phenyl-1H-pyrrole-3-carboxamide

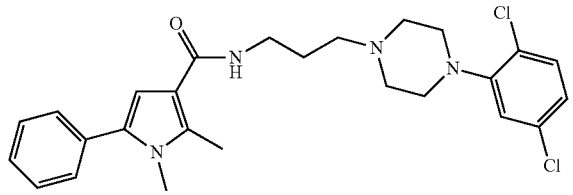 [SMILES: Cc1c(C(=O)NCCCN2CCN(c3cc(Cl)ccc3Cl)CC2)cc(-c2ccccc2)n1C]

¹H NMR (400 MHz, DMSO-d₆) δ 7.67 (brs, 1H), 7.40-7.34 (m, 5H), 7.31-7.26 (m, 1H), 7.09-7.04 (m, 2H), 6.51 (s, 1H), 3.44 (s, 3H), 3.21-3.17 (m, 2H), 3.03-2.92 (m, 4H), 2.49 (s, 3H), 2.58-2.51 (m, 4H), 2.39-2.32 (m, 2H), 1.66-1.61 (m, 2H).
MH+485

Example 157

1,2-Dimethyl-5-phenyl-N-(3-(4-(pyridin-4-yl)piperazin-1-yl)propyl)-1H-pyrrole-3-carboxamide dihydrochloride

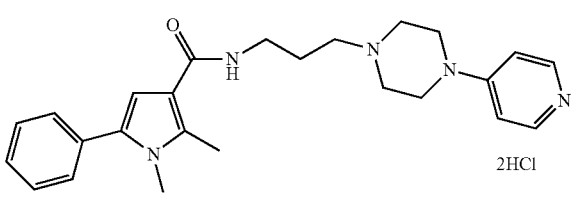 [SMILES: Cc1c(C(=O)NCCCN2CCN(c3ccncc3)CC2)cc(-c2ccccc2)n1C]

¹H NMR (400 MHz, DMSO-d₆) δ 8.32 (d, J=7.6 Hz, 2H), 7.92-7.87 (m, 1H), 7.43-7.35 (m, 4H), 7.32-7.28 (m, 1H), 7.25 (d, J=7.6 Hz, 2H), 6.58 (s, 1H), 3.44 (s, 3H), 4.21-3.88 (m, 4H), 3.34-3.22 (m, 6H), 3.08-3.04 (m, 2H), 2.50 (s, 3H), 1.94-1.92 (m, 2H).
MH+418

Example 158

N-(3-(4-(2,3-dimethoxyphenyl)piperazin-1-yl)propyl)-1,2-dimethyl-5-phenyl-1H-pyrrole-3-carboxamide

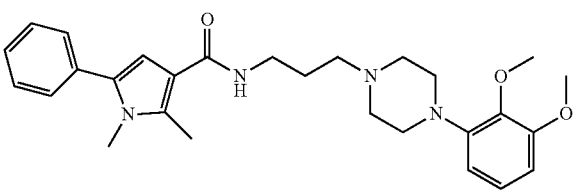 [SMILES: COc1cccc(N2CCN(CCCNC(=O)c3cc(-c4ccccc4)n(C)c3C)CC2)c1OC]

¹H NMR (400 MHz, CDCl₃) δ 7.43-7.37 (m, 1H), 7.31-7.25 (m, 5H), 6.90 (t, J=8.4 Hz, 1H), 6.61 (dd, J=8.4, 1.2 Hz, 1H), 6.41 (dd, J=8.4, 1.2 Hz, 1H), 6.35 (s, 1H), 3.85 (s, 3H), 3.82 (s, 3H), 3.53 (quartet, J=6.0 Hz, 2H), 3.45 (s, 3H), 3.17 (brs, 4H), 2.70-2.62 (m, 7H), 2.58 (t, J=6.0 Hz, 2H), 1.80 (quartet, J=6.0 Hz, 2H).
MH+477

Example 159

N-(3-(4-(2,3-dimethoxyphenyl)piperazin-1-yl)propyl)-2-methyl-5-phenyl-1-propyl-1H-pyrrole-3-carboxamide

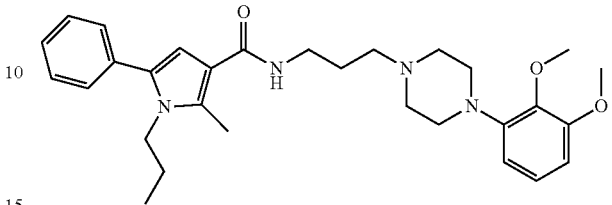

¹H NMR (400 MHz, CDCl₃) δ 7.35-7.25 (m, 6H), 6.90 (t, J=8.0 Hz, 1H), 6.61 (dd, J=8.4, 1.2 Hz, 1H), 6.38 (dd, J=8.4, 1.2 Hz, 1H), 6.31 (s, 1H), 3.87-3.78 (m, 8H), 3.53 (quartet, J=5.6 Hz, 2H), 3.17 (brs, 4H), 2.69-2.55 (m, 9H), 1.78 (quartet, J=6.0 Hz, 2H), 1.62-1.49 (m, 2H), 0.74 (t, J=7.2 Hz, 3H).
MH+505

Example 160

N-(3-(4-(2,3-dichlorophenyl)piperazin-1-yl)propyl)-5-(4-methoxybutyl)-1,2-dimethyl-1H-pyrrole-3-carboxamide hydrochloride

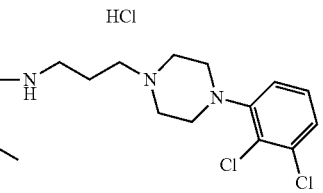

¹H NMR (400 MHz, CDCl₃) δ 7.17-7.13 (m, 2H), 6.94 (dd, J=2.4, 2.4 Hz, 1H), 5.99 (s, 1H), 3.49 (d, J=6.0 Hz, 2H), 3.38 (s, 3H), 3.28 (s, 3H), 3.10 (brs, 4H), 2.68 (brs, 4H), 2.59-2.48 (m, 6H), 2.54 (s, 3H), 1.79-1.76 (m, 2H), 1.66-1.57 (m, 4H).
MH+494

Example 161

2-methyl-5-phenyl-N-(3-(4-(quinolin-6-yl)piperazin-1-yl)propyl)-1H-pyrrole-3-carboxamide

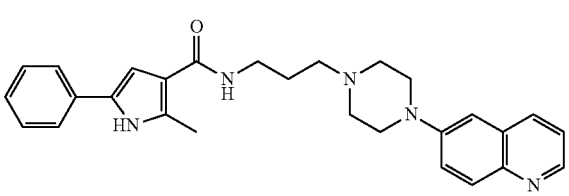 [SMILES: Cc1[nH]c(-c2ccccc2)cc1C(=O)NCCCN1CCN(c2ccc3ncccc3c2)CC1]

¹H NMR (400 MHz, CDCl₃) δ 8.73 (dd, J=1.6, 4.0 Hz, 1H), 7.97 (d, J=8.0 Hz, 1H), 7.91 (d, J=7.6 Hz, 1H), 7.44 (dd, J=2.4, 9.2 Hz, 1H), 7.41 (t, J=2.0 Hz, 1H), 7.31 (dd, J=4.0, 8.0 Hz, 1H), 7.15-7.13 (m, 1H), 7.00-6.93 (m, 4H), 6.28 (s, 1H), 3.58-3.53 (m, 2H), 3.36 (t, J=4.8 Hz, 2H), 2.72 (brs, 5H), 2.64 (s, 3H), 2.64-2.62 (m, 3H), 1.86-1.81 (m, 2H).
MH+453

Example 162

1,2-dimethyl-5-phenyl-N-(3-(4-(quinolin-6-yl)piperazin-1-yl)propyl)-1H-pyrrole-3-carboxamide

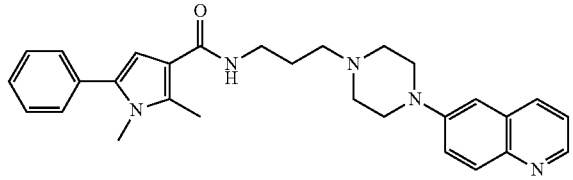 [SMILES: Cc1c(C(=O)NCCCN2CCN(c3ccc4ncccc4c3)CC2)cc(-c2ccccc2)n1C]

$^1$H NMR (400 MHz, CDCl$_3$) δ 8.74 (dd, J=1.6, 4.0 Hz, 1H), 7.98 (d, J=8.0 Hz, 1H), 7.92 (d, J=7.6 Hz, 1H), 7.45 (dd, J=2.4, 9.2 Hz, 1H), 7.41 (t, J=2.0 Hz, 1H), 7.31 (dd, J=4.0, 8.0 Hz, 1H), 7.15-7.13 (m, 1H), 7.00-6.93 (m, 4H), 6.28 (s, 1H), 3.58-3.53 (m, 2H), 3.45 (s, 3H), 3.37 (t, J=4.8 Hz, 2H), 2.72 (brs, 5H), 2.64 (s, 3H), 2.64-2.62 (m, 3H), 1.86-1.80 (m, 2H).
MH+467

Example 163

2-methyl-5-(pyridin-2-yl)-N-(3-(4-(quinolin-6-yl)piperazin-1-yl)propyl)-1H-pyrrole-3-carboxamide

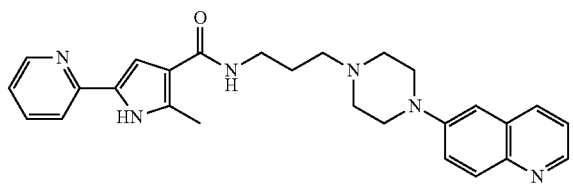 [SMILES: Cc1[nH]c(-c2ccccn2)cc1C(=O)NCCCN1CCN(c2ccc3ncccc3c2)CC1]

$^1$H NMR (400 MHz, CDCl$_3$) δ 9.44 (brs, 1H), 8.74 (dd, J=1.6, 4.4 Hz, 1H), 8.29-8.27 (m, 1H), 7.98 (d, J=9.2 Hz, 1H), 7.86 (d, J=7.6 Hz, 1H), 7.65 (t, J=2.0 Hz, 1H), 7.52 (dd, J=2.4, 8.8 Hz, 1H), 7.29 (dd, J=4.4, 6.4 Hz, 1H), 7.03 (d, J=7.6 Hz, 1H), 6.96 (d, J=6.0 Hz, 1H), 6.76 (d, J=2.4 Hz, 1H), 6.70-6.66 (m, 2H), 3.58 (q, J=6.4 Hz, 2H), 3.44 (t, J=4.8 Hz, 4H), 2.77 (t, J=4.4 Hz, 4H), 2.67 (t, J=5.6 Hz, 2H), 2.62 (s, 3H), 1.88-1.82 (m, 2H).
MH+454

Example 164

1,2-dimethyl-5-(pyridin-2-yl)-N-(3-(4-(quinolin-6-yl)piperazin-1-yl)propyl)-1H-pyrrole-3-carboxamide

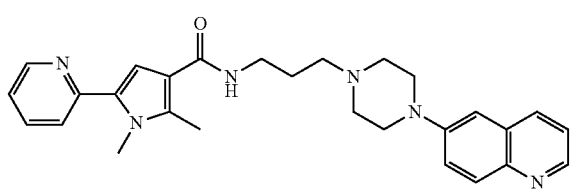 [SMILES: Cc1c(C(=O)NCCCN2CCN(c3ccc4ncccc4c3)CC2)cc(-c2ccccn2)n1C]

$^1$H NMR (400 MHz, CDCl$_3$) δ 8.74 (d, J=2.8 Hz, 1H), 8.33 (d, J=4.4 Hz, 1H), 7.96 (d, J=9.2 Hz, 1H), 7.89 (d, J=7.6 Hz, 1H), 7.58 (t, J=2.0 Hz, 1H), 7.47 (dd, J=2.8, 12.0 Hz, 1H), 7.31 (dd, J=4.0, 8.0 Hz, 1H), 7.13 (d, J=8.0 Hz, 1H), 6.90 (d, J=2.4 Hz, 1H), 6.73-6.62 (m, 2H), 3.80 (s, 3H), 3.56 (q, J=4.8Hz, 2H), 3.40 (t, J=4.4 Hz, 4H), 2.74 (brs, 4H), 2.64 (s, 3H), 1.85-1.82 (m, 2H).
MH+469

Example 165

1,2-dimethyl-N-(3-(4-(2-methylquinolin-8-yl)piperazin-1-yl)propyl)-5-phenyl-1H-pyrrole-3-carboxamide

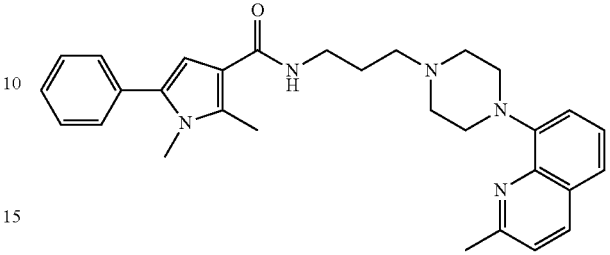

$^1$H NMR (400 MHz, CDCl$_3$) δ 8.12 (dd, J=1.6, 8.0 Hz, 1H), 7.44-7.32 (m, 8H), 7.15 (dd, J=3.6, 5.2 Hz, 1H), 6.46 (brs, 1H), 6.31 (s, 1H), 3.57 (q, J=6.0 Hz, 2H), 3.52 (s, 3H), 3.46 (brs, 3H), 2.87 (brs, 3H), 2.72 (t, J=6.0 Hz, 2H), 2.64 (s, 3H), 2.53 (s, 3H), 1.58-1.52 (m, 2H).
MH+481

Example 166

2-methyl-N-(3-(4-(2-methylquinolin-8-yl)piperazin-1-yl)propyl)-5-phenyl-1-propyl-1H-pyrrole-3-carboxamide

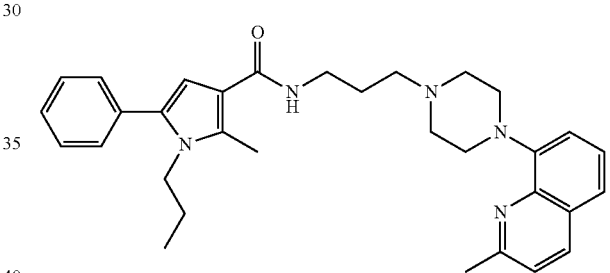

$^1$H NMR (400 MHz, CDCl$_3$) δ 8.14 (dd, J=1.6, 8.0 Hz, 1H), 7.48-7.36 (m, 8H), 7.16 (dd, J=4.0, 5.2 Hz, 1H), 6.50 (brs, 1H), 6.31 (s, 1H), 3.86 (t, J=7.2 H, 2H), 3.55 (q, J=5.6 Hz, 2H), 3.08 (brs, 4H), 2.69 (brs, 4H), 2.61 (t, J=6.0 Hz, 2H), 2.55 (s, 3H), 1.83-1.77 (m, 2H), 1.71-1.61 (m, 3H), 0.79 (t, J=7.6 Hz, 3H).
MH+509

Example 167

N-(3-(4-(3-chloro-2-methylphenyl)piperazin-1-yl)propyl)-1,2-dimethyl-5-phenyl-1H-pyrrole-3-carboxamide

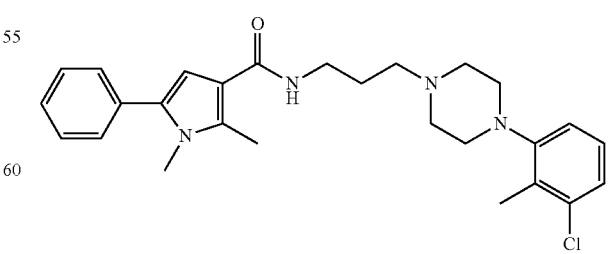

$^1$H NMR (400 MHz, CDCl$_3$) δ 7.38-7.31 (m, 5H), 7.06 (d, J=3.6 Hz, 1H), 6.93 (t, J=8.4 Hz, 1H), 6.65 (d, J=8.0 Hz, 1H), 6.37 (s, 1H), 3.54 (q, J=5.6 Hz, 2H), 3.49 (s, 3H), 2.91 (t,

J=4.8 Hz, 4H), 2.65 (brs, 4H), 2.60 (t, J=6.0 Hz, 2H),2.31 (s, 3H), 2.00 (s, 3H), 1.82-1.78 (m, 2H).
MH+465

Example 168

N-(3-(4-(3-chloro-2-methylphenyl)piperazin-1-yl)propyl)-2-methyl-5-phenyl-1-propyl-1H-pyrrole-3-carboxamide

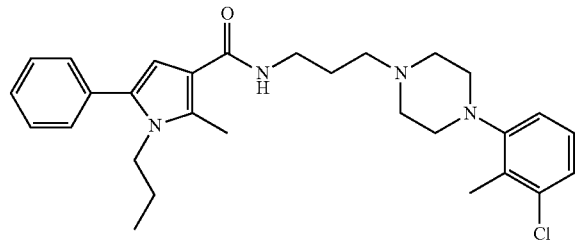 [SMILES: CCCn1c(-c2ccccc2)cc(C(=O)NCCCN2CCN(c3cccc(Cl)c3C)CC2)c1C]

$^1$H NMR (400 MHz, CDCl$_3$) δ 7.41-7.22 (m, 5H), 7.06 (d, J=8.0 Hz, 1H), 6.94 (t, J=8.0 Hz, 1H), 6.64 (d, J=8.4 Hz, 1H), 6.38 (s, 1H), 3.82 (t, J=7.6 Hz, 2H), 3.51 (q, J=4.8 Hz, 2H), 2.91 (t, J=4.8 Hz, 4H), 2.72-2.61 (m, 8H), 2.38 (s, 3H), 2.00 (s, 3H), 1.85-1.79 (m, 2H), 1.57-1.50 (m, 2H), 0.74 (t, J=7.6 Hz, 3H).
MH+493

Example 169

5-tert-butyl-N-(2-(4-(2,3-dichlorophenyl)piperazin-1-yl)ethyl)-1,2-dimethyl-1H-pyrrole-3-carboxamide

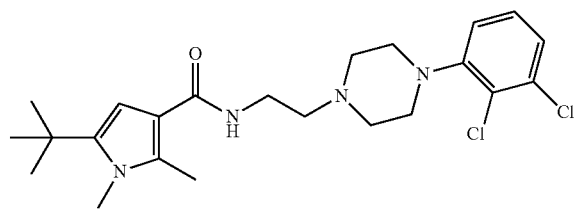 [SMILES: Cc1c(C(=O)NCCN2CCN(c3cccc(Cl)c3Cl)CC2)cc(C(C)(C)C)n1C]

$^1$H NMR (400 MHz, CDCl$_3$) δ 7.17-7.12 (m, 2H), 6.98-6.93 (m, 1H), 6.26 (brs, 1H), 6.00 (s, 1H), 3.59 (s, 3H), 3.51 (q, J=6.0 Hz, 2H), 3.07 (brs, 4H), 2.69 (brs, 4H), 2.64 (t, J=6.4 Hz, 2H), 2.53 (s, 3H),1.36 (s, 9H).
MH+450

Example 170

N-(3-(4-(2,3-dichlorophenyl)piperazin-1-yl)propyl)-2,5-dimethyl-1-phenyl-1H-pyrrole-3-carboxamide

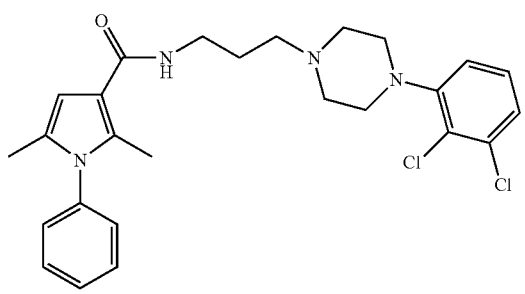 [SMILES: Cc1cc(C(=O)NCCCN2CCN(c3cccc(Cl)c3Cl)CC2)c(C)n1-c1ccccc1]

$^1$H NMR (400 MHz, CDCl$_3$) δ 7.51-7.41 (m, 3H), 7.17-7.12 (m, 3H), 7.10-6.95 (m, 2H), 6.14 (s, 1H), 3.52 (q, J=6.0 Hz, 2H), 3.12 (brs, 4H), 2.70 (brs, 4H), 2.60 (t, J=6.8 Hz, 2H), 2.32 (s, 3H), 1.98 (s, 3H), 1.84-1.78 (m, 2H).
MH+484

Example 171

N-(3-(4-(2,3-dimethylphenyl)piperazin-1-yl)propyl)-2,5-dimethyl-1-phenyl-1H-pyrrole-3-carboxamide

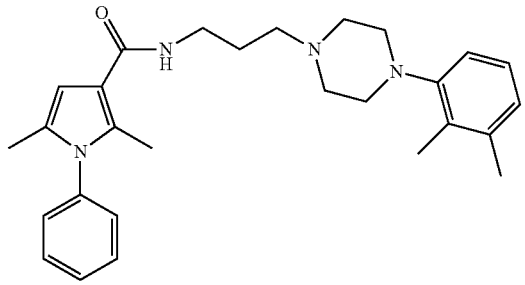 [SMILES: Cc1cccc(N2CCN(CCCNC(=O)c3cc(C)n(-c4ccccc4)c3C)CC2)c1C]

$^1$H NMR (400 MHz, CDCl$_3$) δ 7.51-7.40 (m, 3H), 7.16 (d, J=6.8 Hz, 2H), 7.07-7.03 (m, 1H), 6.95-6.89 (m, 2H), 6.15 (s, 1H), 3.53 (q, J=5.6 Hz, 2H), 2.97 (dd, J=4.8, 6.0 Hz, 4H), 2.67 (brs, 4H), 2.61 (t, J=6.0 Hz, 2H), 2.33 (s, 3H), 2.27 (s, 3H), 2.23 (s, 3H), 1.98 (s, 3H), 1.84-1.77 (m, 2H).
MH+444

Example 172

N-(3-(4-(3-chloro-2-fluorophenyl)piperazin-1-yl)propyl)-1,2-dimethyl-5-phenyl-1H-pyrrole-3-carboxamide

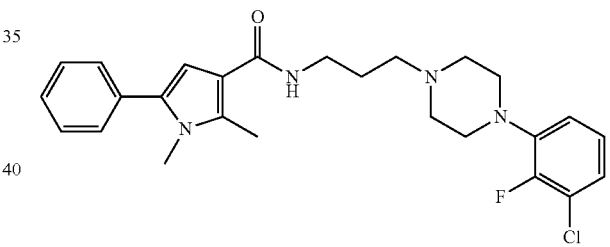

$^1$H NMR (400 MHz, CDCl$_3$) δ 7.35 (brs, 1H), 7.28-7.26 (m, 4H), 7.02-6.98 (m, 1H), 6.89 (dt, J=1.6, 8.4 Hz, 1H), 6.64 (dt, J=1.6, 8.0 Hz, 1H), 6.33 (s, 1H), 3.53 (q, J=5.6 Hz, 2H), 3.49 (s, 3H), 3.13 (t, J=4.4 Hz, 4H), 2.68 (brs, 4H), 2.64 (s, 3H), 2.61 (t, J=6.0 Hz, 2H), 1.83-1.77 (m, 2H).
MH+469

Example 173

N-(3-(4-(3-chloro-2-fluorophenyl)piperazin-1-yl)propyl)-2-methyl-5-phenyl-1-propyl-1H-pyrrole-3-carboxamide

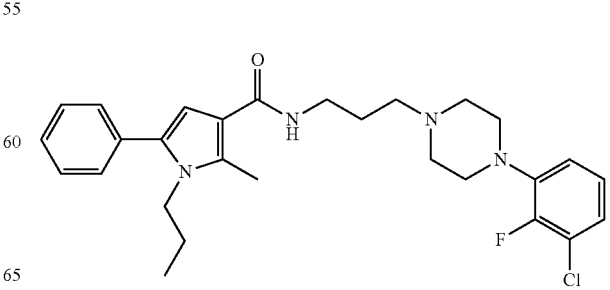

¹H NMR (400 MHz, CDCl₃) δ 7.54-7.21 (m, 5H), 6.99 (dt, J=1.6, 8.4 Hz, 1H), 6.89 (dt, J=1.2, 8.0 Hz, 1H), 6.61 (dt, J=1.2., 8.0 Hz, 1H), 6.29 (s, 1H), 3.81 (t, J=8.0 Hz, 2H), 3.52 (q, J=6.0 Hz, 2H), 3.11 (brs, 3H), 2.67-2.63 (m, 6H), 2.60 (t, J=6.0 Hz, 2H), 1.83-1.77 (m, 2H), 1.64-1.53 (m, 2H), 0.74 (t, J=7.6 Hz, 3H).
MH+497

Example 174

5-tert-butyl-N-(3-(4-(3-chloro-2-fluorophenyl)piperazin-1-yl)propyl)-1,2-dimethyl-1H-pyrrole-3-carboxamide

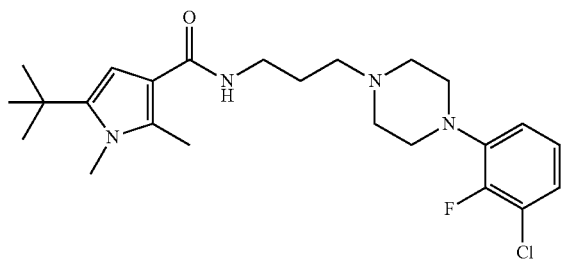 [SMILES: Cc1c(C(=O)NCCCN2CCN(c3cccc(Cl)c3F)CC2)cc(C(C)(C)C)n1C]

¹H NMR (400 MHz, CDCl₃) δ 7.01-6.93 (m, 2H), 6.80 (dt, J=7.6, 1.6 Hz, 1H), 5.98 (s, 1H), 3.57 (s, 3H), 3.50 (q, J=5.2 Hz, 2H), 3.16 (t, J=4.8 Hz, 4H), 2.67 (brs, 4H), 2.65-2.59 (m, H), 2.58 (s, 3H), 1.81-1.75 (m, 2H), 1.33 (s, 9H).
MH+449

Example 175

N-(3-(4-(3-chloro-2-fluorophenyl)piperazin-1-yl)propyl)-2,5-dimethyl-1-phenyl-1H-pyrrole-3-carboxamide

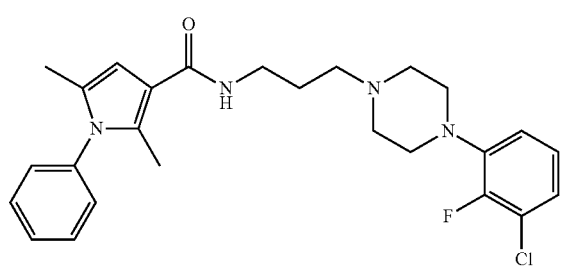 [SMILES: Cc1cc(C(=O)NCCCN2CCN(c3cccc(Cl)c3F)CC2)c(C)n1-c1ccccc1]

¹H NMR (400 MHz, CDCl₃) δ 7.58-7.40 (m, 5H), 7.26-7.22 (m, 1H), 7.17-7.15 (m, 2H), 7.02-6.95 (m, 3H), 6.84 (dt, J=2.4, 7.2 Hz, 1H), 6.13 (s, 1H), 3.53 (q, J=5.6 Hz, 2H), 3.17 (t, J=4.4 Hz, 4H), 2.69 (brs, 3H), 2.60 (t, J=6.4 Hz, 2H), 2.32 (s, 3H), 1.93 (s, 3H), 1.84-1.78 (m, 2H).
MH+469

Example 176

N-(3-(4-(3-chloro-2-methylphenyl)piperazin-1-yl)propyl)-2,5-dimethyl-1-phenyl-1H-pyrrole-3-carboxamide

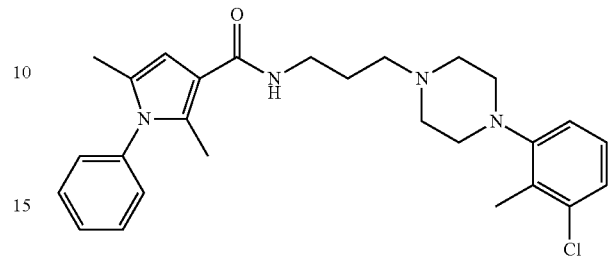

¹H NMR (400 MHz, CDCl₃) δ 7.50-7.42 (m. 3H), 7.18-7.07 (m, 5H), 6.96-6.94 (m, 1H), 6.18 (s, 1H), 3.53 (q, J=5.2 Hz, 2H), 2.97 (t, J=4.4 Hz, 4H), 2.68 (brs, 3H), 2.61 (t, J=6.0 Hz, 2H), 2.35 (s, 3H), 2.33 (s, 3H), 1.97 (s, 3H), 1.84-1.78 (m, 2H).
MH+466

Example 177

5-tert-butyl-N-(3-(4-(3-chloro-2-methylphenyl)piperazin-1-yl)propyl)-1,2-dimethyl-1H-pyrrole-3-carboxamide

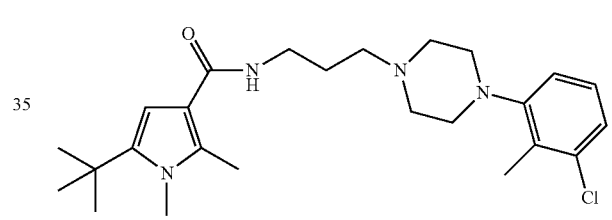

¹H NMR (400 MHz, CDCl₃) δ 7.09-7.04 (m, 2H), 6.89 (dd, J=2.4, 2.4 Hz, 1H), 6.00 (s, 1H), 3.58 (s, 3H), 3.52-3.47 (m, 2H), 2.95 (brs, 4H), 2.65 (brs, 4H), 2.57 (t, J=6.4 Hz, 2H), 2.55 (s, 3H), 2.33 (s, 3H), 1.80-1.77 (m, 2H) 1.34 (s, 9H).
MH+444

Example 178

5-tert-butyl-N-(3-(4-(2,3-dimethylphenyl)piperazin-1-yl)propyl)-1,2-dimethyl-1H-pyrrole-3-carboxamide

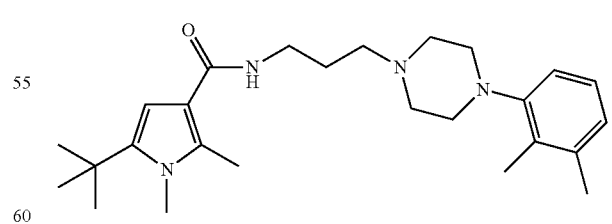

¹H NMR (400 MHz, CDCl₃) δ 7.05 (t, J=7.6 Hz, 1H), 6.93-6.87 (m, 2H), 6.02 (s, 1H), 3.58 (s, 3H), 3.50-3.42 (m, 2H), 2.94(brs, 4H), 2.64 (brs, 4H), 2.57 (t, J=6.0 Hz, 2H), 2.55 (s, 3H), 2.26 (s, 2H), 2.21(s, 3H) 1.80-1.77 (m, 2H), 1.35 (s, 9H).
MH+424

Example 179

N-(2-(4-(2,3-dichlorophenyl)piperazin-1-yl)ethyl)-2,5-dimethyl-1-phenyl-1H-pyrrole-3-carboxamide

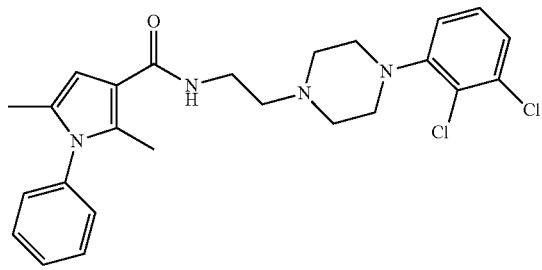 [SMILES: Cc1cc(C(=O)NCCN2CCN(c3cccc(Cl)c3Cl)CC2)c(C)n1-c1ccccc1]

$^1$H NMR (400 MHz, CDCl$_3$) δ 7.52-7.42 (m, 3H), 7.21-7.12 (m, 3H), 6.96 (dd, J=3.6, 5.6 Hz, 2H), 6.33 (brs, 1H), 5.98(s, 1H), 3.54 (q, 5.2 Hz, 2H), 3.09 (brs, 4H), 2.71 (brs, 4H), 2.66 (t, J=6.0 Hz, 2H), 2.32 (s, 3H), 1.99 (s, 3H).
MH+470

Example 180

5-tert-butyl-N-(3-(4-(2,3-dimethylphenyl)piperazin-1-yl)propyl)-2-methyl-1-propyl-1H-pyrrole-3-carboxamide

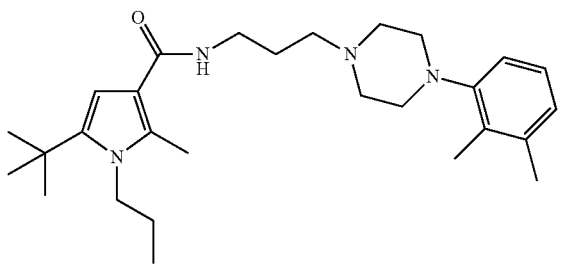 [SMILES: CCCn1c(C(C)(C)C)cc(C(=O)NCCCN2CCN(c3cccc(C)c3C)CC2)c1C]

$^1$H NMR (400 MHz, CDCl$_3$) δ 7.05 (t, J=7.6 Hz, 1H), 6.89-6.87 (m, 2H), 6.83 (brs, 1H), 6.01 (s, 1H), 3.87-3.82 (m, 2H), 3.48 (q, J=5.6 Hz, 2H), 2.95 (brs, 4H), 2.65 (brs, 4H), 2.26 (s, 3H), 2.20 (s, 3H), 1.80-1.76 (m, 2H), 1.71-1.65 (m, 2H), 1.34 (s, 9H), 0.97 (t, J=7.2 Hz, 3H).
MH+452

Example 181

5-tert-butyl-N-(3-(4-(2,3-dichlorophenyl)piperazin-1-yl)propyl)-2-methyl-1-propyl-1H-pyrrole-3-carboxamide

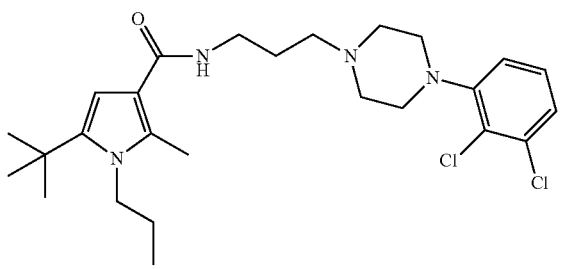 [SMILES: CCCn1c(C(C)(C)C)cc(C(=O)NCCCN2CCN(c3cccc(Cl)c3Cl)CC2)c1C]

$^1$H NMR (400 MHz, CDCl$_3$) δ 7.19-7.10 (m, 2H), 6.92 (dd, J=2.4, 2.0 Hz, 1H), 6.81 (brs, 1H), 5.98 (s, 1H), 3.86-3.82 (m, 2H), 3.48 (q, J=5.6 Hz, 2H), 3.11 (brs, 4H), 2.67 (brs, 4H), 2.57 (t, J=6.4 Hz, 2H), 2.56 (s, 3H), 1.81-1.75 (m, 2H), 1.71-1.65 (m, 2H), 1.32 (s, 9H), 0.98 (t, J=7.6 Hz, 3H).
MH+492

Example 182

5-tert-butyl-N-(3-(4-(2,3-dichlorophenyl)piperazin-1-yl)propyl)-1-ethyl-2-methyl-1H-pyrrole-3-carboxamide

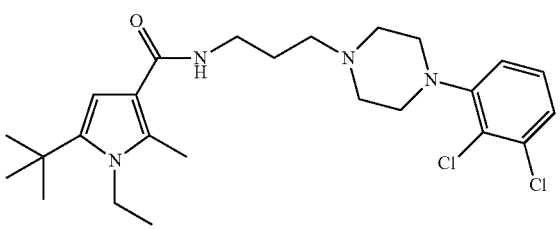 [SMILES: CCn1c(C(C)(C)C)cc(C(=O)NCCCN2CCN(c3cccc(Cl)c3Cl)CC2)c1C]

$^1$H NMR (400 MHz, CDCl$_3$) δ 7.17-7.11 (m, 2H), 6.93 (d, J=7.2 Hz, 1H), 6.80 (brs, 1H), 5.98 (s, 1H), 4.04 (q, J=7.2Hz, 2H), 3.50(q, J=5.6 Hz, 2H), 3.12 (brs, 4H), 267 (brs, 4H), 2.58 (t, J=6.4 Hz, 2H), 2.56 (s, 3H), 1.79 (t, J=6.0 Hz, 2H), 1.34 (s, 9H), 1.30 (t, J=7.2 Hz, 3H).
MH+478

Example 183

N-(2-(4-(3-chloro-2-fluorophenyl)piperazin-1-yl)ethyl)-1,2-dimethyl-5-phenyl-1H-pyrrole-3-carboxamide

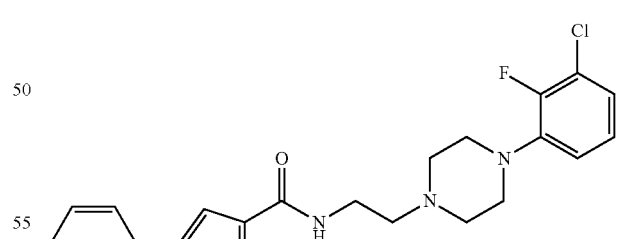

$^1$H NMR (400 MHz, CDCl$_3$) δ 7.43-7.32 (m, 5H), 7.02-6.94 (m, 2H), 6.85-6.77 (m, 1H), 6.33 (brs, 1H), 6.26 (s, 1H), 3.54 (q, J=6.0 Hz, 2H), 3.52 (s, 3H), 3.11 (t, J=4.4 Hz, 3H), 2.68 (brs, 4H), 2.64 (s, 3H).
MH+455

Example 184

N-(2-(4-(3-chloro-2-methylphenyl)piperazin-1-yl)ethyl)-1,2-dimethyl-5-phenyl-1H-pyrrole-3-carboxamide

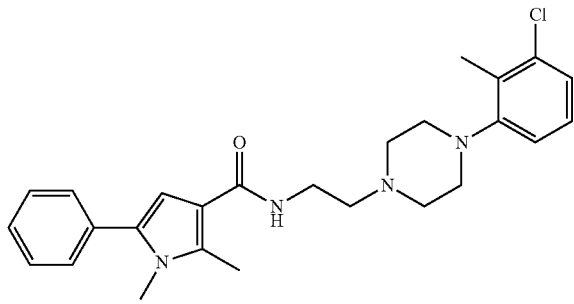 [SMILES: Cc1c(Cl)cccc1N1CCN(CCNC(=O)c2cc(-c3ccccc3)n(C)c2C)CC1]

$^1$H NMR (400 MHz, CDCl$_3$) δ 7.92 (brs, 1H), 7.43-7.27 (m, 5H), 7.16 (d, J=6.8 Hz, 1H), 7.10 (t, J=8.0 Hz, 1H), 6.99 (d, J=7.2 Hz, 1H), 6.75 (s, 1H), 3.94-3.91 (m, 2H), 3.71 (d, J=10.8 Hz, 2H), 3.58 (d, J=12.0 Hz, 2H), 3.49 (s, 3H), 3.36 (t, J=4.8 Hz, 2H), 3.12-3.02 (m, 4H), 2.62 (s, 3H), 2.33 (s, 3H).
MH+451

Example 185

1,2-dimethyl-N-(2-(4-(2-methylquinolin-8-yl)piperazin-1-yl)ethyl)-5-phenyl-1H-pyrrole-3-carboxamide

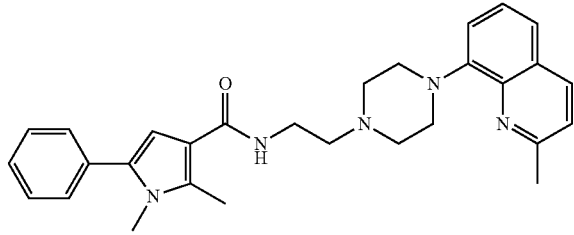 [SMILES: Cc1ccc2cccc(N3CCN(CCNC(=O)c4cc(-c5ccccc5)n(C)c4C)CC3)c2n1]

$^1$H NMR (400 MHz, CDCl$_3$) δ 7.97 (d, J=8.4 Hz, 1H), 7.43-7.30 (m, 7H), 7.24 (d, J=8.4 Hz, 1H), 7.80 (dd, J=2.4, 6.0 Hz, 1H), 6.48 (brs, 1H), 6.30 (s, 1H), 3.61-3.55 (m, 2H), 3.50 (s, 3H), 3.48 (brs, 4H), 2.87 (brs, 4H), 2.73 (s, 3H), 2.72-2.70 (m, 2H), 2.64 (s, 3H).
MH+467.

Example 186

5-tert-butyl-N-(2-(4-(3-chloro-2-fluorophenyl)piperazin-1-yl)ethyl)-1,2-dimethyl-1H-pyrrole-3-carboxamide

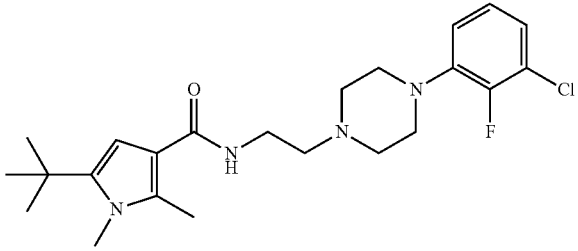 [SMILES: Cc1c(Cl)cccc1N1CCN(CCNC(=O)c2cc(C(C)(C)C)n(C)c2C)CC1]

$^1$H NMR (400 MHz, CDCl$_3$) δ 7.28-6.97 (m, 2H), 6.85-6.78 (m, 1H), 6.20 (brs, 1H), 6.87 (s, 1H), 3.59 (s, 3H), 3.51 (q, J=6.0 Hz, 2H), 3.12 (t, J=4.8 Hz, 4H), 2.68 (t, J=4.8 Hz, 3H), 2.63 (t, J=6.4 Hz, 2H), 2.54 (s, 3H), 1.36 (s, 9H).
MH+435

Example 187

5-tert-butyl-N-(2-(4-(3-chloro-2-methylphenyl)piperazin-1-yl)ethyl)-1,2-dimethyl-1H-pyrrole-3-carboxamide

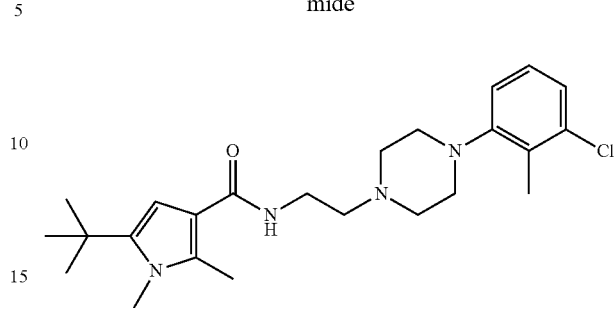

$^1$H NMR (400 MHz, CDCl$_3$) δ 7.10-7.06 (m, 2H), 6.95-6.92 (m, 1H), 6.25 (brs, 1H), 6.00 (s, 1H), 3.59 (s, 3H), 3.51 (q, J=6.4 Hz, 2H), 2.92 (t, J=4.4 Hz, 4H), 2.67-2.62 (m, 6H), 2.54 (s, 3H), 2.34 (s, 3H), 1.36 (s, 9H).
MH+431

Example 188

5-tert-butyl-1,2-dimethyl-N-(2-(4-(2-methylquinolin-8-yl)piperazin-1-yl)ethyl)-1H-pyrrole-3-carboxamide

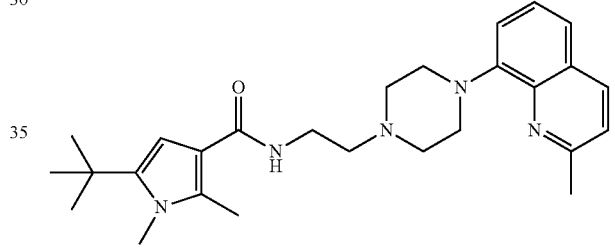

$^1$H NMR (400 MHz, CDCl$_3$) δ 7.98 (d, J=8.4 Hz, 1H), 7.40-7.35 (m, 2H), 7.27-7.23 (m, 1H), 7.12-7.07 (m, 1H), 6.35 (brs, 1H), 6.02 (s, 1H)3.59 (s. 3H), 3.55 (q, J=6.0 Hz, 2H), 2.86 (t, J=2.0 Hz, 4H), 2.73 (s, 3H), 2.70 (t, J=6.0 Hz, 2H), 2.54 (s, 3H), 1.36 (s, 9H).
MH+447

Example 189

5-tert-butyl-N-(2-(4-(2,3-dimethylphenyl)piperazin-1-yl)ethyl)-1,2-dimethyl-1H-pyrrole-3-carboxamide

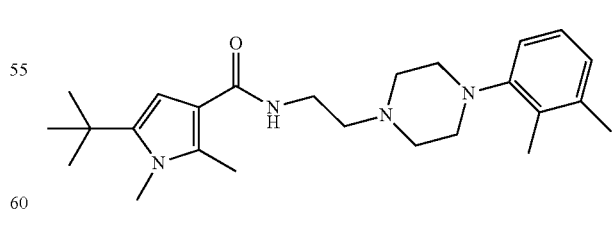

$^1$H NMR (400 MHz, CDCl$_3$) δ 7.08 (t, J=7.6 Hz, 1H), 6.93-6.89 (m, 2H), 6.31 (brs, 1H), 6.01 (s, 1H), 3.59(s, 3H), 3.51 (q, J=5.2 Hz, 2H), 2.92 (brs, 4H), 2.65 (brs, 4H), 2.63 (q, J=6.0 Hz, 2H), 2.54 (s, 3H), 2.27 (s, 3H), 2.23 (s, 3H), 1.37 (s, 9H).
MH+410

Example 190

5-tert-butyl-N-(3-(4-(2,3-dimethylphenyl)piperazin-1-yl)propyl)-1-ethyl-2-methyl-1H-pyrrole-3-carboxamide

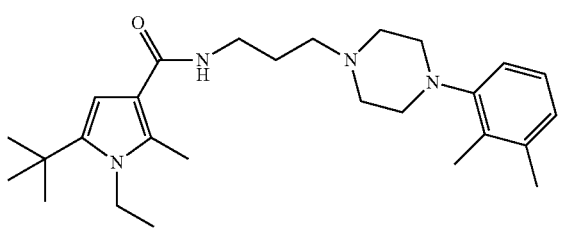 [SMILES: CCn1c(C(C)(C)C)cc(C(=O)NCCCN2CCN(c3cccc(C)c3C)CC2)c1C]

$^1$H NMR (400 MHz, CDCl$_3$) δ 7.06 (t, J=7.6 Hz, 1H), 6.90-6.88 (m, 2H), 6.83 (brs, 1H), 6.01 (s, 1H), 4.03 (q, J=7.2 Hz, 2H), 3.49 (q, J=5.6 Hz, 2H), 2.96-2.93 (m, 4H), 2.64 (brs, 4H), 2.58 (s, 3H), 2.57 (t, J=6.0 Hz, 2H), 2.27 (s, 3H), 221 (s, 3H), 1.81-1.77 (m, 2H), 1.35 (s, 9H), 1.30 (t, J=6.8 Hz, 3H).
MH+438

Example 191

5-tert-butyl-N-(3-(4-(2,3-dichlorophenyl)piperazin-1-yl)-2-hydroxypropyl)-1,2-dimethyl-1H-pyrrole-3-carboxamide

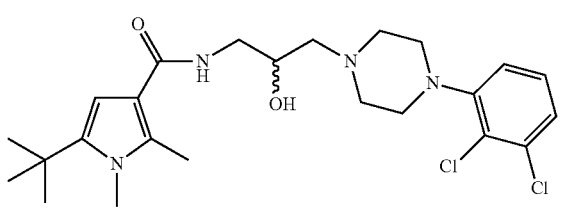 [SMILES: Cc1c(C(=O)NCC(O)CN2CCN(c3cccc(Cl)c3Cl)CC2)cc(C(C)(C)C)n1C]

$^1$H NMR (400 MHz, CDCl$_3$) δ 7.20-7.11 (m, 2H), 6.94 (dd, J=2.4, 2.4 Hz, 1H), 6.16 (t, J=6.0 Hz, 1H), 6.00 (s, 1H), 3.94-3.89 (m, 2H), 3.69-3.61 (m, 1H), 3.59 (s, 3H), 3.39-3.33 (m, 2H), 3.06 (brs, 4H), 2.85-2.82 (m, 2H), 2.63-2.61 (m, 2H), 2.53 (s, 3H), 2.50-2.44 (m, 2H), 1.36 (s, 9H).
MH+480

Example 192

N-(3-(4-(2,3-dichlorophenyl)piperazin-1-yl)propyl)-4-methoxy-1,2-dimethyl-5-phenyl-1H-pyrrole-3-carboxamide

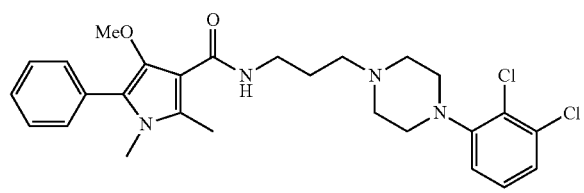 [SMILES: COc1c(C(=O)NCCCN2CCN(c3cccc(Cl)c3Cl)CC2)c(C)n(C)c1-c1ccccc1]

$^1$H NMR (400 MHz, CDCl$_3$) δ 7.47 (br, 1H), 7.45-7.41 (m, 2H), 7.38-7.33 (m, 3H), 7.19-7.14 (m, 2H), 6.97 (dd, J=7.6, 2.4 Hz, 1H), 3.53-3.49 (m, 3H), 3.48 (s, 3H), 3.36 (s, 3H), 3.24-3.16 (m, 4H), 2.82-2.65 (m, 5H), 2.62 (s, 3H), 1.96-1.86 (m, 2H).
MH+515

Example 193

N-(2-(4-(2,3-Dichlorophenyl)piperazin-1-yl)ethyl)-4-methoxy-1,2-dimethyl-5-phenyl-1H-pyrrole-3-carboxamide

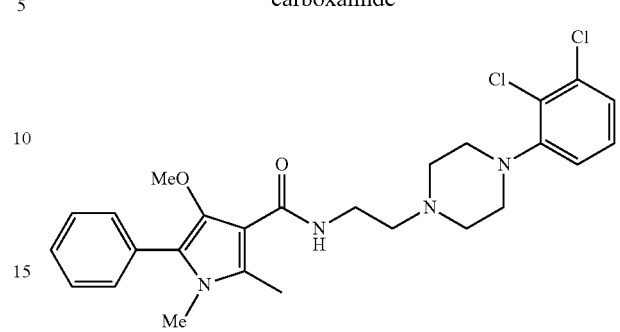

$^1$H NMR (400 MHz, CDCl$_3$) δ 7.74 (br, 1H), 7.48-7.42 (m, 2H), 7.39-7.36 (m, 2H), 7.33-7.24 (m, 2H), 7.19 (t, J=8.0 Hz, 1H), 7.00 (d, J=7.2 Hz, 1H), 3.99-3.90 (m, 2H), 3.84-3.76 (m, 2H), 3.46 (s, 3H), 3.44-3.35 (m, 6H), 3.33 (s, 3H), 3.22-3.12 (m, 2H), 2.61 (s, 3H).
MH+501

Example 194

1,2-dimethyl-5-phenyl-N-(2-(4-(quinolin-8-yl)piperazin-1-yl)ethyl)-1H-pyrrole-3-carboxamide

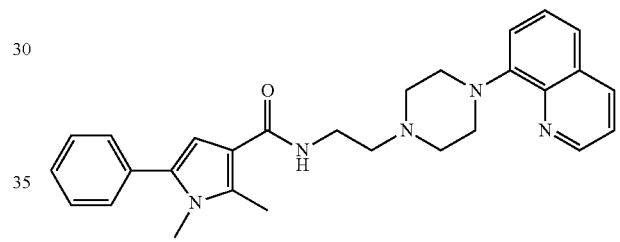

$^1$H NMR (400 MHz, CDCl$_3$) δ 8.87 (dd, J=1.6, 4.0 Hz, 1H), 8.10 (dd, J=1.6, 8.0 Hz, 1H), 7.46-7.35 (m, 8H), 7.13 (dd, J=3.6, 5.2 Hz, 1H), 6.46 (brs, 1H), 6.30 (s, 1H), 3.58 (q, J=5.6 Hz, 2H), 3.50 (s, 3H), 3.49-3.45 (m, 3H), 2.87 (brs, 3H), 2.72 (t, J=6.0 Hz, 2H), 2.64 (s, 3H).
MH+454

Example 195

N-(3-(4-(3-chloro-2-methylphenyl)piperazin-1-yl)-2-hydroxypropyl)-1,2-dimethyl-5-phenyl-1H-pyrrole-3-carboxamide

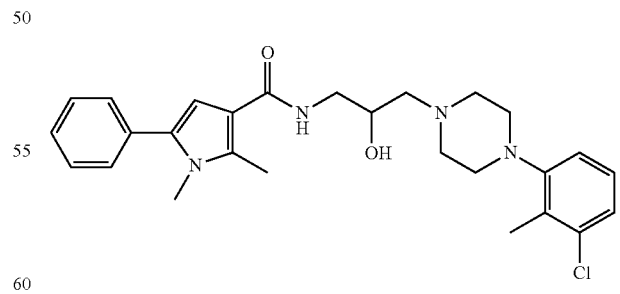

$^1$H NMR (400 MHz, CDCl$_3$) δ 7.43-7.39 (m, 2H), 7.35-7.31 (m, 2H), 7.26-7.05 (m, 2H), 6.92-6.87 (m, 1H), 6.30 (s, 1H), 6.29 (brs, 1H), 3.96-3.91 (m, 1H), 3.69-3.63 (m, 1H), 3.50 (s, 1H), 3.44-3.37 (m, 1H), 2.94-2.81 (m, 5H), 2.63 (s, 3H), 2.54 (brs, 2H), 2.54-2.45 (m, 2H), 2.33 (s, 3H).
MH+481

Example 196

N-(2-(4-(2,3-dichlorophenyl)piperazin-1-yl)-3-fluoropropyl)-1,2-dimethyl-5-phenyl-1H-pyrrole-3-carboxamide hydrochloride

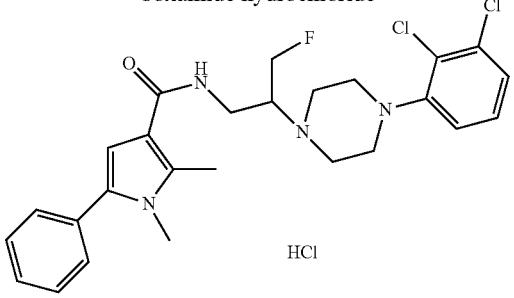 [SMILES: Cc1c(C(=O)NCC(CF)N2CCN(c3cccc(Cl)c3Cl)CC2)cc(-c2ccccc2)n1C ; Cl]

$^1$H NMR (400 MHz, DMSO-d$_6$) δ 11.24 (bs, 1H), 8.21 (br 1H), 7.43-7.30 (m, 6H), 7.21 (d, J=2.8Hz, 1H), 5.09-4.79 (m, 2H), 3.82-3.72 (m, 5H), 3.45 (s, 3H), 3.43-3.33 (m, 4H), 3.32-3.27 (m, 2H), 2.52 (s, 3H).
MH+503

Example 197

N-(2-(4-(2,3-dichlorophenyl)piperazin-1-yl)-3-fluoropropyl)-2-methyl-5-phenyl-1-propyl-1H-pyrrole-3-carboxamide hydrochloride

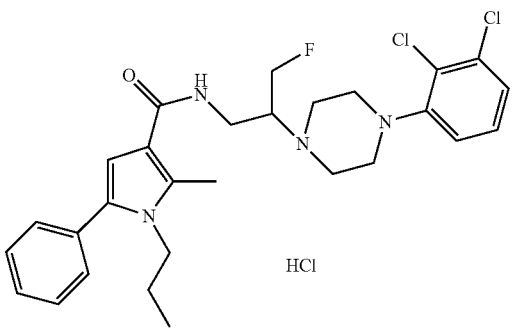 [SMILES: CCCn1c(-c2ccccc2)cc(C(=O)NCC(CF)N2CCN(c3cccc(Cl)c3Cl)CC2)c1C ; Cl]

$^1$H NMR (400 MHz, DMSO-d$_6$) δ 11.21 (bs, 1H), 8.20 (br 1H), 7.43-7.40 (m, 2H), 7.40-7.30 (m, 5H), 7.17 (dd, J=7.2, 2.4Hz, 1H), 6.60 (s, 1H), 5.09-4.80 (m, 2H), 3.84-3.67 (m, 7H), 3.46-3.30 (m, 4H), 3.30-3.40 (m, 2H), 2.53 (s, 3H), 1.46-1.37 (m, 2H), 0.63 (t, J=7.2Hz, 3H).
MH+531

Example 198

N-(3-(4-(2,3-dichlorophenyl)piperazin-1-yl)-2,2-difluoropropyl)-1,2-dimethyl-5-phenyl-1H-pyrrole-3-carboxamide

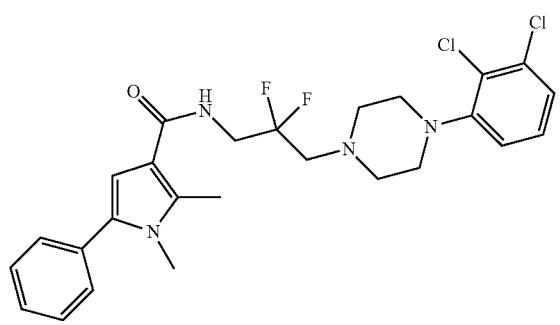 [SMILES: Cc1c(C(=O)NCC(F)(F)CN2CCN(c3cccc(Cl)c3Cl)CC2)cc(-c2ccccc2)n1C]

$^1$H NMR (400 MHz, DMSO-d$_6$) δ 7.82 (m, 1H), 7.42-7.25 (m, 7H), 7.10-7.08 (m, 1H), 6.62 (s, 1H), 3.73 (m, 2H), 3.44 (s, 3H), 2.95 (m, 4H), 2.86-2.78 (m, 2H), 2.71 (m, 4H), 2.50 (s, 3H).
MH+521

Example 199

5-tert-butyl-N-(3-(4-(2,3-dimethylphenyl)piperazin-1-yl)-2-hydroxypropyl)-1,2-dimethyl-1H-pyrrole-3-carboxamide

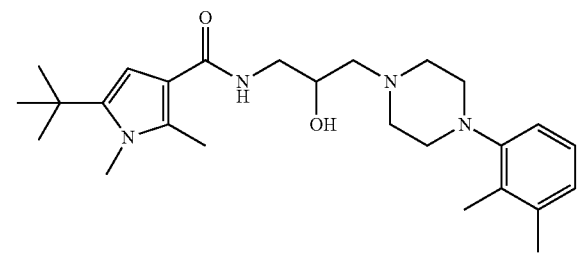 [SMILES: Cc1cccc(N2CCN(CC(O)CNC(=O)c3cc(C(C)(C)C)n(C)c3C)CC2)c1C]

MH+440

Example 200

5-tert-butyl-N-(4-(4-(2,3-dimethylphenyl)piperazin-1-yl)butyl)-1,2-dimethyl-1H-pyrrole-3-carboxamide

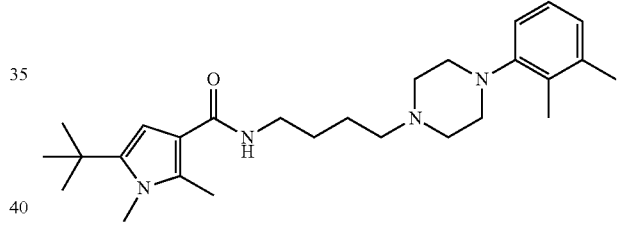

MH+438

Example 201

N-(2-(4-(2,3-dimethylphenyl)piperazin-1-yl)ethyl)-4-methoxy-1,2-dimethyl-5-phenyl-1H-pyrrole-3-carboxamide

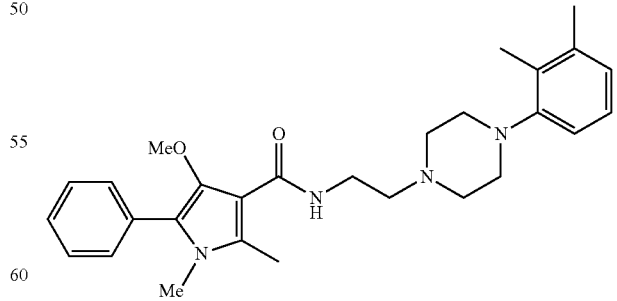

$^1$H NMR (400 MHz, CDCl$_3$) δ 7.53-7.33 (m, 5H), 7.19-7.14 (m, 2H), 7.13-7.06 (m, 1H), 4.29-3.87 (m, 4H), 3.82-3.72 (m, 3H), 3.49 (s, 3H), 3.48-3.36 (m, 3H), 3.33 (s, 3H), 3.30 (m, 2H), 2.29 (s, 6H).
MH+461

Example 202

N-(3-(4-(2,3-Dimethylphenyl)piperazin-1-yl)propyl)-4-methoxy-1,2-dimethyl-5-phenyl-1H-pyrrole-3-carboxamide

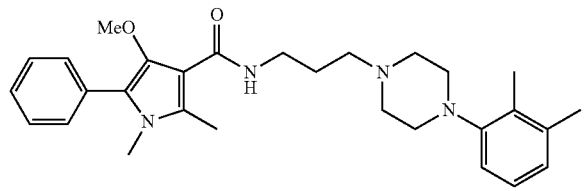 [SMILES: COc1c(C(=O)NCCCN2CCN(c3cccc(C)c3C)CC2)c(C)n(C)c1-c1ccccc1]

$^1$H NMR (400 MHz, CDCl$_3$) δ 7.46-7.39 (m, 2H), 7.38-7.35 (m, 3H), 7.17-7.06 (m, 1H), 6.99-6.95 (m, 2H), 3.63-3.50 (m, 4H), 3.49 (s, 3H), 3.34 (s, 3H), 3.24-2.95 (m, 4H), 2.62 (s, 3H), 2.25-2.10 (m, 4H), 2.27 (s, 6H), 2.05-1.82 (m, 2H).
MH+475

Example 203

N-(3-(4-(2,3-Dichlorophenyl)piperazin-1-yl)propyl)-4-hydroxy-1,2-dimethyl-5-phenyl-1H-pyrrole-3-carboxamide

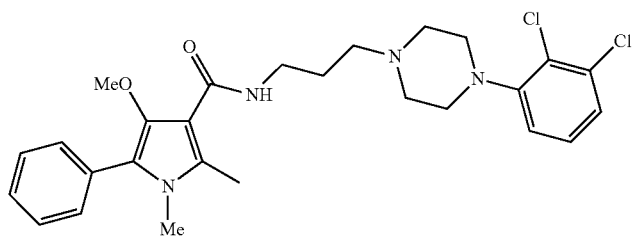

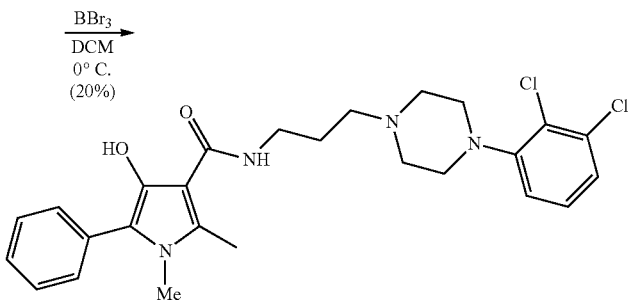

To a solution of N-(3-(4-(2,3-dichlorophenyl)piperazin-1-yl)propyl)-4-methoxy-1,2-dimethyl-5-phenyl-1H-pyrrole-3-carboxamide (375 mg, 0.60 mmol) was added BBr$_3$ (0.77 ml, 17% in DCM) slowly at 0° C. After stirring at 0° C. for 2~3 hours, the mixture was quenched with saturated sodium bicarbonate solution and extracted with DCM (50 mL) MeI (2.13 mL, 34.2 mmol). The organic phase was dried over MgSO$_4$ and evaporated under vacuum. The residue was further purified by prep HPLC (Gilson, C18 column) to provide title compound (73 mg, 20%).

$^1$H NMR (400 MHz, CDCl$_3$) δ 7.47-7.34 (m, 3H), 7.24-7.14 (m, 2H), 7.01-6.95 (m, 1H), 3.74-3.62 (m, 4H), 3.40-3.32 (m, 4H), 3.25-3.16 (m, 3H), 3.07-3.04 (m, 1H), 2.97 (s, 3H), 2.76 (s, 3H), 2.06-1.90 (m, 2H).
MH+501

Experimental Example 1

Measurement of Binding Affinity for Serotonin 5-HT$_{2A}$ and 5-HT$_{2C}$ Receptors Receptor binding affinities of the compounds for serotonin receptors were measured by the method described in the literature [Park W K et al., *Pharmacol Biochem Behav.* 2005, 82(2), 361-372].

For serotonin 5-HT$_{2A}$ binding, an aliquot of human recombinant serotonin 5-HT$_{2A}$ receptor (PerkinElmer Life and Analytical Sciences, USA) expressed in CHO-K1 cells (5 ug/well) and 1 nM [$^3$H]Ketanserin (PerkinElmer) were used in the presence of mianserin (20 uM) as nonspecific. The reaction mixture was incubated for 60 min at 27 using 50 mM Tris-HCl (pH 7.4) buffer containing 4 mM CaCl$_2$ and 0.1% ascorbic acid, and harvested through filtermate A glass fiber filter (Wallac, Finland) presoaked in 0.5% polyethyleneimine (PEI) by microbeta filtermate-96 harvester (PerkinElmer) to terminate the reaction, and then washed with ice cold 50 mM Tris-HCl buffer solution (pH 7.4). The filter was then covered with MeltiLex, sealed in a sample bag, dried in an oven. The radioactivity retained in the filter was finally counted using MicroBeta Plus (Wallac).

The binding affinity (IC$_{50}$) of a compound for the receptor was calculated by computerized nonlinear regression analysis (GraphPad Prism Program, San Diego, USA) using 7-8 varied concentrations of the compound run in duplicate tubes.

For serotonin 5-HT$_{2C}$ binding, frozen membranes from stable CHO-K1 cell line expressing the human recombinant 5-HT$_{2C}$ receptor (PerkinElmer, 4 ug/well), [$^3$H]Mesulergine (Amersham, 1.3 nM) and test compounds were added into 50 mM Tris-HCl (pH 7.4) buffer containing 0.1% ascorbic acid and 4 mM CaCl$_2$. Nonspecific binding was determined using 100 uM mianserin. The incubations were performed for 60 min at 27, and these were terminated by rapid filtration through filtermate. A glass fiber filter presoaked in 0.5% PEI.

The results are shown in the following Table 1(unit: nM).

TABLE 1

| Compound | 5-HT$_{2A}$ | 5-HT$_{2C}$ |
| --- | --- | --- |
| Example 1 | 92 | 160 |
| Example 3 | 57 | 133 |
| Example 4 | 92 | 192 |
| Example 5 | 75 | 139 |
| Example 6 | 191 | 273 |
| Example 10 | 46.2 | 12 |
| Example 11 | 376 | 66 |
| Example 12 | 324 | 628 |
| Example 13 | 67.1 | 795 |
| Example 14 | 22.9 | 443 |
| Example 15 | 6.9 | 162 |
| Example 16 | 4.1 | 466 |
| Example 18 | 224 | 297 |
| Example 19 | 354 | 220 |
| Example 20 | 1067 | 611 |
| Example 21 | 1233 | 638 |
| Example 22 | 4383 | 1034 |
| Example 23 | 245 | 280 |
| Example 24 | 300 | 615 |
| Example 25 | 300 | 599 |
| Example 27 | 897 | 1298 |
| Example 28 | 406 | 342 |
| Example 31 | 33.2 | 20.7 |
| Example 33 | 792 | 149 |
| Example 34 | 104 | 20.9 |
| Example 35 | 61 | 61 |
| Example 36 | 28 | 32 |
| Example 37 | 38.8 | 34.5 |
| Example 38 | 40 | 37 |
| Example 39 | 408 | 310 |
| Example 40 | 10 | 63 |
| Example 41 | 13 | 14 |
| Example 42 | 10 | 17 |
| Example 43 | 28 | 28 |
| Example 44 | 92 | 189 |
| Example 45 | 105 | 106 |
| Example 46 | 32 | 88 |
| Example 47 | 56 | 62 |
| Example 48 | 175 | 156 |
| Example 49 | 100 | 96 |
| Example 61 | 213 | 129 |
| Example 62 | 232 | 39 |
| Example 63 | 151 | 39 |
| Example 64 | 153 | 22 |
| Example 65 | 192 | 26 |
| Example 66 | 333 | 41 |
| Example 67 | 100 | 23 |
| Example 68 | 292 | 24 |
| Example 69 | 412 | 29 |
| Example 71 | 188 | 32 |
| Example 72 | 300 | 68 |
| Example 73 | 37 | 201 |
| Example 74 | 108 | 101 |
| Example 75 | 141 | 35 |
| Example 76 | 37 | 13 |
| Example 77 | 39 | 16 |
| Example 78 | 19 | 10 |
| Example 79 | 33 | 16 |
| Example 80 | 47 | 42 |
| Example 81 | 25 | 75 |
| Example 82 | 138 | 43 |
| Example 83 | 20 | 20 |
| Example 84 | 953 | 1408 |
| Example 87 | 647 | 4830 |
| Example 88 | 221 | 633 |
| Example 90 | 269 | 637 |
| Example 91 | 21 | 211 |
| Example 92 | 43 | 267 |
| Example 93 | 58 | 639 |
| Example 96 | 410 | 619 |
| Example 100 | 49 | 209 |
| Example 101 | 46 | 344 |
| Example 106 | 39 | 175 |
| Example 107 | 34 | 420 |
| Example 114 | 22 | 107 |
| Example 116 | 69 | 136 |
| Example 124 | 23 | 106 |
| Example 127 | 107 | 1392 |
| Example 128 | 163 | 1021 |
| Example 135 | 65 | 157 |
| Example 136 | 108 | 173 |
| Example 137 | 68 | 133 |
| Example 138 | 134 | 268 |
| Example 154 | 213 | 349 |
| Example 155 | 22 | 493 |
| Example 156 | 585 | 806 |
| Example 158 | 666 | 782 |
| Example 159 | 874 | 977 |
| Example 165 | 832 | 653 |
| Example 169 | 57 | 109 |
| Example 170 | 132 | 98 |
| Example 176 | 170 | 127 |
| Example 184 | 152 | 233 |
| Example 185 | 761 | 554 |
| Example 186 | 121 | 293 |
| Example 187 | 54 | 210 |
| Example 188 | 1483 | 1497 |
| Example 189 | 36 | 227 |
| Example 190 | 386 | 1145 |

Experimental Example 2

Measurement of Binding Affinity for Serotonin Transporter

For serotonin transporter binding assays, a reaction mixture with a final volume of 0.25 ml was prepared by mixing a test compound, human serotonin transporter membrane expressed in HEK-293 cells (PerkinElmer, 5 ug/well), [$^3$H] Imipramine (PerkinElmer, 2 nM) and 50 mM Tris-HCl (pH 7.4) buffer containing 120 mM NaCl and 5 mM KCl. The reaction mixture was incubated for 30 min at 27, and harvested through filtermate. A glass fiber filter presoaked in 0.5% PEI with ice cold 50 mM Tris-HCl buffer (pH 7.4) containing 0.9% NaCl. The results are shown in the following Table 2 (unit: nM).

TABLE 2

| Compound | Serotonin Transporter |
| --- | --- |
| Example 1 | 11.1 |
| Example 3 | 11.8 |
| Example 4 | 25.8 |
| Example 5 | 35.9 |
| Example 6 | 93 |
| Example 10 | 61.7 |
| Example 11 | 182 |
| Example 12 | 420 |
| Example 13 | 298 |
| Example 14 | 80.2 |
| Example 15 | 53.6 |
| Example 16 | 266 |
| Example 18 | 14.3 |
| Example 19 | 125 |
| Example 20 | 213 |
| Example 21 | 352 |
| Example 22 | 412 |
| Example 23 | 92 |
| Example 24 | 77 |
| Example 25 | 133 |
| Example 27 | 350 |
| Example 28 | 381 |
| Example 31 | 102 |
| Example 33 | 76 |
| Example 34 | 76 |

TABLE 2-continued

| Compound | Serotonin Transporter |
|---|---|
| Example 35 | 149 |
| Example 36 | 93 |
| Example 37 | 98 |
| Example 38 | 87 |
| Example 39 | 32 |
| Example 40 | 21 |
| Example 41 | 21 |
| Example 42 | 65 |
| Example 43 | 64 |
| Example 44 | 19 |
| Example 45 | 56 |
| Example 46 | 98 |
| Example 47 | 122 |
| Example 48 | 57 |
| Example 49 | 85 |
| Example 61 | 129 |
| Example 62 | 733 |
| Example 63 | 93 |
| Example 64 | 629 |
| Example 65 | 131 |
| Example 66 | 1159 |
| Example 67 | 233 |
| Example 68 | 176 |
| Example 69 | 220 |
| Example 71 | 642 |
| Example 72 | 1190 |
| Example 73 | 204 |
| Example 74 | 76.2 |
| Example 75 | 100 |
| Example 76 | 162 |
| Example 77 | 36 |
| Example 78 | 74 |
| Example 79 | 80 |
| Example 80 | 97 |
| Example 81 | 78 |
| Example 82 | 196 |
| Example 83 | 59 |
| Example 84 | 1084 |
| Example 87 | 628 |
| Example 88 | 225 |
| Example 90 | 223 |
| Example 91 | 28 |
| Example 92 | 110 |
| Example 93 | 397 |
| Example 96 | 381 |
| Example 100 | 92 |
| Example 101 | 133 |
| Example 106 | 85 |
| Example 107 | 78 |
| Example 114 | 59 |
| Example 116 | 1093 |
| Example 124 | 54 |
| Example 127 | 860 |
| Example 128 | 375 |
| Example 135 | 144 |
| Example 136 | 347 |
| Example 137 | 62 |
| Example 138 | 334 |
| Example 154 | 23 |
| Example 155 | 183 |
| Example 156 | 134 |
| Example 158 | 1259 |
| Example 159 | 1981 |
| Example 165 | 300 |
| Example 169 | 45 |
| Example 170 | 20 |
| Example 176 | 15 |

Experimental Example 3

Measurement of Anti-Depressants Activity in Forced Swimming Test

To evaluate the anti-depressants activity of the compounds, the inhibitory effects on immobility in forced swimming test in mice were measured according to the methods described by Porsolt et al. [Porsolt R D et al., *Eur J Pharmacol.* 1978, 51, 291-294].

Each mouse was placed in a 25-cm glass cylinder (10 cm diameter) containing 15 cm of water maintained at 22±1, and was forced to swim for 10 min. Twenty-four hours later, the mouse was replaced into the cylinder and the total duration of immobility was recorded during the last 5 min of the 6-min testing period. Mice are judged immobile when they float in an upright position and make only small movements to keep their head above water. Test drugs were suspended in 3% Tween 80 solution, and administered orally (po) 60 min before the testing. The results are shown in the following Table 3 (unit: %).

TABLE 3

| Compound | 100 mg/kg | 50 mg/kg | 25 mg/kg | 10 mg/kg |
|---|---|---|---|---|
| Example 5 | — | 67.4 ± 4.8 | 70.1 ± 6.0 | 95.2 ± 2.3 |
| Example 9 | 68.3 ± 11.7 | — | — | — |
| Example 10 | 3.9 ± 2.5 | — | 40.7 ± 10.4 | 80.7 ± 5.7 |
| Example 11 | 18.7 ± 10.1 | — | — | — |
| Example 12 | — | — | 48.6 ± 7.3 | 79.0 ± 5.7 |
| Example 13 | 26.9 ± 9.9 | — | 61.0 ± 10.9 | — |
| Example 15 | 52.1 ± 6.4 | — | — | — |
| Example 16 | 58.3 ± 8.4 | — | — | — |
| Example 18 | 45.3 ± 12.5 | — | — | — |
| Example 19 | 21.8 ± 10.5 | — | — | — |
| Example 22 | — | 34.6 ± 11.5 | — | — |
| Example 25 | 24.5 ± 8.3 | — | 55.1 ± 10.5 | 103.2 ± 4.8 |
| Example 27 | — | 57.9 ± 8.6 | — | — |
| Example 30 | 48.3 ± 7.1 | — | — | — |
| Example 31 | — | 54.7 ± 10.5 | — | — |
| Example 34 | 8.3 ± 5.9 | — | — | — |
| Example 36 | 27.3 ± 12.6 | — | — | — |
| Example 37 | 25.3 ± 9.2 | — | — | — |
| Example 38 | 44.1 ± 10.7 | — | — | — |
| Example 39 | 20.5 ± 10.3 | — | — | — |
| Example 45 | 34.9 | — | — | — |
| Example 48 | 26.1 | — | — | — |
| Example 49 | 54.3 | — | — | — |
| Example 62 | 16.6 ± 2.4 | — | — | — |
| Example 64 | 25.7 ± 6.3 | — | — | — |
| Example 67 | 63.8 ± 8.1 | — | — | — |
| Example 71 | 9.3 ± 9.3 | — | — | — |
| Example 72 | 31.1 ± 7.5 | — | — | — |
| Example 73 | 23.0 ± 8.8 | — | — | — |
| Example 74 | 2.5 ± 2.5 | — | — | — |
| Example 75 | 2.7 ± 2.1 | — | — | — |
| Example 81 | 25.7 ± 9.3 | — | — | — |
| Example 82 | 14.3 ± 7.8 | — | — | — |
| Example 83 | 52.8 ± 5.8 | — | — | — |
| Example 90 | — | 42.6 ± 6.4 | — | — |
| Example 91 | — | 51.5 ± 8.7 | — | — |
| Example 92 | — | 46.3 ± 4.0 | — | — |
| Example 93 | — | 13.3 ± 4.1 | — | — |
| Example 100 | — | 65.3 ± 5.3 | — | — |
| Example 101 | — | 55.3 ± 5.6 | — | — |
| Example 107 | — | 61.7 ± 6.4 | — | — |
| Example 116 | — | 57.5 ± 7.2 | — | — |
| Example 126 | — | 58.4 ± 7.1 | 32.5 ± 7.9 | 85.1 ± 5.1 |
| Example 128 | — | 12.5 ± 4.8 | 57.4 ± 5.2 | 88.5 ± 4.3 |
| Example 129 | — | 11.9 | — | — |
| Example 131 | — | 24.14 | — | — |
| Example 132 | — | 42.86 | — | — |
| Example 133 | — | 66.65 | — | — |
| Example 134 | — | 61.51 | — | — |
| Example 135 | — | 66.0 ± 5.7 | — | — |
| Example 139 | — | 49.52 | — | — |
| Example 140 | — | 48.22 | — | — |
| Example 141 | — | 56.93 | — | — |
| Example 142 | — | 46.26 | — | — |
| Example 147 | — | 46.50 | — | — |
| Example 148 | — | 51.64 | — | — |
| Example 149 | — | 27.27 | — | — |
| Example 152 | — | 19.07 | — | — |
| Example 153 | — | 14.04 | — | — |

TABLE 3-continued

| Compound | 100 mg/kg | 50 mg/kg | 25 mg/kg | 10 mg/kg |
|---|---|---|---|---|
| Example 160 | — | 50.55 | — | — |
| Example 165 | — | 47.60 | — | — |
| Example 167 | — | 57.56 | — | — |
| Example 168 | — | 56.65 | — | — |
| Example 169 | — | 47.86 | — | — |
| Example 170 | — | 31.42 | — | — |
| Example 171 | — | 54.07 | — | — |
| Example 176 | — | 28.77 | — | — |
| Example 179 | — | — | 52.1 ± 7.7 | — |
| Example 181 | — | — | 33.3 ± 11.5 | — |
| Example 187 | — | — | 49.1 ± 14.5 | — |
| Example 189 | — | — | 37.7 ± 10.0 | — |

As can be seen from Table 3, the compounds of the present invention showed immobilities of 70% or less at 100 mg/kg. And a control compound, fluoxetine showed immobility of 59.5% at 100 mg/kg and 70.4% at 50 mg/kg. From the result of the above, it is found that the compounds of the present invention showed anti-depressants activities of equal levels or more compared with fluoxetine, which are suitable for a therapeutic agent for depressive disorders.

While the invention has been described with respect to the above specific embodiments, it should be recognized that various modifications and changes may be made to the invention by those skilled in the art which also fall within the scope of the invention as defined by the appended claims.

What is claimed is:
1. A compound selected from the group consisting of:
N-(3-(4-(3-chlorophenyl)piperazin-1-yl)propyl)-1,2-dimethyl-5-phenyl-1H-pyrrole-3-carboxamide;
N-(3-(4-(3-chlorophenyl)piperazin-1-yl)propyl)-1,2-dimethyl-5-phenyl-1H-pyrrole-3-carboxamide hydrochloride;
N-(3-(4-(2,3-dimethylphenyl)piperazin-1-yl)propyl)-1,2-dimethyl-5-phenyl-1H-pyrrole-3-carboxamide;
N-(3-(4-(3-chlorophenyl)piperazin-1-yl)propyl)-1-ethyl-2-methyl-5-phenyl-1H-pyrrole-3-carboxamide;
N-(3-(4-(2,3-dimethylphenyl)piperazin-1-yl)propyl)-1-ethyl-2-methyl-5-phenyl-1H-pyrrole-3-carboxamide;
N-(3-(4-(3-chlorophenyl)piperazin-1-yl)propyl)-2-methyl-5-phenyl-1-propyl-1H-pyrrole-3-carboxamide;
N-(3-(4-(2,3-dimethylphenyl)piperazin-1-yl)propyl)-2-methyl-5-phenyl-1-propyl-1H-pyrrole-3-carboxamide;
N-(3-(4-(3-chlorophenyl)piperazin-1-yl)propyl)-2-methyl-5-phenyl-1-(piperidin-1-yl)-1H-pyrrole-3-carboxamide;
N-(3-(4-(2,3-dimethylphenyl)piperazin-1-yl)propyl)-2-methyl-5-phenyl-1-(piperidin-1-yl)-1H-pyrrole-3-carboxamide;
N-(3-(4-(2,3-dichlorophenyl)piperazin-1-yl)propyl)-1,2-dimethyl-5-phenyl-1H-pyrrole-3-carboxamide;
N-(3-(4-(2,3-dichlorophenyl)piperazin-1-yl)propyl)-1-ethyl-2-methyl-5-phenyl-1H-pyrrole-3-carboxamide;
N-(3-(4-(2,3-dichlorophenyl)piperazin-1-yl)propyl)-2-methyl-5-phenyl-1-propyl-1H-pyrrole-3-carboxamide;
N-(3-(4-(2,3-dichlorophenyl)piperazin-1-yl)propyl)-2-methyl-5-phenyl-1-(piperidin-1-yl)-1H-pyrrole-3-carboxamide;
N-(3-(4-(3-chlorophenyl)piperazin-1-yl)propyl)-1-(4-fluorophenyl)-2-methyl-5-phenyl-1H-pyrrole-3-carboxamide;
N-(3-(4-(2,3-dimethylphenyl)piperazin-1-yl)propyl)-1-(4-fluorophenyl)-2-methyl-5-phenyl-1H-pyrrole-3-carboxamide;
N-(3-(4-(2,3-dichlorophenyl)piperazin-1-yl)propyl)-1-(4-fluorophenyl)-2-methyl-5-phenyl-1H-pyrrole-3-carboxamide;
1-Benzyl-N-(3-(4-(3-chlorophenyl)piperazin-1-yl)propyl)-2-methyl-5-phenyl-1H-pyrrole-3-carboxamide;
1-Benzyl-N-(3-(4-(2,3-dimethylphenyl)piperazin-1-yl)propyl)-2-methyl-5-phenyl-1H-pyrrole-3-carboxamide;
1-Benzyl-N-(3-(4-(2,3-dichlorophenyl)piperazin-1-yl)propyl)-2-methyl-5-phenyl-1H-pyrrole-3-carboxamide;
N-(3-(4-(3-chlorophenyl)piperazin-1-yl)propyl)-1-(cyclohexylmethyl)-2-methyl-5-phenyl-1H-pyrrole-3-carboxamide;
1-(Cyclohexylmethyl)-N-(3-(4-(2,3-dimethylphenyl)piperazin-1-yl)propyl)-2-methyl-5-phenyl-1H-pyrrole-3-carboxamide;
1-(Cyclohexylmethyl)-N-(3-(4-(2,3-dichlorophenyl)piperazin-1-yl)propyl)-2-methyl-5-phenyl-1H-pyrrole-3-carboxamide;
N-(3-(4-(3-chlorophenyl)piperazin-1-yl)propyl)-1-isobutyl-2-methyl-5-phenyl-1H-pyrrole-3-carboxamide;
N-(3-(4-(2,3-dimethylphenyl)piperazin-1-yl)propyl)-1-isobutyl-2-methyl-5-phenyl-1H-pyrrole-3-carboxamide;
N-(3-(4-(2,3-dichlorophenyl)piperazin-1-yl)propyl)-1-isobutyl-2-methyl-5-phenyl-1H-pyrrole-3-carboxamide;
N-(3-(4-(2,3-dimethylphenyl)piperazin-1-yl)propyl)-1-ethyl-2-methyl-5-phenyl-1H-pyrrole-3-carboxamide hydrochloride;
N-(3-(4-(2,3-dimethylphenyl)piperazin-1-yl)propyl)-1-ethyl-2-methyl-5-phenyl-1H-pyrrole-3-carboxamide hydrochloride;
N-(3-(4-(2,3-dichlorophenyl)piperazin-1-yl)propyl)-N,2-dimethyl-5-phenyl-1-propyl-1H-pyrrole-3-carboxamide hydrochloride;
1-benzyl-N-(3-(4-(2,3-dimethylphenyl)piperazin-1-yl)propyl)-N,2-dimethyl-5-phenyl-1H-pyrrole-3-carboxamide hydrochloride;
N-(3-(4-(2,3-dichlorophenyl)piperazin-1-yl)propyl)-N,1,2-trimethyl-5-phenyl-1H-pyrrole-3-carboxamide hydrochloride;
N-(2-(4-(2,3-dichlorophenyl)piperazin-1-yl)ethyl)-2-methyl-5-phenyl-1-propyl-1H-pyrrole-3-carboxamide hydrochloride;
N-(2-(4-(2,3-dichlorophenyl)piperazin-1-yl)ethyl)-1-ethyl-2-methyl-5-phenyl-1H-pyrrole-3-carboxamide hydrochloride;
N-(2-(4-(2,3-dichlorophenyl)piperazin-1-yl)ethyl)-5-(4-methoxyphenyl)-1,2-dimethyl-1H-pyrrole-3-carboxamide hydrochloride;
N-(2-(4-(2,3-dichlorophenyl)piperazin-1-yl)ethyl)-1-ethyl-5-(4-methoxyphenyl)-2-methyl-1H-pyrrole-3-carboxamide hydrochloride;
N-(2-(4-(2,3-dichlorophenyl)piperazin-1-yl)ethyl)-5-(4-methoxyphenyl)-2-methyl-1-propyl-1H-pyrrole-3-carboxamide hydrochloride;
N-(3-(4-(2,3-dichlorophenyl)piperazin-1-yl)propyl)-5-(4-methoxyphenyl)-1,2-dimethyl-1H-pyrrole-3-carboxamide hydrochloride;
N-(3-(4-(2,3-dichlorophenyl)piperazin-1-yl)propyl)-1-ethyl-5-(4-methoxyphenyl)-2-methyl-1H-pyrrole-3-carboxamide hydrochloride;
N-(3-(4-(2,3-dimethylphenyl)piperazin-1-yl)propyl)-5-(4-methoxyphenyl)-2-methyl-1-propyl-1H-pyrrole-3-carboxamide hydrochloride;

N-(4-(4-(2,3-dichlorophenyl)piperazin-1-yl)butyl)-5-(4-methoxyphenyl)-2-methyl-1-propyl-1H-pyrrole-3-carboxamide hydrochloride;
N-(4-(4-(2,3-dichlorophenyl)piperazin-1-yl)butyl)-1-ethyl-5-(4-methoxyphenyl)-2-methyl-1H-pyrrole-3-carboxamide hydrochloride;
5-(4-chlorophenyl)-N-(3-(4-(2,3-dimethylphenyl)piperazin-1-yl)propyl)-1,2-dimethyl-1H-pyrrole-3-carboxamide hydrochloride;
5-(4-chlorophenyl)-N-(3-(4-(2,3-dichlorophenyl)piperazin-1-yl)propyl)-1,2-dimethyl-1H-pyrrole-3-carboxamide hydrochloride;
5-(4-chlorophenyl)-N-(3-(4-(2,3-dimethylphenyl)piperazin-1-yl)propyl)-1-ethyl-2-methyl-1H-pyrrole-3-carboxamide hydrochloride;
5-(4-chlorophenyl)-N-(3-(4-(2,3-dichlorophenyl)piperazin-1-yl)propyl)-1-ethyl-2-methyl-1H-pyrrole-3-carboxamide hydrochloride;
5-(4-chlorophenyl)-N-(3-(4-(2,3-dimethylphenyl)piperazin-1-yl)propyl)-2-methyl-1-propyl-1H-pyrrole-3-carboxamide hydrochloride;
5-(4-chlorophenyl)-N-(3-(4-(2,3-dichlorophenyl)piperazin-1-yl)propyl)-2-methyl-1-propyl-1H-pyrrole-3-carboxamide hydrochloride;
5-(4-chlorophenyl)-N-(2-(4-(2,3-dichlorophenyl)piperazin-1-yl)ethyl)-1,2-dimethyl-1H-pyrrole-3-carboxamide hydrochloride;
5-(4-chlorophenyl)-N-(2-(4-(2,3-dichlorophenyl)piperazin-1-yl)ethyl)-1-ethyl-2-methyl-1H-pyrrole-3-carboxamide hydrochloride;
5-(4-chlorophenyl)-N-(2-(4-(2,3-dichlorophenyl)piperazin-1-yl)ethyl)-2-methyl-1-propyl-1H-pyrrole-3-carboxamide hydrochloride;
1-butyl-N-(3-(4-(2,3-dichlorophenyl)piperazin-1-yl)propyl)-2-methyl-5-phenyl-1H-pyrrole-3-carboxamide hydrochloride;
N-(3-(4-(2,3-dichlorophenyl)piperazin-1-yl)propyl)-5-(4-methoxyphenyl)-1,2-dimethyl-1H-pyrrole-3-carboxamide hydrochloride;
N-(3-(4-(2,3-dichlorophenyl)piperazin-1-yl)propyl)-1-ethyl-5-(4-methoxyphenyl)-2-methyl-1H-pyrrole-3-carboxamide hydrochloride;
N-(3-(4-(2,3-dichlorophenyl)piperazin-1-yl)propyl)-1,2,4-trimethyl-5-phenyl-1H-pyrrole-3-carboxamide hydrochloride;
N-(3-(4-(2,3-dichlorophenyl)piperazin-1-yl)propyl)-1-ethyl-2,4-dimethyl-5-phenyl-1H-pyrrole-3-carboxamide hydrochloride;
N-(3-(4-(2,3-dichlorophenyl)piperazin-1-yl)propyl)-2,4-dimethyl-5-phenyl-1-propyl-1H-pyrrole-3-carboxamide hydrochloride;
N-(3-(4-(2,3-dichlorophenyl)piperazin-1-yl)propyl)-5-(3-methoxyphenyl)-2-methyl-1-propyl-1H-pyrrole-3-carboxamide hydrochloride;
N-(3-(4-(2,3-dichlorophenyl)piperazin-1-yl)propyl)-1,2-dimethyl-5-(pyridin-2-yl)-1H-pyrrole-3-carboxamide dihydrochloride;
N-(3-(4-(2,3-dichlorophenyl)piperazin-1-yl)propyl)-2-methyl-1-propyl-5-(pyridin-2-yl)-1H-pyrrole-3-carboxamide dihydrochloride;
N-(2-(4-(2,3-dichlorophenyl)piperazin-1-yl)ethyl)-1,2-dimethyl-5-(pyridin-2-yl)-1H-pyrrole-3-carboxamide dihydrochloride;
N-(2-(4-(2,3-dichlorophenyl)piperazin-1-yl)ethyl)-2-methyl-1-propyl-5-(pyridin-2-yl)-1H-pyrrole-3-carboxamide dihydrochloride;
N-(3-(4-(2,3-dichlorophenyl)piperazin-1-yl)propyl)-1,2-dimethyl-5-(pyridin-3-yl)-1H-pyrrole-3-carboxamide;
N-(3-(4-(2,3-dichlorophenyl)piperazin-1-yl)propyl)-2-methyl-1-propyl-5-(pyridin-3-yl)-1H-pyrrole-3-carboxamide;
N-(2-(4-(2,3-dichlorophenyl)piperazin-1-yl)ethyl)-1,2-dimethyl-5-(pyridin-3-yl)-1H-pyrrole-3-carboxamide;
N-(2-(4-(2,3-dichlorophenyl)piperazin-1-yl)ethyl)-2-methyl-1-propyl-5-(pyridin-3-yl)-1H-pyrrole-3-carboxamide;
N-(3-(4-(2,3-dichlorophenyl)piperazin-1-yl)propyl)-1,2-dimethyl-5-(pyridin-4-yl)-1H-pyrrole-3-carboxamide;
N-(3-(4-(2,3-dichlorophenyl)piperazin-1-yl)propyl)-2-methyl-1-propyl-5-(pyridin-4-yl)-1H-pyrrole-3-carboxamide;
N-(2-(4-(2,3-dichlorophenyl)piperazin-1-yl)ethyl)-1,2-dimethyl-5-(pyridin-4-yl)-1H-pyrrole-3-carboxamide;
N-(2-(4-(2,3-dichlorophenyl)piperazin-1-yl)ethyl)-2-methyl-1-propyl-5-(pyridin-4-yl)-1H-pyrrole-3-carboxamide;
2-chloro-N-(3-(4-(2,3-dichlorophenyl)piperazin-1-yl)propyl)-1-methyl-5-phenyl-1H-pyrrole-3-carboxamide;
2-chloro-N-(3-(4-(2,3-dichlorophenyl)piperazin-1-yl)propyl)-1-propyl-5-(pyridin-4-yl)-1H-pyrrole-3-carboxamide;
N-(3-(4-(2,3-dichlorophenyl)piperazin-1-yl)propyl)-1-methyl-5-phenyl-1H-pyrrole-3-carboxamide;
N-(3-(4-(2,3-dichlorophenyl)piperazin-1-yl)propyl)-5-phenyl-1-propyl-1H-pyrrole-3-carboxamide;
5-tert-Butyl-N-(3-(4-(2,3-dichlorophenyl)piperazin-1-yl)propyl)-1,2-dimethyl-1H-pyrrole-3-carboxamide;
N-(3-(4-(2-carbamoylbenzofuran-5-yl)piperazin-1-yl)propyl)-1,2-dimethyl-5-phenyl-1H-pyrrole-3-carboxamide;
N-(3-(4-(2-carbamoylbenzofuran-5-yl)piperazin-1-yl)propyl)-2-methyl-5-phenyl-1-propyl-1H-pyrrole-3-carboxamide;
1,2-dimethyl-5-phenyl-N-(3-(4-(quinolin-8-yl)piperazin-1-yl)propyl)-1H-pyrrole-3-carboxamide;
2-methyl-5-phenyl-1-propyl-N-(3-(4-(quinolin-8-yl)piperazin-1-yl)propyl)-1H-pyrrole-3-carboxamide;
N-(3-(4-(benzo[d]isothiazol-3-yl)piperazin-1-yl)propyl)-1,2-dimethyl-5-phenyl-1H-pyrrole-3-carboxamide;
N-(3-(4-(benzo[d]isothiazol-3-yl)piperazin-1-yl)propyl)-2-methyl-5-phenyl-1-propyl-1H-pyrrole-3-carboxamide;
5-(But-3-enyl)-N-(3-(4-(2,3-dichlorophenyl)piperazin-1-yl)propyl)-1,2-dimethyl-1H-pyrrole-3-carboxamide;
5-Butyl-N-(3-(4-(2,3-dichlorophenyl)piperazin-1-yl)propyl)-1,2-dimethyl-1H-pyrrole-3-carboxamide;
N-(3-(4-(2,3-dichlorophenyl)piperazin-1-yl)propyl)-1,2,5-trimethyl-1H-pyrrole-3-carboxamide;
N-(3-(4-(2,3-dichlorophenyl)piperazin-1-yl)propyl)-5-(4-hydroxybutyl)-1,2-dimethyl-1H-pyrrole-3-carboxamide;
N-(3-(4-(2,3-dihydrobenzo[b][1,4]dioxin-5-yl)piperazin-1-yl)propyl)-1,2-dimethyl-5-phenyl-1H-pyrrole-3-carboxamide;
N-(3-(4-(2,3-dihydrobenzo[b][1,4]dioxin-5-yl)piperazin-1-yl)propyl)-2-methyl-5-phenyl-1-propyl-1H-pyrrole-3-carboxamide;
1,2-dimethyl-5-(pyridin-2-yl)-N-(3-(4-(quinoxalin-5-yl)piperazin-1-yl)propyl)-1H-pyrrole-3-carboxamide;
2-methyl-1-propyl-5-(pyridin-2-yl)-N-(3-(4-(quinoxalin-5-yl)piperazin-1-yl)propyl)-1H-pyrrole-3-carboxamide;

1,2-dimethyl-5-(pyridin-2-yl)-N-(3-(4-(quinolin-8-yl)piperazin-1-yl)propyl)-1H-pyrrole-3-carboxamide dihydrochloride;
2-methyl-1-propyl-5-(pyridin-2-yl)-N-(3-(4-(quinolin-8-yl)piperazin-1-yl)propyl)-1H-pyrrole-3-carboxamide dihydrochloride;
N-(3-(4-(benzo[d][1,3]dioxol-4-yl)piperazin-1-yl)propyl)-1,2-dimethyl-5-phenyl-1H-pyrrole-3-carboxamide;
N-(3-(4-(benzo[d][1,3]dioxol-4-yl)piperazin-1-yl)propyl)-2-methyl-5-phenyl-1-propyl-1H-pyrrole-3-carboxamide;
N-(3-(4-(2,3-dichlorophenyl)piperazin-1-yl)-2-hydroxypropyl)-1,2-dimethyl-5-phenyl-1H-pyrrole-3-carboxamide hydrochloride;
N-(3-(4-(2,3-dichlorophenyl)piperazin-1-yl)-2-hydroxypropyl)-2-methyl-5-phenyl-1-propyl-1H-pyrrole-3-carboxamide hydrochloride;
N-(3-(4-(2,3-dichlorophenyl)piperazin-1-yl)propyl)-5-(4-methoxybutyl)-1,2-dimethyl-1H-pyrrole-3-carboxamide hydrochloride;
1,2-dimethyl-5-phenyl-N-(3-(4-(quinolin-6-yl)piperazin-1-yl)propyl)-1H-pyrrole-3-carboxamide;
1,2-dimethyl-5-(pyridin-2-yl)-N-(3-(4-(quinolin-6-yl)piperazin-1-yl)propyl)-1H-pyrrole-3-carboxamide;
1,2-dimethyl-N-(3-(4-(2-methylquinolin-8-yl)piperazin-1-yl)propyl)-5-phenyl-1H-pyrrole-3-carboxamide;
2-methyl-N-(3-(4-(2-methylquinolin-8-yl)piperazin-1-yl)propyl)-5-phenyl-1-propyl-1H-pyrrole-3-carboxamide;
N-(3-(4-(3-chloro-2-methylphenyl)piperazin-1-yl)propyl)-1,2-dimethyl-5-phenyl-1H-pyrrole-3-carboxamide;
N-(3-(4-(3-chloro-2-methylphenyl)piperazin-1-yl)propyl)-2-methyl-5-phenyl-1-propyl-1H-pyrrole-3-carboxamide;
5-tert-Butyl-N-(2-(4-(2,3-dichlorophenyl)piperazin-1-yl)ethyl)-1,2-dimethyl-1H-pyrrole-3-carboxamide;
N-(3-(4-(2,3-dichlorophenyl)piperazin-1-yl)propyl)-2,5-dimethyl-1-phenyl-1H-pyrrole-3-carboxamide;
N-(3-(4-(2,3-dimethylphenyl)piperazin-1-yl)propyl)-2,5-dimethyl-1-phenyl-1H-pyrrole-3-carboxamide;
N-(3-(4-(3-chloro-2-fluorophenyl)piperazin-1-yl)propyl)-1,2-dimethyl-5-phenyl-1H-pyrrole-3-carboxamide;
N-(3-(4-(3-chloro-2-fluorophenyl)piperazin-1-yl)propyl)-2-methyl-5-phenyl-1-propyl-1H-pyrrole-3-carboxamide;
5-tert-Butyl-N-(3-(4-(3-chloro-2-fluorophenyl)piperazin-1-yl)propyl)-1,2-dimethyl-1H-pyrrole-3-carboxamide;
N-(3-(4-(3-chloro-2-fluorophenyl)piperazin-1-yl)propyl)-2,5-dimethyl-1-phenyl-1H-pyrrole-3-carboxamide;
N-(3-(4-(3-chloro-2-methylphenyl)piperazin-1-yl)propyl)-2,5-dimethyl-1-phenyl-1H-pyrrole-3-carboxamide;
5-tert-Butyl-N-(3-(4-(3-chloro-2-methylphenyl)piperazin-1-yl)propyl)-1,2-dimethyl-1H-pyrrole-3-carboxamide;
5-tert-Butyl-N-(3-(4-(2,3-dimethylphenyl)piperazin-1-yl)propyl)-1,2-dimethyl-1H-pyrrole-3-carboxamide;
N-(2-(4-(2,3-dichlorophenyl)piperazin-1-yl)ethyl)-2,5-dimethyl-1-phenyl-1H-pyrrole-3-carboxamide;
5-tert-Butyl-N-(3-(4-(2,3-dimethylphenyl)piperazin-1-yl)propyl)-2-methyl-1-propyl-1H-pyrrole-3-carboxamide;
5-tert-Butyl-N-(3-(4-(2,3-dichlorophenyl)piperazin-1-yl)propyl)-2-methyl-1-propyl-1H-pyrrole-3-carboxamide;
5-tert-Butyl-N-(3-(4-(2,3-dichlorophenyl)piperazin-1-yl)propyl)-1-ethyl-2-methyl-1H-pyrrole-3-carboxamide;
N-(2-(4-(3-chloro-2-fluorophenyl)piperazin-1-yl)ethyl)-1,2-dimethyl-5-phenyl-1H-pyrrole-3-carboxamide;
N-(2-(4-(3-chloro-2-methylphenyl)piperazin-1-yl)ethyl)-1,2-dimethyl-5-phenyl-1H-pyrrole-3-carboxamide;
1,2-dimethyl-N-(2-(4-(2-methylquinolin-8-yl)piperazin-1-yl)ethyl)-5-phenyl-1H-pyrrole-3-carboxamide;
5-tert-Butyl-N-(2-(4-(3-chloro-2-fluorophenyl)piperazin-1-yl)ethyl)-1,2-dimethyl-1H-pyrrole-3-carboxamide;
5-tert-Butyl-N-(2-(4-(3-chloro-2-methylphenyl)piperazin-1-yl)ethyl)-1,2-dimethyl-1H-pyrrole-3-carboxamide;
5-tert-Butyl-1,2-dimethyl-N-(2-(4-(2-methylquinolin-8-yl)piperazin-1-yl)ethyl)-1H-pyrrole-3-carboxamide;
5-tert-Butyl-N-(2-(4-(2,3-dimethylphenyl)piperazin-1-yl)ethyl)-1,2-dimethyl-1H-pyrrole-3-carboxamide;
5-tert-Butyl-N-(3-(4-(2,3-dimethylphenyl)piperazin-1-yl)propyl)-1-ethyl-2-methyl-1H-pyrrole-3-carboxamide;
5-tert-Butyl-N-(3-(4-(2,3-dichlorophenyl)piperazin-1-yl)-2-hydroxypropyl)-1,2-dimethyl-1H-pyrrole-3-carboxamide;
N-(3-(4-(2,3-dichlorophenyl)piperazin-1-yl)propyl)-4-methoxy-1,2-dimethyl-5-phenyl-1H-pyrrole-3-carboxamide;
N-(2-(4-(2,3-Dichlorophenyl)piperazin-1-yl)ethyl)-4-methoxy-1,2-dimethyl-5-phenyl-1H-pyrrole-3-carboxamide;
1,2-dimethyl-5-phenyl-N-(2-(4-(quinolin-8-yl)piperazin-1-yl)ethyl)-1H-pyrrole-3-carboxamide;
N-(3-(4-(3-chloro-2-methylphenyl)piperazin-1-yl)-2-hydroxypropyl)-1,2-dimethyl-5-phenyl-1H-pyrrole-3-carboxamide;
N-(2-(4-(2,3-dichlorophenyl)piperazin-1-yl)-3-fluoropropyl)-1,2-dimethyl-5-phenyl-1H-pyrrole-3-carboxamide hydrochloride;
N-(2-(4-(2,3-dichlorophenyl)piperazin-1-yl)-3-fluoropropyl)-2-methyl-5-phenyl-1-propyl-1H-pyrrole-3-carboxamide hydrochloride;
N-(3-(4-(2,3-dichlorophenyl)piperazin-1-yl)-2,2-difluoropropyl)-1,2-dimethyl-5-phenyl-1H-pyrrole-3-carboxamide;
5-tert-Butyl-N-(3-(4-(2,3-dimethylphenyl)piperazin-1-yl)-2-hydroxypropyl)-1,2-dimethyl-1H-pyrrole-3-carboxamide;
N-(2-(4-(2,3-dimethylphenyl)piperazin-1-yl)ethyl)-4-methoxy-1,2-dimethyl-5-phenyl-1H-pyrrole-3-carboxamide;
N-(3-(4-(2,3-dimethylphenyl)piperazin-1-yl)propyl)-4-methoxy-1,2-dimethyl-5-phenyl-1H-pyrrole-3-carboxamide; and
N-(3-(4-(2,3-dichlorophenyl)piperazin-1-yl)propyl)-4-hydroxy-1,2-dimethyl-5-phenyl-1H-pyrrole-3-carboxamide, or a pharmaceutically acceptable salt thereof.

2. A pharmaceutical composition, which comprises the compound according to claim 1 or the pharmaceutically acceptable salt thereof as an active ingredient, and a pharmaceutically acceptable carrier.

3. A method for treating depressive disorders in a mammal, which comprises administering the compound according to claim 1 or the pharmaceutically acceptable salt thereof to the mammal.

* * * * *